US012778580B2

(12) United States Patent
Hirotsuka et al.

(10) Patent No.: US 12,778,580 B2
(45) Date of Patent: Nov. 3, 2026

(54) MEDICAL DEVICE FOR JOINING MATERIALS

(71) Applicant: BioBolt Medical Corporation, Tucson, AZ (US)

(72) Inventors: Mark Y. Hirotsuka, San Jose, CA (US); William R. George, Santa Cruz, CA (US); Joseph R. Rimsa, Palo Alto, CA (US); Geoffrey C. Gurtner, Portola Valley, CA (US)

(73) Assignee: BioBolt Medical Corporation, Tucson, AZ (US)

( * ) Notice: Subject to any disclaimer, the term of this patent is extended or adjusted under 35 U.S.C. 154(b) by 0 days.

(21) Appl. No.: 18/656,458

(22) Filed: May 6, 2024

(65) Prior Publication Data

US 2024/0398407 A1 Dec. 5, 2024

Related U.S. Application Data

(63) Continuation of application No. 17/770,994, filed as application No. PCT/US2020/057188 on Oct. 23, 2020.

(Continued)

(51) Int. Cl.

| | |
|---|---|
| ***A61B 17/068*** | (2006.01) |
| ***A61B 17/00*** | (2006.01) |
| ***A61B 17/04*** | (2006.01) |

(52) U.S. Cl.

CPC .. *A61B 17/068* (2013.01); *A61B 2017/00747* (2013.01); *A61B 2017/0419* (2013.01)

(58) Field of Classification Search

CPC .............. A61B 17/068; A61B 17/0401; A61B 17/06066; A61B 2017/00747;

(Continued)

(56) References Cited

U.S. PATENT DOCUMENTS 4,006,747 A 2/1977 Kronenthal et al.
4,558,810 A 12/1985 Mulllauser et al.

(Continued)

FOREIGN PATENT DOCUMENTS

JP 2000-515054 11/2000
JP 2002-537058 11/2002

(Continued)

OTHER PUBLICATIONS

Anthrex; Arthroscopic Meniscal Repair; Arthroscopic All-Inside Meniscal Repair; 6 pages; 2009.

(Continued)

*Primary Examiner* — Shaun L David
*Assistant Examiner* — Cherie M Poland
(74) *Attorney, Agent, or Firm* — Levine Bagade Han LLP

(57) ABSTRACT

A medical device for joining materials is provided. The device comprises a piercing element configured to penetrate materials to be joined. The piercing element is sufficiently sharp to penetrate materials to be joined and comprises a hollow interior along at least a portion of its length configured to distal advancement of a fastener therethrough; and an open tip through which the fastener can be pushed. The device can be used for fastening materials including tissue, synthetic mesh, and biologic mesh (e.g., ADM).

19 Claims, 118 Drawing Sheets

Related U.S. Application Data

(60) Provisional application No. 63/022,286, filed on May 8, 2020, provisional application No. 62/926,273, filed on Oct. 25, 2019.

(58) Field of Classification Search
CPC .. A61B 2017/0419; A61B 2017/00349; A61B 2017/0417; A61B 2017/0409; A61B 2090/0807; A61B 17/0682; A61B 17/064; A61B 2017/0042; A61B 2017/2943; A61B 2017/2923; A61B 2017/2904; A61B 2017/2908; A61B 2017/00738; A61F 2002/0072
See application file for complete search history.

(56) References Cited

U.S. PATENT DOCUMENTS

| | | | | |
|---|---|---|---|---|
| 4,621,639 | A | 11/1986 | Transue et al. | |
| 5,085,661 | A | 2/1992 | Moss | |
| 5,203,684 | A * | 4/1993 | Henriksen | F01C 9/002 417/482 |
| 5,203,864 | A | 4/1993 | Phillips | |
| 5,549,617 | A | 8/1996 | Green et al. | |
| 6,056,778 | A | 5/2000 | Grafton et al. | |
| 6,086,600 | A | 7/2000 | Kotenbach | |
| 6,716,234 | B2 | 4/2004 | Grafton | |
| 6,736,828 | B1 | 5/2004 | Adams et al. | |
| 7,833,234 | B2 | 11/2010 | Bailly et al. | |
| 8,337,514 | B2 | 12/2012 | Baker et al. | |
| 8,337,523 | B2 | 12/2012 | Baker et al. | |
| 8,361,112 | B2 | 1/2013 | Carroll, II et al. | |
| 8,636,188 | B2 | 1/2014 | Buesseler et al. | |
| 8,961,540 | B2 | 2/2015 | Baker et al. | |
| 9,358,007 | B2 | 6/2016 | Baker et al. | |
| 9,572,578 | B2 | 2/2017 | Baker et al. | |
| 9,795,375 | B2 | 10/2017 | Lore et al. | |
| 10,299,905 | B2 * | 5/2019 | Cardinale | A61F 2/0063 |
| 10,357,245 | B2 | 7/2019 | Baker et al. | |
| 10,646,325 | B2 | 5/2020 | Willard et al. | |
| 10,675,015 | B2 | 6/2020 | Guo et al. | |
| 11,484,305 | B2 | 11/2022 | Baker et al. | |
| 12,035,908 | B2 | 7/2024 | Lee et al. | |
| 2002/0010490 | A1 | 1/2002 | Schaller et al. | |
| 2003/0187465 | A1 * | 10/2003 | Bailly | A61B 17/068 606/143 |
| 2005/0187567 | A1 * | 8/2005 | Baker | A61B 17/10 606/151 |
| 2005/0203552 | A1 | 9/2005 | Laufer et al. | |
| 2006/0235446 | A1 * | 10/2006 | Godin | A61B 17/0401 606/151 |
| 2007/0073316 | A1 * | 3/2007 | Sgro | A61B 17/068 606/151 |
| 2009/0090763 | A1 * | 4/2009 | Zemlok | A61B 17/07207 227/175.2 |
| 2012/0298719 | A1 * | 11/2012 | Shelton, IV | A61B 17/072 227/176.1 |
| 2014/0031835 | A1 * | 1/2014 | Viker | A61B 17/3468 606/151 |
| 2017/0181826 | A1 * | 6/2017 | Cardinale | A61F 2/0063 |
| 2018/0064442 | A1 * | 3/2018 | Shelton, IV | H01M 10/48 |

FOREIGN PATENT DOCUMENTS

| | | |
|---|---|---|
| JP | 2005-526549 | 9/2005 |
| JP | 2016-531675 | 10/2016 |
| WO | WO 2004/000104 | 12/2003 |
| WO | WO 2008/005465 | 1/2008 |
| WO | WO2021/081422 | 4/2021 |

OTHER PUBLICATIONS

Con Med; Reflex Skin Stapiers—Procedure for Clinical Use; 2 pages; retrieved from the internet (https://www.conmed.com/en/medical-specialities/iaparnsocpic-robotic-and-open-surgery/urology/instruments/closure/skin-staplers) on Jun. 10, 2019.
Coviden; Single Use Skin Staplers; 2 pages: retrieved from the internet (https://www.medtronic.com/covidien/en-US/products/surgical-stapling/skin-staplers.html) on Jun. 10, 2019.
Dipaola et al.; Meniscus Repair Fixation Devices; Musculoskeletal Key; 9 pages; retrieved from.
The internet (https://musculoskeletalkey.com/meniscus-repair-fixation-devices/); Jun. 22, 2016.

* cited by examiner

MEDICAL DEVICE FOR JOINING MATERIALS

CROSS REFERENCE TO RELATED APPLICATIONS

This application is a continuation of U.S. patent application Ser. No. 17/770,994 filed Apr. 21, 2022, which is a national stage of International Application No. PCT/US2020/057188 filed Oct. 23, 2020, which claims the benefit of U.S. Prov. Pat. Apps. 62/926,273 filed on Oct. 25, 2019 and 63/022,286 filed May 8, 2020, each of which is incorporated herein by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of surgical fastening devices.

BACKGROUND

Joining soft tissues and soft tissues to materials (such as synthetic, biological or resorbable mesh) is performed in many surgical procedures and is typically accomplished using sutures, staples or tacks. However, these fixation methods come with tradeoffs. Placing multiple sutures takes a lot of time. Stapling and tacking can be relatively fast; but, they can be undesirable if metal or rigid, sharp-tipped fasteners present issues (e.g. pain, imaging, perforating structures, retention). Additionally, most existing staplers and tackers are unsuitable for tougher materials such as acellular dermal matrix (also known as ADM, a biological mesh), and require time-consuming suturing.

Acellular dermal matrix (ADM) is a material that is made from donor skin, typically of human or porcine origin, and processed to remove the cellular contents and preserve the collagen and elastin fiber matrix. ADM is used to treat a range of conditions where intact dermal scaffolding is needed and is approximated to tissue using suture. Examples of surgical procedures that use ADM include breast reconstruction, cosmetic breast procedures, abdominal wall repair (e.g. ventral/incisional hernia repair, wall reinforcement/prophylaxis), burns and wounds (e.g. diabetic foot ulcers), and orthopedic procedures (e.g. quadriceps tendon reinforcement, Achilles tendon repair, and augmentation in shoulder, hip and knee).

Currently there are no staplers that can penetrate ADM, so doctors use sutures to fix ADM to tissue, which is a time-consuming procedure. In procedures with other materials where staplers can be used (e.g. with mesh), doctors push the stapler into tissue using a good amount of force to ensure a good connection. The pushing, however, risks damaging underlying tissues or organs, as it causes the tissues to be stapled to abut underlying tissues during the stapling.

As an example, in ventral and incisional hernia repair, mesh is used to reinforce the midline closure to prevent hernia recurrence. If ADM is used in an open onlay approach, as shown in FIG. 1, the ADM 2 is placed on the abdominal muscles 4 and sutured in place. Multiple sutures 6 are carefully placed to fix the ADM 2 to muscle 4 so that the ADM 2 is taut, lays flat and has enough fixation points. Suturing is not only time-consuming, but also relatively difficult and technique dependent, which could negatively affect clinical outcomes.

A fast, easy to use fastener device that can pierce ADM or other mesh, facilitate ADM (or other mesh) positioning and tensioning, fix ADM (or other mesh) to soft tissue using a non-metal (polymeric or resorbable) fastener, and work with onlay procedures would be an advantageous tool that reduces the surgeon's workload/procedure time and provides a repeatable fixation construct.

SUMMARY OF THE DISCLOSURE

In a first aspect, a fastening device is provided. The device comprises a shaft; a handle; a needle extending from the shaft, the needle comprising a slot extending along at least a portion of the needle. The device can be configured to receive a fastener comprising a first bar and a second bar connected by a bar connector, the first bar positioned within the needle and the second bar positioned outside the needle.

The device can further comprise at least one fastener comprising a first bar and a second bar connected by a bar connector, the first bar positioned within the needle and the second bar positioned outside the needle; and a push member configured to push the fastener out of the needle.

The device can further comprise a push member configured to push the fastener out of the needle.

In some embodiments, the device further comprises a fastener reservoir within the shaft. The second bar can be positioned within the shaft. In some embodiments, the device comprises at least one ramp near a distal end of the device, the ramp configured to reorient the second bar while the fastener is pushed distally. The device can comprise a shoulder positioned at a fixed or adjustable distance proximal to the distal end of the needle. In some embodiments, the device comprises a trigger configured to deploy a fastener by engaging the push member. The shaft can comprise one or more of an articulating end and a rotating end. In some embodiments, the shaft comprises a bent end.

The shaft can comprise a replaceable cartridge. The replaceable cartridge can comprise the entire shaft or a distal portion of the shaft.

In some embodiments, the needle can be retracted and/or advanced relative to the shaft. A distal portion of the shaft can be retracted and/or advanced relative to the needle.

In some embodiments, the needle comprises one or more barbs. The barbs can be ejectable/retractable. In some embodiments, the needle comprises on or more bumps. The needle can comprise one or more notches. In some embodiments, the needle comprises an area of enlarged diameter proximal to an end of the needle.

The needle can comprise one or more blades. The one or more blades can be retractable. The one or more blades can be actuated. In some embodiments, the device comprises one or more auxiliary needles.

The one or more auxiliary needles can comprise one or more auxiliary needle barbs. In some embodiments, the one or more auxiliary needle barbs are ejectable/retractable.

The device can comprise a first ramp extending from a surface close to the needle, the first ramp extending away from the surface and configured to lift the bar connector and second bar above the needle as the fastener is being pushed distally. In some embodiments, the device comprises a ramp extending from a sidewall, the ramp extending away from the sidewall and configured to rotate the second bar as the fastener is being pushed distally, such that the second bar is moved towards an orientation approximately parallel to a material being fastened. The device can comprise a surface or sidewall configured to maintain the rotated position of the second bar.

In some embodiments, at least a portion of the needle's slot is in a helical shape. The device can comprise a support configured to provide countertraction to materials being fastened while the needle is withdrawn from the materials.

The device can comprise a support configured to provide countertraction to materials being fastened while the needle is withdrawn from the materials.

In some embodiments, the needle is bent or curved.

A width of the needle slot can be larger than a width of the bar connector or the fastener. In some embodiments, edges of the needle slot comprise rounded, broken, polished, or other non-sharp edge configurations.

A size of an inner diameter of the needle and a size of an outer diameter of the needle can be selected to provide a sufficiently sized passageway through the material to be joined so the fastener's bar and bar connector pass through the material to be joined with minimal force. In some embodiments, the size of the inner diameter and outer diameter of the needle is selected to provide minimal insertion force in the material to be joined.

The bevel angle of the needle tip can be configured to provide minimal insertion force in the material to be joined. In some embodiments, the bevel angle of the needle tip is configured to withstand repeated use.

A length of the needle can be selected to minimize trauma to tissue and structures surrounding a repair site. In some embodiments, the length of the needle is selected to be suitable for depositing one end or more than one end of the fastener in tissue.

In another aspect, a tissue fastener configured for joining tissue to another material or tissue is provided. The fastener comprises a first bar; a second bar; and a connector joining the first bar to the second bar, wherein the connector is configured to be strong enough to withstand the deployment of the first bar.

In some embodiments, at least one of the first and second bar has one or more blunt ends. At least one of a height, length, or width of the second bar can be different from a corresponding dimension of the first bar. In some embodiments, the second bar is configured to flex. At least one of the first bar and the second bar can be curved.

In some embodiments, at least one of the second bar and the first bar comprises downward and/or upward facing protrusions. At least one of the first bar, the second bar and the connector bar can comprise one or more barbs. In some embodiments, at least one of the first bar and the second bar comprises expanding wings. At least one of the first bar and the second bar can comprise curling arms.

In some embodiments, the first bar comprises a circular cross section. At least one of the first bar, the second bar, and the connector can comprise a circular, ovular, square or rectangular cross section.

In some embodiments, a thickness or diameter of the connector is smaller than a thickness or diameter of the first bar or second bar.

In some embodiments, the connector material is stretched or prestretched. The first arm and the second arm can extend in different directions. In some embodiments, at least one of the first bar and the second bar comprises an end feature. At least one of the first bar and the second bar can comprise a bend. In some embodiments, a length of the connector is adjustable. The connector can be positioned at an angle other than perpendicular relative to the first bar and the second bar. In some embodiments, at least one of the first bar, the second bar and the connector bar comprises one or more materials. The connector bar can be bent or curved.

In some embodiments, a length of the tissue fastener is sized to embed one or more ends of the fastener in tissue. The one or more ends of the fastener that are embedded in tissue can comprise one or more features configured to resist pulling out of tissue.

In some embodiments, one or more ends of the fastener that are not embedded in tissue comprise one or more features configured to retain an onlay material.

In some embodiments, a method for fastening an onlay material to tissue is provided. The method comprises piercing the onlay material and tissue with a needle comprising a slot, the needle forming part of a fastening device; and advancing a fastener comprising a first bar positioned within the needle, the first bar connected to a second bar by a connector.

The method can comprise using a stop to control the insertion depth of the needle.

In some embodiments, the method comprises withdrawing the needle out of the tissue from a first location in tissue, positioning or tensioning the material on the needle, and piercing the tissue at a second location.

In some embodiments, the method comprises reorienting the second bar.

The method can comprise advancing the fastener comprising activating a trigger on the fastening device. In some embodiments, the method comprises maintaining/stabilizing the position of the needle within the onlay material and tissue while deploying the fastener.

The method can comprise reorienting the second bar comprises using one or more ramps positioned near a distal end of the device. In some embodiments, reorienting the second bar comprises moving or lifting the second bar to avoid engaging the slot of the needle. Reorienting the second bar can comprise moving the second bar towards a position parallel to a surface of the onlay material. In some embodiments, reorienting the second bar comprises rotating the second bar such that the second bar moves towards being parallel to the surface of the onlay material.

In some embodiments, the method comprises deploying the first bar within the tissue. The method can comprise deploying the second bar such that it rests adjacent to the onlay material. In some embodiments, the method comprises deploying the fastener such that the tissue and onlay material are approximated and fixed together by the fastener. The method can comprise withdrawing the needle from the onlay material and tissue after the fastener is deployed. In some embodiments, the method comprises supporting the onlay material and tissue while withdrawing the needle. The method can comprise holding the onlay material and tissue away from underlying structures while the fastener is deployed.

In another aspect, a fastening device is provided. The device comprises two needles extending from the device, each needle comprising a slot extending along at least a portion of the needle; at least one fastener comprising a first bar and a second bar connected by a bar connector; the first bar positioned within one needle and the second bar positioned within the other needle; and push members configured to push the bars distally within and out of the needles.

In yet another aspect, a method for fastening an onlay material to tissue is provided. The method comprises piercing the onlay material and tissue with two needles, each needle comprising a slot, the needles forming part of a fastening device; advancing a fastener comprising a first bar positioned within one needle, a second bar positioned within the other needle, the first bar connected to a second bar by a connector; and deploying the first and second bars in tissue such that the tissue and onlay material are approximated and fixed together by the fastener.

In still another aspect, a fastening device is provided. The device comprises a needle extending from the device, the needle comprising a slot extending along at least a portion of the needle; at least one fastener comprising a first bar and a second bar connected by a bar connector, the first bar and second bar positioned within the needle; and a push member configured to push the bars distally within and out of the needle.

In another aspect, a method for fastening an onlay material to tissue is provided. The method comprises piercing the onlay material and tissue with a needle comprising a slot, the needle forming part of a fastening device; advancing a fastener comprising a first bar and second bar positioned within the needle, the first bar connected to a second bar by a connector; deploying the first bar in tissue at a first location; removing the needle from the onlay material and tissue at the first location; and deploying the second bar in tissue at a second location such that the tissue and onlay material are approximated and fixed together by the fastener.

In yet another aspect, a fastening device is provided. The device comprises a first jaw comprising a needle comprising a slot; and a second jaw, opposing the first jaw.

The device can comprise an opening configured to receive the needle when the first jaw and second jaw are moved towards one another.

In a further aspect, a method for fastening tissues or materials is provided. The method comprises piercing a first tissue or material with a needle comprising a slot, the needle forming part of a fastening device, wherein piercing the first tissue or material comprises moving opposing jaws of the fastening device towards one another; piercing a second tissue or material with the needle and approximating the first and second tissues or materials, wherein piercing the second tissue or material comprises moving the opposing jaws towards one another; and advancing a fastener comprising a first bar positioned within the needle, the first bar connected to a second bar by a connector.

In some embodiments, the method comprises deploying the first bar through the tissues or materials such that the first bar rests on the surface of one of the tissues or materials and the second bar rests on the surface of another of the other tissues or materials. The method can comprise deploying the fastener such that the tissues or materials are approximated and fixed together by the fastener.

In another aspect, a method for fastening tissues or materials is provided. The method comprises piercing a first tissue or material with a first needle comprising a slot, the first needle forming part of the fastening device; piercing a second tissue or material with a second needle comprising a slot, the second needle forming part of the fastening device; approximating the first and second tissues or materials, wherein approximating the tissues or materials comprises moving the first tissue or material using the first needle, and piercing the second tissue or material with the second needle; advancing the fastener comprising a first bar positioned within the first needle, a second bar positioned within the second needle, the first bar connected to a second bar by a connector; and deploying the first bar and second bars through the tissues or materials such that the tissues or materials are approximated and fixed together by the fastener.

In yet another aspect, a method for fastening an onlay material to tissue is provided. The method comprises placing an onlay material adjacent to the tissue; embedding a first bar of a fastener in the tissue; and positioning a second bar of the fastener adjacent to the onlay material, thereby fixing the onlay material to the tissue, wherein the fastener comprises a connector joining the first bar to the second bar.

In another aspect, a method for fastening a material to tissue is provided. The method comprises placing a material adjacent to the tissue; placing a first bar of a fastener adjacent to the tissue; and placing a second bar of the fastener adjacent to the material, thereby fixing the material to the tissue, wherein the fastener comprises a connector joining the first bar to the second bar.

In a first aspect, a surgical device for joining materials is provided. The device comprises a head portion, a first and second fang comprising sharp ends and a hollow or partially hollow interior; and a deployment member configured to push a staple out of the head portion.

The first fang can be configured to receive a first leg of a staple; and a second fang configured to receive a second leg of a staple. The device can also comprise a retractable backstop configured to be actuated towards the first and second fangs, comprising a first hole or partial perimeter configured to receive the first fang; and a second hole or partial perimeter configured to receive the second fang; and a joint connecting the head portion and retractable backstop and configured to enable retractable backstop to actuate towards the head portion.

In some embodiments, at least one of the first and second fangs comprises an open side shaped to allow passage of a staple leg. The open side can comprise a slot. The deployment member can comprise two outer dies configured to be moved down towards a center die. In some embodiments, the deployment member comprises a center die and two outer dies configured to be moved down towards the center die. At least one of the first and second fangs can comprise an angled or sharpened tip.

In some embodiments, the fangs can be attached to a retractable shuttle. The device can comprise a staple positioned in a retractable shuttle with a first staple leg positioned within the first fang and a second staple leg positioned within the second fang. In some embodiments, the retractable shuttle is configured to retract the fangs.

In some embodiments, the device comprises a staple positioned in the retractable head with a first leg positioned within the first fang and a second leg positioned within the second fang. The retractable head can be configured to be retracted while the head portion maintains its position. The head portion can be configured to hold a plurality of staples. In some embodiments, the head portion comprises a staple cartridge configured to hold a plurality of staples.

In some embodiments, the head portion is on an end of a shaft. The head portion can be configured to rotate or articulate.

One or more fangs can comprise an attached blade. In some embodiments, one or more fangs comprises an actuatable blade. The blade can taper from a base of the fang toward an end of the fang. In some embodiments, one or more fangs is configured to articulate. One or more fangs can comprise internal features shaped to guide the staple into a closed position. In some embodiments, the one or more fangs is adjustable. The one or more fangs can comprise threads. In some embodiments, wherein one or more fangs comprises at least one of a barb, notch or neck. The fangs can be replaceable. In some embodiments, the fangs are covered by an actuatable shroud or backstop.

In another aspect, a surgical device for joining materials is provided. The device comprises a head portion comprising a fang and a deployment member configured to push the staple out of the head portion.

The fang can be configured to receive legs of the staple.

The device can comprise a retractable backstop configured to be actuated towards the fang. The retractable backstop comprises a first hole or partial perimeter configured to receive the fang and a joint connecting the head portion and the retractable backstop and configured to actuate the retractable backstop towards the fang.

In some embodiments, the head portion is configured to rotate at least 180°. In some embodiments, the fang comprises an open side shaped to allow passage of a staple leg.

The head portion can be configured to articulate. In some embodiments, the first fang comprises a blade attached to it. The blade can taper from a base of the fang towards an end of the fang. In some embodiments, the fang is configured to articulate. The fang can comprise internal features shaped to guide the staple into a closed position. In some embodiments, a position of the first fang is adjustable. The first fang can be threaded. In some embodiments, the fang comprises at least one of barbs, notches, and necks. The fang can be replaceable. In some embodiments, the fang is configured to flip down from the head portion.

In yet another aspect, a method for joining materials is provided. The method comprises piercing a first material and a second material with fangs, the fangs forming part of a fastening device; and deploying a staple through the fangs.

The method can comprise first piercing the first material with the fangs. The method can comprise first piercing only the first material with the fangs by positioning the first material between the fang and backstop, moving the backstop toward the fangs thereby pushing the first material onto the fangs. In some embodiments, the method comprises comprising moving the backstop away from the fangs and retracting the backstop. The method can comprise positioning the first material to the second material using the fangs to which the first material is attached. The method can comprise piercing the second material with the fangs. In some embodiments, the method comprises retracting the first and second materials using one or more of the fangs or partially deployed staple. The method can comprise deploying the staple to join the first material to the second material. In some embodiments, the method comprises removing the fangs from the first and second materials. The method can comprise comprising deploying the staple by pushing the staple out of the head portion. In some embodiments, the method comprises deploying the staple by forming the staple around a center die. The method can comprise deploying the staple using outer dies to form the staple around a center die. The first material can comprise an onlay material. The second material can comprise tissue.

In another aspect, a surgical device for joining materials is provided. The device comprises a head portion, comprising a first staple exit configured to allow passage of a first staple leg; a second staple exit configured to allow passage of a second staple leg; and a deployment member configured to push a staple out of the head portion.

The device can also comprise a retractable backstop configured to be actuated towards the staple legs, comprising a first hole or partial perimeter configured to receive the first staple leg; and a second hole or partial perimeter configured to receive the second staple leg; and a joint connecting the head portion and retractable backstop and configured to enable the retractable backstop to actuate towards the staple legs.

In some embodiments, the deployment member comprises a center die and two outer dies configured to be moved down towards the center die.

In some embodiments, the first and second staple legs comprise angled or sharpened tips.

The device can comprise a staple that can be positioned in a retractable shuttle. In some embodiments, the device comprises a staple positioned in a retractable shuttle with the first staple leg positioned at or in the first staple exit and a second staple leg positioned at or in the second staple exit. The retractable shuttle can be configured to retract the staple legs.

The head portion can comprise a staple cartridge configured to hold a plurality of staples. The head portion can comprise a staple cartridge configured to hold a plurality of staples. The head portion can be on an end of a shaft. The head portion can be configured to rotate or articulate. The head portion can comprise one or more attached blades. The head portion can comprise one or more actuatable blades. The blade can taper from the base of the head portion toward and end of the staple leg. The staple legs can be configured to flip down from the head. The staple legs can be covered by an actuatable shroud or backstop.

In another aspect, a surgical device for joining materials is provided. The device comprises a first arm, comprising a channel configured for holding a staple; an opening in the channel to allow passage of the staple during staple deployment; and a push member configured to advance the staple out of the first hole. The device also comprises a second arm comprising a second hole or partial perimeter; and a hinge connecting first arm and second arm and configured to allow the first arm and second arm to be moved away from each other and to be moved towards one another.

The first arm can comprise a stop configured to interact with a formed feature of the staple to arrest motion of the staple. The stop can be configured to disengage.

In some embodiments, the first arm comprises a first forming member configured to form the staple. In some embodiments, the first arm comprises a moveable second forming element configured to advance and work in conjunction with the first forming element to form the staple. In some embodiments, the second arm comprising a hole or portion of a perimeter (such as a slot) moves toward the first arm to receive the piercing end of the staple. In some embodiments, the first arm comprises a push member configured to push the staple. The first arm can comprise a push member configured to push the staple through forming elements to form the staple. In some embodiments, the staple has a first preformed end configured to pierce the materials to be joined. The staple can have a second preformed end configured to interact with the stop and retain a material to be joined.

In another aspect, a method of joining materials is provided. The method comprises moving opposing arms or jaws towards one another to pierce the materials to be joined with an end of a staple; securing the materials to be joined between the opposing arms or jaws; and deploying and forming the staple to fix the materials to be joined.

The method can comprise advancing a first end of the staple out of a channel opening in the first arm or jaw. In some embodiments, the method comprises advancing a second forming element to shape a first end of the staple for piercing materials to be joined. The method can comprise using a stop to interact with a formed feature of the staple to arrest motion of the staple during the advancement of the second forming feature.

In some embodiments, the method comprises positioning a first material of the materials between the opposing arms or jaws. The method can comprise moving the opposing arms or jaws towards one another to pierce the first material on the staple. The method can comprise moving the opposing arms away from one another. The method can comprise further comprising positioning a second material of the materials between the opposing arms or jaw. The method can comprise moving the opposing arms or jaws towards one another to pierce the second material on the staple. The method can comprise securing the materials to be joined between the opposing arms or jaws. In some embodiments, the method comprises pushing the staple through one or more forming members to fully form and close the staple, fixing the materials together. The method can comprise releasing the staple from the first arm or jaw, leaving the materials fixed together by the staple. The method can comprise moving the opposing arms or jaws away from one another to release the materials.

In another aspect, a tissue fastener or staple configured for joining tissue to another material or tissue is provided. The fastener or staple comprises a first leg; a second leg; and a span connecting the first leg and second leg. The first leg and second leg can be approximately perpendicular to the span. In some embodiments, the first leg and second leg have an acute angle to the span. In some embodiments, the bend between the span and the legs comprises bend radius of about 0.005-0.020". In some embodiments, the bend between the span and the legs comprises a bend radius of about 0.021-0.100". In some embodiments, ends of the closed staple legs reside relatively in the same plane above and below each other. In some embodiments, the span is configured with bumps or humps on the lateral aspects of the span. The fastener can comprise a metal, a polymer, and/or a resorbable material.

In another aspect, a tissue fastener or staple configured for joining tissue and/or materials is provided. The staple comprises comprising one or more preformed bends on a first end of the staple; and a sharpened tip on a second end of the staple. In some embodiments, the one or more preformed bends on the first end of the staple are configured to retain materials to be joined. In some embodiments, the sharpened tip on the second end of the staple is configured to pierce materials to be joined. In some embodiments, the second end of the staple comprises one or more preformed bends. The fastener can comprise a metal, a polymer, and/or a resorbable material.

In another aspect, a tissue fastener or staple configured for joining tissue and/or materials. The fastener comprises one or more heads on a first end of the staple; and a sharpened tip on a second end of the staple. The fastener can comprise a metal, a polymer, and/or a resorbable material.

In another aspect, a surgical device for joining materials is provided. The device comprises a moveable housing comprising a track; a push member configured to be advanced along the track; a first linkage connected to the housing and a first articulating fang; and a second linkage connected to the housing and a second articulating fang.

In some embodiments, the fangs have sharpened tips configured to pierce materials to be joined. The articulating fangs can be configured to rotate the fang tips toward each other. The fangs can have internal grooves configured to guide a staple or fastener to be formed. The fangs can have internal grooves configured to form a staple. In some embodiments, the fangs have internal grooves configured to shield the staple from surrounding tissue and bodily structures. The push member can be configured to have end features for pushing a staple or fastener to be formed. In some embodiments, the articulating fangs are located at an end of a shaft.

In another aspect, a surgical device for joining materials is provided. The device comprises a first jaw; a second jaw, wherein the first jaw and/or the second jaw are configured to be actuated towards one another; a hook positioned within the first jaw, an end of the hook extending up towards the second jaw, the end of the hook configured to be deployed from the first jaw; and one or more staples positioned within the second jaw and configured to be deployed in a direction towards the first jaw.

In some embodiments the second jaw comprises a window with a frame at least partially surrounding the window on a side of the second jaw facing the first jaw. The hook can be rigid of flexible.

In another aspect, a method of joining materials is provided. The method comprises clamping a first material between the first jaw and the second jaw of a device; deploying a hook from the first jaw to capture the and stabilize the first material to the first jaw; unclamping the first jaw and the second jaw; positioning a second material adjacent to the first material and between the first jaw and the second jaw; clamping the materials between the first jaw and the second jaw; and deploying a staple from the second jaw to join the first material and the second material.

In some embodiments, deploying a staple or fastener comprises deploying a staple or fastener from the second jaw. In some embodiments, deploying a staple or fastener comprises deploying a staple or fastener from the first jaw. The method can comprise retracting the hook from the first material.

In yet another aspect, a device for stabilizing materials is provided. The device comprises a first jaw comprising one or more piercing elements; a second jaw comprising one or more openings or recesses, wherein the first jaw and the second jaw, are configured to be moved towards one another In some embodiments, the one or more piercing elements positioned on the first jaw and extending towards the second jaw, are configured to interact with the one or more openings or recesses on the second jaw when the first jaw and second jaw are moved sufficiently towards one another. In some embodiments, the one or more piercing elements positioned on the first jaw and extending towards the second jaw, is configured to enter the one or more openings or recesses on the second jaw when the first jaw and second jaw are moved sufficiently towards one another.

In another aspect, a method for stabilizing materials to be joined is provided. The method comprises positioning a first material between the first jaw and the second jaw of a device; moving the first jaw and the second jaw towards one another such that one or more piercing elements positioned on the first jaw pierces the first material; separating the first jaw and the second jaw; positioning a second material between the first jaw and the second jaw; and moving the first jaw and the second jaw towards one another such that one or more piercing elements positioned on the first jaw pierces the second material.

In some embodiments, the method comprises moving the first jaw and the second jaw towards one another such that the one or more piercing elements positioned on the first jaw pierce material by entering the one or more openings or recesses on the second jaw.

The method can comprise comprising moving or retracting the device to move or retract the first and second materials. The method can comprise approximating a stapling mechanism to the stabilized materials. The method can comprise stapling the first material and the second material. The method can comprise joining the first material and the second material using other joining means, such as suture, tacks, fasteners, glue, etc.

In another aspect, a device for stabilizing material to be surgically stapled is provided. The device comprises a first jaw comprising a sharp tip; and a second jaw comprising a sharp tip, wherein the first jaw and/or second jaw is configured to be moved towards the other jaw.

In another aspect, a method for stabilizing materials to be joined is provided. The method comprises positioning a first material between the first jaw and the second jaw of a device, the first and second jaws each comprising sharpened tips; moving the first jaw and the second jaw towards one another such that the sharp tips pierce the first material.

The method can comprise separating the first jaw and the second jaw while keeping the first material on sharp tips, moving the first jaw and second jaw towards one another such that the sharp tips pierce the second material. The method can comprise moving or retracting the device to more or retract the first and second materials. The method can comprise approximating a stapling mechanism to the stabilized materials. The method can comprise joining the first material and the second material using other joining means, such as suture, tacks, fasteners, glue, etc. In some embodiments, the method comprises stapling the first material to the second material.

In another aspect, a surgical device for joining materials is provided. The device comprises an elongate shaft; and a curved staple positioned at a distal end of the elongate shaft.

The staple can be positioned in a plane perpendicular to the elongate shaft. In some embodiments, the staple is positioned in a plane oriented at an angle other than perpendicular to the elongate shaft. A second arm or shaft can comprise a slot or opening at its end configured to support the material and receive an end of the staple. The second arm or shaft can be configured to actuate or rotate to form or close the staple.

In another aspect, a method for joining materials is provided. The method comprises advancing a device comprising an elongate shaft and a curved staple positioned at a distal end of the elongate shaft, the staple positioned in a plane perpendicular to the elongate shaft to a surgical site; positioning a first material on a second material; rotating the elongate shaft such that a piercing end of the curved staple pierces the first material and the second material; and closing the staple.

In some embodiments, an edge of the first material is joined to the second material. The method can comprise positioning a second arm or shaft comprising a slot or opening at the end to support the material and receive the piercing end of the staple. The method can comprise actuating or rotating the second arm or shaft to form or close the staple. The method can comprise comprising releasing the staple from the device. The method can comprise actuating or rotating of the elongate shaft to form or close the staple. At least one of the first and second materials can comprise ADM.

In another aspect, a device for joining materials is provided. The device comprises a first elongate shaft configured to hold a first leg of a staple; a second elongate shaft configured to hold a second leg of a staple, the first and second elongate shaft positioned adjacent to and substantially parallel to one another, wherein rotation of the elongate shafts causes the staple legs to move towards one another.

In some embodiments, the first and second staple legs are curved towards one another.

In another aspect, a method of surgically stapling materials is provided. The method comprises advancing a device to the surgical site, the device comprising a first elongate shaft comprising a first leg of a staple a second elongate shaft comprising a second leg of a staple; positioning a first material on a second material; and rotating the first and second elongate shafts relative to one another such that the first and second legs pierce the first and second materials and close the staple.

In some embodiments, the method comprises releasing the staple from the device. In some embodiments, at least one of the first materials and the second materials comprises ADM.

In another aspect, a surgical device for joining materials is provided. The device comprises a first jaw configured to hold a first end of a staple, the first end of the staple comprising a preformed feature, and the second end configured to pierce material; and a second jaw comprising a slot or opening, the first jaw and the second jaw configured to move towards one another.

In some embodiments, the preformed feature comprises a loop or hook shape. In some embodiments, the slot or opening in the second jaw is configured to receive the second end of the staple when the first jaw and second jaw are moved towards one another. In some embodiments, the second jaw is configured to actuate or rotate to form or close the staple. In some embodiments, the second jaw is advanceable and retractable with respect to the first jaw. The second jaw can comprise an anvil. The first jaw can comprise an actuator configured to advance the staple into the anvil on the second jaw. The second end of the staple can comprise a bend. The first jaw can comprise a piercing shroud or fang configured to cover the staple tip.

In another aspect, a method for joining materials is provided. The method comprises advancing a device comprising a first jaw and a second jaw, the first jaw holding a first end of a staple comprising a preformed feature; positioning a first material between the first jaw and the second jaw; moving the first jaw and the second jaw towards one another such that a second end of the staple pierces the first material and enters a slot or opening on the second jaw; moving the first jaw and the second jaw away from one another; positioning a second material between the first jaw and the second jaw; and moving the first jaw and second jaw towards one another, such that the second end of the staple pierces the second material.

The method can comprise moving the first material into the preformed feature on the staple. The method can comprise moving or retracting the device to move or retract the first and second materials.

The method can comprise actuating or rotating the second jaw to close the staple. In some embodiments, the method comprises sliding the second jaw to align the staple tip with an anvil on the second jaw prior to positioning the second material. The method can comprise moving the jaws towards one another such that the second end of the staple pierces the second material, enters the anvil and curls, forms or closes the staple. The method can comprise releasing the staple from the device.

In another aspect, a staple configured to be used with any of the devices or methods disclosed herein is provided. The staple comprises a central portion; a first leg extending from a first end of the central portion at a first bend; and a second leg extending from a second end of the central portion at a second bend, wherein the first bend and the second bend each comprise a hump.

In yet another aspect, a staple configured to be used with any of the devices or methods disclosed herein is provided. The staple comprises a first leg extending from a first end of the central portion at a first intersection; and a second leg extending from a second end of the central portion at a second intersection, wherein the central portion comprises at least one bump proximate to the intersections.

In another aspect, a device for joining materials is provided. The device comprises a first arm comprising a first fang and a first hole; a second arm comprising a second fang and a second hole, wherein the first arm is connected to the second arm at a joint, and wherein the first arm and the second arm are configured to rotate towards one another about the joint, and wherein, when rotated, the first fang is configured to enter the second hole and the second fang is configured to enter the first hole. The fangs can comprise one or more of notches, barbs, or necks, etc. to retain the first material on the fang. The fangs can comprise a lubricious coating so the opposing fang can be removed from the first material.

In another aspect, a method for joining materials is provided. The method comprises advancing a device comprising a first arm comprising a first fang and a first hole; and a second arm comprising a second fang and a second hole, the first arm and the second arm connected at and configured to rotate about a joint; positioning the device above a first material, the device in an open position; piercing the first material with the first and second fangs; rotating the first arm and the second arm about the joint such that the first fang enters the second hole and the second fang enters the first hole; rotating the first arm and the second arm away from one another; positioning the device and the attached first material over a second material; and piercing the second material with the first and second fangs.

The method can comprise deploying a staple to join the first and second materials. The method can comprise moving or retracting the device to move or retract the first and second materials.

In another aspect, a device for joining materials is provided. The device comprises carriers configured to extend from a head, the head configured to deploy a staple; and sharp elements configured to extend from the carriers wherein tips of the sharp elements are configured to move toward one another to grasp target materials, the carriers configured to retract while the sharp elements remain extended to approximate the head to the target materials.

The tips of the sharp elements can be configured to overlap one another to grasp and/or pierce target materials. The sharp elements can be configured with surfaces that prevent the staple ends from protruding past the sharp elements.

In another aspect a prosthetic material comprising a plurality or array of holes is provided. The plurality or array of holes can be configured for a size that allows a staple or fastener, or portions of a staple or fastener, to pass through the material.

In another aspect, a device for joining materials is provided. The device comprises a body comprising features for anchoring in bone; and a wire extending from the body, forming an exposed end of the wire.

The exposed end of the wire can comprise a point.

The wire can be configured to bend in order to retain material or tissue.

In another aspect, a method for joining materials is provided. The method comprises inserting into bone one or more devices for joining materials to bone, wherein the device comprises a body comprising features for anchoring in bone, and a wire extending from the body; piercing the one or more materials to be joined to bone using the wire; and forming or closing the wire to secure the one or more materials to bone.

In another aspect, a device for joining materials is provided. The device comprises a fastener or staple in the shape of a loop comprising at least one sharp end; a shaft configured to expand the loop of one or more staples, wherein the shaft resides in the inner diameter of the loop of one or more staples and rotate and push on the end of one or more staples.

The staple can be located at the end of the shaft is configured to pierce the materials to be joined with the sharp end as staple is rotated by the shaft. In some embodiments, a diameter of the staple loop recovers or contracts to fix the materials to be joined.

In another aspect, a device for joining materials is provided. The device comprises a polymer strand comprising a series of openings, wherein the openings are configured to receive and end of the polymer strand and configured to melt and fuse the joint between the opening and strand passed through the opening, creating a fixed loop.

The device can comprise a guide tube comprising a point configured to pierce materials to be joined and form a loop shape; and a slot down a length or a portion of the length of the tube, wherein the slotted lumen of the guide tube is sized to allow the polymer strand with openings to pass.

In another aspect, a device for joining materials is provided. The device comprises a first curved tubular lumen with a point; and a second curved tubular lumen with a point, wherein the first and second curved tubular lumens articulate to pierce a first and second material to be joined and mate the opposing points of both tubular lumens to one another.

In some embodiments, the mated points of both tubular lumens create a continuous lumen configured to receive a material, the continuous lumen forming a loop shape. The tubular lumens can be configured to be removed, leaving the polymeric loop that approximates and fixes the materials together.

In yet another aspect, a device for joining materials is provided. The device comprises a curved cannula with a point on one end configured to pierce materials to be joined and create a passageway through the materials so a suture or strand can be passed through the materials. In some embodiments, the curved cannula can be removed, leaving the suture or strand in the materials to be joined. In some embodiments, a cinching element can cinch a loop with the suture or strand to approximate the materials to be joined. In some embodiments, the cinching element or separate element can fuse the loop In some embodiments, excess lengths of the suture or strand can be removed, leaving a loop that fixes the materials together.

In still another aspect, a device for stabilizing materials is provided. The device comprises an inner tube comprising angled barbs on one end; and an outer tube comprising angled bard on the same end, wherein an angled barb on the inner tube and an angled barb on the outer tube point toward each other creating a pair; and one or more pairs of barbs that pinch or secure one or more materials to be joined when the inner or outer tube is rotated in a direction that brings the tips of one or more pairs of barbs together.

The inner tube can have a lumen through which instruments can be passed. In some embodiments, walls of the inner and outer tubes comprise windows to provide visibility and access to a working area of stabilized tissue.

In another aspect, a device for stabilizing materials is provided. The device comprises at least two pincers, wherein the tips of the pincers point toward one another and a portion of each pincer has an outward profile, a tube surrounding the pincers and configured to advance and bring tips of the pincers together. In some embodiments, the tips of the pincers are configured to grasp material when the tips of the pincers are moved toward one another.

In yet another aspect, a fastening device is provided. The device comprises a shaft; a needle extending from the shaft, the needle comprising a slot extending along at least a portion of the needle; the device configured to receive at least one fastener comprising a first bar and a second bar connected by a bar connector, the first bar configured to be positioned within the needle and the second bar configured to be positioned outside the needle; a push member configured to push the fastener out of the needle; one or more control rods comprising a connector, the connector configured for connection to a surgical robot.

In some embodiments, the shaft is configured to rotate and/or articulate. In some embodiments, at least one control rod provides the motion for moving a fastener from a conveyance zone through a transition zone. In some embodiments, at least one control rod is configured to provide the motion for moving a fastener from a transition zone through a manipulation zone and deploying the fastener. One or more control rod connectors can be configured for connection to one or more control rods of the surgical robot. In some embodiments, the one or more control rod connectors comprise a connection clamp or union configured to interact with a ball or end feature on the surgical robot. In some embodiments, the connection clamp or union comprises a first position in the device to receive the ball or end feature on the surgical robot. In some embodiments, the connection clamp or union comprises a second position in the device to secure the control rod connection to the surgical robot. In some embodiments, the connector on the fastening device comprises a collar that attaches to the surgical robot. In some embodiments, the connector on the fastening device threads onto the surgical robot. In some embodiments, the device is configured to receive a fastener cartridge comprising one or more fasteners. The fastener cartridge can be replaceable. The fastener cartridge can be configured for replacement while the device remains connected to the surgical robot. In some embodiments, the fastener cartridge comprises features to secure the cartridge to the device. The fastener cartridge can comprise spring loading features to secure the cartridge to the device. In some embodiments, the fastener cartridge comprises features that align the cartridge to a transition zone of the device. In some embodiments, the fastener cartridge comprises features that align the cartridge to the control rods or push rods of the device. The fastener cartridge can be flexible. In some embodiments, the needle of the device is configured for replacement while the device remains connected to the surgical robot.

In another aspect, a fastening device configured for fixation in soft tissue is provided. The device comprises one or more piercing elements comprising a sharp tip and a hollow or partially hollow interior in communication with an opening near or through the tip, wherein the hollow or partially hollow interior is configured to allow advancement of a fastener.

The device can comprise a push member configured to advance a fastener. In some embodiments, the device comprises a fastener configured to advance along the interior of the piercing element and out of the opening near or through the tip. A length of the fastener can be sized to allow embedding one or more ends of the fastener in tissue. In some embodiments, one or more ends of the fastener that are configured to be embedded in tissue comprise one or more features configured to resist pulling out of tissue. One or more ends of the fastener that are not embedded in tissue can comprise one or more features configured to retain an onlay material. In some embodiments, a length of the piercing element is selected to minimize trauma to tissue and structures surrounding a repair site. In some embodiments, a length of the piercing element is selected to be suitable for depositing one end or more than one end of the fastener in tissue.

In another aspect, a method for fixation in soft tissue is provided. The method comprises piercing a material to be joined using one or more piercing elements of a fastening device; advancing a fastener along an interior of the piercing element; and pushing the fastener out of an opening near or through a tip of the piercing element.

The method can comprise using a stop, shoulder, etc. that controls an insertion depth of the piercing element(s). The method can comprise depositing one end or more than one end of the fastener in tissue.

In another aspect, a method for fixation in soft tissue is provided. The method comprises piercing a material to be joined using one or more piercing elements of a fastening device, wherein the piercing element creates one or more openings or passages through the material to be joined.

The method can comprise pushing a fastener through the opening(s) or passage(s) created by the one or more piercing elements in the material to be joined. The method can comprise depositing one end or more than one end of the fastener in tissue.

In another aspect, a device for fastening materials is provided. The device comprises a piercing element configured to penetrate materials to be joined, wherein the piercing element is sufficiently sharp to penetrate the materials, wherein the piercing element comprises a hollow interior along at least a portion of its length, the hollow interior configured for distal advancement of a fastener therethrough; and an open tip through which the fastener can be pushed.

The device can comprise a push member to advance the fastener distally within and out of the piercing element. In some embodiments, a length of the piercing element can be selected to minimize and/or avoid trauma to surrounding structures. In some embodiments, a length of the piercing element can be selected to be suitable for depositing one end of the fastener in tissue. In some embodiments, the length of the piercing element is about 0.100 in-0.380". The piercing element can comprise a needle or a fang.

In another aspect, a method for joining materials is provided. The method comprises inserting a piercing element of a fastening device into or through a material; advancing a fastener along an interior of the piercing element; pushing the fastener or a portion of the fastener through the material and out of a distal tip of the piercing element.

In another aspect, a method for joining materials is provided. The method comprises inserting a piercing element of a fastening device into a material creating one or more openings or passages through the material; and passing a fastener through the openings or passages created by the piercing element.

The material can comprise synthetic mesh, biologic mesh (e.g., ADM), and/or tissue.

In another aspect, a method for joining materials is provided. The method comprises inserting a piercing element of a fastening device into a mesh; advancing a fastener along an interior of the piercing element; pushing the fastener or a portion of the fastener through the material and out of a distal tip of the piercing element.

In another aspect, a method for joining materials is provided. The method comprises inserting a piercing element of a fastening device into or through a mesh creating one or more openings or passages through the material; and passing a fastener through the openings or passages created by the piercing element.

The mesh can comprise a synthetic mesh and/or a biologic mesh.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 27A-31 show additional embodiments of fastening devices comprising features that can reduce/eliminate the amount of stabilization force required during fastener deployment.

FIGS. 103A-10H show an embodiment of a device configured to clamp and staple materials.

DETAILED DESCRIPTION

Figure 1:
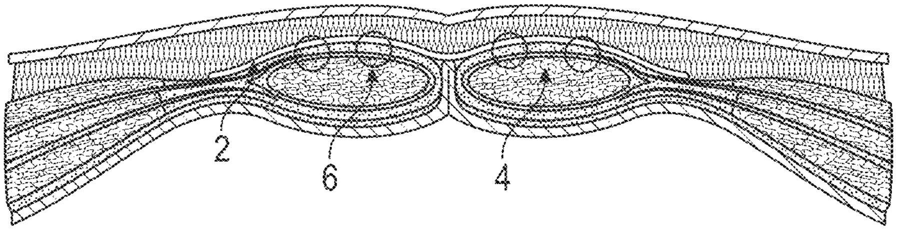
FIG. 1 is a schematic of an onlay procedure.

Disclosed herein are embodiments of a fastener device that can pierce ADM or other material (e.g. synthetic mesh, resorbable mesh, tissue), facilitate ADM (or other material) positioning and tensioning, fix ADM (or other material) to soft tissue using a (polymeric, resorbable or metal) fastener, and work with onlay procedures. The tool could also be used for any other procedure that joins soft tissues together or soft tissues to materials. The devices can comprise a stapler. The device can require little, if any pushing force into tissue during deployment, and can be compatible for use in multiple procedures. Such devices are unique tools that will reduce the surgeon's workload and procedure time, and prevent damage to underlying tissues and organs.

The devices disclosed herein can advantageously provide the ability to access confined locations. Embodiments of the device can also conceal sharp features during device insertion and removal. The devices can penetrate the toughness of the material (e.g., ADM). The devices can be used target/control the position of the material to be stapled (e.g., ADM). The devices can be configured for use during onlay procedures. The device can be configured to grasp the desired tissue or material (e.g., ADM) and retract it away to avoid underlying structures. Some of the devices can be configured to shield/protect underlying structures. Embodiments of the device can also be configured to recruit tissue and close the staple. The concepts described herein can apply to a number of procedures (e.g., pelvic sling, dural closure) that could benefit from the advantages listed above. It will be appreciated that the devices disclosed herein can be used to manipulate material, such as ADM, but can also be used to manipulate other materials such as other mesh, membranes, etc.

Some examples of procedures utilizing mesh (e.g., ADM) in which the devices disclosed herein could be used include breast reconstruction, abdominal wall procedures, treatment of diabetic foot ulcers, and orthopedic procedures (e.g., reinforcing a quadriceps tendon repair, reinforcing an Achilles tendon repair, and reinforcing a rotator cuff repair). Breast reconstruction following a mastectomy traditionally occurred in two stages, the tissue expansion stage and the implant stage. The introduction of ADM provided the option to convert the two-stage process into a single-stage (also known as direct-to-implant reconstruction). The following describes two techniques used in direct-to-implant reconstruction. In the subpectoral technique, the pectoralis muscle is released from the chest wall at the inframammary fold. The ADM is sutured to the chest wall at the inframammary fold. The implant is inserted into the subpectoral pocket. The ADM is attached to the pectoralis muscle to close the implant pocket. In the prepectoral technique, the implant is wrapped with ADM. The implant/ADM is placed into mastectomy pocket on top of the pectoralis muscle. The ADM is secured to the chest wall.

In abdominal wall procedures, ADM is used to repair ventral/incisional hernias and prophylactically reinforce the abdominal wall to prevent incisional hernias. ADM can be placed in multiple locations to repair the abdominal wall, and the devices disclosed herein could facilitate the ADM onlay procedure.

When treating diabetic foot ulcers, after the wound is debrided, ADM is secured in place over the wound so dermal integration and healing can occur. For reinforcing a quadriceps tendon repair, the ADM is placed over the repair and secured in place. For reinforcing an Achilles tendon repair, the ADM is wrapped around the repaired tendon and secured in place. As noted in the preceding examples, there are numerous procedures in which devices and methods for piercing, manipulating, and joining materials, including ADM, would be very useful.

Throughout the disclosure, the term 'target material(s)' is used to refer to materials that can be joined or otherwise manipulated by the devices and using the methods described herein. The target materials can include mesh (e.g., ADM, synthetic mesh) tissue, membranes, etc. In some embodiments, a first target material comprises ADM to be joined to a second target material comprising tissue. In some embodiments, a first target material comprises tissue to be joined to a second target material comprising tissue. Other combinations are also possible.

Throughout the disclosure, the terms 'fang' and 'needle' can be used to refer to a sharp element that may or may not have a hollow area along at least a portion of its interior.

Described herein are embodiments of fastening devices (e.g., staplers, etc.) that are able to fasten materials and tissue (e.g. tissue to tissue, material to tissue), including synthetic mesh and tough biologic mesh such as acellular dermal matrix (ADM). As described herein, tough materials (such as ADM) typically require time consuming suturing as they are unsuitable for traditional fastening devices.

The fastening devices described herein utilize one or more sharp piercing elements (e.g., needle or fang) to penetrate the material, and then deploy a fastener (e.g., staple) therethrough. The piercing element is sufficiently sharp to penetrate the material (e.g., synthetic mesh, ADM). The piercing element comprises a hollow interior along at least a portion of its length. The fastener or a portion of the fastener can be advanced distally within this hollow portion. The piercing element comprises an open tip through which the fastener or a portion of the fastener can be pushed through a material to be joined. A push member can be used to advance the fastener distally within and out of the piercing element.

In some embodiments, the length of the piercing element can be selected to minimize/avoid trauma to surrounding structures. For example, in an onlay procedure, the length of the piercing element can be selected to minimize or avoid contact with tissues and structures underlying the repair site. The length of the piercing element can also be selected to be suitable for depositing one end of the fastener at a depth in tissue.

For example, the length of the piercing element can be about 0.240 in (or about 0.100 in-0.380", or about 0.140 in-0.340 in, or about 0.190 in-0.290 in, or about, 0.220 in-0.260 in, or about 0.230 in-0.250", or about 0.235 in-0.245 in, etc.).

There are known devices that deliver a fastener through a hollow needle. Examples of such devices are taught in U.S. Pat. No. 4,006,747. Such devices however are taught as having long needles used to pass through the tissues to be joined, such that the needle exits the tissue on the opposite side of a wound to be closed. These needles would be unsuitable for preventing trauma to underlying structures (e.g., in an onlay procedure). Additionally, such devices are generally configured to use with more than one operator. The fastening devices described herein can be used by a single person to perform repairs.

The fastening devices can comprise a design including, but not limited to those shown in any or a combination of FIGS. 2-9, 11-19, 22-51C, 72A-84B, 98A-101G, 103A-107H, 121A-148D.

A method for using such fastening devices comprises inserting one or more piercing elements of a fastening device into or through a material (e.g., synthetic mesh, ADM, or tissue). The method further comprises advancing a fastener (e.g., stapler, other fastener, etc.) along an interior of the piercing element. The method comprises pushing the fastener or a portion of the fastener through the material and out of the distal tip of the piercing element.

The method can comprise creating one or more openings or passages through material by inserting the piercing element(s) into or through the material. The method can comprise passing a fastener or a portion of a fastener through the openings or passages created by the piercing element.

As noted above, the devices that are disclosed herein can be particularly advantageous in onlay procedures such as abdominal wall repairs. The devices and methods disclosed herein provide many advantages over what is currently available. Currently, other options for securing onlay mesh in open abdominal wall repairs include suture, metal staples or tacks, and fibrin glue. If a surgeon uses ADM, they would likely have to use suture (with a needle) in order to penetrate the toughness of ADM. However, suturing greatly increases the procedure time and is relatively difficult and technique dependent, which could affect clinical outcomes. Stapling and tacking are unsuitable for penetrating the toughness of ADM, and fibrin glue is costly. The devices disclosed herein can advantageously penetrate the toughness of ADM or other mesh, and can deploy repeatable fasteners quickly, providing solutions to these problems.

In intraperitoneal onlay mesh repairs (IPOM repairs), devices including barbed tacks and spiral metal tacks can be used. In such repairs, the mesh is generally introduced into the abdominal cavity and covers the hernia defect on the abdominal cavity side of the peritoneum. The tacks are deployed outwards and embed in the abdominal muscle, which generally results in pain for the patient. When using resorbable tacks, the pain is supposed to subside as the tacks resorb. When using metal tacks, the patient may have to return for a second surgery to remove the tacks to alleviate pain. The devices disclosed herein could advantageously secure the material being joined (e.g. mesh) by anchoring one end of the fastener against the fascia. This would eliminate the need to embed a portion of the fastener in muscle, increasing patient comfort.

Figure 2:
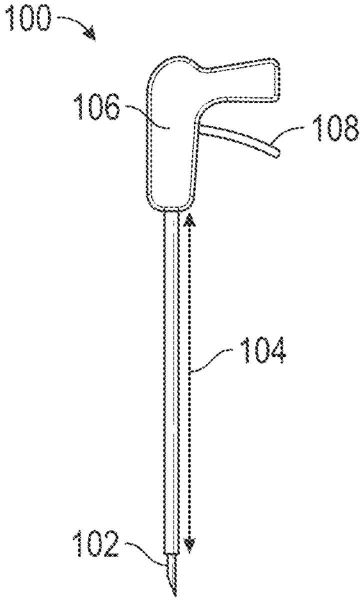
FIG. 2 shows an embodiment of a fastener device.
Figure 8:
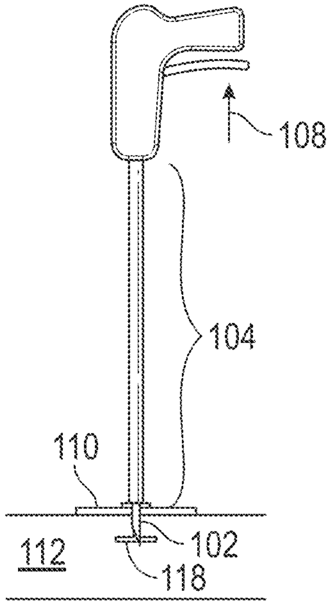

FIG. 2 shows an embodiment of a fastener device 100 that includes the needle 102, shaft/fastener reservoir 104, handle 106, deployment trigger 108, and fastener 118 (FIG. 8). The needle 102 can be sharp enough to penetrate a tough material like ADM and be configured to allow passage of a fastener therethrough.

Figure 3:
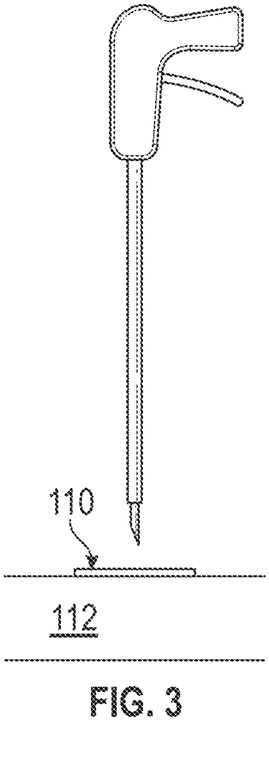
FIGS. 3-9 show an embodiment of a method for using the device of FIG. 2 in an onlay procedure.
Figure 4:
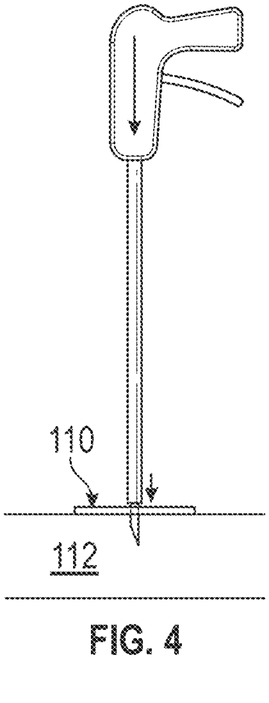

FIG. 3 shows the onlay material (e.g., ADM) 110 and tissue 112 to be joined. FIGS. 4-9 show the basic procedure for fixing the material 110 (e.g., ADM) to tissue 112 using the fastener device 100. In FIG. 4, the user applies a distal force via the handle to pierce the material 110 and tissue 112 with the needle 102.

Figure 5:
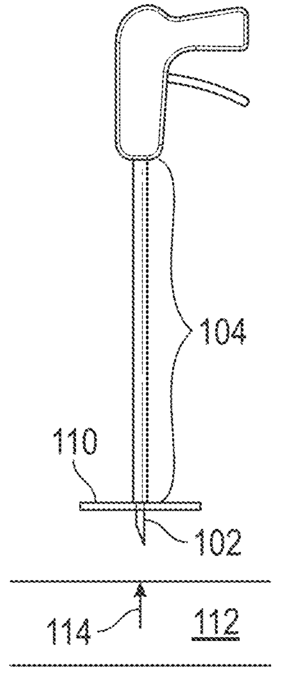
Figure 6:
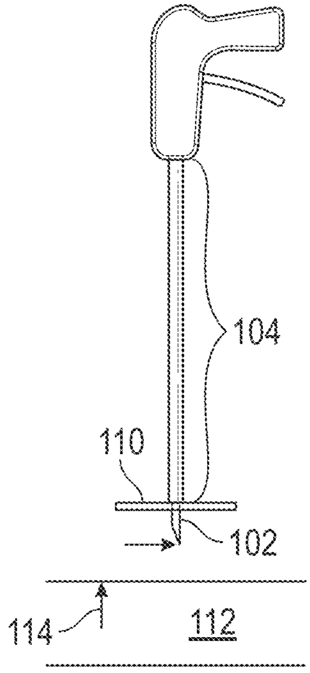
Figure 7:
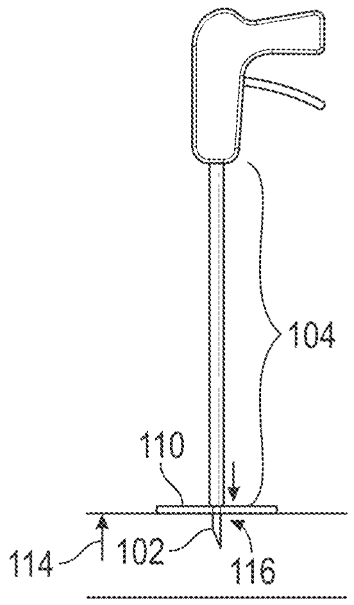

In FIGS. 5-7, the user has the option to withdraw the needle out of the tissue from the first location 114 (FIG. 5), position or tension the material (e.g., ADM) as needed (FIG. 6), and then pierce the tissue at a second location 116 (FIG. 7).

Because there is friction/compression between the material (e.g., ADM) and needle, the material can stay on the needle when the user withdrawals the needle out of the tissue. Described in more detail below (e.g., with respect to FIGS. 23-26) are a number of features that facilitate repositioning.

In FIG. 8, the user applies a stabilizing force against the material (e.g., ADM) and tissue, and simultaneously actuates the deployment trigger 108. This deploys the fastener 118 and fixes the material 110 to tissue 112. Described in more detail below (e.g., with respect to FIGS. 23-31) are a number of ways to reduce/eliminate the required stabilizing force.

Figure 9:
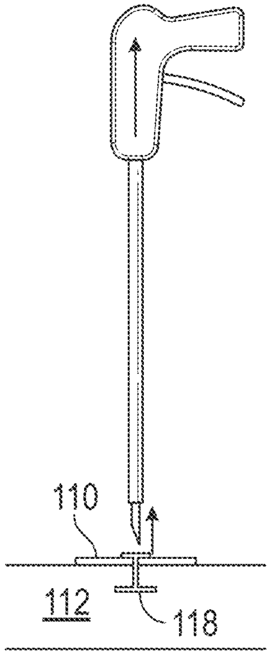

In FIG. 9, the user applies a proximal force via the handle to withdraw the needle out of the material (e.g., ADM) and tissue. Described in more detail below (e.g., with respect to FIGS. 44-51) are a number of features that aid needle withdrawal.

Figure 10:
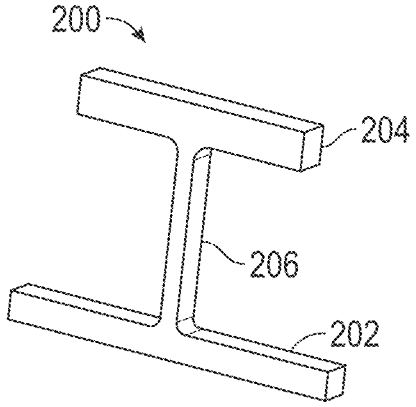
FIG. 10 shows an embodiment of a fastener.
Figure 11:
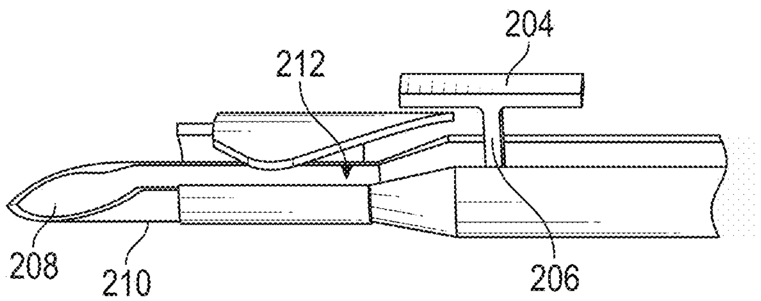
FIG. 11 shows an embodiment of a fastener positioned within a needle of a fastening device.

FIG. 10 shows an embodiment of a fastener implant 200 that is made of a polymeric or resorbable material, or metal. For example, the implant can comprise nylon, polyethylene, polypropylene, various resorbable polymers or Nitinol. The fastener has a first bar 202 and second bar 204 on either end of a connector 206 (e.g., filament). In FIG. 11, the first bar resides in the lumen 208 of the slotted delivery needle 210. The fastener can comprise a rectangular cross section, as shown in FIG. 10. The rectangular cross section of the first bar contains flat faces to improve the resistance of the fastener pulling out of tissue. Other shape cross section are also possible (e.g., circular, ovular, etc.). In some embodiments, different portions of the fastener can comprise the same or different cross sections. In some embodiments, different portions of the fastener can comprise the same or different dimensions. The fastener's filament 206 exits the delivery needle slot 212, and the second bar 204 resides on the outside of the needle. The filament length is sized to approximate and/or compress the tissue and mesh to be joined. For example, in an open onlay repair, the filament length can be selected so that the bar embeds in muscle. Examples of suitable dimensions are described with respect to FIGS. 95A-96C. In a laparoscopic IPOM repair, the filament length can be selected so that the bar gets deployed on the opposite side of the peritoneum/fascia, and does not embed in muscle, to avoid pain to the patient.

Figure 12:
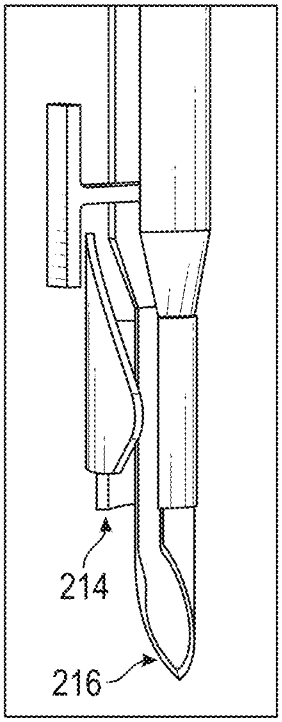
FIGS. 12-15 show an embodiment of a method for using the fastening device of FIG. 11 in an onlay procedure that includes an embodiment of a deflector that interacts with the fastener's filament.

FIG. 12 shows a shoulder 214 that controls and limits the insertion depth of the needle. The shoulder could have a fixed or adjustable distance from the needle tip 216. The shoulder can control the deployment depth of the fastener's first bar and control the amount of approximation and/or compression between the onlay material and the tissue. In embodiments comprising a fixed distance shoulder, the distance can be about 0.235" (or about 0.17-0.30" or about 0.185-0.285" or about 0.20-0.27", etc.).

Figure 13:
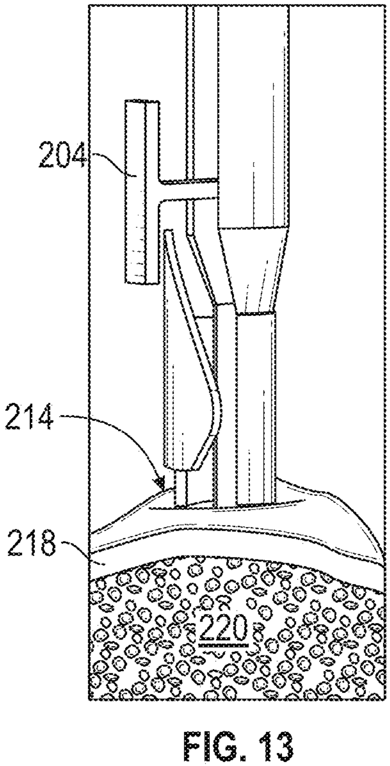

In FIG. 13, the needle 216 pierces the onlay material 218 (e.g., ADM or other mesh) and tissue 220 until the shoulder 214 contacts the material 218 (e.g., ADM). The user has the option to advantageously withdraw the needle out of the tissue 220 before deploying the fastener (with the material remaining on the needle) to position or tension the onlay material 218 as needed.

Figure 14:
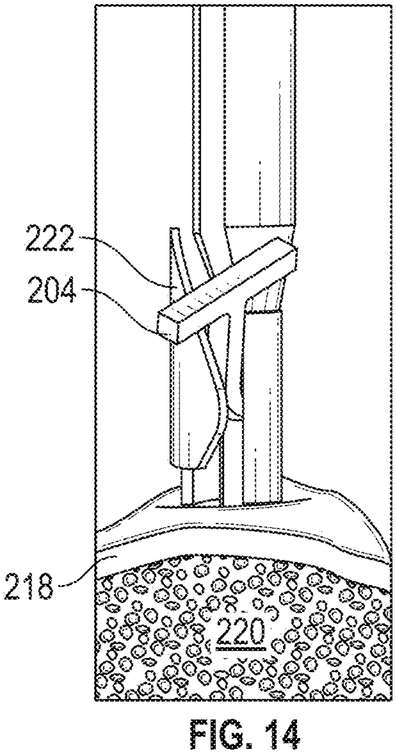

In FIG. 14, as the push rod (not shown, inside the needle lumen) advances the first bar down the needle's lumen, the deflector 222 acts on the fastener's filament. This action reorients the second bar 204 and prepares it to seat on the surface of the onlay material (e.g., ADM). Described in more detail below (e.g., FIGS. 32-43D) are a number of other embodiments to optimize the placement of the second bar 204 and the onlay material/tissue approximation and/or compression.

Figure 15:
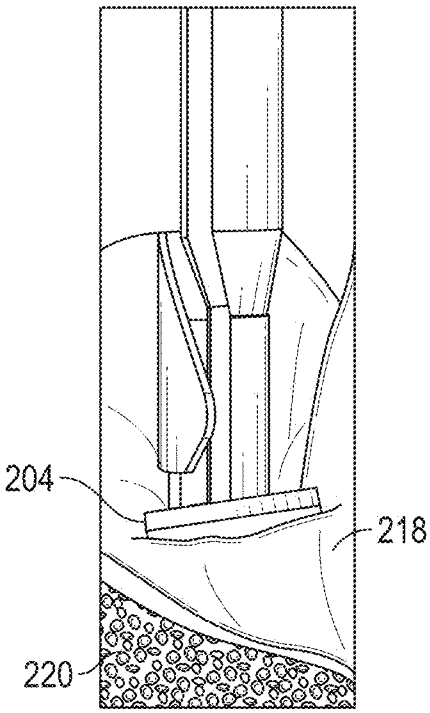

In FIG. 15, the first bar and filament get delivered through the onlay material 218 (e.g., ADM) and embedded into tissue 220 by traveling through the hole in the material 218 that the slotted needle created. Concurrently, the second bar 204 seats on the surface of the onlay material 218 (e.g., ADM). During this step the user applies a stabilizing force against the onlay material 218 and tissue 220 to ensure that the material does not get pushed off of the needle.

Figure 16:
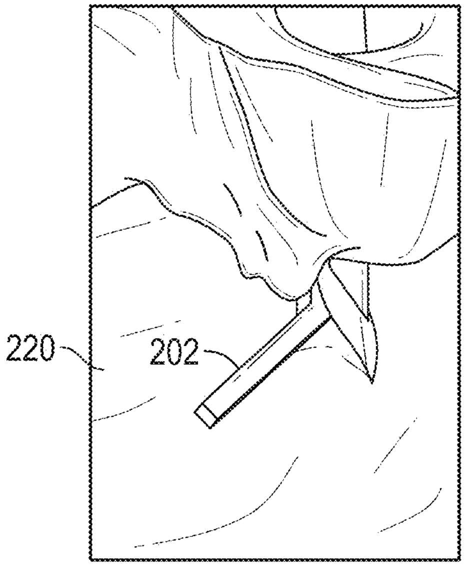
FIGS. 16-19 show an embodiment of a method for using the fastening device of FIG. 11 in an only procedure with clear materials to allow visualization.
Figure 17:
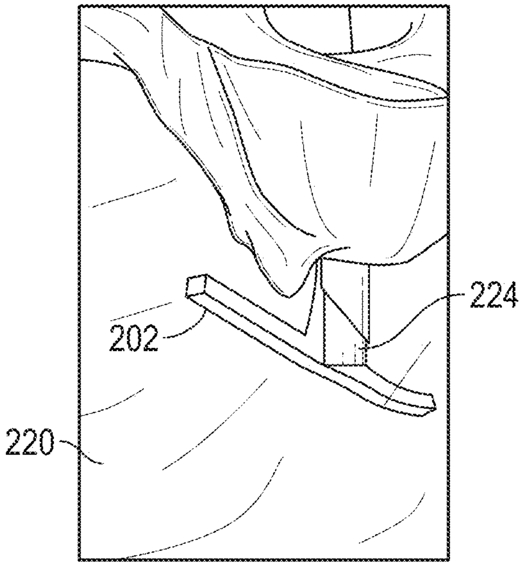

In FIGS. 16 and 17, the push rod 224 deploys the first bar 202 into tissue 220 (represented as clear to allow visualization).

Figure 18:
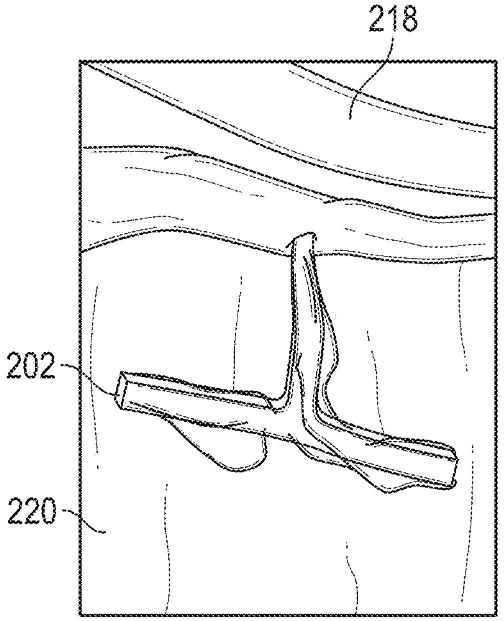
Figure 19:
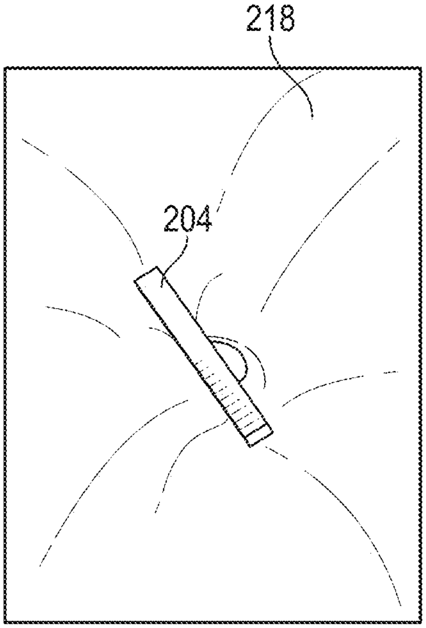

In FIGS. 18 and 19, the push rod is retracted, and the needle is withdrawn from the tissue 220 and onlay material 218 (e.g., ADM), leaving the onlay material and tissue approximated and/or compressed and fixed together by the fastener.

Figure 20:
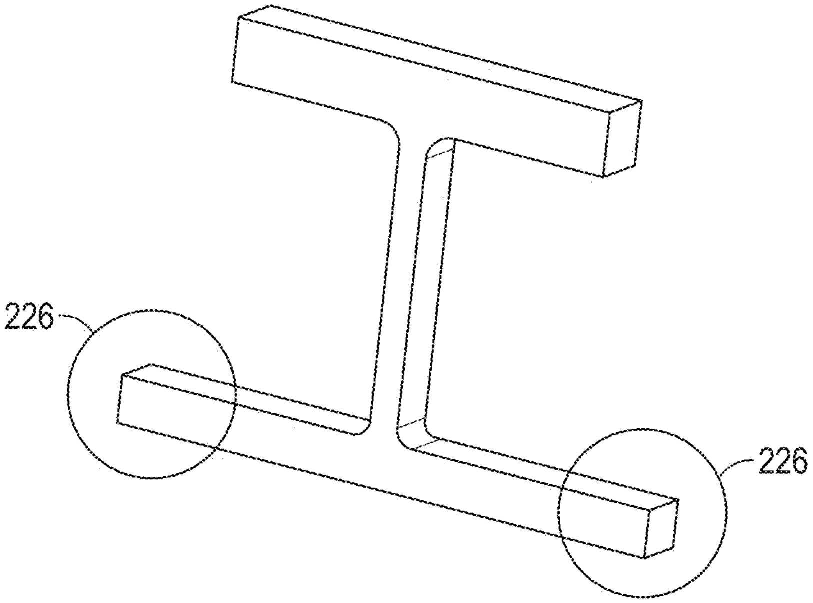
FIG. 20 shows an embodiment of a fastener comprising blunt ends.

In some embodiments, as shown in FIG. 20, the fastener's bar comprises blunt ends 226. The blunt ends can advantageously prevent the bar from unintentionally penetrating any fascia that may lie below the target muscle tissue. Because the needle handles the piercing through the onlay material (e.g., ADM), it is not necessary for the fastener to comprise sharpened ends. The blunt ends can comprise square or rectangular ends as shown in FIG. 20. The blunt ends can be rounded, in some embodiments.

Figure 21:
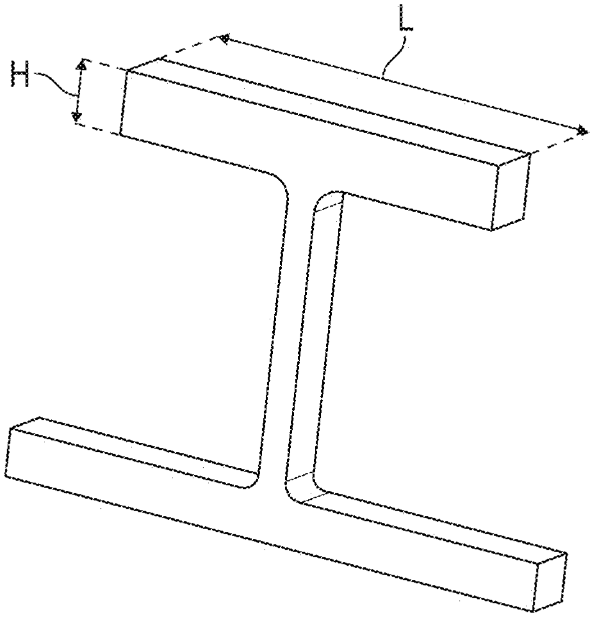
FIG. 21 shows an embodiment of a fastener where the second bar has a shorter length L and different height H than the first bar.

FIG. 21 shows an embodiment of a fastener where the second bar has a different (in this example, shorter) length L and different (in this example, taller) height H than the first bar. The shorter length allows the fastener to be positioned close to the edges of the onlay material (e.g., ADM) without the ends of the bar protruding significantly past the edge(s) of the material. The taller height increases the stiffness and strength of the bar. In another embodiment, a shorter height reduces the bar's profile on the onlay material (e.g., ADM), which could benefit the repair. In some embodiments, a larger width of the second bar can be used to increase contact surface area of the bar.

Figure 22:
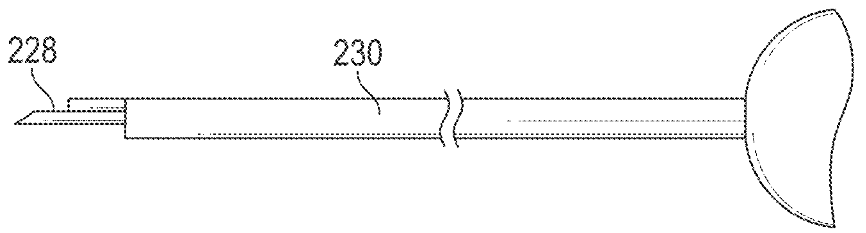
FIG. 22 show an embodiment of a fastening device comprising a needle at a distal end of a shaft.

FIG. 22 shows an embodiment of a needle 228 on the end of a shaft 230. The shaft (e.g. diameter and length) is sized to enable access to do open or laparoscopic procedures.

Embodiments of Features that Facilitate Repositioning

Figure 23:
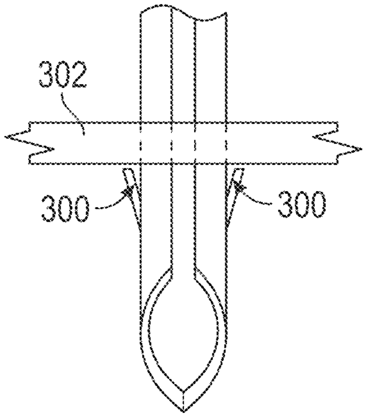
FIGS. 23-26 show embodiments of fastening devices comprising features that can assist with keeping onlay material on a needle of a fastening device and reduce/eliminate the amount of stabilization force required during fastener deployment.

FIG. 23 shows an embodiment of a needle comprising one or more barbs 300 that assist with keeping the onlay material 302 (e.g., ADM) on the needle to (re) position and/or tension the material 302. The needle pierces the onlay material 302, and the barbs 300 keep the onlay material 302 on the needle. The user pulls the needle out of the tissue from a first location, but the barbs keep the onlay material on the needle. The user repositions the needle to (re) position or tension the onlay material, then inserts the needle in tissue at a second location. To enable needle withdrawal from the ADM, a support (e.g. FIGS. 46-48) could be used to withdraw the barbed needle out of the ADM. Alternatively, the barbs could retract to facilitate needle withdrawal.

Figure 24:
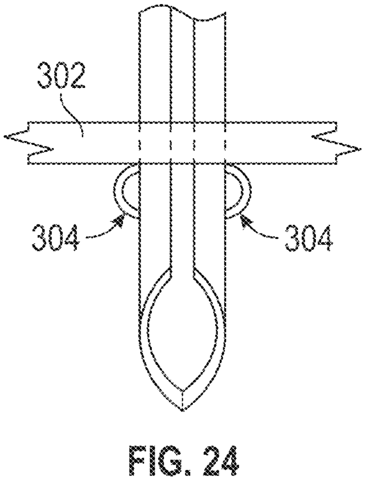

FIG. 24 shows an embodiment comprising one or more raised bumps 304 that assist with keeping the onlay material (e.g., ADM) on the needle to (re) position and/or tension the onlay material.

Figure 25:
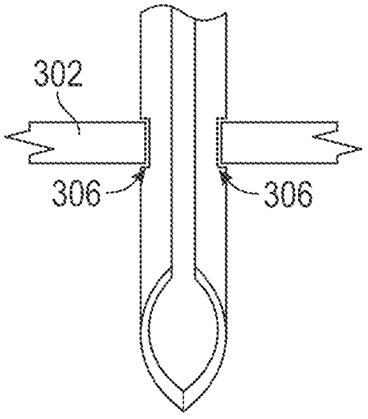

FIG. 25 shows an embodiment comprising one or more notches 306 that assist with keeping the onlay material (e.g., ADM) on the needle to (re) position and/or tension the onlay material.

Figure 26:
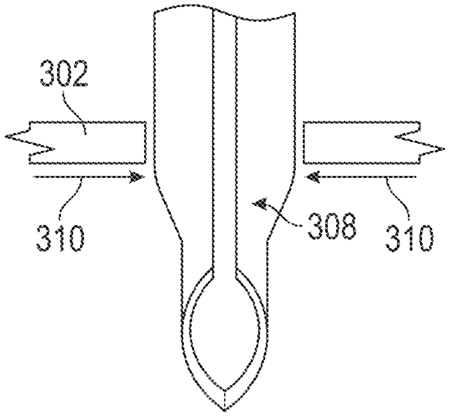

FIG. 26 shows an embodiment comprising an enlargement 308 on the needle. The enlargement increases the compressive force 310 of the onlay material (e.g., ADM) on the needle. The increased compressive force assists with keeping the onlay material on the needle to (re) position and/or tension the onlay material.

Embodiments of Features to Reduce or Eliminate the Amount of Stabilization Force Required During Fastener Deployment When the first bar and filament pass through the hole in the onlay material (e.g., ADM) created by the needle, the amount of interference the first bar and filament encounter with the onlay material depends on the size of the passageway through the onlay material created by the needle. The amount of interference affects the force required to push the first bar and filament through the needle's passageway in the onlay material. The force the first bar and filament apply to the onlay material must have a counteracting "stabilization" force on the onlay material so the first bar and filament can pass through the passageway without pushing the onlay material off the needle. One way to keep the onlay material on the needle is for the user to apply a distal force to the device/needle during fastener deployment. Current design features balance competing needs between 1) reducing the amount of force required for the needle to pierce the ADM, and 2) reducing the required stabilizing force. To reduce the required stabilizing force, the needle's inner and outer diameters are sized to create a sufficiently sized passageway in the ADM so the fastener's first bar and (folded) filament are able to pass through the ADM with minimal force. By minimizing the force to pass the fastener through the ADM, the stabilizing force required by the user is also reduced. Using a larger size needle would create a larger passageway in the ADM that would further reduce the force to pass the fastener through the ADM (and further reduce the stabilizing force required by the user). However, a larger size needle would also increase the amount of force required for the needle to pierce the ADM. Consequently, the needle design achieves a balance between the two competing needs by using a tri-bevel tip design with a primary bevel angle that minimizes the amount of force required for the needle to pierce ADM. The tri-bevel tip design also maintains durability for the needle tip's repeated use. Examples of primary bevel angles include 20-24 degrees, and 14-30 degrees. The following concepts describe embodiments of features than can help to further minimize the amount of stabilization force required by the user during fastener deployment.

The features shown in FIGS. 23-26 could also be used to assist with keeping the onlay material (e.g., ADM) on the needle during fastener deployment. This assistance could reduce or eliminate the amount of stabilization force the user needs to apply during fastener deployment. To enable needle withdrawal, a support (e.g. FIGS. 46-48) could be used to withdraw the needle out of the onlay material. Alternatively, with reference to FIG. 23, the barbs could retract to facilitate needle withdrawal.

Figures 27A, 27B:
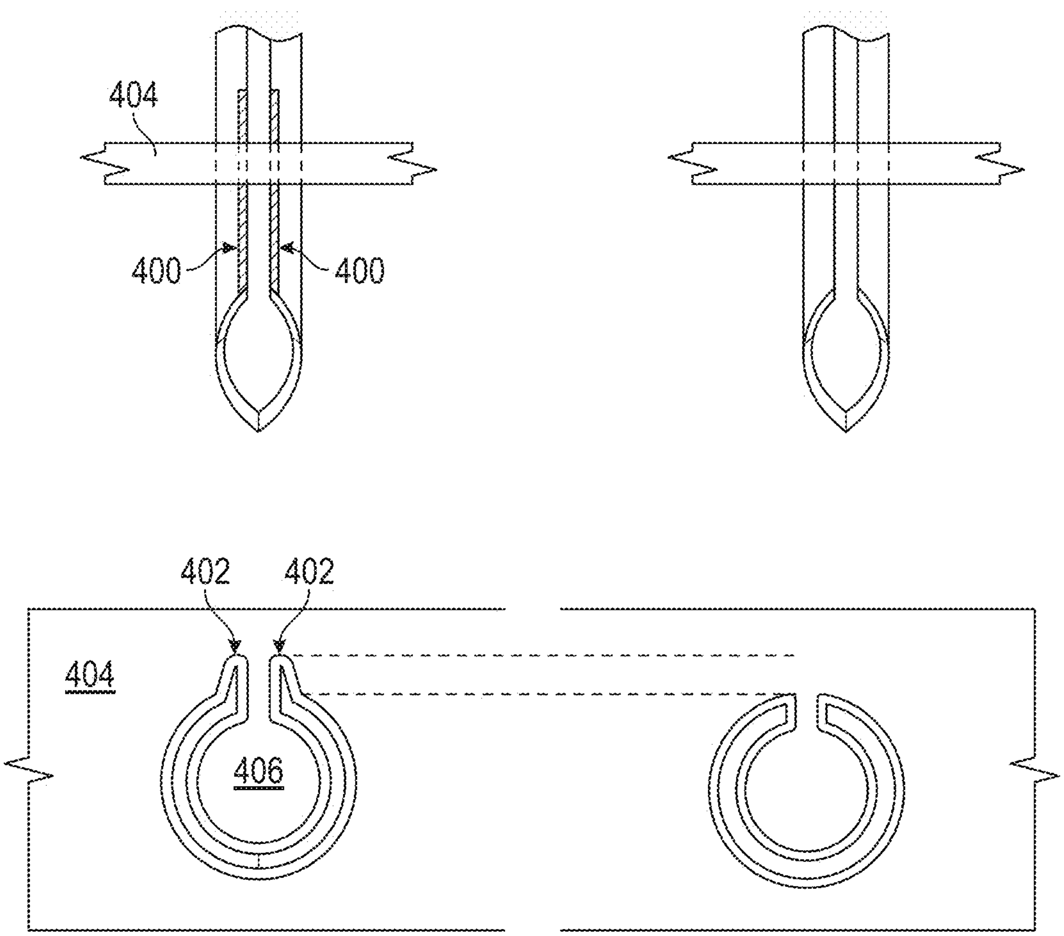

FIG. 27A shows an embodiment comprising one or more blades 400 on the needle. The blades cut slits 402 through the onlay material (e.g., ADM) 404 so that when the onlay material flap 406 in needle lumen folds when the first bar and filament pass through the onlay material, the taller flap creates more space through the onlay material. As a result, the first bar and filament can pass through the onlay material with less force so that the user can also apply less force on the onlay material during fastener deployment. FIG. 27B shows a comparison to a smaller flap size (without slits).

Figure 28:
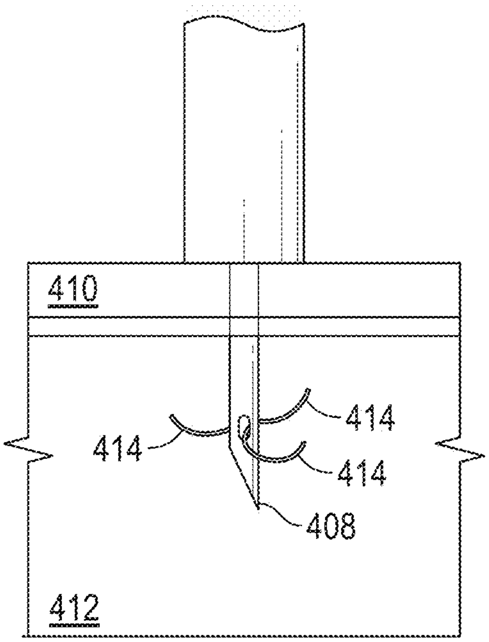

As shown in the embodiment of FIG. 28, after the fastener delivery needle 408 pierces through onlay material 410 (e.g., ADM) and into tissue 412, one or more barbs 414 can deploy from the fastener delivery needle into tissue. The user could then lift/keep the onlay material and tissue away from any underlying structures and deploy the fastener without unintentionally fastening underlying structures. Unintentionally fastening underlying structures can sometimes be caused by having to push into the onlay material/tissue during deployment.

Figure 29:
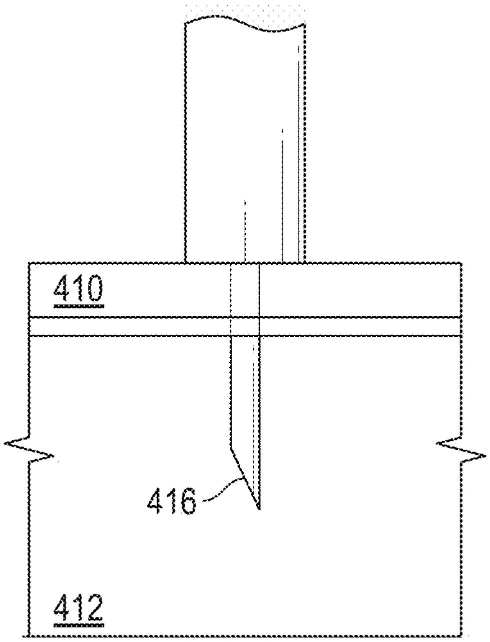
Figure 30:
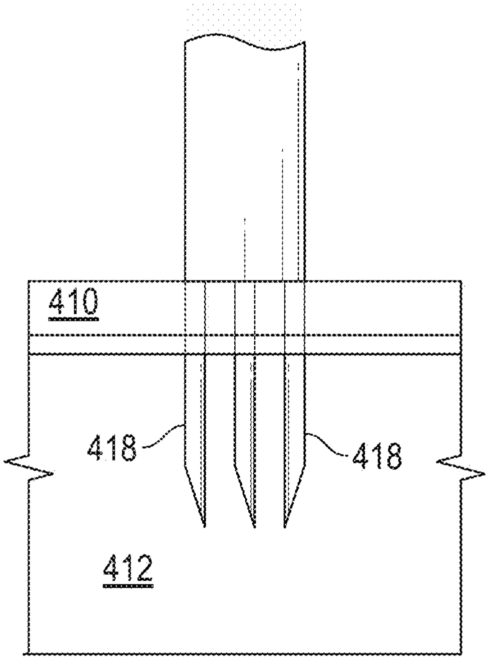
Figure 31:
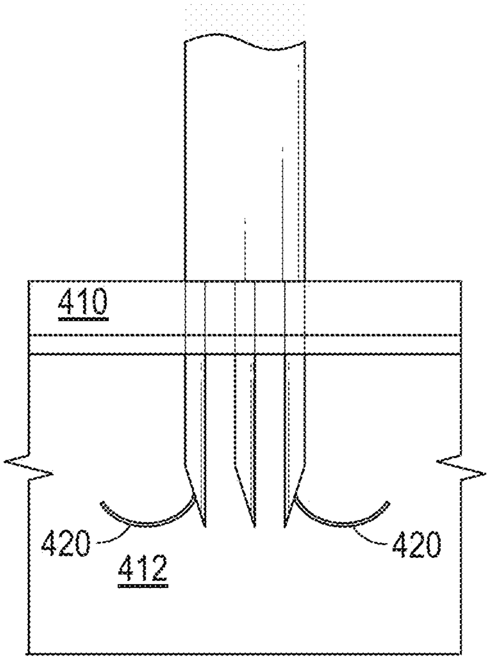

As shown in the embodiments of FIGS. 29-31, after the fastener delivery needle 416 pierces through onlay material 410 (e.g., ADM) and into tissue 412 (FIG. 29), one or more barb deployment needles 418 pierce through onlay material and into tissue (FIG. 30). Then, barbs 420 deploy from the barb deployment needles into tissue. The user could then lift/keep the onlay material and tissue away from any underlying structures and deploy the fastener without unintentionally fastening underlying structures. Unintentionally fastening underlying structures can sometimes be caused by having to push into the onlay material/tissue during deployment.

Embodiments of Features to Optimize the Placement of the Second Bar

Figure 32:
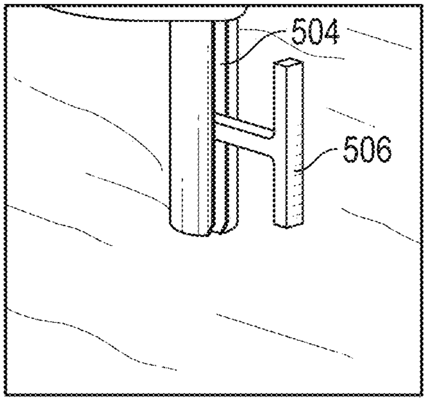
FIGS. 32-35 show an embodiment of a fastener being deployed and inadequate placement of the second bar.
Figure 33:
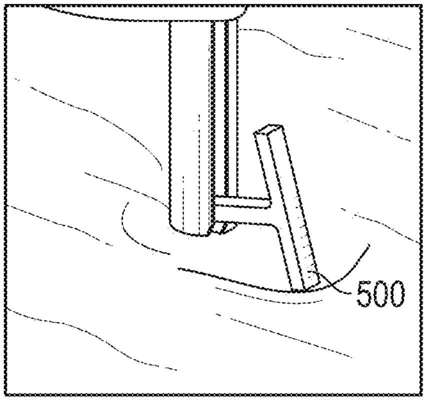
Figure 34:
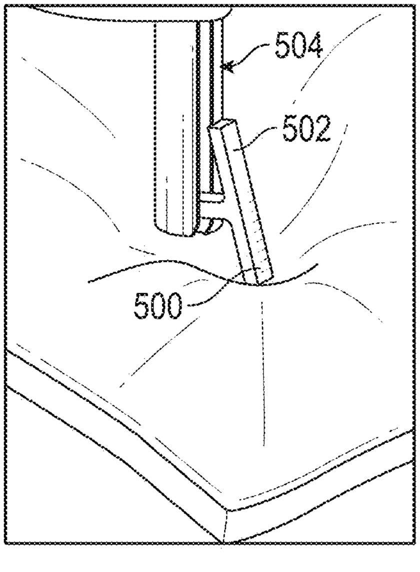
Figure 35:
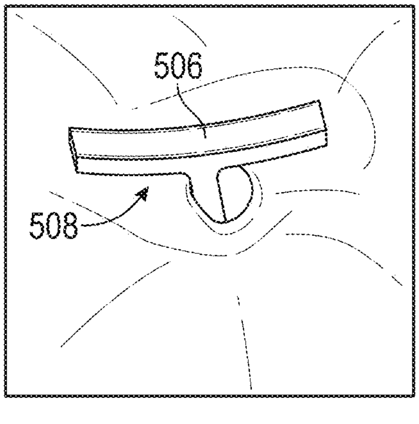

Without one or more deflectors (e.g., deflector 222 of FIG. 14), the second bar's deployment can get arrested resulting in suboptimal approximation and/or compression between the onlay material (e.g., ADM) and tissue. FIG. 32 shows the second bar 506 outside the needle slot 504 as it moves towards the onlay material. As shown in FIGS. 33 and 34, the distal end of the bar 500 seats itself on the onlay material, and the proximal end of the bar 502 can enter the needle slot 504. This configuration prevents the second bar 506 from seating on the onlay material during deployment. As shown in FIG. 35, the resulting gap 508 between the second bar 506 and onlay material prevents the second bar 506 from approximating and/or compressing the onlay material to tissue. The deflector 222 solves this problem by deflecting the fastener's filament to reorient the second bar 506 so that it seats on the onlay material to approximate and/or compress the onlay material to tissue. The following concepts describe alternate ways to optimize the placement of the second bar and the onlay material/tissue approximation and/or compression.

Figure 36:
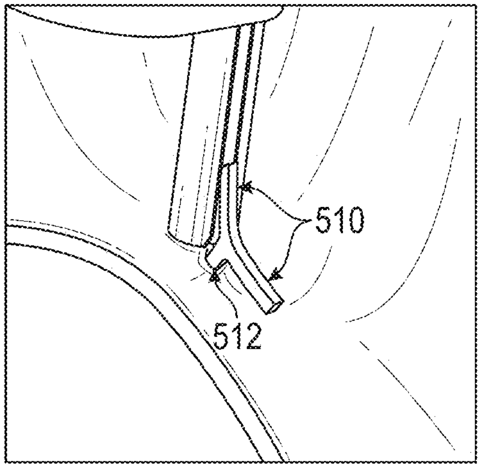
FIGS. 36-37 show an embodiment of a fastener with a flexible second bar being deployed from a fastening device.
Figure 37:
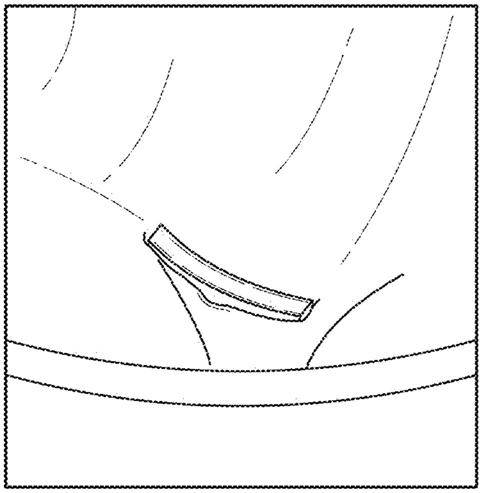

FIG. 36 shows an embodiment of a fastener with a second bar that has a shorter height. The shorter height makes the second bar more flexible so that when the second bar encounters the configuration illustrated in FIG. 34, the bar flexes. The flexed second bar 510 enables the junction 512 between the filament and second bar to advance to the onlay material. By allowing the junction between the filament and second bar to advance to the onlay material, the gap between the second bar and onlay material is eliminated, and the fastener can approximate and/or compress the onlay material to tissue, as shown in FIG. 37.

Figure 38:
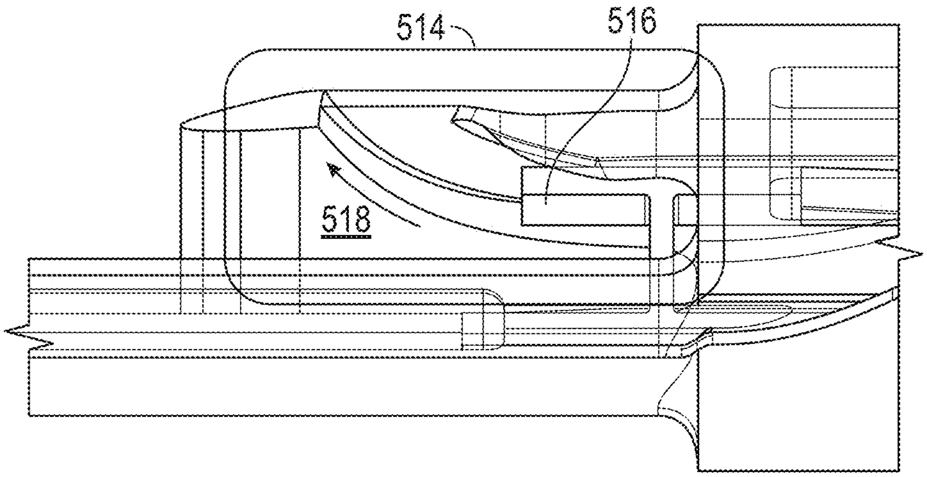
FIGS. 38-39 show an embodiment of a deflector that interacts with the fastener's second bar.
Figure 39:
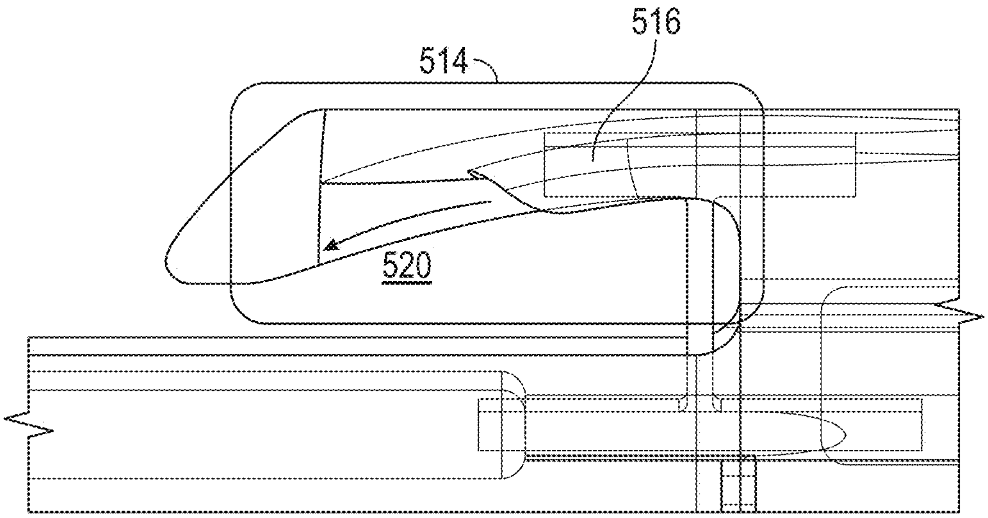

FIGS. 38 and 39 show an embodiment of a deflector 514 that interacts directly with the fastener's second bar 516. The deflector curves in one or more directions, shown by a first direction 518 (e.g., upward, shown in the side view of FIG. 38) and a second direction 520 (e.g., inward, shown in the top view of FIG. 39). Both curvatures or directions act together to deflect the second bar. The deflector 514 reorients the second bar 516 to seat on the onlay material (e.g., ADM).

Figure 40:
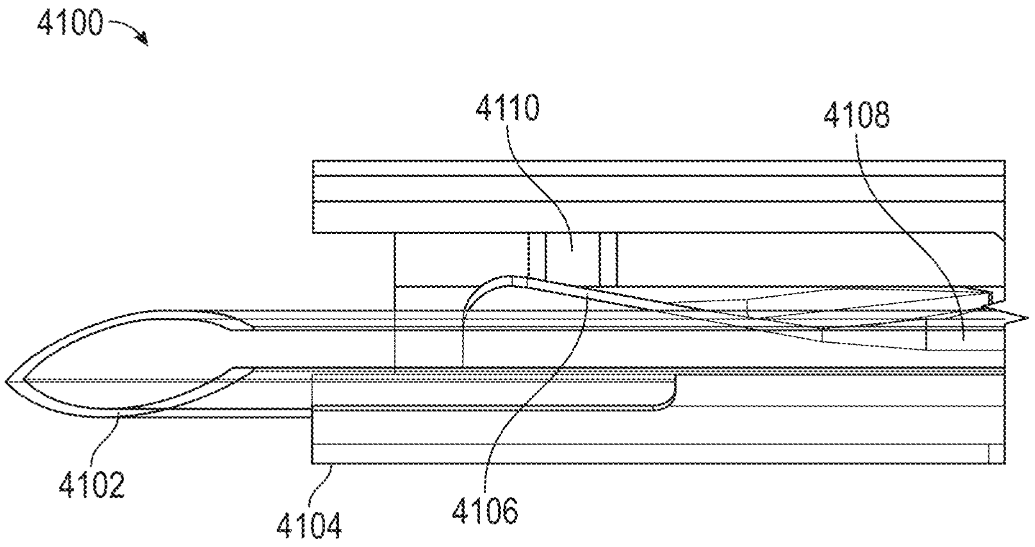
FIGS. 40-42O illustrate another embodiment of a fastener deflector configured to interact with the fastener's filament and second bar to reorient the second bar.
Figure 41:
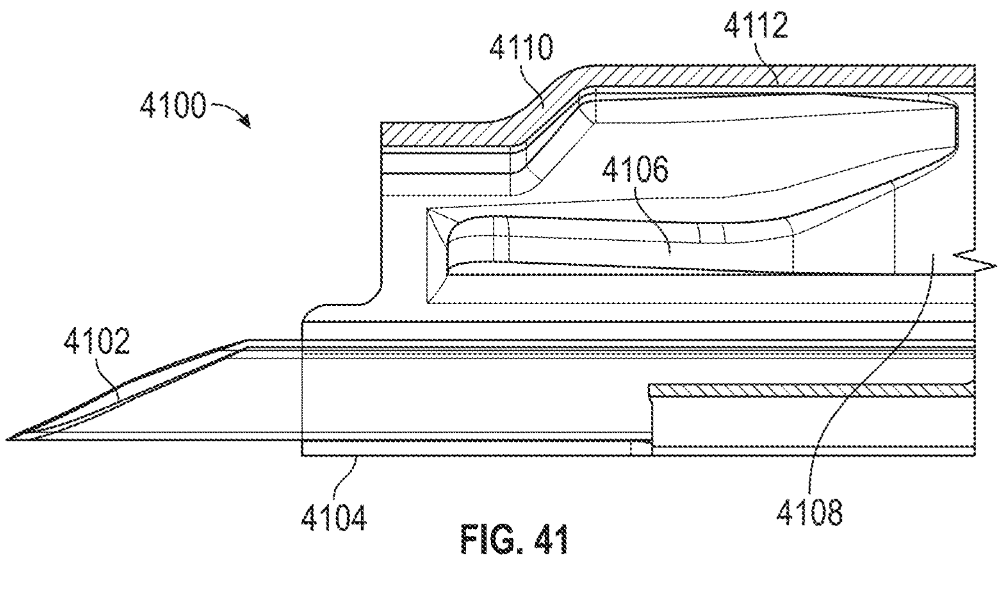

FIGS. 40-42O illustrate another embodiment of a fastener deflector configured to interact with the fastener's filament and second bar to reorient the second bar so that it seats on the onlay material (e.g., ADM). FIGS. 40 and 41 show the side and top views, respectively, of the distal end of a fastening device 4100. FIGS. 40 and 41 show slotted needle 4102 extending from the distal end of shaft 4104. Moving distally along the shaft 4104, a first or bottom ramp 4106 extends upwards or away from a bottom side 4108 of the shaft. Positioned distal to the start of the first ramp 4106 is a second or side ramp 4110 which projects from a side wall 4112.

Figure 42A:
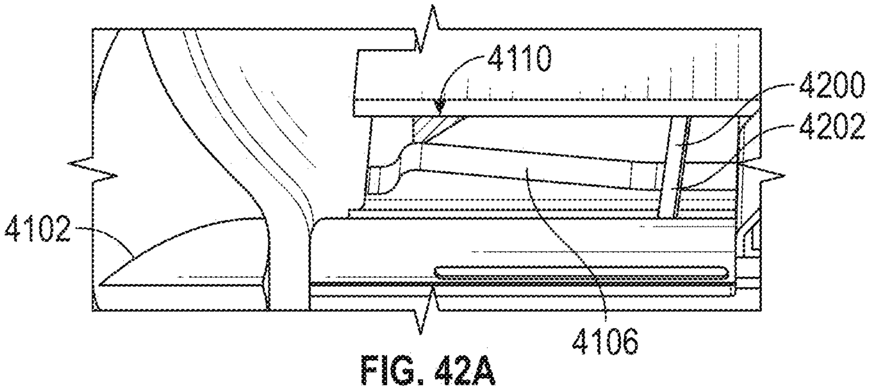
Figure 42B:
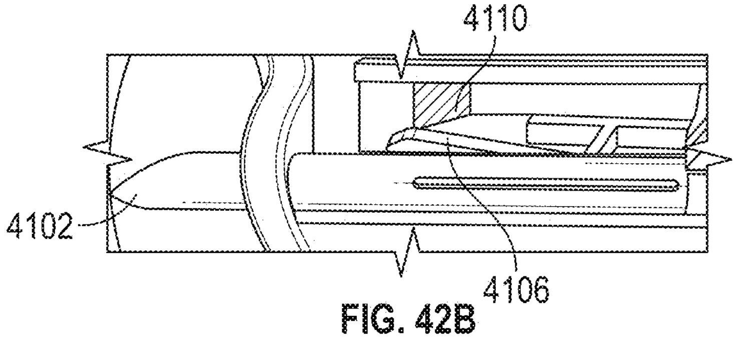
Figure 42C:
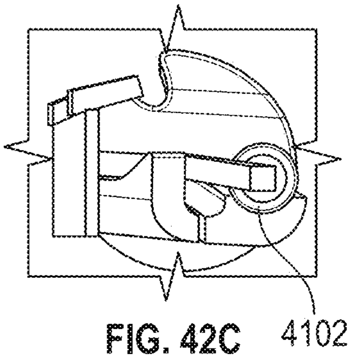
Figure 42D:
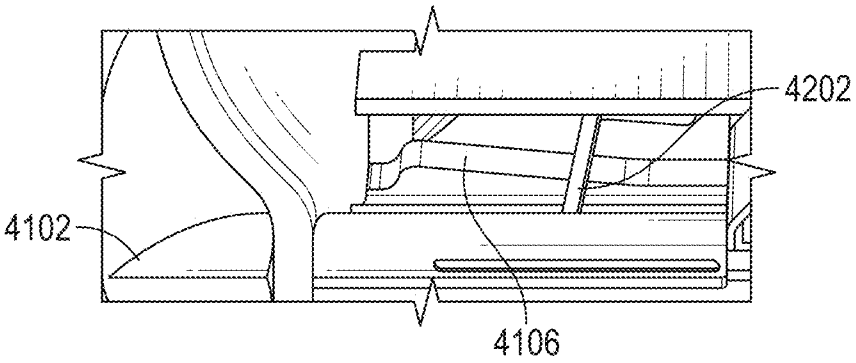
Figure 42E:
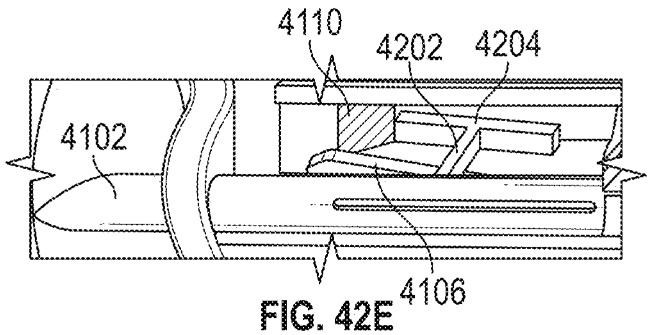
Figure 42F:
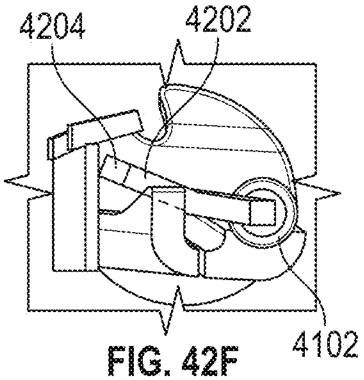
Figure 42G:
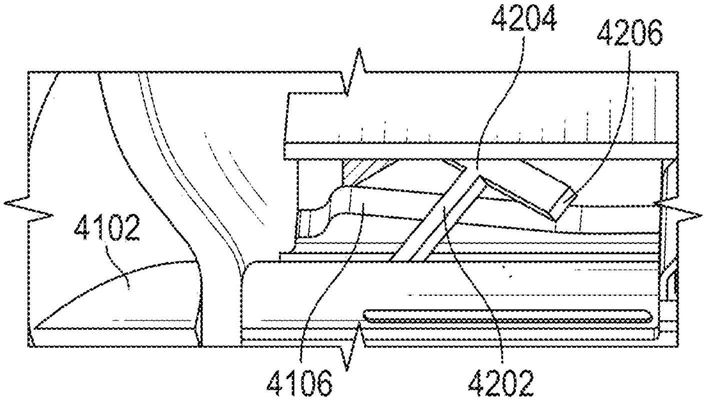
Figure 42H:
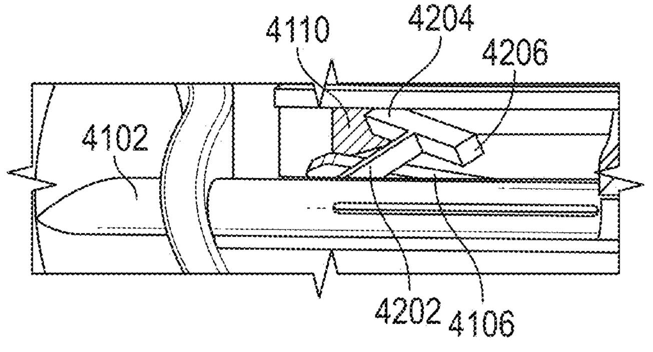
Figure 42I:
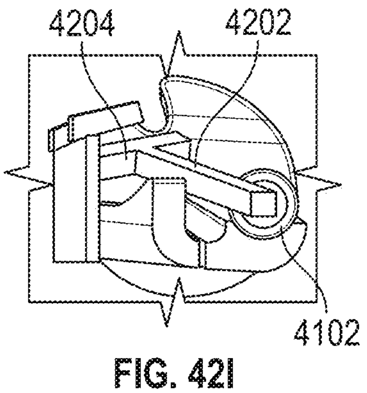
Figure 42J:
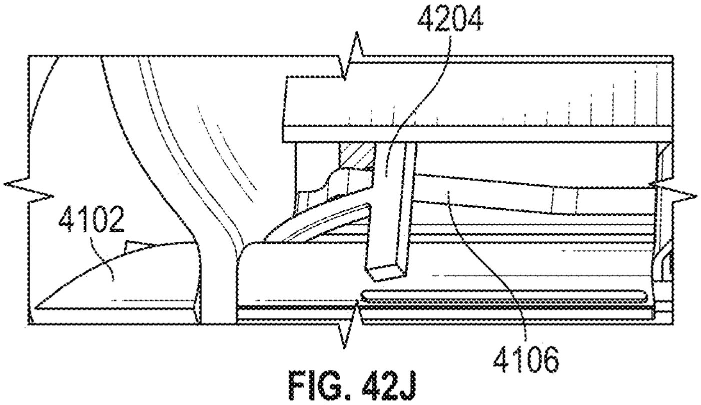
Figure 42K:
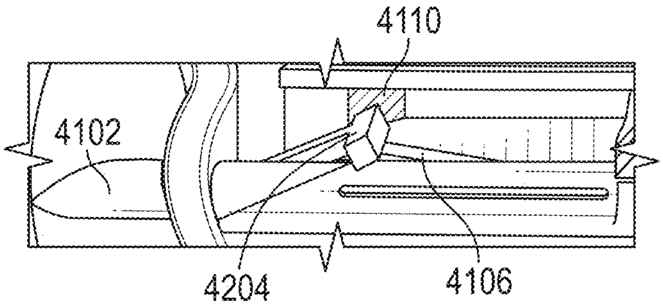
Figure 42L:
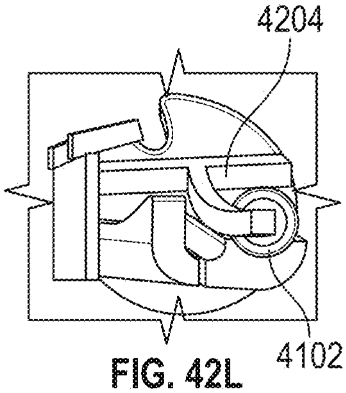
Figure 42M:
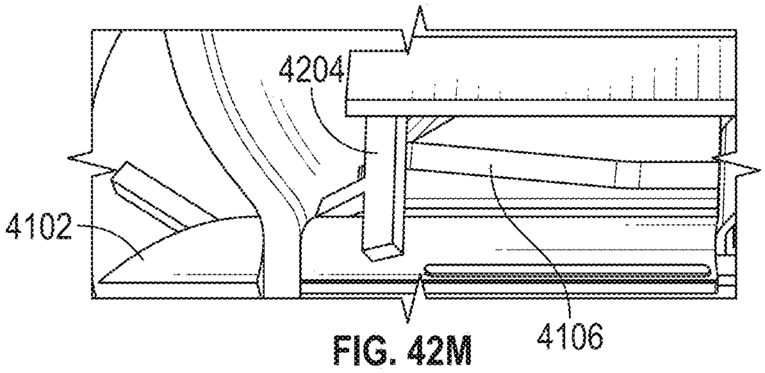
Figure 42N:
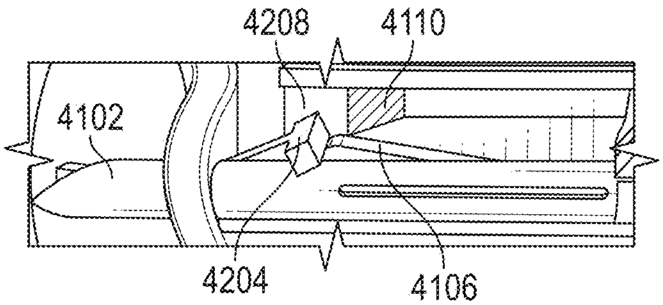
Figure 42O:
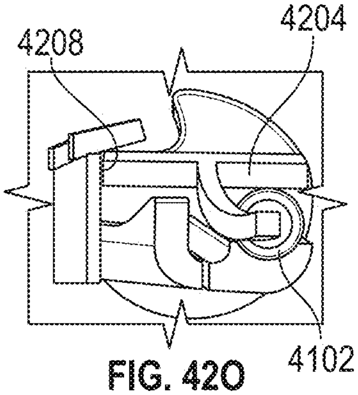
Figure 43A:
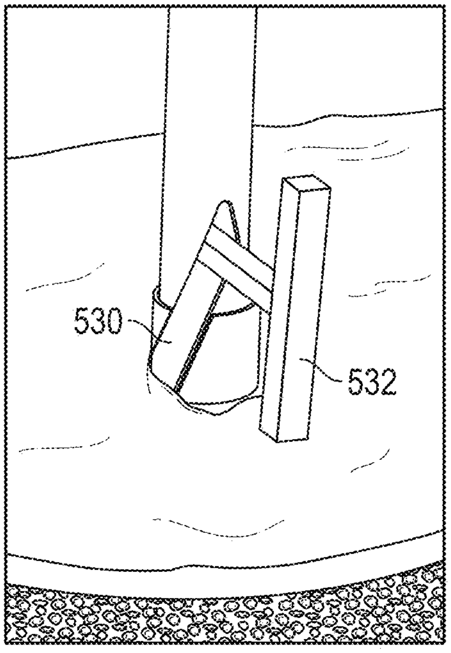
FIGS. 43A-43D show an embodiment of a needle comprising a helical slot.
Figure 43B:
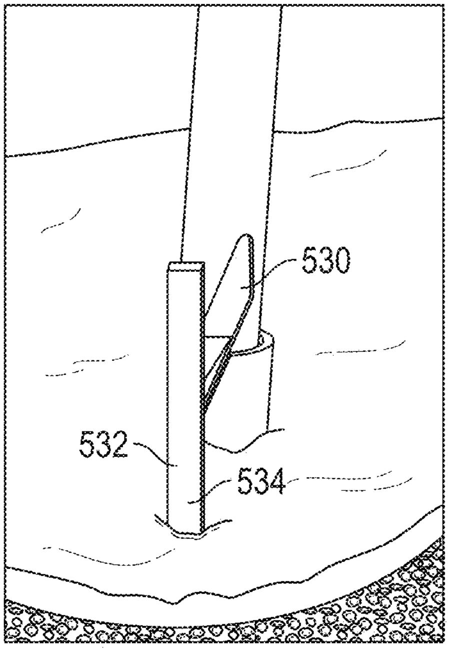
Figure 43C:
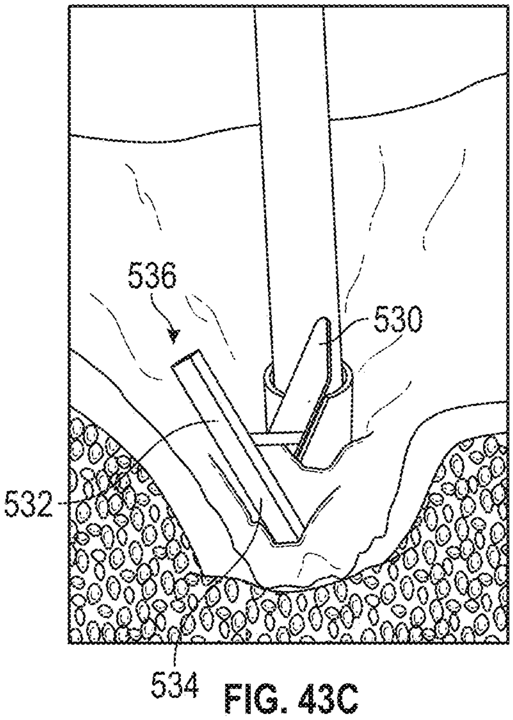
Figure 43D:
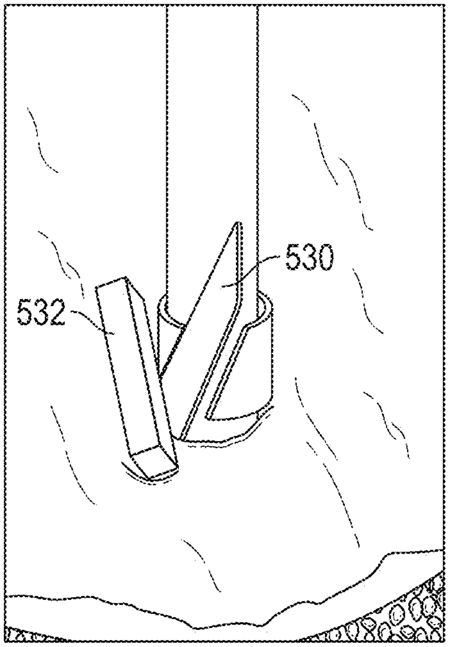

FIGS. 42A-O show an embodiment of a fastener 4200 being deployed from a fastening device 4100 like that shown in FIGS. 40 and 41. FIGS. 42A-C show top, side, and front views, respectively, of the fastener's filament 4202 extending from the slotted needle 4102.

FIGS. 42D-F show top, side, and front views, respectively, of the fastener 4200 being pushed distally along the slotted needle 4102, causing the bottom ramp 4106 to lift the fastener's filament 4202, elevating the fastener's second bar 4204 above the needle 4102.

FIGS. 42G-I show top, side, and front views, respectively, of the fastener 4200 continuing to be pushed distally along the needle 4102, causing the bottom ramp 4106 to continue to lift the filament 4202 and second bar 4204, and causing the side ramp 4110 to rotate the second bar 4204 so that an end 4206 of second bar rotates towards the needle 4102.

FIGS. 42J-L show top, side, and front views, respectively, of the fastener 4200 continuing to be pushed distally along the needle 4102, causing the bottom ramp 4106 continuing to lift the second bar 4204 and the side ramp 4110 continuing to rotate the second bar 4204 above the needle 4102. As shown in this set of figures, the second bar 4204 is now largely parallel to the surface of the onlay material.

FIGS. 42M-O show top, side, and front views, respectively, of the side wall 4208, best shown in FIG. 42N maintaining the position of the second bar 4204 during deployment of the fastener.

FIGS. 43A-43D show an embodiment of a needle comprising a helical slot 530 in the needle. The helical slot reorients the second bar 532 to seat on the onlay material (e.g., ADM) as the fastener is being deployed from the needle. When the end 534 of the second bar 532 makes contact with the onlay material (e.g., ADM), the rotational movement of the fastener 536 causes the second bar 532 to pivot about the end 534 so that it seats on the onlay material.

Reorienting the second bar so that it moves towards a position parallel to a surface of the onlay material provides the advantage of improved approximation and/or compression of the onlay material and tissue, as described above. It also provides the advantage of allowing the surgeon to hold the fastening device at an angle other than perpendicular relative to the onlay material and tissue. The surgeon can approach the treatment site from any angle while still being assured of reliable and consistent positioning of the fastener.

Embodiments of Features that Aid Needle Withdrawal

Figure 44:
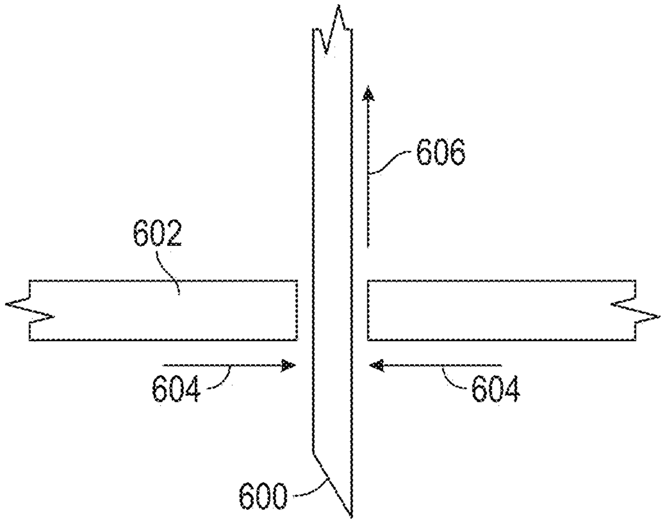
FIGS. 44-45 depict a withdrawal force occurring on a needle.
Figure 45:
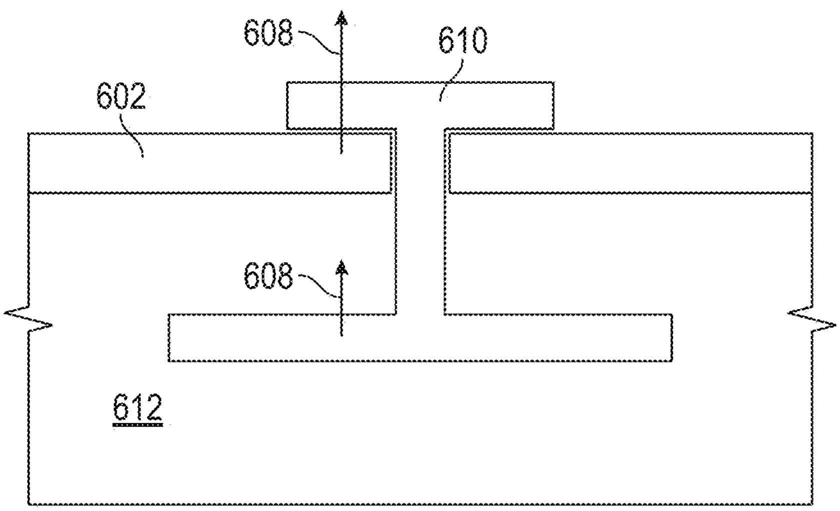

After the needle 600 pierces the onlay material 602 (e.g., ADM), there is a compressive force 604 between the onlay material and the needle that acts to keep the onlay material on the needle. Consequently, a "withdrawal" force 606 is required to pull the needle out of the onlay material (FIG. 44). This withdrawal force also causes the onlay material 602 to apply a "pull out" force 608 that acts to pull the fastener 610 out of tissue 612 and/or compromise the fastener's retention in tissue (FIG. 45). The following concepts describe ways to aid needle withdrawal to preserve the fastener's retention in tissue. The following concepts would also aid needle withdrawal when used with any features that assist with keeping the onlay material on the needle to (re) position and/or tension the onlay material (e.g., like those described with respect to FIGS. 23-26).

Figure 48:
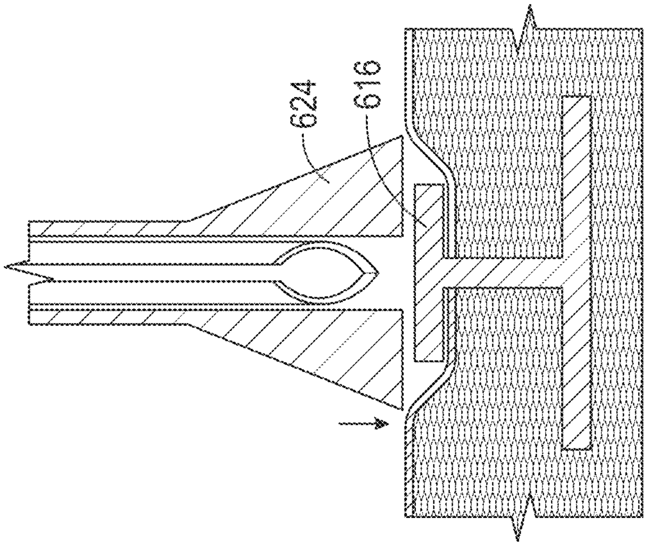
FIGS. 46-48 show embodiments of supports for fastening devices.
Figure 47:
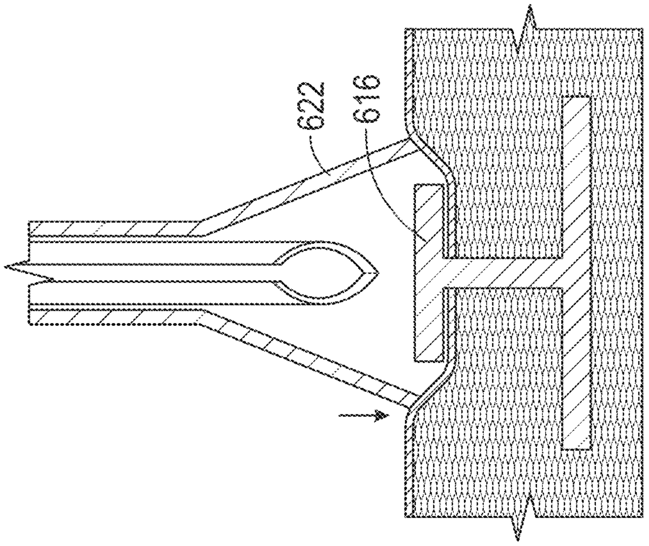
Figure 46:
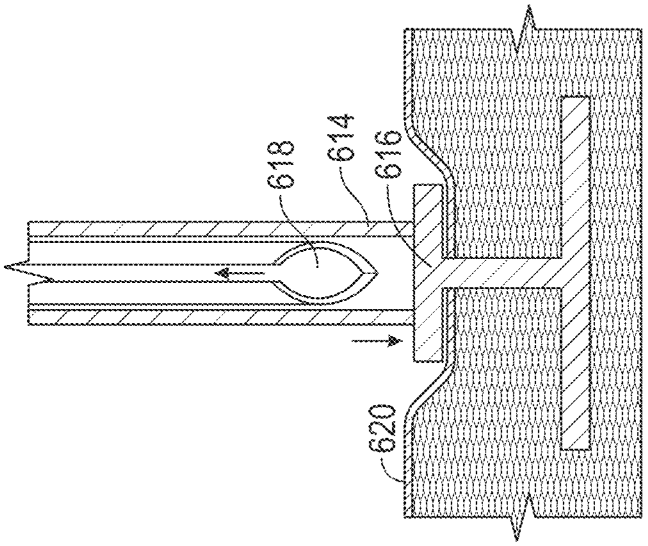

FIG. 46 shows an embodiment of a support 614 that actuates and contacts the fastener 616 to provide countertraction while the needle 618 withdraws from the onlay material 620 (e.g., ADM). The support can comprise one or more elongated features or a shaft that extends past the needle and can provide a force on the onlay material while the needle is being withdrawn. FIG. 47 shows an alternative embodiment of a support 622 that contacts the onlay material to provide countertraction. The support 622 has a distal feature that extends radially outward so that the support 622 does not contact the fastener 616, and only contacts the onlay material around the fastener. FIG. 48 shows another embodiment of a support 624 that contacts both the fastener and the onlay material to provide countertraction. In FIGS. 46-48, the shoulder 214 (above) could also serve as the support. Alternatively, the support could be a separate element. In some embodiments, the support is dual purposed to also serve as a needle protector/cover.

Figure 49A:
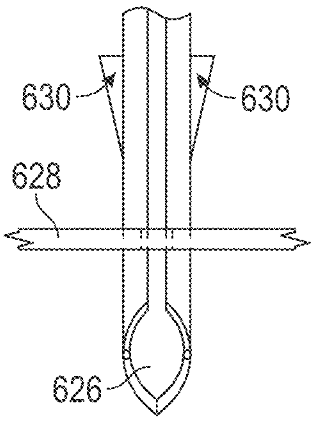
FIGS. 49A-51C show embodiments of needles comprising one or more blades.
Figure 50A:
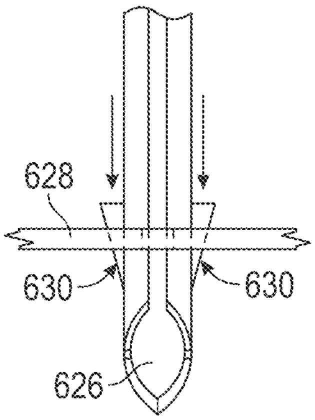

FIG. 49A shows a front view of an embodiment of a needle 626 through onlay material 628 (e.g., ADM). FIG.

49B shows a bottom view of the onlay material hole compressing the outside diameter (OD) of the needle. One or more blades 630 are positioned around the perimeter of the needle 626. In the front view of FIG. 50A and bottom view of FIG. 50B, the blades 630 are actuated (e.g., advanced distally) to cut slits through the perimeter of the hole, thereby relieving the onlay material's compression on the OD of the needle. With the compression relieved, the needle can be easily withdrawn from the onlay material.

Figure 51A:
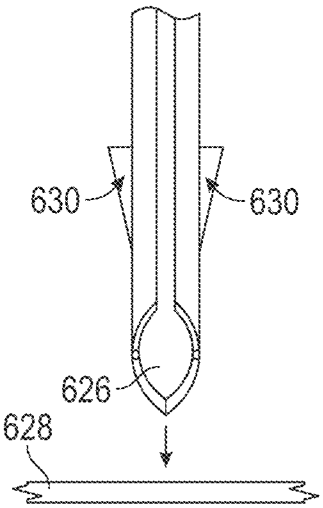
Figure 49B:
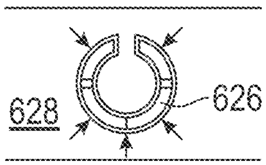
Figure 50B:
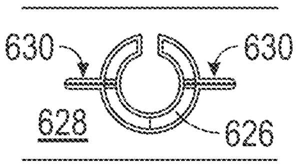
Figure 51B:
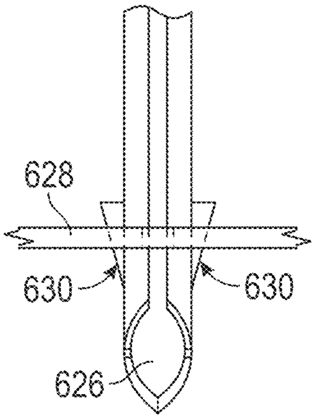
Figure 51C:
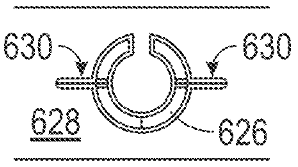

FIGS. 51A-51C show an alternative embodiment where one or more blades 630 are fixed around the perimeter of the needle 626. When the needle pierces the onlay material 628 (e.g., ADM), the blades simultaneously cut slits through the perimeter of the hole, thereby relieving the onlay material's compression on the OD of the needle. With the compression relieved, the needle can be easily withdrawn from the onlay material.

Other Fastener Embodiments

Figure 52:
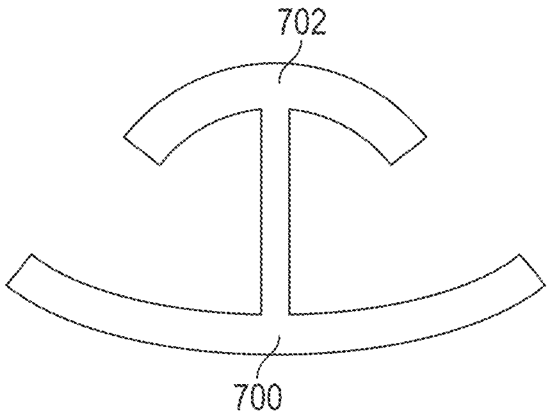
FIG. 52 shows an embodiment of a fastener with one or more curved bars.

FIG. 52 shows an embodiment of a fastener with a curved first bar 700 to improve the fastener's retention in tissue, and a curved second bar 702 to improve the fastener's retention to the onlay material (e.g., ADM). The curved bars would also assist approximating and/or compressing the onlay material to tissue. The curved second bar 702 could also prevent the bar's ends from pointing upward (e.g. away from the onlay material like a "V") and from moving (e.g. spinning) on the onlay material.

Figure 53:
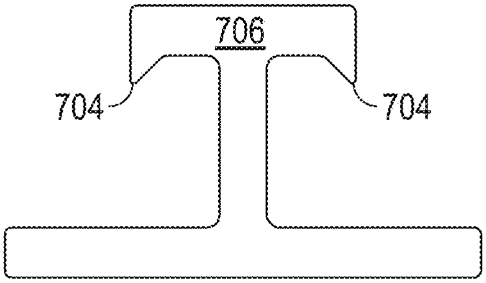
FIG. 53 shows an embodiment of a fastener with one or more protrusions.

FIG. 53 shows an embodiment of a fastener that has one or more downward pointing (e.g., pointing towards the first bar) protrusions 704 on the second bar 706 that prevent the second bar from moving (e.g. spinning) on the onlay material (e.g., ADM).

Figure 54:
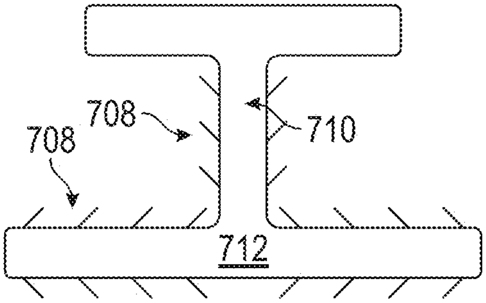
FIG. 54 shows an embodiment of a fastener comprising barbs.

FIG. 54 shows an embodiment of a fastener with multiple barbs 708 on both/either the fastener's filament 710 and/or the fastener's first bar 712. The barbs are oriented to allow the filament and first bar to be easily deployed through the onlay material (e.g., ADM) and into tissue, but make it difficult to pull the fastener out of tissue and the onlay material.

Figure 55:
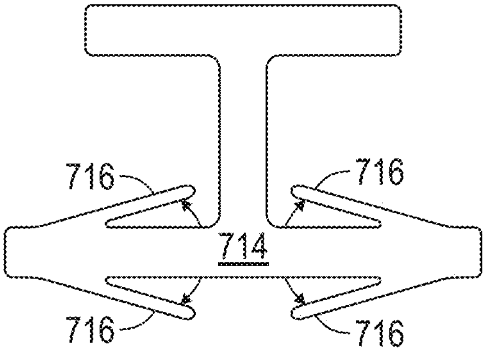
FIGS. 55-56B show embodiments of fasteners comprising expanding wings.

FIG. 55 shows an embodiment of a fastener with a first bar 714 that has one or more expanding wings 716. The wings are oriented to allow the first bar to be easily deployed into tissue, but make it difficult to pull the fastener out of tissue. The wings are oriented in a same plane as the fastener.

Figure 56A:
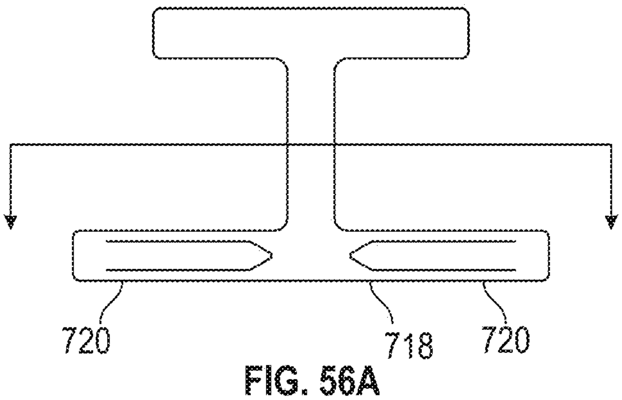
Figure 56B:
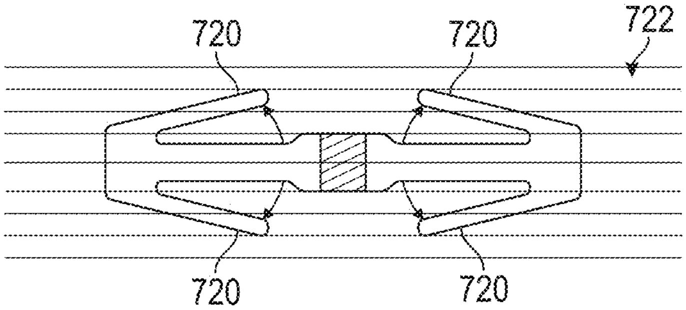

FIGS. 56A and 56B show an embodiment of a fastener with a first bar 718 that has one or more expanding wings 720. The wings are oriented to allow the first bar to be easily deployed into tissue, but make it difficult to pull the fastener out of tissue. The wings are also oriented to expand out of the fastener's plane, as shown in FIG. 56B, so that if the first bar 718 is deployed in the same direction as the muscle fibers 722, the wings expand across the muscle fibers to improve the fastener's retention strength in tissue.

Figure 57:
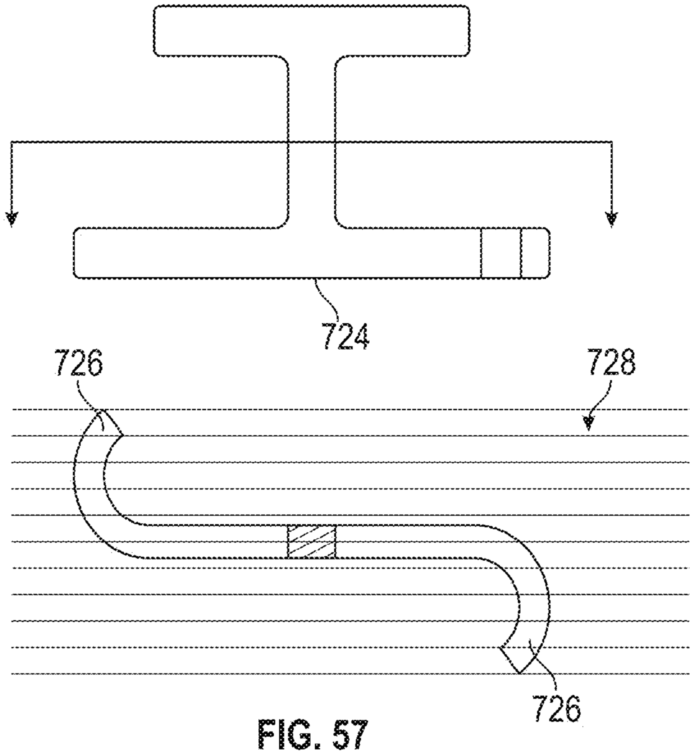
FIG. 57 shows an embodiment of a fastener comprising curling arms.

FIG. 57 shows an embodiment of a fastener with a first bar 724 with arms that curl 726 when deployed from the needle. The arms curl out of the fastener's plane across the muscle fibers 728 so that if the first bar is deployed in the same direction as the muscle fibers, the curled arms improve the fastener's retention strength in tissue.

Figure 58C:
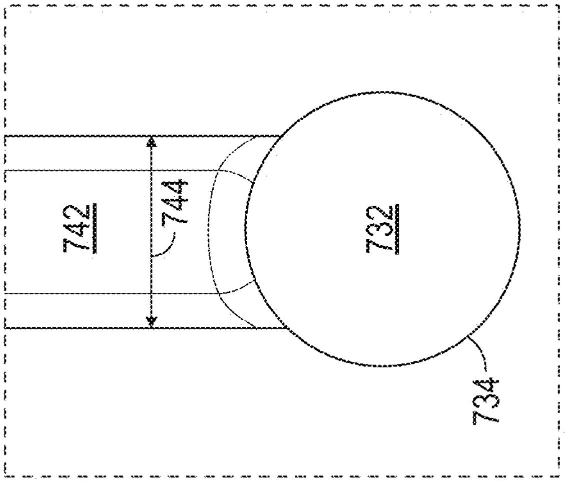
FIGS. 58A-59C show various views of two embodiments of fasteners comprising different cross-sectional geometries.
Figure 58B:
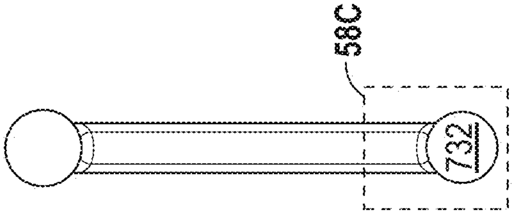
Figure 58A:
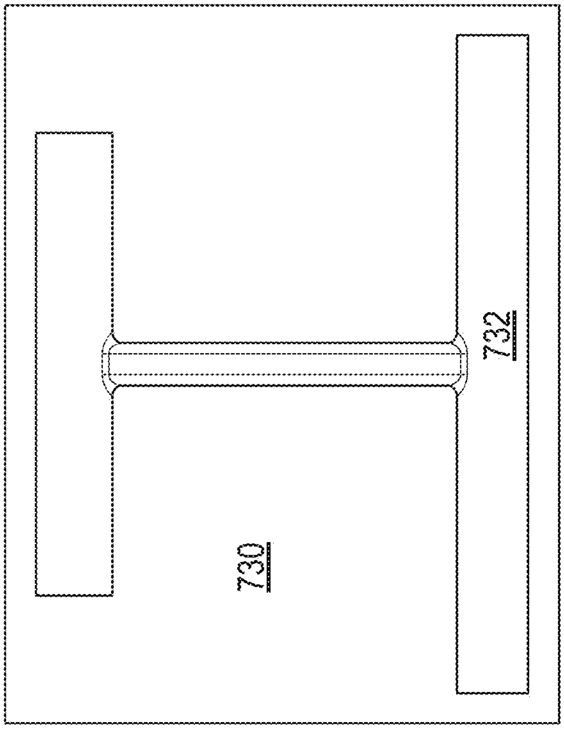
Figure 59C:
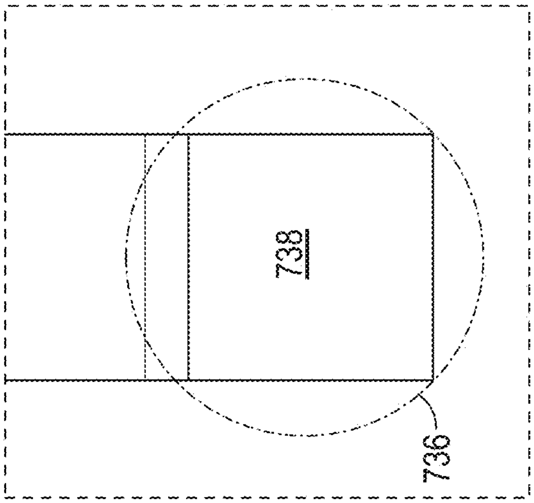
Figure 59B:
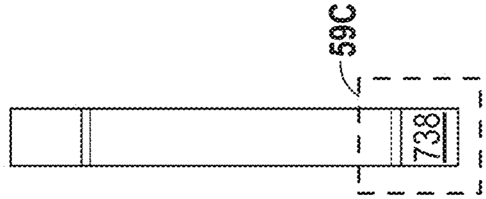
Figure 59A:
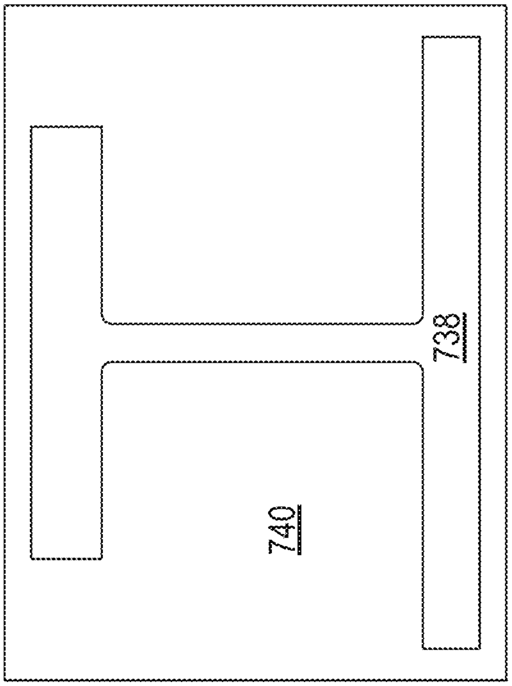

FIGS. 58A-C and 59A-C show a front view, a side view, and a blown up side view, respectively, of two fasteners. FIGS. 58A-C show a fastener 730 that has a first bar 732 with a circular cross-section. The circular cross-section has a diameter 734 that is less than the diameter 736 of a circumscribed circle around a first bar 738 of a fastener 740 that has a rectangular/square cross-section of comparable stiffness/strength, shown in FIGS. 59A-C. The smaller diameter 734 allows the first bar 732 to fit inside a needle that has a smaller inner diameter (ID). In other words, a fastener with a rectangular/square cross section would need a larger diameter slotted needle than a fastener with a circular cross section of comparable stiffness/strength. The potential benefits of a needle with a corresponding smaller outer diameter (OD) include lower force to pierce the onlay material (e.g., ADM) with the needle and lower force to withdraw the needle from the onlay material. Another potential benefit of the smaller diameter 734 first bar 732 is additional space in a needle that is sized for the rectangular/square cross section. The additional space could reduce the amount of stabilization force required by the user during fastener deployment (e.g., as described above with respect to FIGS. 23-31).

Figure 60:
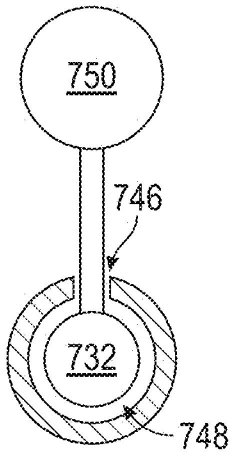
FIG. 60 shows an embodiment of a fastener's first bar positioned within a needle.

As shown in FIGS. 58A-C, in some embodiments, the fastener 730 could also have a connector or filament 742 with a height 744 that is smaller than the diameter 734 of the first bar 732. As shown in FIG. 60, this allows the needle slot 746 to prevent the first bar 732 from unintentionally coming out of the needle's lumen 748. The second bar 750 could have a different or the same diameter as the first bar 732.

Figure 61A:
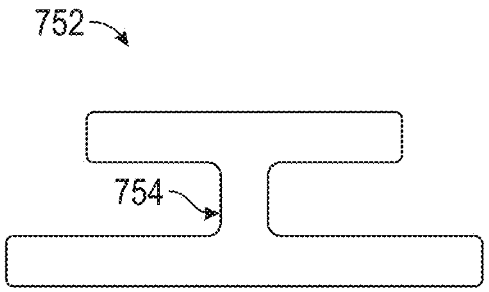
FIGS. 61A and 61B show an embodiment of a fastener manufactured in multiple steps.
Figure 61B:
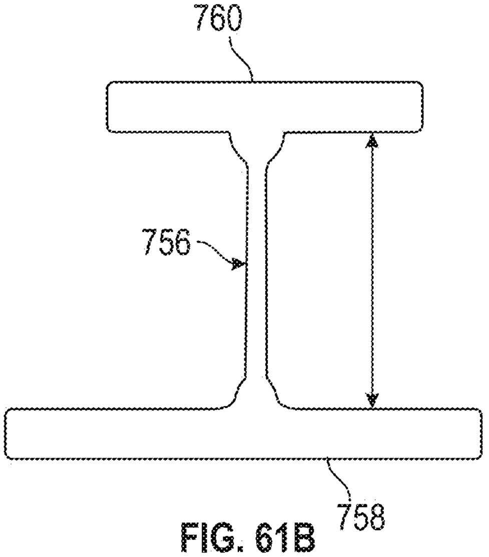

As shown in FIGS. 61A and B, in some embodiments, the fastener 752 could be fabricated in multiple steps, with the initial step producing a preliminary shorter filament length 754 (FIG. 61A). In a subsequent manufacturing step, the filament could be stretched to a longer length 756 (FIG. 61B). The stretching could serve multiple purposes. First, for polymers susceptible to stretch under certain loads, the stretching manufacturing process could reduce/eliminate stretch that could occur after implantation. As a result, the approximation and/or compression between the onlay material (e.g., ADM) and tissue achieved at the time of implantation could be better maintained over time to benefit healing. Second, the stretching will reduce the filament's cross-sectional geometry. This could create more space in the needle's lumen for the first bar 758 and filament 756 to pass through the onlay material. The additional space could reduce the amount of stabilization force required by the user during fastener deployment (e.g., as described above with respect to FIGS. 23-31). The filament's smaller cross-sectional geometry would also enable a smaller needle slot width that can prevent the first bar from unintentionally coming out of the needle's lumen (as illustrated in FIG. 60). Third, the stretching will make the filament more flexible. The additional filament flexibility could facilitate reorientation of the second bar 760 to optimize placement of the second bar and the onlay material/tissue approximation and/or compression (e.g., as described above with respect to FIGS. 32-43D).

Alternatively, the stretching could also be done in the device at the time of deployment to a variable or predetermined length.

Figure 62A:
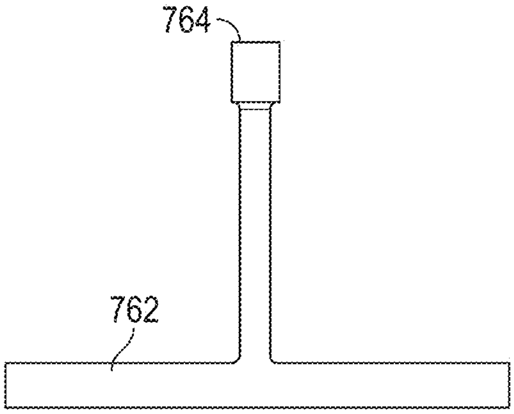
FIGS. 62A-C show an embodiment of a fastener with bars extending in different directions.
Figure 62B:
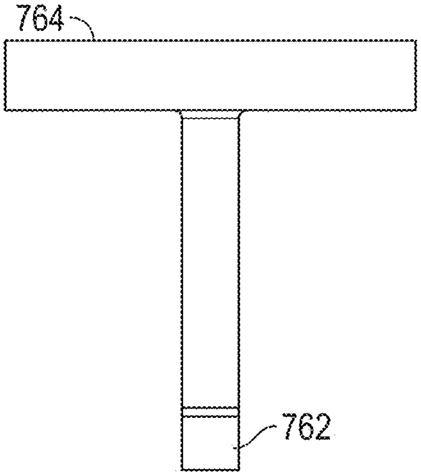
Figure 62C:
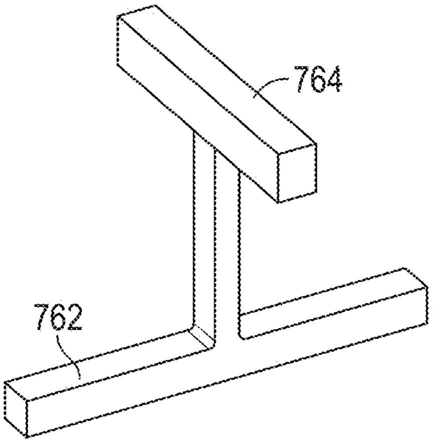

FIGS. 62A-C shows an embodiment of a fastener with a first bar 762 and a second bar 764 extending in different directions. The directions could be different than what is illustrated in FIG. 62. Having the second bar extend in a different direction than the first bar could optimize placement of the second bar and the onlay material (e.g., ADM)/tissue approximation and/or compression (e.g., as described above with respect to FIGS. 32-43D). The fasteners could convey down the shaft/fastener reservoir 104 in an unstressed configuration as shown in FIG. 62 and deploy. Alternatively, the fasteners could convey down the shaft/fastener reservoir 104 with the bars deformed/stressed into the same plane (e.g. like an "H" as shown in FIG. 10) and then recover to the unstressed (out-of-plane) configuration (e.g. as shown in FIG. 62) for deployment.

Figure 63:
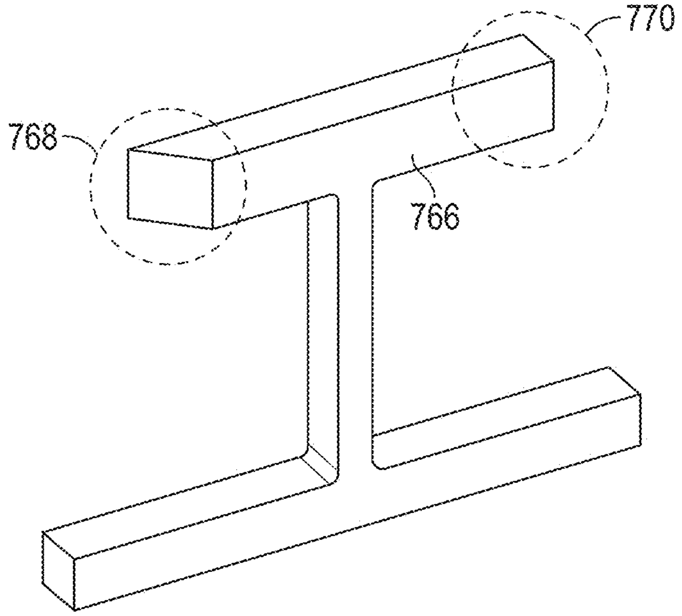
FIG. 63 shows an embodiment of a fastener with a bar comprising an end feature.

FIG. 63 shows an embodiment of a fastener with a second bar 766 that has an end feature 768 (such as a chamfer). When the end feature contacts the onlay material (e.g., ADM) during deployment, the end feature causes the proximal end 770 of the second bar to tilt and avoid the needle slot. This could optimize placement of the second bar and the onlay material (e.g., ADM)/tissue approximation and/or compression (e.g., as described above with respect to FIGS. 32-43D).

Figure 64:
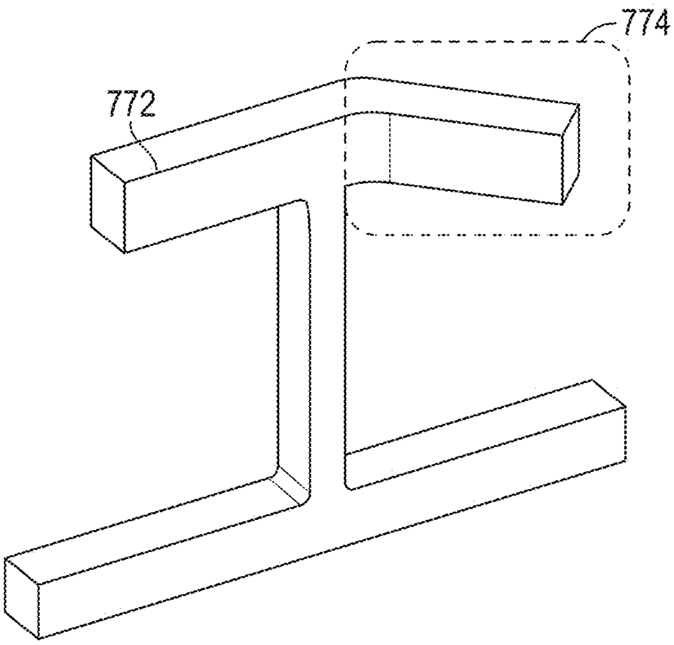
FIG. 64 shows an embodiment of a fastener with a bar comprising a bend.

FIG. 64 shows an embodiment of a fastener with a second bar 772 that has a bend 774. When the bent end travels towards the needle slot during deployment, the bend causes the second bar to glance off the needle and avoid the needle slot. This could optimize placement of the second bar and the onlay material (e.g., ADM)/tissue approximation and/or compression (e.g., as described above with respect to FIGS. 32-43D).

Figure 65:
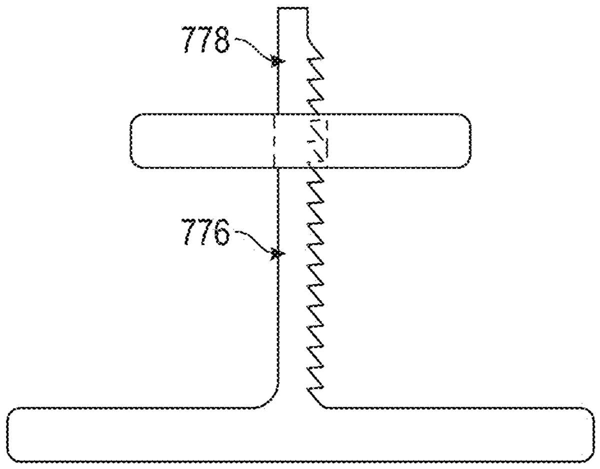
FIG. 65 shows an embodiment of a fastener comprising an adjustable connector or filament.

To provide additional control over the onlay material (e.g., ADM)/tissue approximation and/or compression, the fastener could incorporate an adjustable length filament. One such embodiment is shown in FIG. 65, with adjustable length filament 776. After adjusting the filament to the proper length (either before or after implantation), the excess filament 778 could be trimmed if desired.

Figure 66:
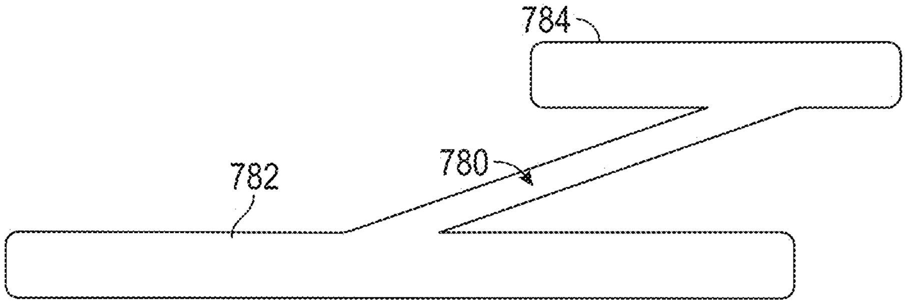
FIGS. 66-70 show embodiments of a fastener comprising a connector or filament positioned at an oblique angle relative to the bars of the fastener.
Figure 67:
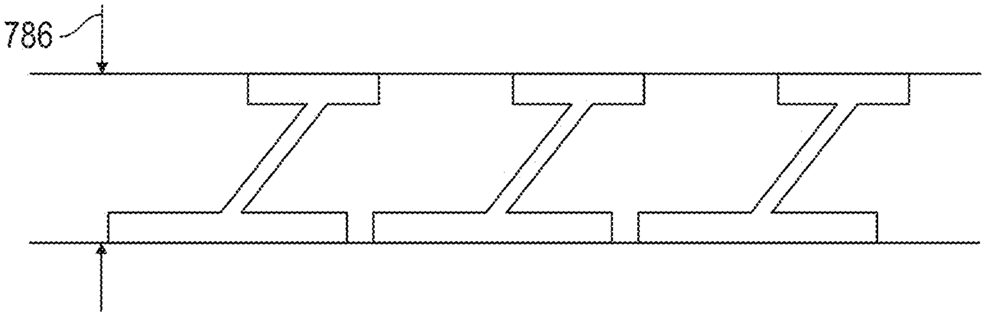
Figure 68:
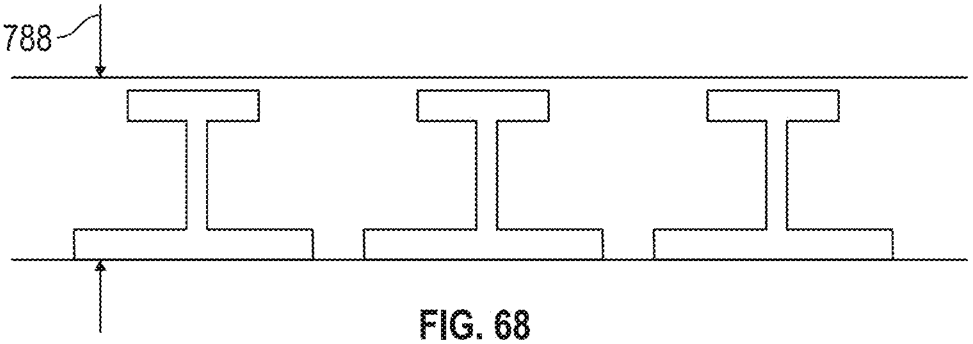
Figure 69:
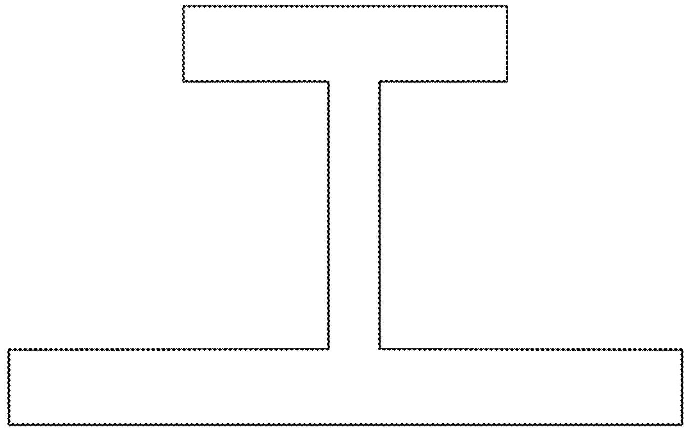

FIGS. 66 and 67 show an embodiment of a fastener that has a filament 780 at an oblique angle to the fastener's first bar 782 and second bar 784 in order to facilitate a smaller crossing profile 786 for the shaft/fastener reservoir 104. FIG. 67 shows the smaller crossing profile 786 compared to the larger crossing profile 788 (FIG. 68) of the shaft/fastener reservoir containing fasteners that have a filament perpendicular to the fastener's bars (FIG. 69).

Figure 70:
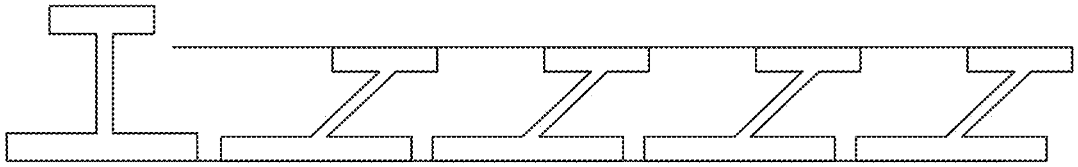

The fasteners could convey down the shaft/fastener reservoir 104 in an unstressed configuration as shown in FIGS. 66 and 67 and deploy. Alternatively (as shown in FIG. 70), the fasteners could be deformed/stressed from the configuration shown in FIG. 69 to the configuration shown in FIG. 66 while they convey down the shaft/fastener reservoir 104. The fasteners could recover to the unstressed configuration (shown in FIG. 69) for deployment.

Figure 71:
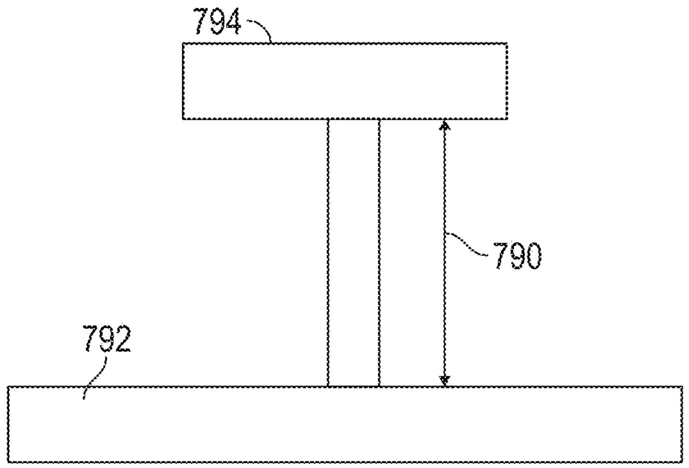
FIG. 71 shows an embodiment of a fastener comprising more than one material.

FIG. 71 shows an embodiment of a fastener that could comprise or be made from more than one material that would 1) have more favorable strain-related properties in the filament direction 790 that may facilitate an elastic benefit holding/approximating and/or compressing the onlay material (e.g., ADM)/tissue, and/or 2) have different properties on both/either the first bar 792 and/or second bar 794 to prevent mobility.

Figure 95A:
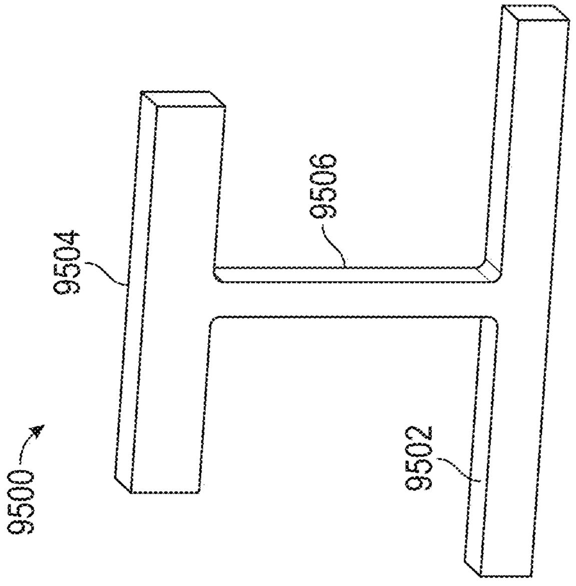
FIGS. 95A-96F show embodiments of fasteners.
Figure 95B:
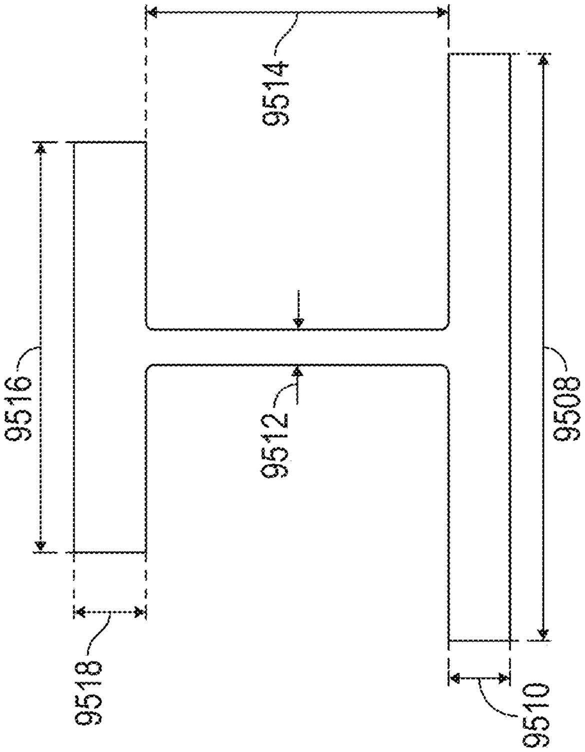
Figure 95C:
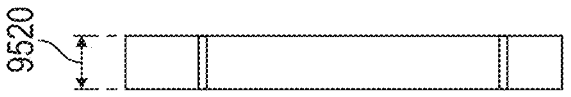

FIGS. 95A-95C show front perspective, front and side views, respectively, of an embodiment of a fastener 9500 having a single thickness. The thickness 9520 (FIG. 95C) of the fastener can be about 0.03 in (or about 0.01 in-0.05 in, about 0.02 in-0.04 in, about 0.025 in-0.035 in, etc.). In some embodiments, the dimensions of the first bar and second bar are selected such that the first bar has a flexibility or stiffness to curl (or disengage from the needle) upon being deployed from the fastening device, and the filament or connector connecting the first bar and the second bar is strong enough to withstand the forces exerted on it when the first bar is deployed from the needle. In some embodiments, a length 9508 of the first bar is about 0.33 in (or about 0.23 in-0.43 in, or about 0.325 in-0.335 in, etc.). In some embodiments, a height 9510 of the first bar is about 0.03 in (or about 0.01 in-0.05 in, about 0.02 in-0.04 in, about 0.025 in-0.035 in, etc.). In some embodiments, a width 9512 of the filament or connector is about 0.02 in (or about 0.01 in-0.03 in or about 0.015 in-0.025 in, etc.). In some embodiments, a length 9514 of the filament or connector 9506 is about 0.17 in (or about 0.10 in-0.24 in, 0.15 in-0.19 in, 0.16 in-0.18 in, 0.165 in-0.175 in, etc.). In some embodiments, a length 9516 of the second bar is about 0.23 in (or about 0.13 in-0.33 in or about 0.225 in-0.235 in, etc.). In some embodiments, a height 9518 of the second bar is about 0.04 in (or about 0.01 in-0.07 in, 0.02 in-0.06 in, 0.03 in-0.05 in, 0.035 in-0.045 in, etc.).

Figure 96C:
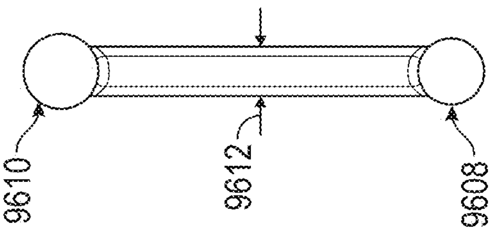
Figure 96B:
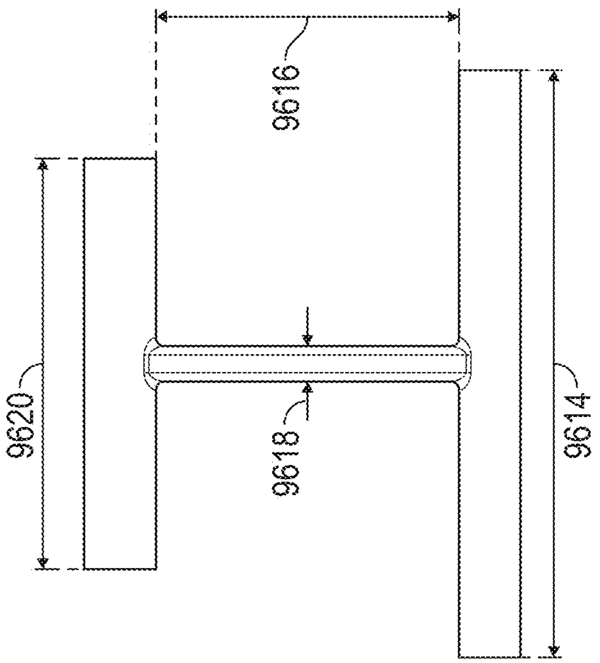
Figure 96A:
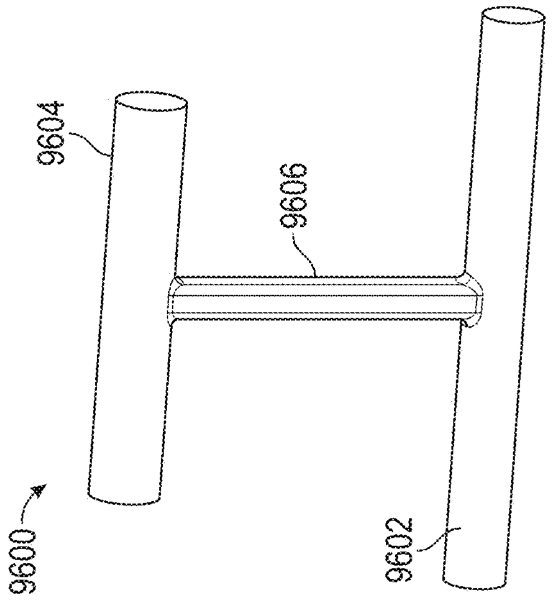

FIGS. 96A-C show another embodiment of a fastener 9600 comprising unique sizes for the first bar 9602, the second bar 9604, and the filament 9606. For example, the first bar 9602 and the second bar 9604 have circular cross sections. As described above, the dimensions of the first bar and second bar are selected such that the first bar has a flexibility or stiffness to curl (or disengage from the needle) upon being deployed from the fastening device, and the filament or connector connecting the first bar and the second bar is strong enough to withstand the forces exerted on it when the first bar is deployed from the needle. In some embodiments, a diameter 9608 of the first bar 9602 is about 0.035 in (or about 0.02 in-0.05 in, 0.025 in-0.045 in, or about 0.03 in-0.04 in, etc.). In some embodiments, a diameter 9610 of the second bar 9604 is about 0.04 in (or about 0.01 in-0.07 in, 0.02 in-0.06 in, 0.03 in-0.05 in, 0.035 in-0.045 in, etc.). In some embodiments, a thickness 9612 of the filament or connector 9606 is about 0.026 in (or about 0.016 in-0.036 in or about 0.021 in-0.031 in, etc.). In some embodiments, a length 9614 of the first bar 9602 is about 0.33 in (or about 0.23 in-0.43 in, or about 0.325 in-0.335 in, etc.). In some embodiments, a length 9616 of the filament or connector 9606 is about 0.17 in (or about 0.10 in-0.24 in, 0.15 in-0.19 in, 0.16 in-0.18 in, 0.165 in-0.175 in, etc.). In some embodiments, a width 9618 of the filament or connector 9606 is about 0.020 in (or about 0.01 in-0.03 in or about 0.015 in-0.025 in, etc.). In some embodiments, a length 9620 of the second bar 9604 is about 0.23 in (or about 0.13 in-0.33 in or about 0.225 in-0.235 in, etc.).

Figure 96F:
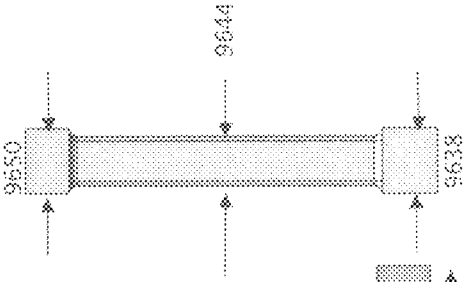
Figure 96E:
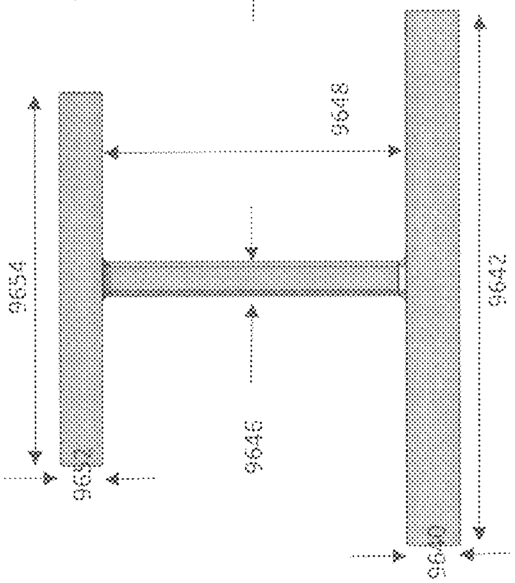
Figure 96D:
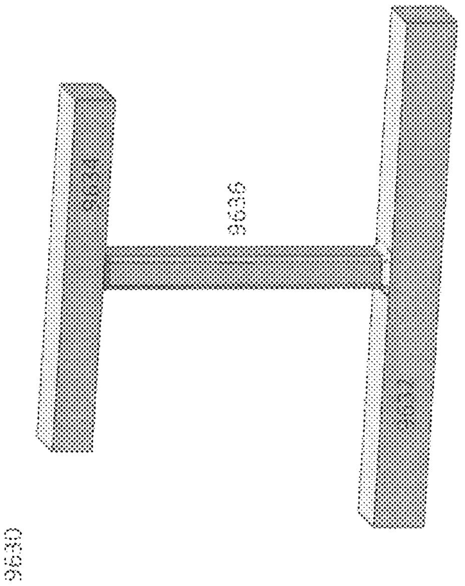

FIGS. 96D-F show another embodiment of a fastener 9630 comprising unique sizes for the first bar 9632, the second bar 9634, and filament 9636. For example, the first bar 9632, the second bar 9634, and filament 9636 have rectangular cross sections. As described above, the dimensions of the first bar and second bar are selected such that the first bar has a flexibility or stiffness to curl (or disengage from the needle) upon being deployed from the fastening device, and the filament or connector connecting the first bar and the second bar is strong enough to withstand the forces exerted on it when the first bar is deployed from the needle. In some embodiments, the thickness 9638 of the first bar (FIG. 96F) can be about 0.039 in (or about 0.019 in-0.059 in, about 0.029 in-0.049 in, about 0.034 in-0.044 in, etc.), the height 9640 of the first bar (FIG. 96E) can be about 0.033 in (or about 0.013 in-0.053 in, about 0.023 in-0.043 in, about 0.028 in-0.038 in, etc.), and the length 9642 of the first bar (FIG. 96E) can be about 0.33 in (or about 0.23 in-0.43 in, or about 0.325 in-0.335 in, etc.). In some embodiments, the thickness 9644 (FIG. 96F) of the filament or connector 9636 can be about 0.030 in (or about 0.010 in-0.050 in, about 0.020 in-0.040 in, about 0.025 in-0.035 in), the width 9646 (FIG. 96E) of the filament or connector 9636 can be about 0.021 in (or about 0.011 in-0.031 in or about 0.016 in-0.026 in, etc.), and the length 9648 (FIG. 96E) of the filament or connector 9636 can be about 0.188 in (or about 0.118 in-0.258 in, about 0.138 in-0.238 in, about 0.168 in-0.208 in, about 0.178 in-0.198 in, about 0.183 in-0.193 in). In some embodiments, the thickness 9650 of the second bar (FIG. 96F) can be about 0.039 in (or about 0.019 in-0.059 in, about 0.029 in-0.049 in, about 0.034 in-0.044 in, etc.), the height

9652 of the second bar (FIG. 96E) can be about 0.026 in (or about 0.016 in-0.036 in, about 0.021 in-0.031 in), and the length 9654 of the second bar (FIG. 96E) can be about 0.23 in (or about 0.13 in-0.33 in or about 0.225 in-0.235 in, etc.).

Figure 97A:
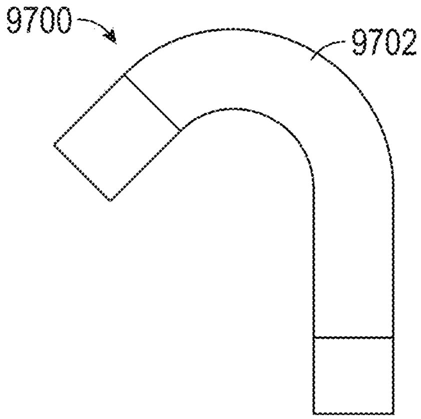
FIGS. 97A-97D show embodiments of a fastener comprising a bent filament or connector in comparison to a fastener having a straight filament or connector.
Figure 97B:
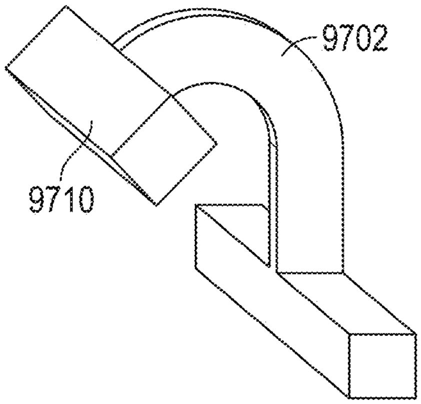
Figure 97C:
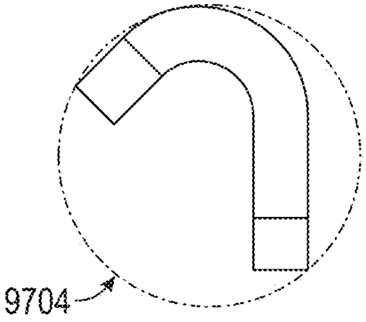
Figure 97D:
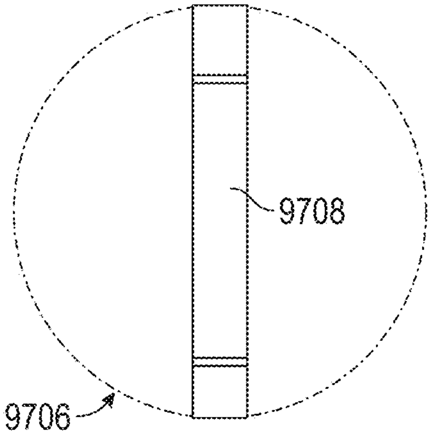

FIGS. 97A-D show another embodiment of a fastener 9700 that has a bent filament or connector 9702. The bent filament or connector can facilitate a smaller crossing profile 9704 for the shaft/fastener reservoir 104. FIG. 97C shows the smaller crossing profile 9704 compared to the larger crossing profile 9706 (FIG. 97D) of a fastener that has a straight filament or connector 9708. The bent filament could also serve to optimize placement of the second bar 9710 and onlay material (e.g., ADM)/tissue approximation and/or compression (e.g., as described above with respect to FIGS. 32-43D).

Other Delivery Device Embodiments

Figure 72A:
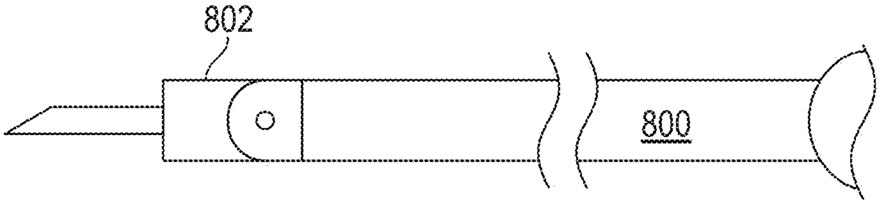
FIGS. 72A-C show embodiments of a shaft having an articulating and/or rotating end.
Figure 72B:
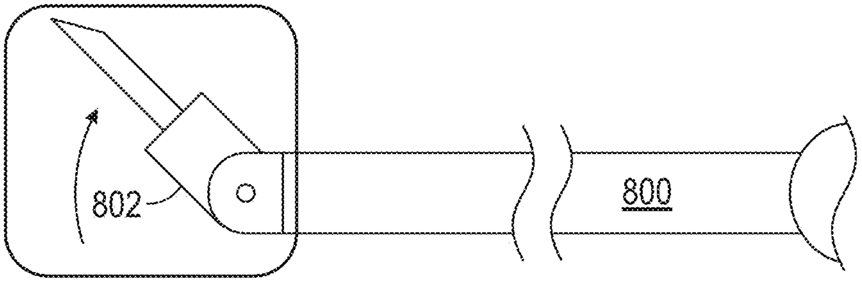
Figure 72C:
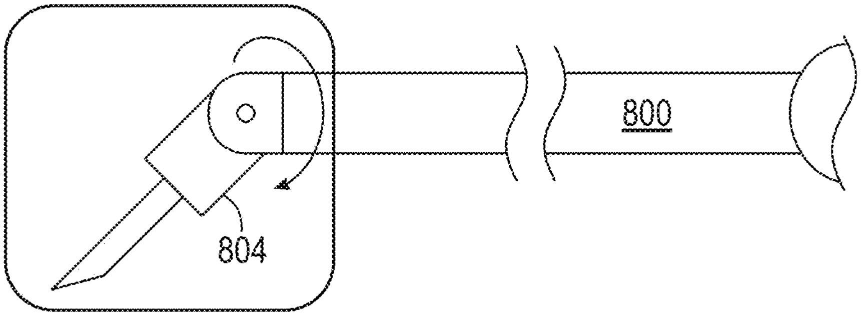

As shown in FIGS. 72A-C, in some embodiments, the shaft 800 could have an articulating end 802 (FIGS. 72A&B) and/or a rotating end 804 (FIG. 72C) to facilitate access in open and/or laparoscopic procedures.

Figure 73:
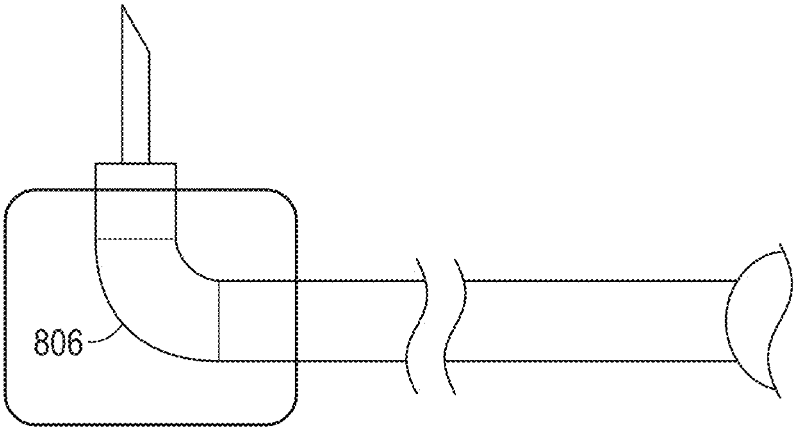
FIG. 73 shows an embodiment of a shaft having a bend at its distal end.

As shown in FIG. 73, the shaft can have a fixed bend 806 at the distal end to facilitate access in open procedures.

Figure 74A:
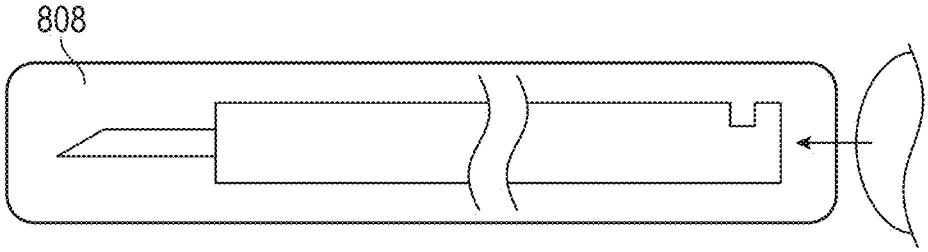
FIGS. 74A and 74B show an embodiment of a fastening device having a replaceable cartridge.
Figure 74B:
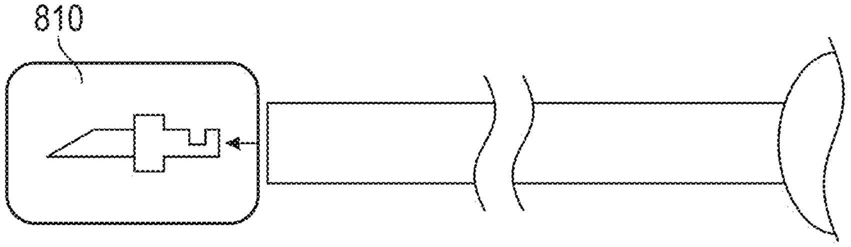

As shown in FIGS. 74A and 74B, in some embodiments, the delivery device could have a replaceable cartridge (e.g. when the fasteners are depleted). The replaceable cartridge could involve the entire shaft 808 (FIG. 74A) or just the distal portion 810 of the shaft (FIG. 74B). If the needle were part of the replaceable cartridge, the user would also benefit from the new needle on the cartridge.

Figure 75A:
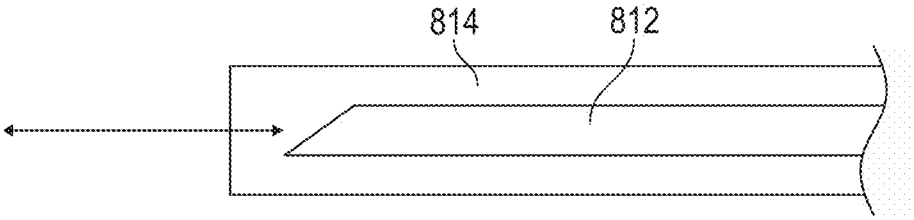
FIGS. 75A and 75B show an embodiment of a shaft having a needle that can retract and/or advance relative to the shaft.
Figure 75B:
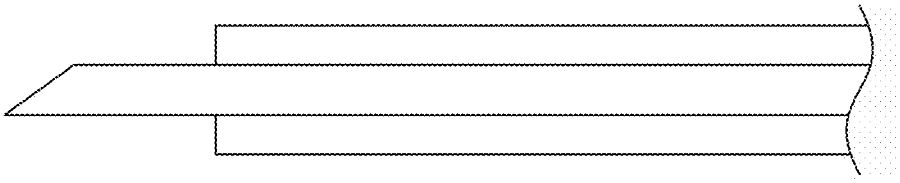

As shown in FIGS. 75A and 75B, in some embodiments, the needle 812 could advance out of the shaft 814 (FIG. 75B) and retract back into the shaft (FIG. 75A). With the needle in the retracted position, the sharp needle point is protected and prevents atraumatic injury while the user inserts the device to the repair site (e.g. via laparoscopic or open approach). Once the device is at the repair site, the user advances the needle out of the shaft.

Figure 76A:
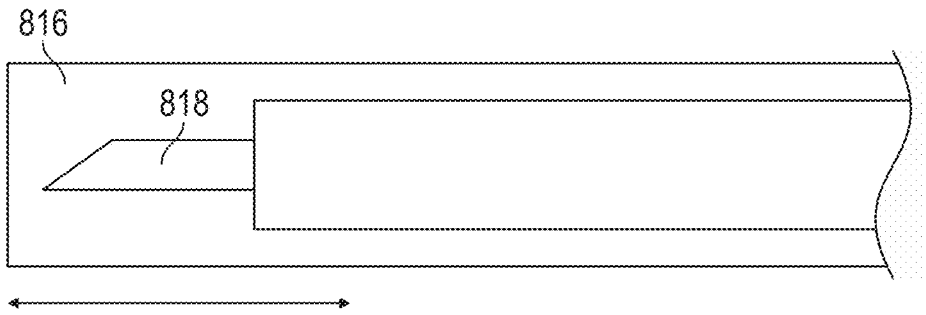
FIGS. 76A and 76B show an embodiment of a shaft having a sheath that can retract and/or advance relative to the needle/shaft.
Figure 76B:
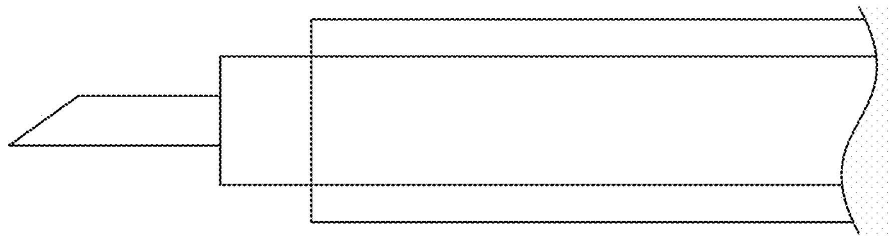

As shown in FIGS. 76A and 76B, in some embodiments, a sheath 816 could advance over the needle 818 (FIG. 76A) and retract to expose the needle (FIG. 76B). With the sheath in the advanced position, the sharp needle point is protected and prevents atraumatic injury while the user inserts the device to the repair site (e.g. via laparoscopic or open approach). Once the device is at the repair site, the user retracts the sheath to expose the needle. After deploying the fastener, the sheath could be advanced to also apply countertraction to the onlay material (e.g., ADM) while the user withdraws the needle out of the onlay material (e.g., similar to the embodiments that aid needle withdrawal described with respect to FIGS. 44-51).

Figure 98A:
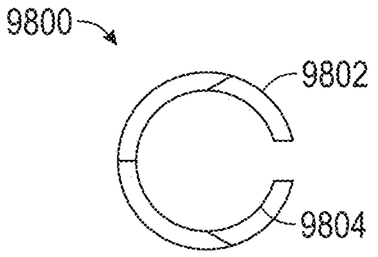
FIGS. 98A-B show embodiments of slotted needles.
Figure 98B:
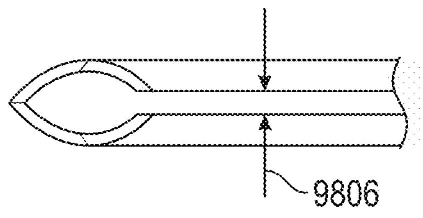

FIGS. 98A-B show another embodiment of a slotted needle 9800 comprising a unique outer diameter (OD) 9802, inner diameter (ID) 9804, and slot width 9806. As described above, the ID dimension is selected such that the bar of the fastener can reside in the ID, and the slot width dimension is selected such that the bar connector (a.k.a. filament) can travel down the length of the slot (with either an interference or clearance fit with the slot). In some embodiments, an OD 9802 is about 0.078 in (or about 0.018 in-0.148 in, 0.048 in-0.108 in, 0.068 in-0.088 in, etc.). In some embodiments, an ID 9804 is about 0.063 in (or about 0.010 in-0.140 in, 0.040 in-0.100 in, 0.060 in-0.080 in, etc.). In some embodiments a slot width 9806 is about 0.035 in (or about 0.020 in-0.050 in, 0.025 in-0.045 in, 0.030 in-0.040 in, etc.) such that the slot width is larger than the filament to minimize or eliminate deformation and/or denting on the fastener's filament during deployment, and smaller than the fastener's bar to prevent the bar from unintentionally coming out of the needle's lumen.

Figure 99A:
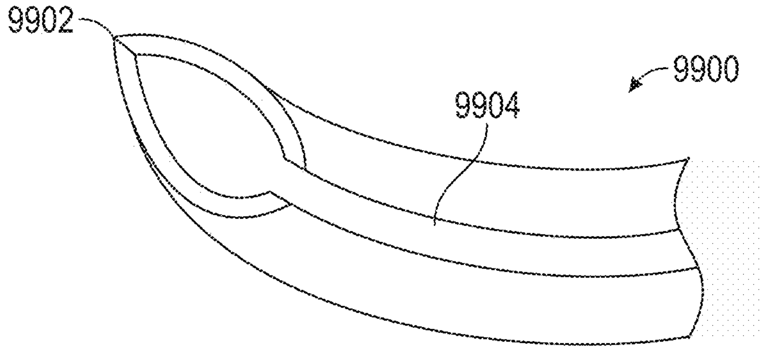
FIGS. 99A-B show embodiments of curved slotted needles.
Figure 99B:
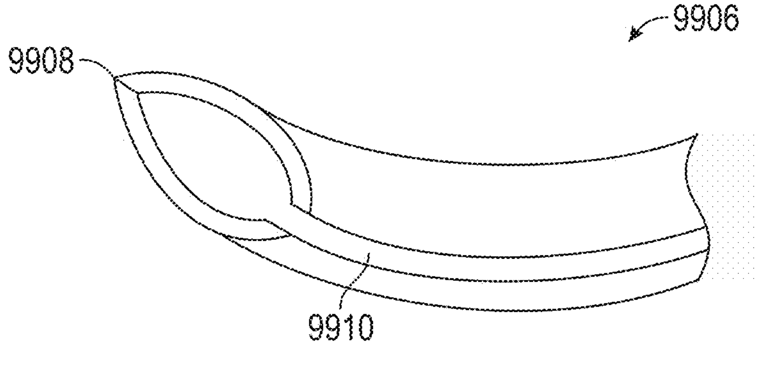

FIG. 99A shows another embodiment of a slotted needle 9900 that is curved (not straight) where the needle tip 9902 is on the outside of the curvature and the slot 9904 is on the inside of the curvature. FIG. 99B shows another embodiment of a slotted needle 9906 that is curved where the needle tip 9908 is on the inside of the curvature and the slot 9910 is on the outside of the of the curvature.

Figure 100B:
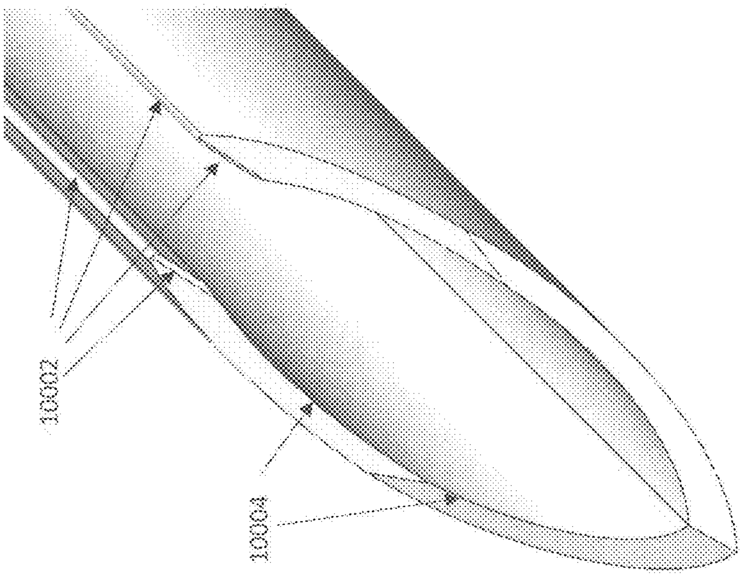
FIGS. 100A-B show embodiments of slotted needles.
Figure 100A:
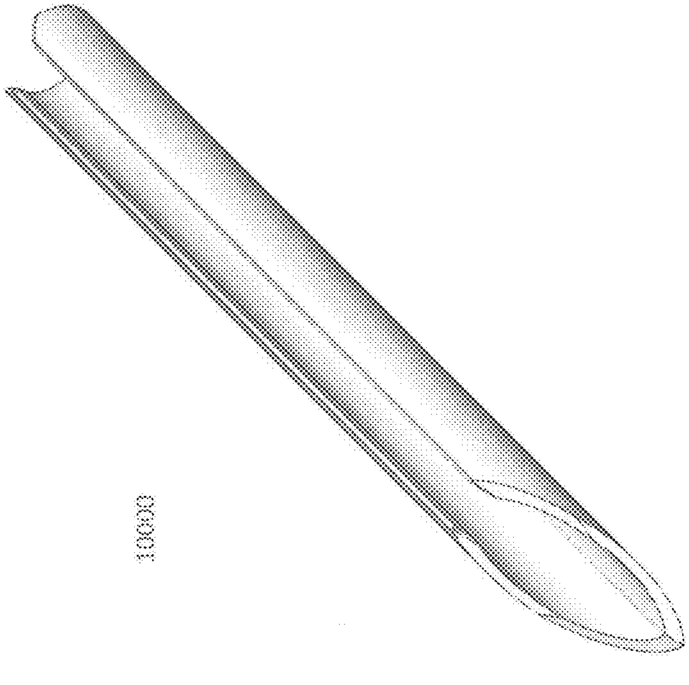

FIG. 100A-B show an embodiment of a slotted needle 10000 (FIG. 100A) comprising non-sharp edges 10002 (FIG. 100B) such as broken edges, radiused edges, polished edges, etc. for a length of the slot such that the non-sharp slot edges do not slice, cut or damage the fastener's filament during deployment.

Additional Embodiments of Devices and Methods to Fasten Onlay Material

Figure 77:
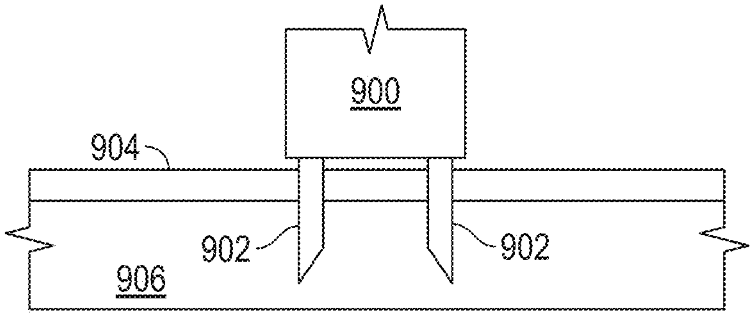
FIGS. 77-79 show an embodiment of a fastening device.
Figure 78:
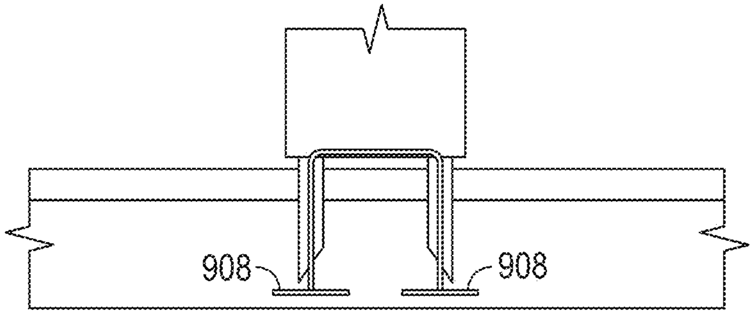
Figure 79:
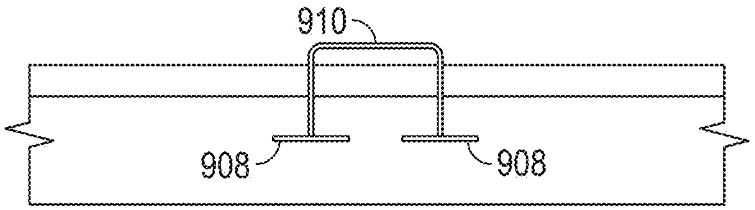

FIG. 77 shows an embodiment of a device 900 containing two deployment needles 902. Both needles pierce the onlay material 904 (e.g., ADM) and tissue 906. Each needle deploys one bar 908 of the fastener in tissue as shown in FIG. 78. The filament 910 holds and approximates and/or compresses the onlay material to tissue as shown in FIG. 79.

Figure 80:
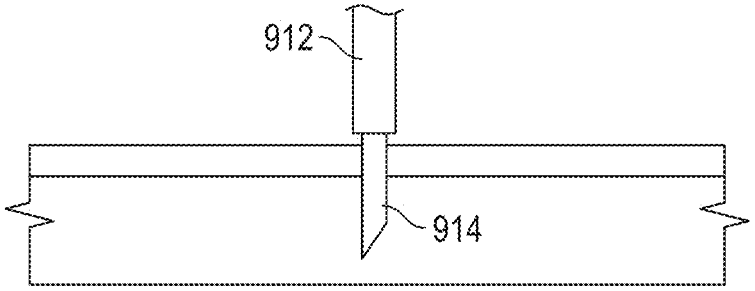
FIGS. 80-83 show another embodiment of a fastening device.
Figure 81:
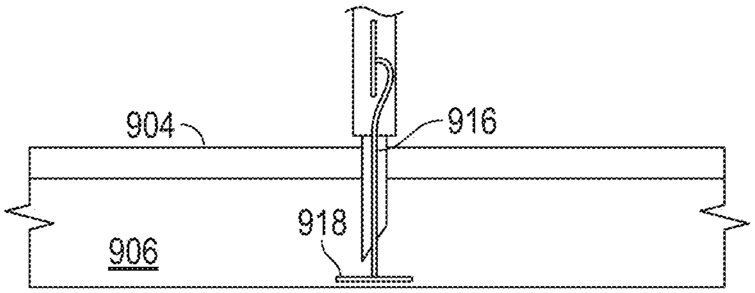
Figure 82:
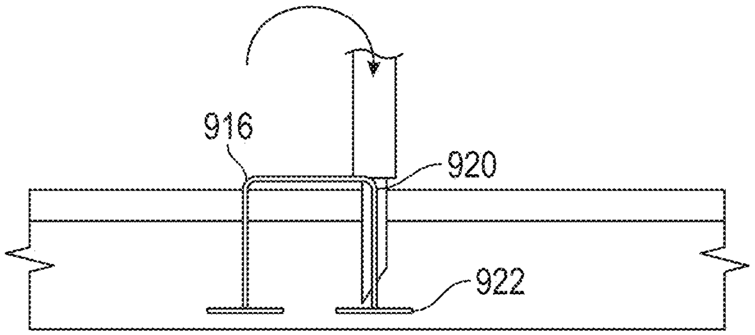
Figure 83:
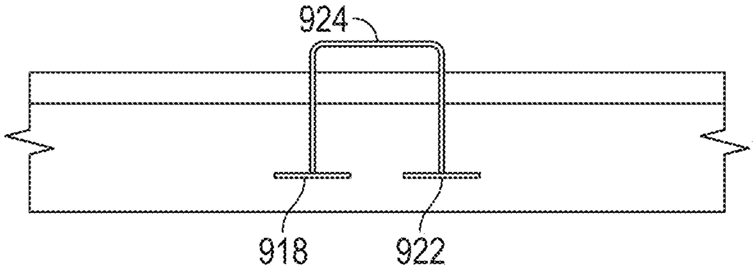

FIG. 80 shows an embodiment of a device 912 containing one deployment needle 914. In FIG. 81, the needle pierces the onlay material 904 (e.g., ADM) and tissue 906 at a first location 916 and deploys the first bar 918 in tissue. In FIG. 82, the needle is withdrawn from the first location 916, pierces the onlay material and tissue at a second location 920, and deploys the second bar 922 in tissue. The filament 924 holds and approximates and/or compresses the onlay material to tissue as shown in FIG. 83.

Embodiments of Devices and Methods Allowing Interrupted Suture

The following concepts illustrate how the fastener could be used in other device platforms to deliver a fast, interrupted stitch for joining two or more tissues.

Figure 84:
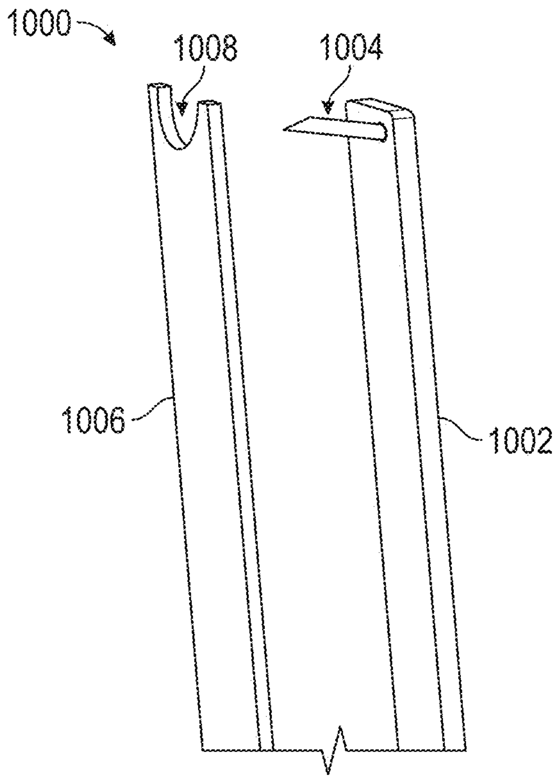
FIGS. 84-89 show an embodiment of a fastening device comprising opposing jaws.

FIG. 84 shows an embodiment of a device 1000 with opposing jaws. The first jaw 1002 has a slotted needle 1004 (to deploy the fastener), and the second jaw 1006 has an opening or slot 1008 at the end of the jaw.

Figure 85:
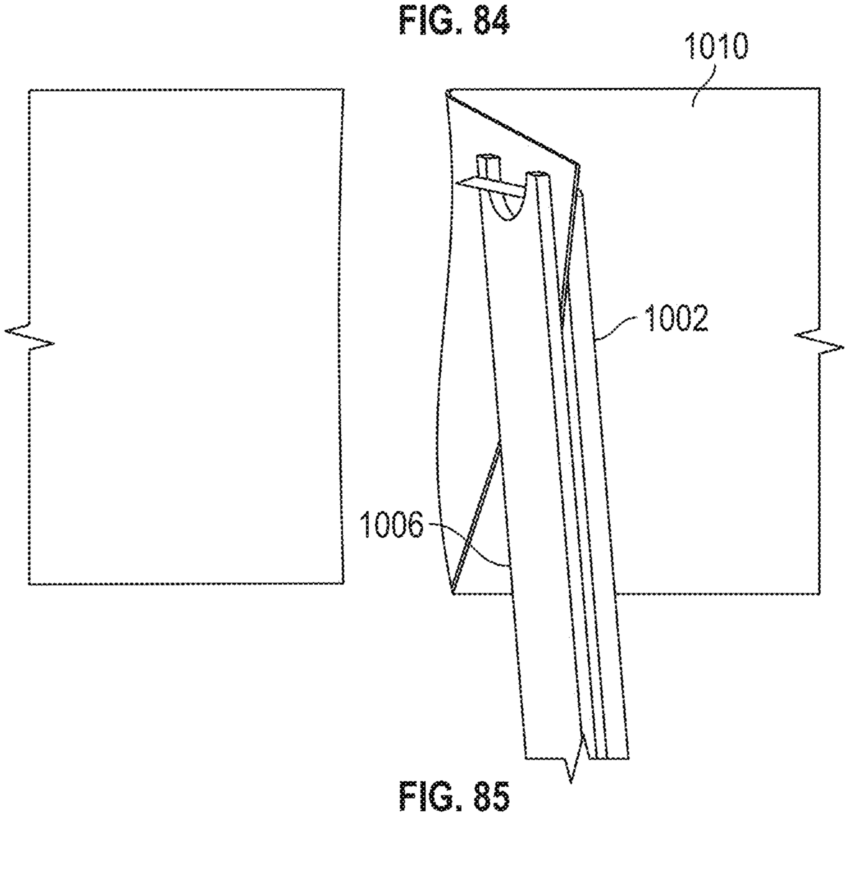

In FIG. 85, the user targets the fixation location on the first tissue 1010 (or other material) using the needle tip, then closes the opposing jaws 1002, 1006, so the needle punctures the first tissue at the target fixation location and moves through the opening 1008 at the end of the second jaw 1006.

Figure 86:
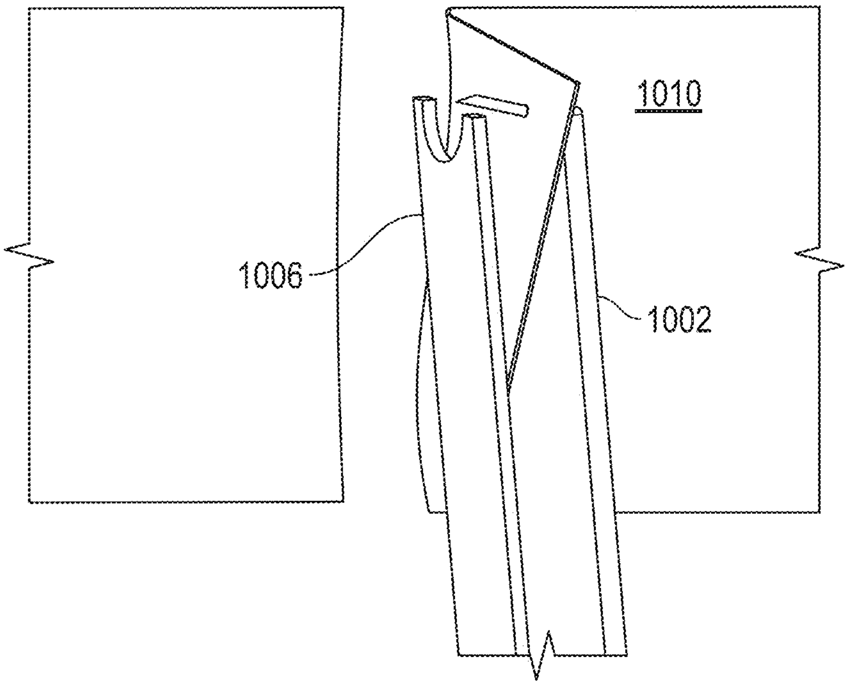

In FIG. 86, the user opens the opposing jaws 1002, 1006, keeping the first tissue 1010 on the needle.

Figure 87:
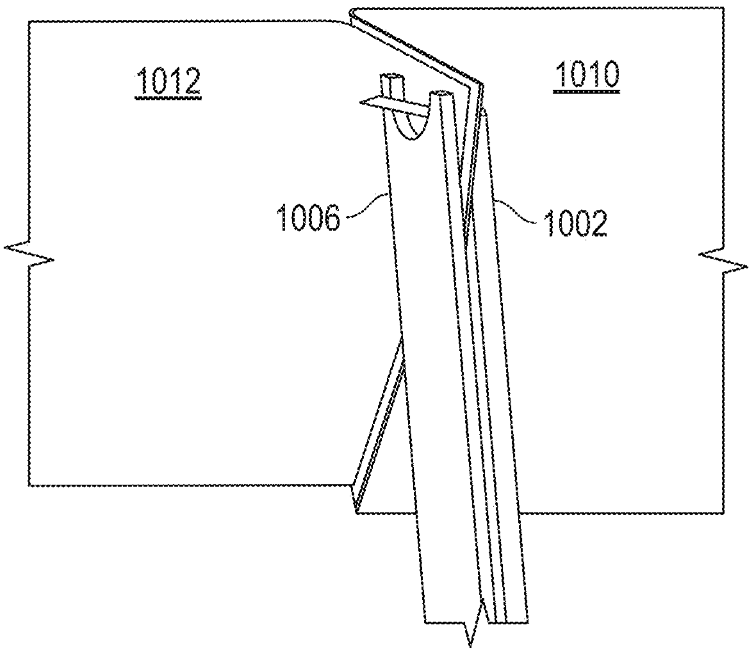

In FIG. 87, with the first tissue 1010 on the needle, the user can move the device to approximate the first tissue 1010 to the second tissue 1012 (or other material). The user targets the fixation location on the second tissue using the needle tip, then closes the opposing jaws 1002, 1006, so the needle punctures the second tissue at the target fixation location and moves through the opening 1008 at the end of the second jaw 1006.

Figure 88:
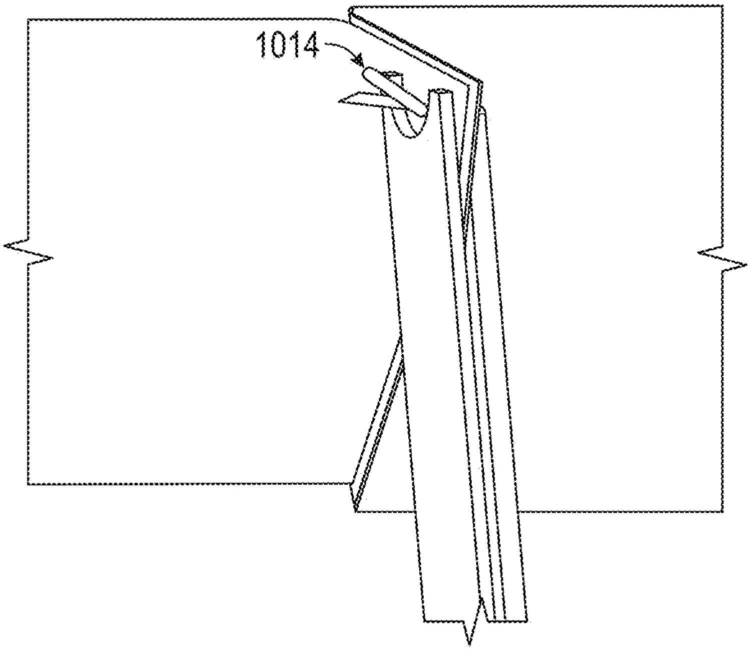
Figure 89:
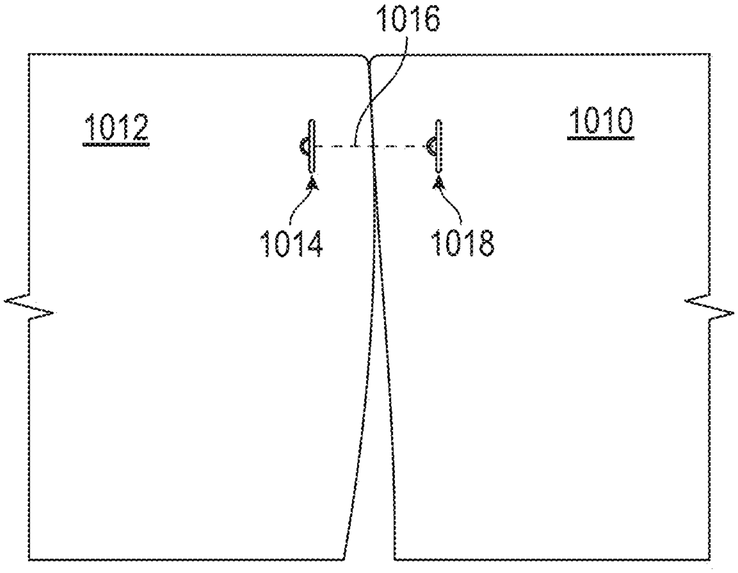

In FIGS. 88 and 89, the user deploys the fastener's first bar 1014 and filament 1016 through both tissues so the first bar 1014 and second bar 1018 holds/fixes/approximates the second tissue 1012 and first tissue 1010, respectively, together.

In FIG. 89, the user opens the opposing jaws to remove the needle and device from the fixation site, leaving the tissues approximated and fixed together by the fastener. The user repeats the process for the next fixation site.

The benefit of this platform over existing methods is the ability for the user to quickly approximate tissues and/or materials and fix them together with an interrupted fixation using only one hand or without the need of an assistant.

The opposing jaws could be joined by a single hinge (e.g. to close like scissors/hemostats). The opposing jaws could also be joined by multiple hinges (e.g. to close like parallel jaw pliers).

In some embodiments, the device shown in FIGS. 84-89 comprises features described with respect to other embodiments of fastening devices described herein. For example, in some embodiments, the device comprises one or more ramps (e.g., as described with respect to FIGS. 38-42O) configured to reorient a portion of the fastener (e.g., the second bar) as it is being deployed. Examples also include features (such as FIGS. 23-26 and FIGS. 28-31) that could assist with keeping the tissue on the needle, and/or allow the user to lift the tissue away from underlying structures and deploy the fastener without unintentionally fastening underlying structures.

Figure 90:
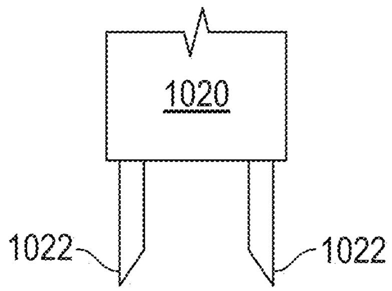
FIGS. 90-94B show another embodiment of a fastening device.
Figure 91:
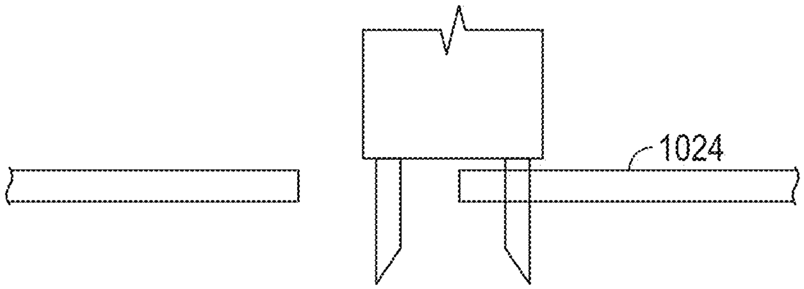
Figure 92:
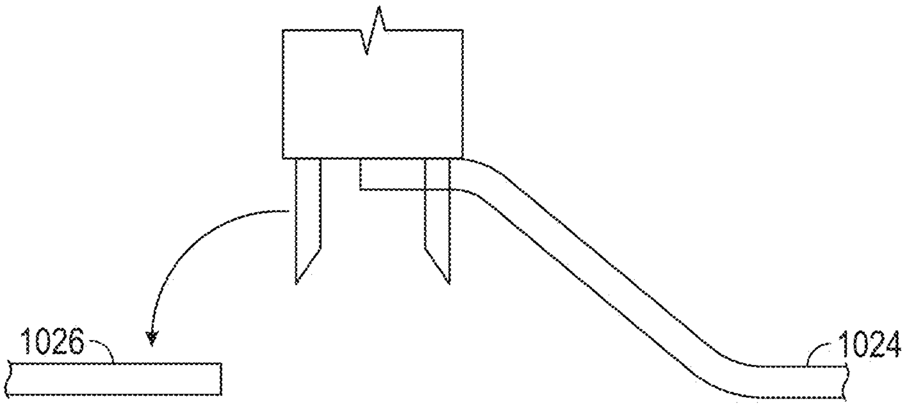
Figure 93:
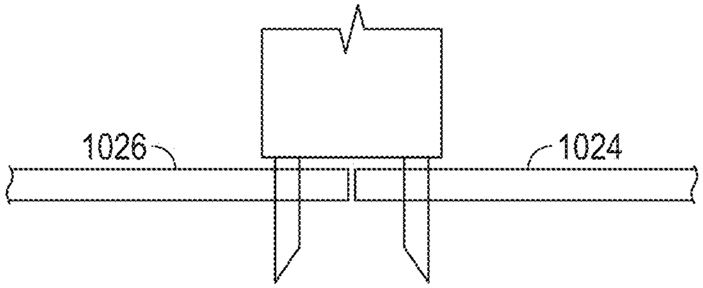
Figure 94A:
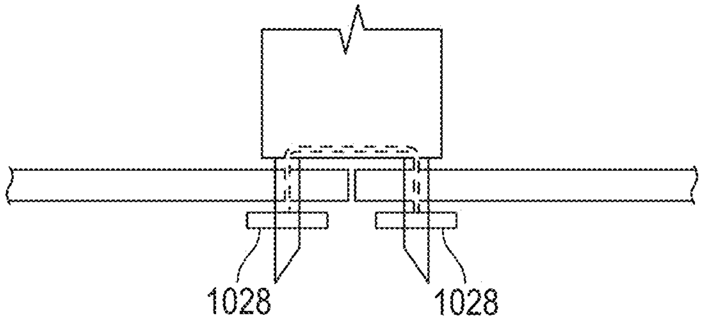
Figure 94B:
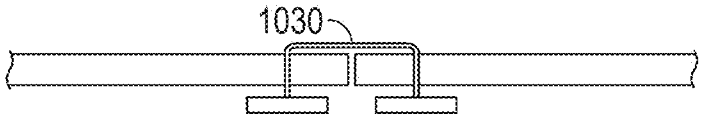

FIG. 90 shows an embodiment of a device 1020 containing two deployment needles 1022. As shown in FIG. 91, one of the deployment needles pierces a first tissue 1024. In FIGS. 92 and 93, the device is moved to approximate the first tissue 1024 to a second tissue 1026 by piercing the second tissue with the other deployment needle. In FIG. 94A, each needle deploys one bar 1028 of the fastener through/in tissue. In FIG. 94B, the filament 1030 holds and approximates and/or compresses the tissues together. The device could also incorporate any embodiment described in this document to facilitate the procedure. Examples include features (such as FIGS. 23-26 and FIGS. 28-31) that could assist with keeping the tissue on the needle, and/or allow the user to lift the tissue away from underlying structures and deploy the fastener without unintentionally fastening underlying structures. For another example, in some embodiments, the device comprises one or more ramps (e.g., as described with respect to FIGS. 38-42O) configured to reorient a portion of the fastener (e.g., the second bar) as it is being deployed.

The benefit of this platform over existing methods is the ability for the user to quickly approximate tissues and/or materials and fix them together with an interrupted fixation using only one hand or without the need of an assistant.

Embodiments of Features Allowing Robotic Control

In some embodiments, the fastening devices and mechanisms described herein can be configured to function under robotic control. It will be appreciated that any embodiment or combination of embodiments and features described herein can be utilized in robotic applications.

In the handled embodiments of the fastening device described above, the fastener manipulation and deployment occurs within the distal end of the device. The proximal handle provides the required interface/motion for conveying fasteners within the shaft and transitioning the fastener to the distal end where the fastener is manipulated into the needle or fang for deployment.

For surgical robotic applications, rather than the robot holding the fastening device by the handle and squeezing the trigger like a surgeon, the device's distal end is converted to an end effector (which could include the transition elements), and the handle's mechanistic action is replaced with functions basic to a surgical robotic arm.

Figure 158:
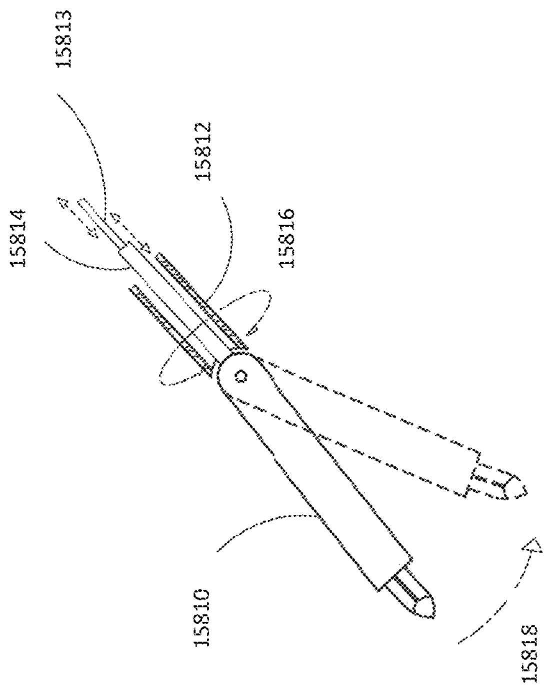
FIG. 158 shows an embodiment of a surgical robot effector end comprising a fastening device as described herein.

FIG. 158 shows the end effector 15810 attached to the surgical robot 15812. Using a combination of rotation 15816 and articulation 15818, the surgical robot can position the end effector, and in combination with other robotic tools (e.g. forceps) as needed, position and pierce the mesh (or vice versa) over the tissue before deploying the fastener.

Figure 159:
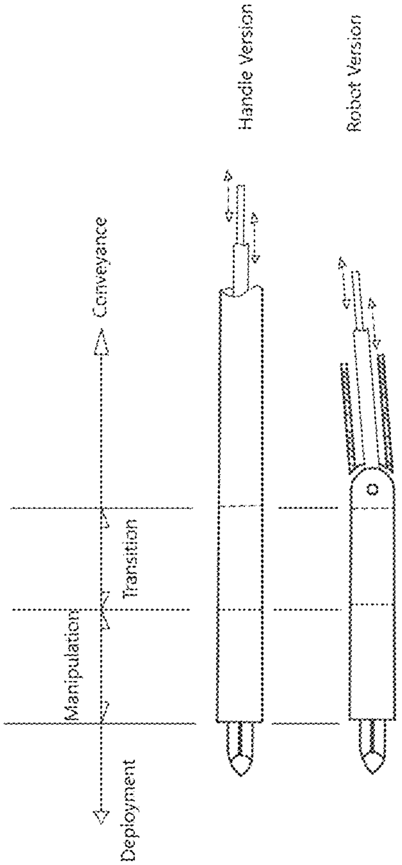
FIG. 159 shows a comparison of embodiments of a robotic end effector fastening device and a handled fastening device.

FIG. 159 compares embodiments of the path the fastener takes as it moves from conveyance to deployment within the handled and robot end effector versions of the fastening device. In some embodiments, the end effector functions to transition the fastener from conveyance and manipulate it, preparing it for deployment. As previously described, the conveyance can comprise multiple configurations and hold as few as one and up to as many fasteners desired.

A unique aspect to the robot interface can be replicating the cyclic action of the handle mechanism to convey and transition the fastener from a conveyance reservoir to the end effector, preparing the fastener for another element that deploys the fastener. In some embodiments, the conveyance advancer 15814 advances in increments of approximately the same length as the length of the fastener. The increments can be long enough to transition the fastener from the conveyance reservoir to a location in front of the deployment element 15813. The conveyance advancer 15814 is held in place to prevent other fasteners in queue from advancing prematurely and jamming the mechanism before the deployment element 15813 is activated. Once activated, the deployment element 15813 pushes the fastener through the end effector, manipulating the fastener's configuration before moving the fastener through the needle/fang, onlay material (e.g., mesh), into the tissue and releasing from the needle/fang. The deployment element 15813 can start and stop during deployment but must be completely extended prior to retraction, to ensure the fastener is fully deployed and the transition zone is clear and ready to repeat the cycle.

Figure 160:
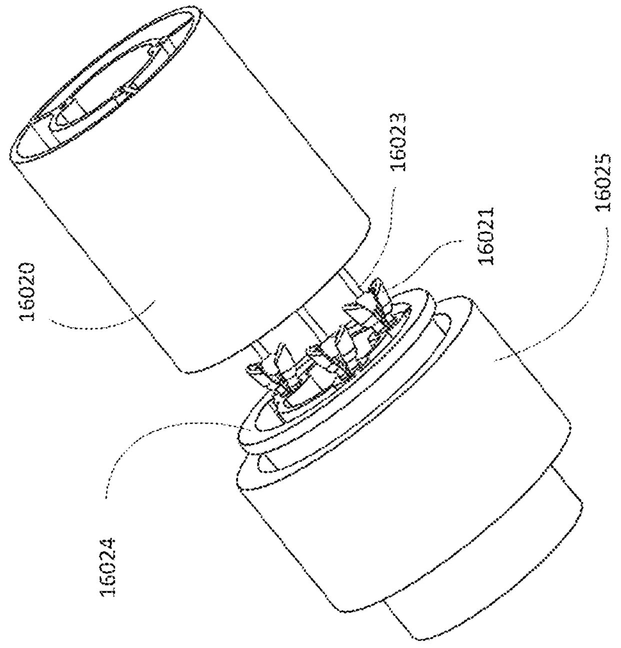
FIGS. 160-162 show an embodiment of a connection between a fastening device and a surgical robot.
Figure 161:
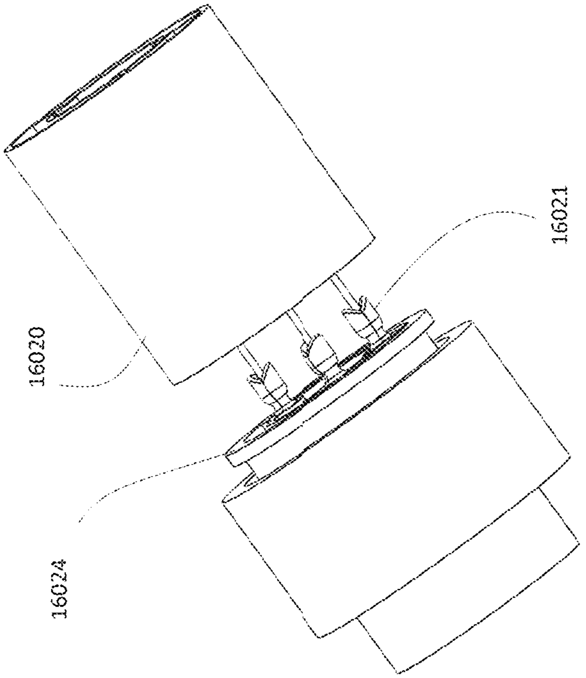

FIG. 160 illustrates a quick connect between the proximal end 16024 of a fastener end effector and distal end of a surgical robot 16020. The distal end of the surgical robot controls the end effector position (e.g., moving in, moving out, rotation and articulation) and internal push/pull control rods to replicate the fastener handle motions to deploy the fastener.

Figure 162:
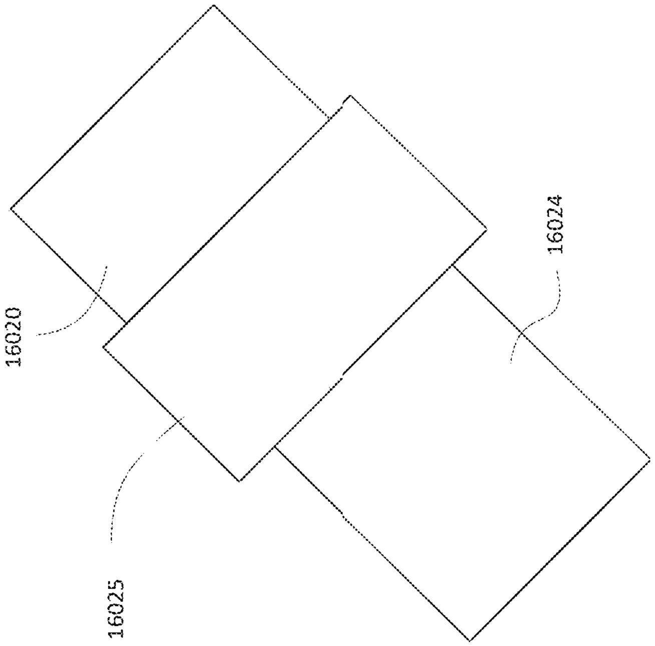

The fastening device's proximal end has the necessary features to quickly connect the fastening device to the surgical robot. The internal push/pull rods in the fastening device 16021 are oriented and advanced to capture the mating features on the push/pull rods 16023 in the surgical robot 16020. The fastening device is then rigidly fixed to the robot by advancing the clamping collar 16025 over the device end 16024 and threaded onto the robot 16020 (FIG. 162). Additional interface/indexing features, such as pin/hole and or slot/key, for example, can be used for improved control/rigidity. In some embodiments, hollowing features to pass other mechanical/electrical/fluid interfaces or supply lines (e.g. additional fasteners) are utilized.

Removing the fastening device for a quick exchange requires the robot to position the control rods 16023 for release ("home"), unscrew the threaded collar 16025, and pull the fastening device off the end.

Figure 165:
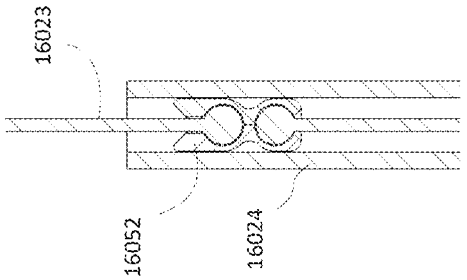
FIGS. 163-165 show a detailed view of an embodiment of a connection between a fastening device and a surgical robot.
Figure 164:
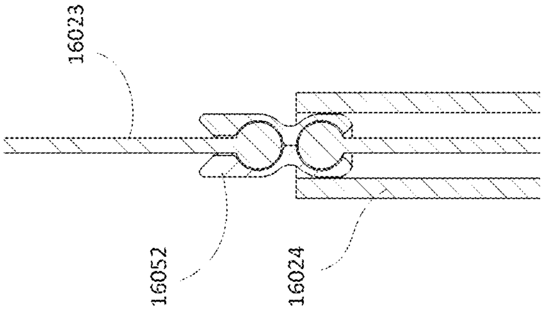
Figure 163:
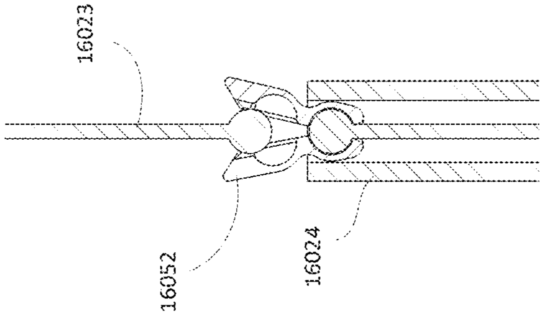

FIGS. 163-165 illustrate a more detailed view of an embodiment of an interface between the robotic device and the push/pull rods 16021 of the fastening device. Orienting and approximating the push/pull rods on the fastening device to the robot moves the ball portion of the connecting rod 16023 and spreads the connecting clamp 16052 (FIG. 163). As the fastening device is advanced toward the robot, the connecting rod advances into the connecting clamp pivots within the tube in the fastening device 16024 capturing the connecting rod 16023 (FIG. 164). When connected to the robot, the push rod/clamp assembly is pushed farther into the fastening device, establishing the control rod connection that the robot can use to replicate the handle mechanistic action to advance and deploy the fastener.

In some embodiments, the robotic conveyance section (that stores the plurality of fasteners) comprises a quick change interface, allowing the surgeon to replace an empty fastener cartridge with a new, full cartridge.

Figure 166:
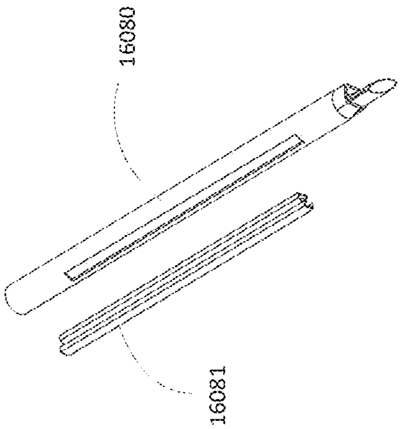

In some embodiments, the fastener cartridge is replaceable with/without the need to remove the fastening device from the robot. The conveyance section of the device holds the fasteners where they are moved along toward the transition area and deployed. In some embodiments, the conveyance section (e.g., cartridge) is removeable. When the fastener supply is exhausted, instead of having to remove/replace the fastening device from the robot, the conveyance cartridge can be removed and replaced. As shown in FIG. 166, the conveyance cartridge 16081 is filled with fasteners. The cartridge can have the features to lock the cartridge into the device housing 16080.

Figure 168:
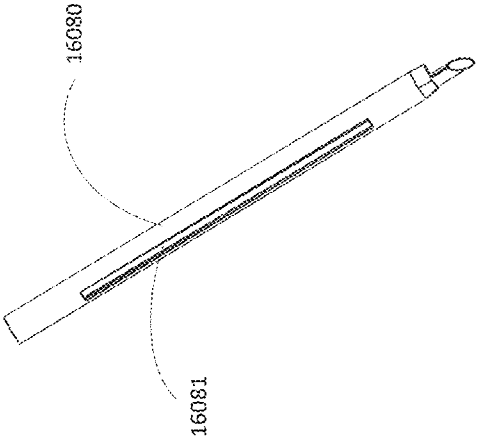
FIGS. 166-168 show an embodiment of a conveyance cartridge insertion into a fastening device.
Figure 167:
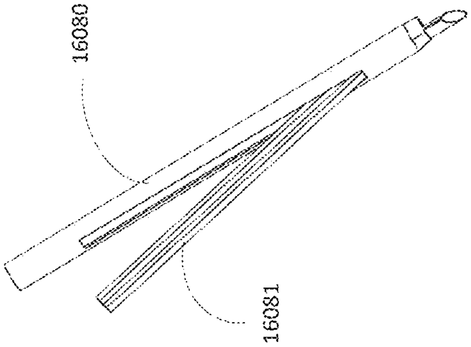

Referring to FIG. 167, the cartridge 16081 is inserted into the device housing. Guides ensure the cartridge lines up with features in the transition zone of the fastening device. Referring now to FIG. 168, the cartridge interface can be spring loaded to lock the cartridge 16081 in place and ensure the deployment and conveyance push rods (from proximal end of fastener) are aligned to move the fasteners into the transition zone and deploy the fastener.

In some embodiments, the conveyance reservoir, conveyance advancer, and deployment elements are flexible. The conveyance cartridge can be made from flexible plastics such as high and low density polyethylene allowing it to flex within the fastener head and with the transition and deployment zones as the head is articulated.

Additional Embodiments of Fastening Devices

In some of the embodiments disclosed herein a target material to be joined to another material (e.g., ADM) is held against a backstop or other portion of the component while a fang or staple is inserted into the target material. Stabilizing the target material in this manner allows for the insertion of a staple into tough material like ADM. Currently, only suture is used in tough materials like ADM. Devices and mechanisms such as those described herein allow for stapling devices to be used to join ADM during surgical procedures.

Figure 101A:
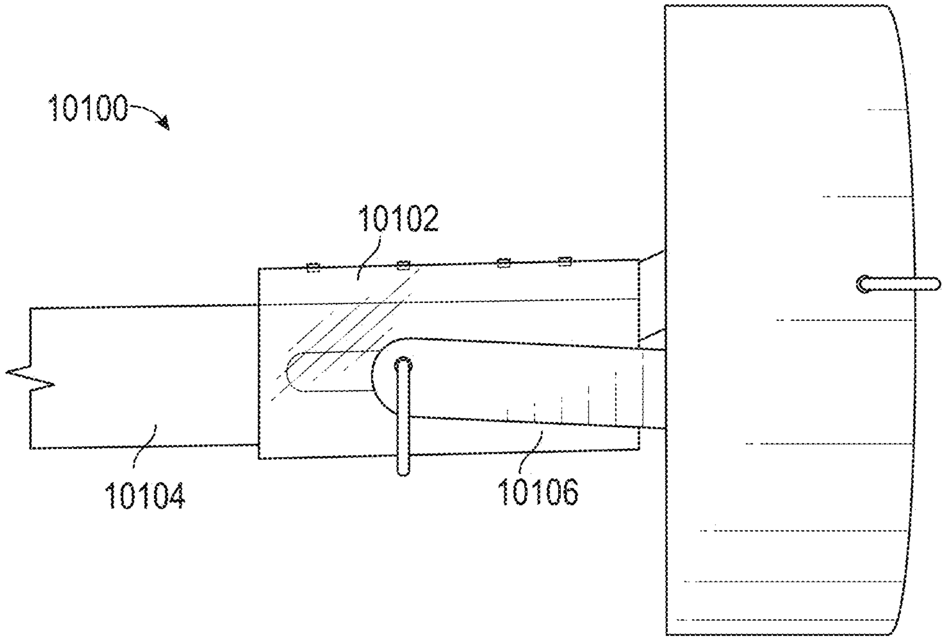
FIGS. 101A-101G show an embodiment of a device configured to grasp and staple materials.
Figure 101B:
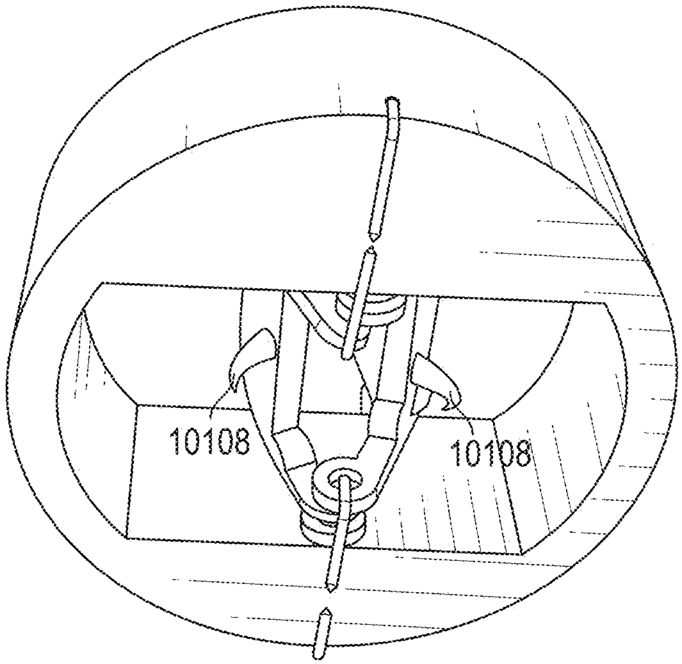
Figure 101C:
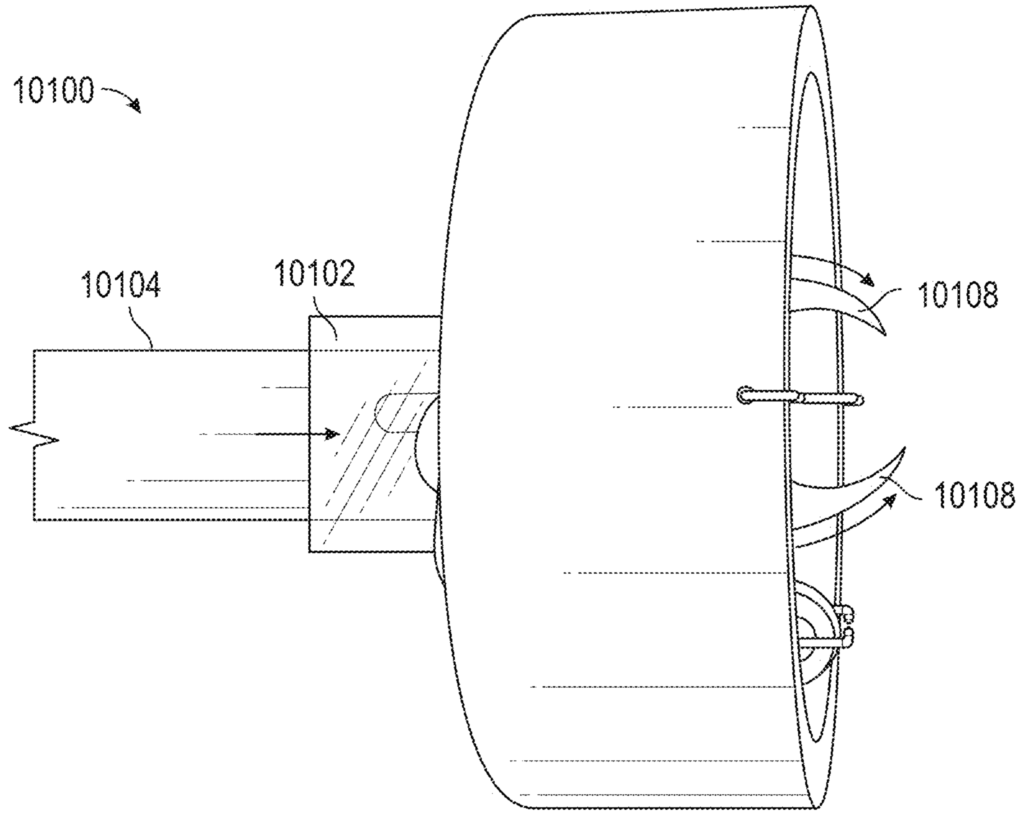

FIGS. 101A-1G show embodiments of a device configured to grasp and join material such as tissue or ADM. As shown in FIG. 101A, the device 10100 comprises a housing 10102, a push rod 10104, and linkages 10106. FIG. 101B shows pincers 10108, which are each connected to a linkage 10106 by a hinge. When the housing 10102 is advanced, as shown in FIG. 101C, the pincers 10108 close and grasp the first target material (e.g., ADM). The device 10100 can be used to position the material as needed. The pincers 10108 can be opened, placed on the second target tissue or material and actuated to pierce the two target materials. After the pincers 10108 have pierced the two materials, the entire device 10100 may be maneuvered to retract the materials in order to avoid underlying structures during staple deployment.

Figure 101D:
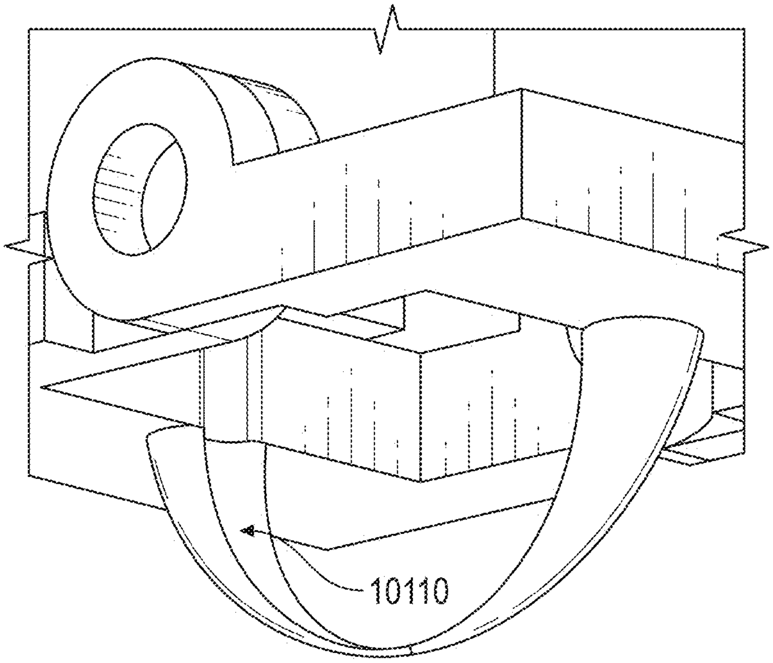
Figure 101E:
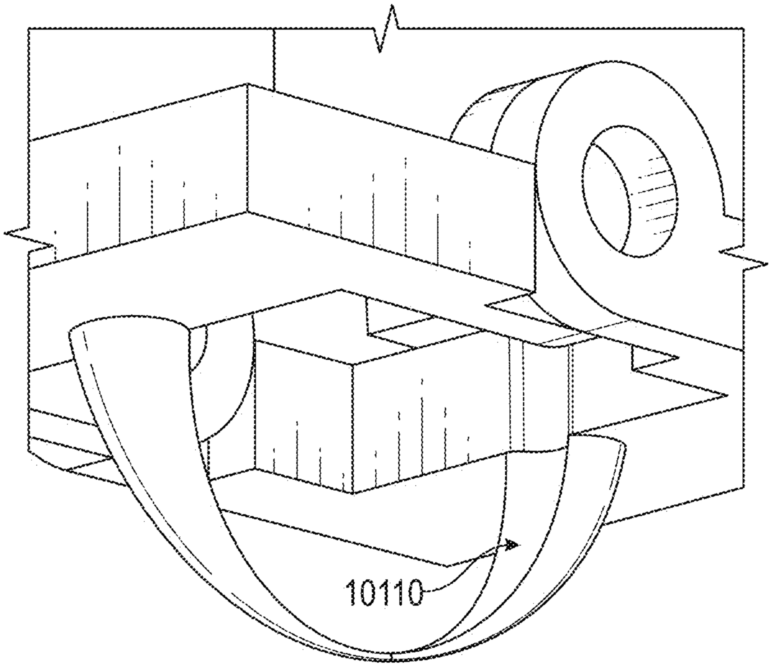
Figure 101F:
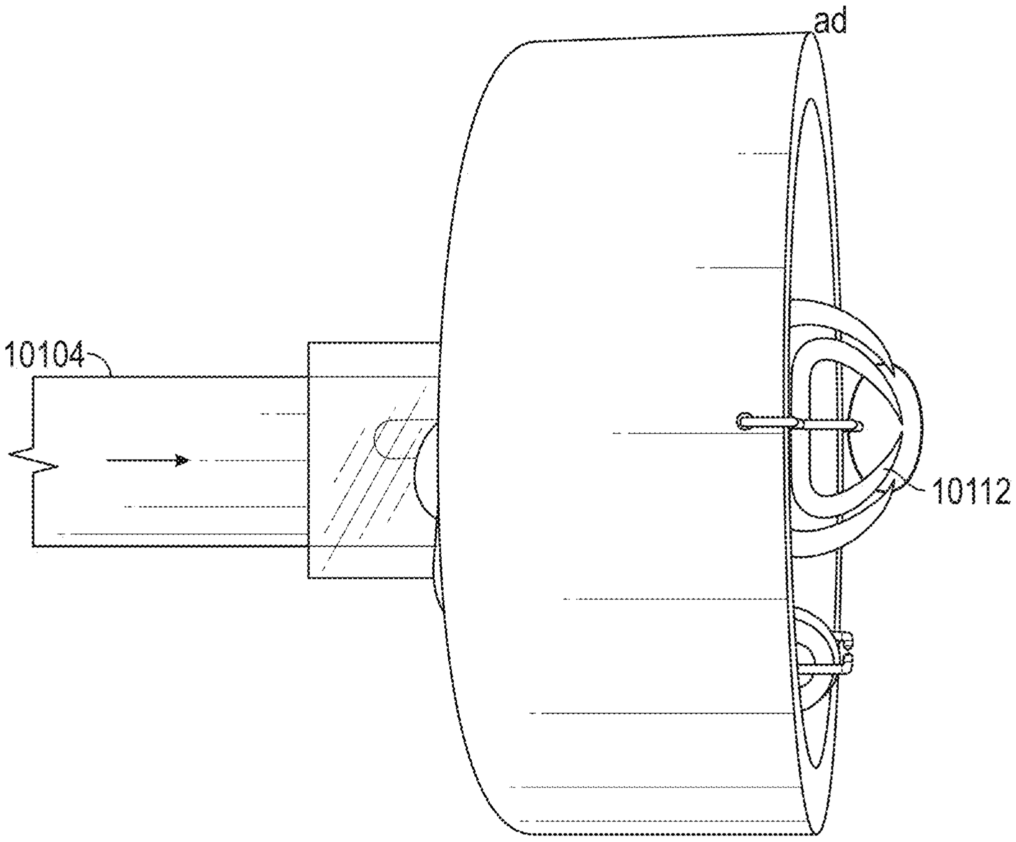

Then the push rod 10104 is advanced, the staple legs track along the pincer grooves 10110, shown in FIGS. 101D and 101E, causing the staple 10112 (FIG. 101F) to close and fix the target materials to one another. The pincers 10108 can also serve as a guard to prevent the staple legs from grabbing unintended material during staple formation. Additional pincer actuation may be applied to close the staples even smaller, thereby increasing the compression on the joined materials, if desired.

Figure 101G:
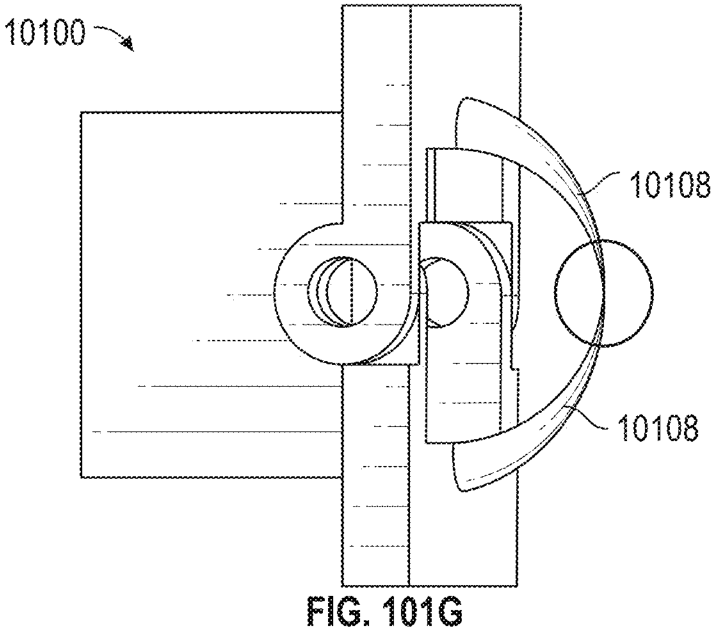

FIG. 101G shows another embodiment of a device 10100, in which the tips of the pincers 10108 meet after actuation. This ability can improve the pincers' grasp on materials (e.g., when pulling tissue or ADM away from an underlying structure).

In some embodiments, the mechanisms shown in the device 10100 are located at the end of a shaft to facilitate access to confined locations.

Figure 102A:
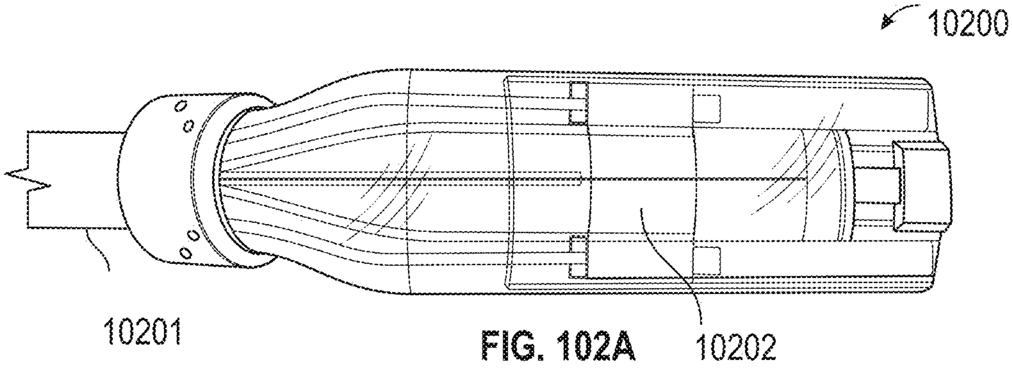
FIGS. 102A-102F show an embodiment of a device configured to grasp and staple materials.
Figure 102B:
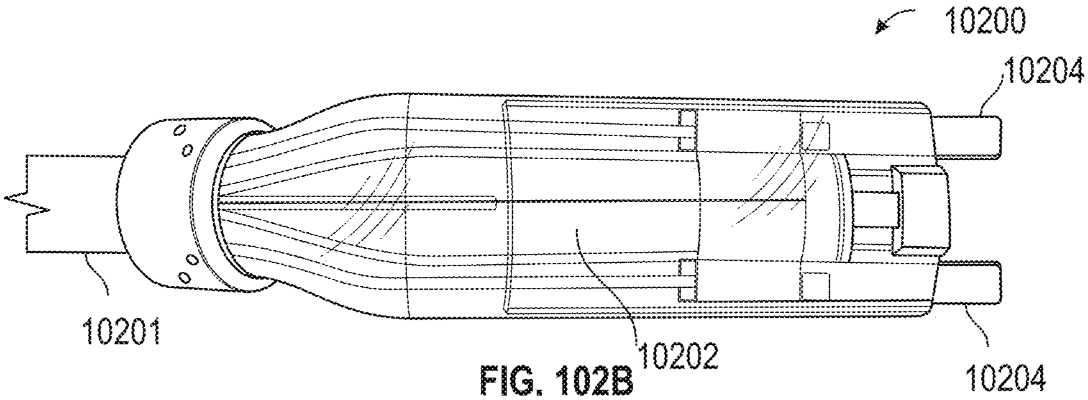
Figure 102C:
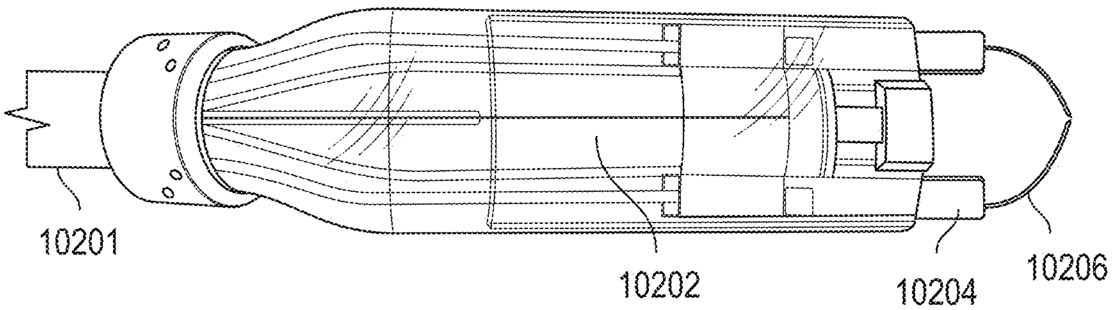
Figure 102D:
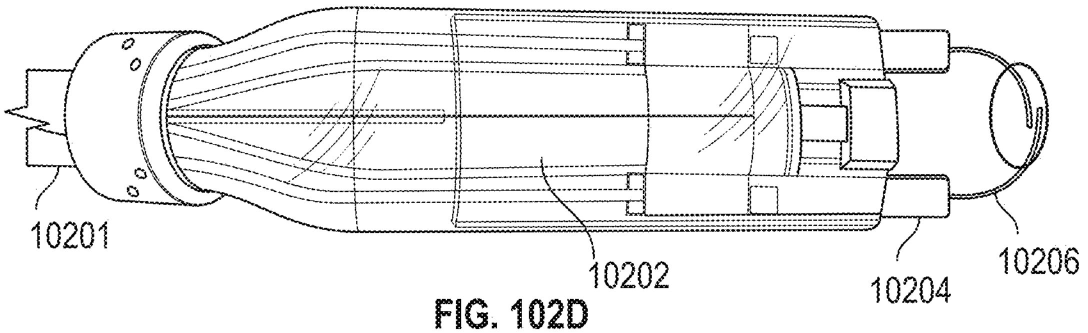
Figure 102E:
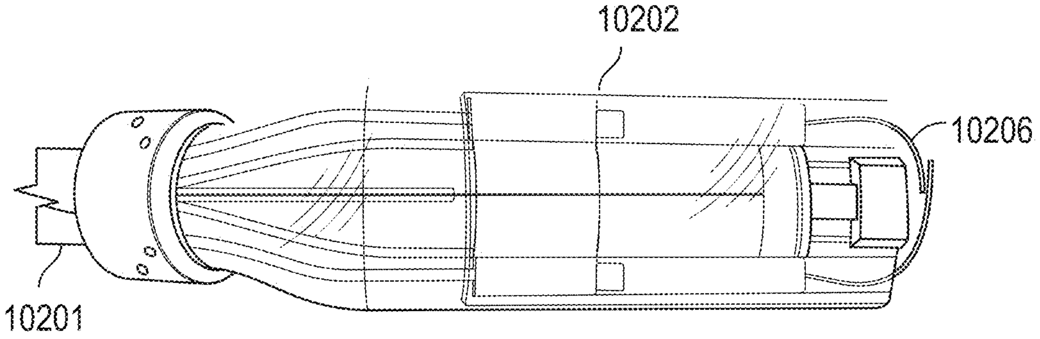
Figure 102F:
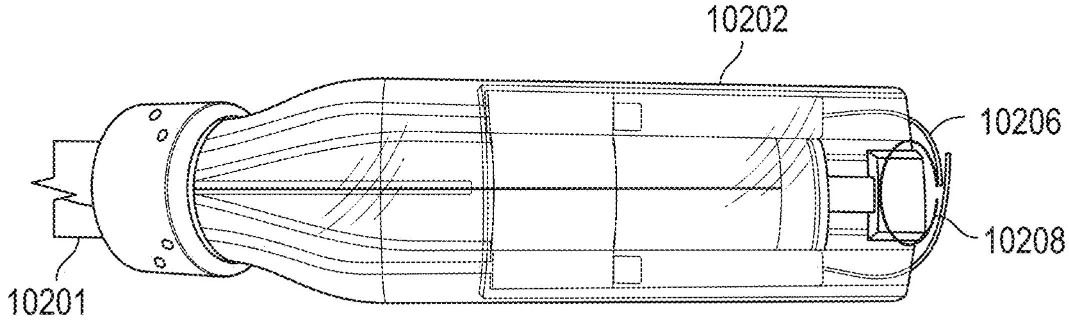

FIGS. 102A and B show a device 10200 comprising a head 10202 located at the end of shaft 10201. Carriers 10204 extend (e.g., upon actuation) from head 10202. As shown in FIG. 102C, tongs 10206 can be actuated and deployed from the carriers 10204 to grasp target material(s) so that a user can position the material(s) if needed. Once the material(s) are positioned, the tongs 10206 can be retracted, the carriers 10204 placed against the material, and the tongs 10206 actuated to pierce the material(s), as shown in FIG. 102D. As shown in FIG. 102E, while the tongs 10206 maintain their piercing through the material(s), the carriers 10204 are retracted, positioning the material(s) against the head 10202. The device 10200 may be maneuvered to retract the material(s) in order to avoid underlying structures during staple deployment. As shown in FIG. 102F, the staple 10208 is deployed to fix the materials to one another. The tongs 10206 also serve as a guard to prevent the staple legs from grabbing unintended materials during staple formation.

Figure 103A:
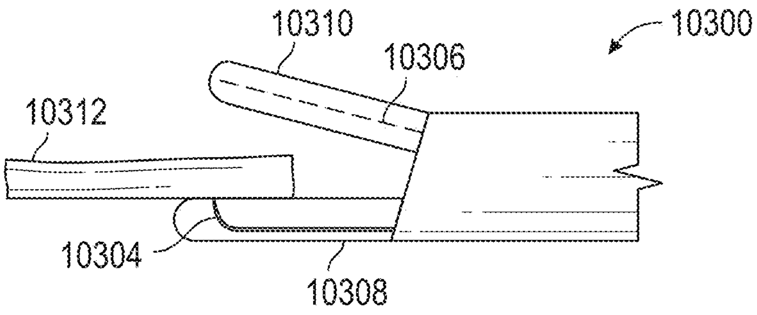
Figure 103B:
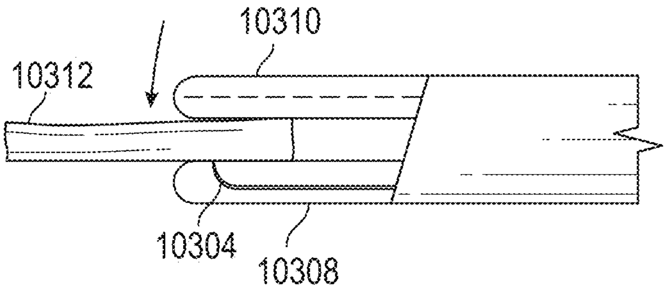
Figure 103C:
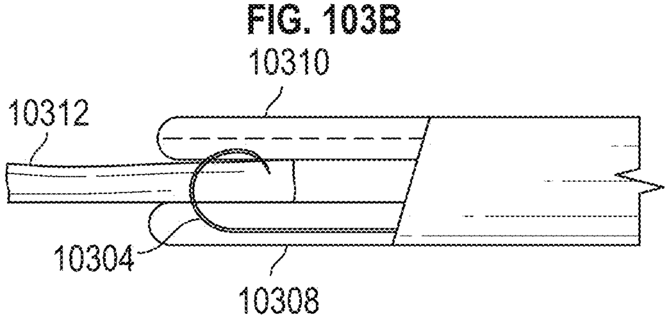
Figure 103D:
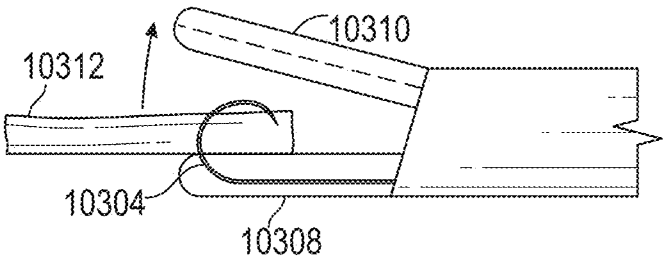
Figure 103E:
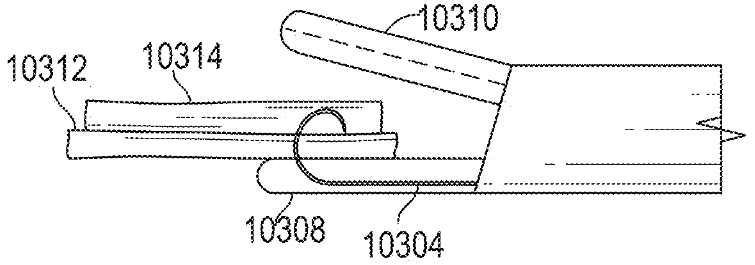
Figure 103F:
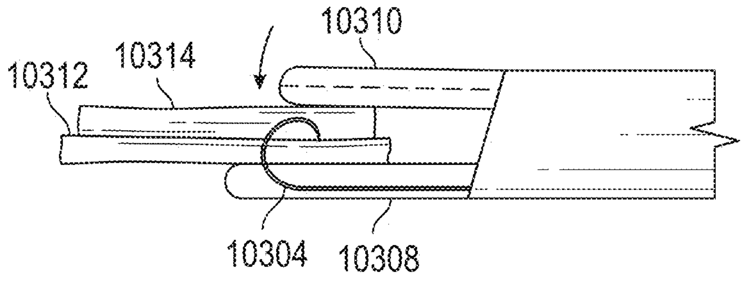
Figure 103G:
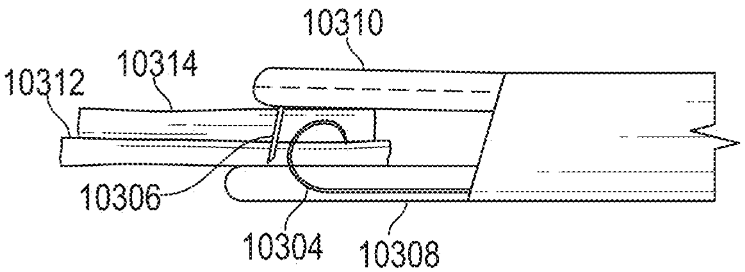
Figure 103H:
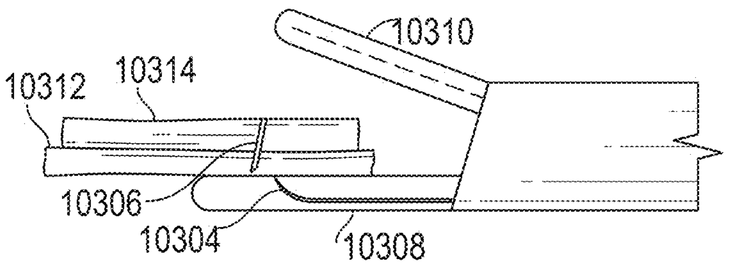

FIGS. 103A-H show an embodiment of using a device 10300 with clamping jaws, a hook 10304 (e.g., a flexible hook, a nitinol hook) configured to deploy from a lower jaw 10308, and staples 10306 that deploy from an upper jaw 10310. As shown in FIG. 103A, the hook 10304 resides in the lower jaw 10308 while the device is inserted to the surgical site. FIG. 103B shows the upper jaw 10310 clamping down on the target material 10312 (e.g., ADM or tissue). FIG. 103C shows the hook 10304 actuated, and the target material secured to the device. FIG. 103D shows the upper jaw 10310 opened to allow positioning of the target material to the second target material 10314 (to be joined). In FIG. 103E, the two materials are positioned together (e.g., ADM positioned on tissue). FIG. 103F shows the upper jaw 10310 clamping both materials. As shown in FIG. 103G, the staple 10306 is deployed to fix the materials together. The lower jaw 10308 also serves as a guard to prevent the staple legs from grabbing unintended material during staple formation. FIG. 103H shows the hook 10304 being retracted, allowing movement or removal of the device 10300.

Figure 104:
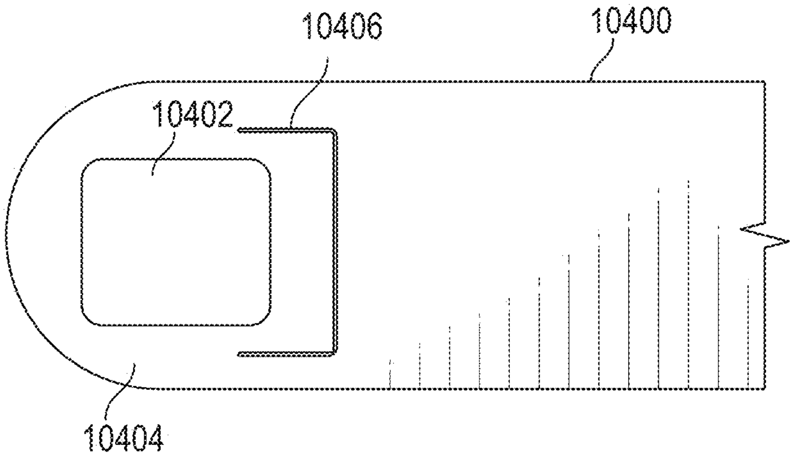
FIG. 104 shows an embodiment of an upper jaw of a device configured to clamp materials.

FIG. 104 illustrates an embodiment of an upper jaw 10400 comprising a window 10402. The frame 10404 around the window 10402 serves to clamp the materials to be joined (e.g., ADM and tissue) between the upper and lower jaws. A staple 10406 is shown in the upper jaw 10400 near the window 10402. The clamping keeps the materials tensioned for the hook to penetrate through the materials and window.

Figure 105A:
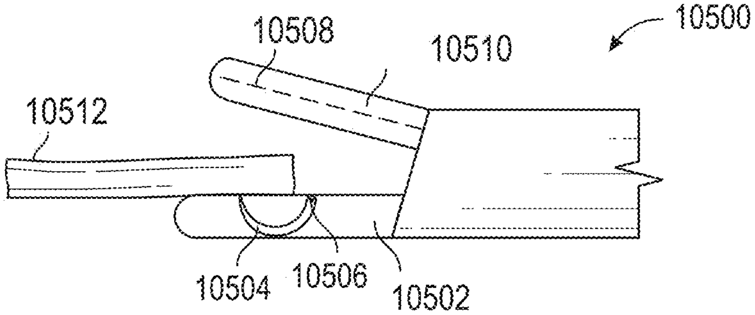
FIGS. 105A-105G shows an embodiment of a lower jaw comprising a hook.
Figure 105B:
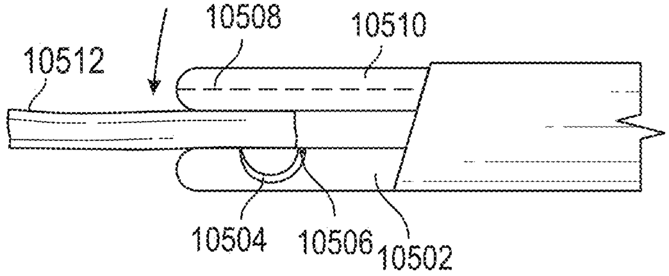
Figure 105C:
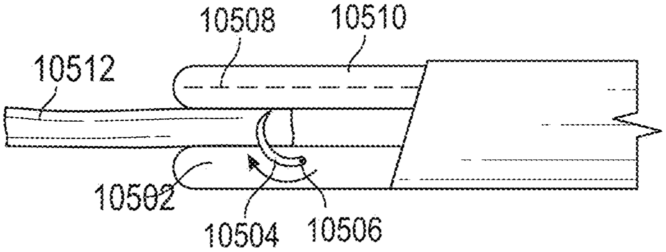
Figure 105D:
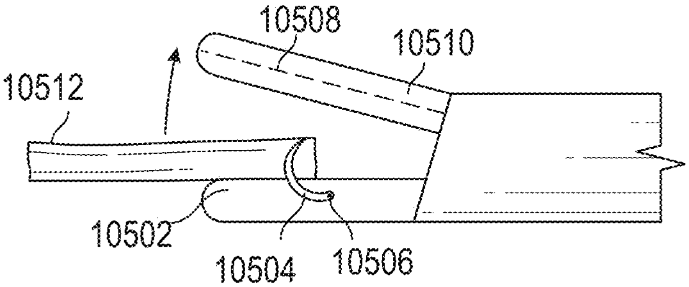
Figure 105E:
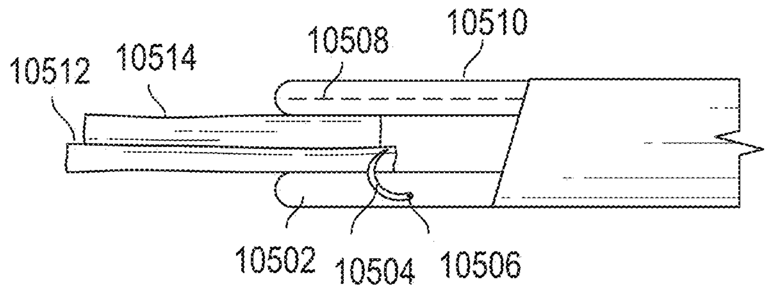
Figure 105F:
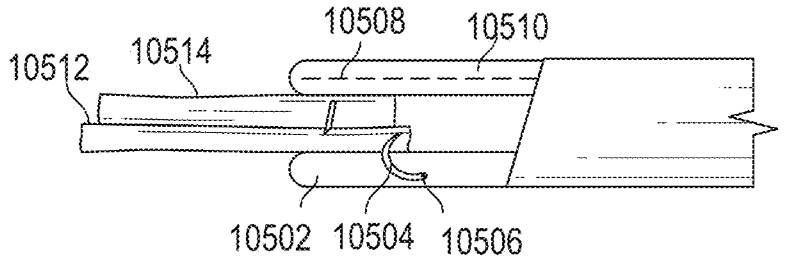

FIG. 105A-G show an alternate embodiment of a device 10500 with clamping jaws, a rigid hook 10504 (instead of a flexible (e.g. nitinol) hook) attached to the lower jaw 10502 by a hinge 10506, and staples 10508 that deploy from an upper jaw 10510. FIG. 105B shows the upper jaw 10510 clamping down on the target material 10512 (e.g. ADM or tissue). FIG. 105C shows the rigid hook 10504 actuated, and the target material secured to the device. FIG. 105D shows the upper jaw 10510 opened to allow positioning of the target material to the second target material 10514 (to be joined). In FIG. 105E, the two materials are positioned together (e.g. ADM positioned on tissue). FIG. 105F shows the upper jaw 10510 clamping both materials and the staple 10508 deployed to fix the materials together. The lower jaw

Figure 105G:
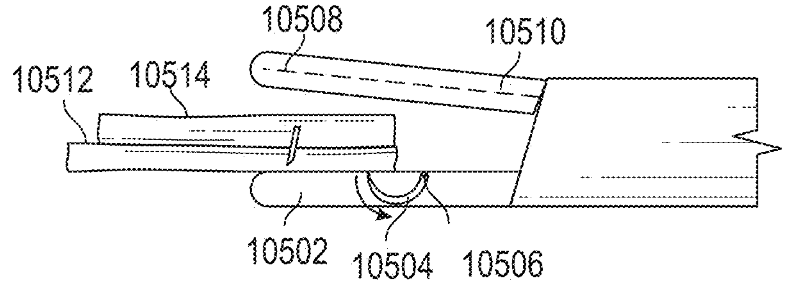

10502 also serves as a guard to prevent the staple legs from grabbing unintended material during staple formation. FIG. 105G shows the rigid hook 10504 retracted, allowing movement or removal of the device 10500.

FIGS. 106A-108B show an embodiment of a device that can be used to secure and stabilize a first material and second material to be joined. Such a device can be particularly useful to position and stabilize tough materials (like ADM) for staple penetration. An integrated or separate (e.g., currently available) stapler or stapling mechanism can be used to perform the stapling to fix the materials together.

Figure 106A:
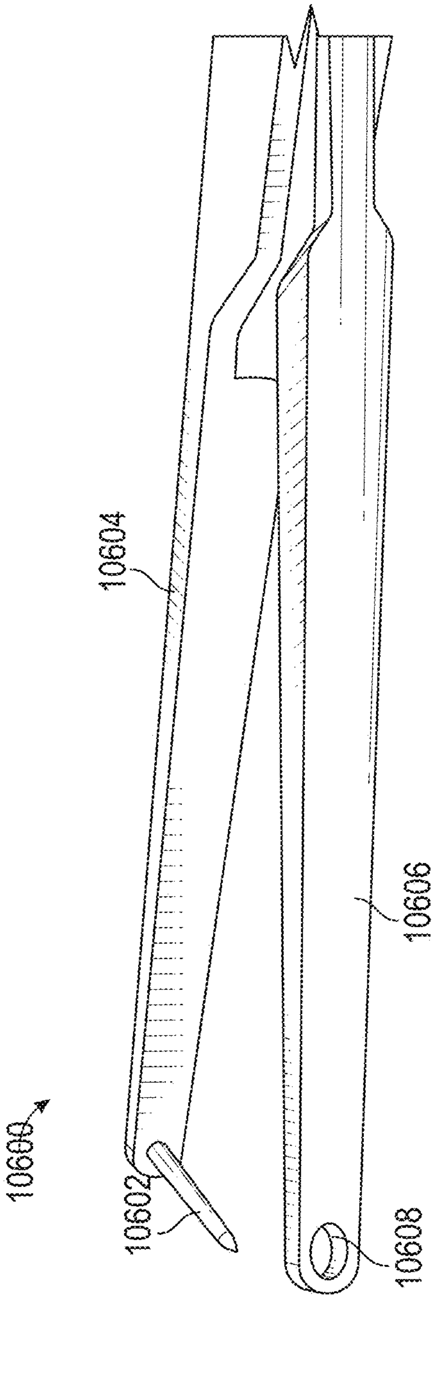
FIGS. 106A-106B show an embodiment of a device for grasping and positioning materials to be stapled.
Figure 106B:
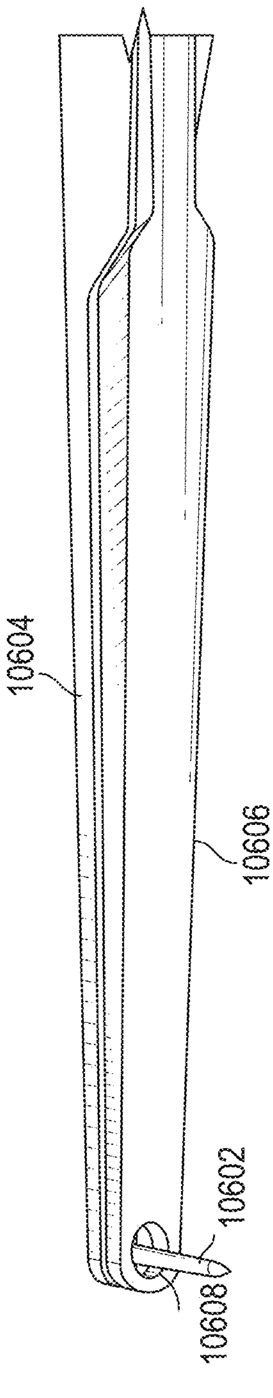

FIGS. 106A and 106B show views of the device 10600 comprising a needle 10602 (or other piercing member) attached to a first jaw 10604. The second jaw 10606 comprises an opening hole 10608. The needle 10602 and hole 10608 are positioned and configured such that the needle 10602 enters the hole 10608 when the jaws 10604, 10606 are closed, as shown in FIG. 106B.

Figure 107A:
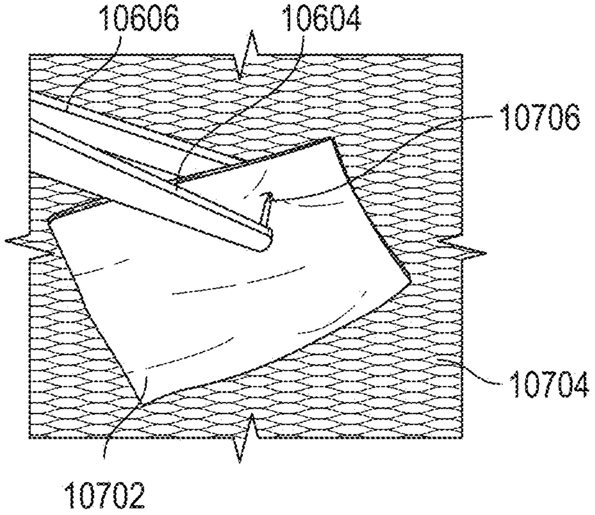
FIGS. 107A-107H show an embodiment of a method of using the device of FIGS. 106A-106B.
Figure 107B:
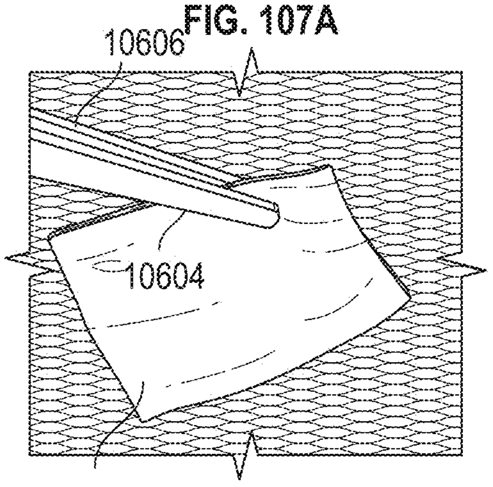
Figure 107C:
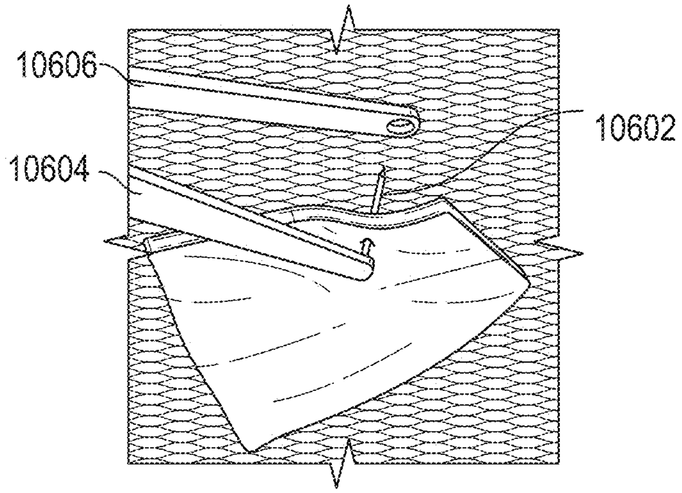
Figure 107D:
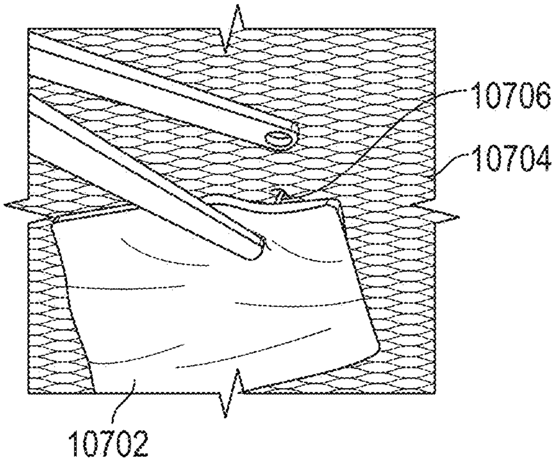
Figure 107E:
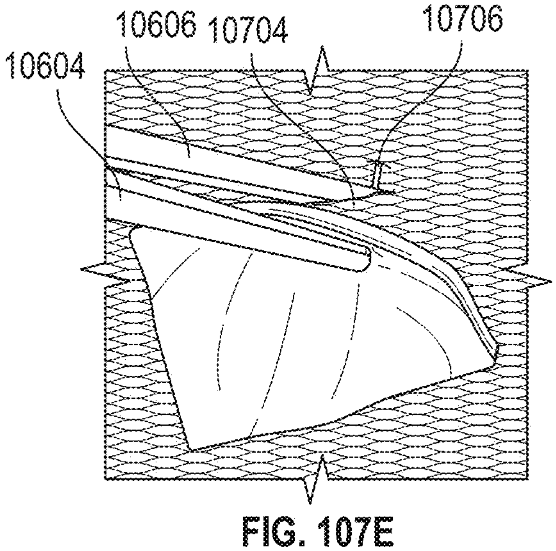
Figure 107F:
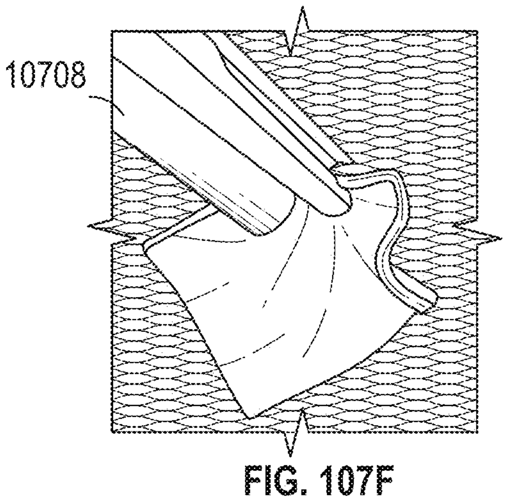
Figure 107G:
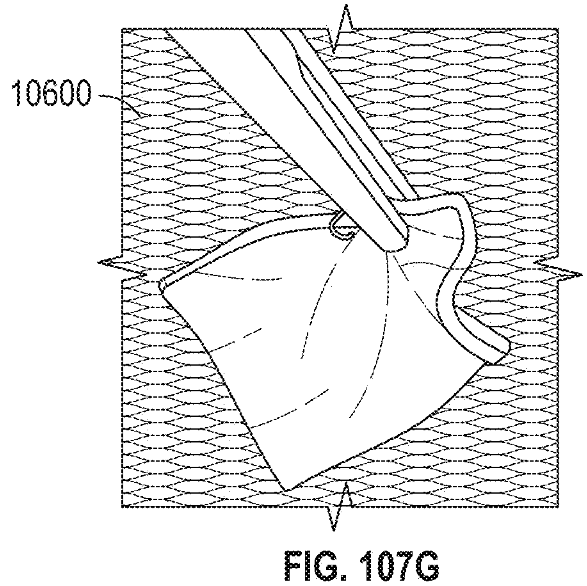
Figure 107H:
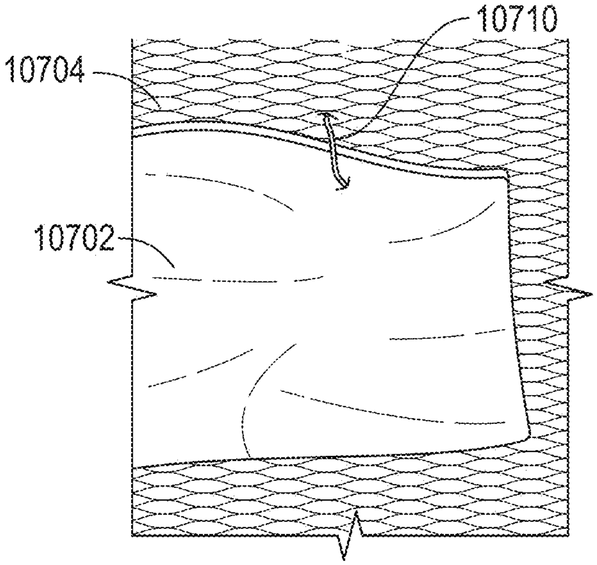

FIGS. 107A-H illustrate an embodiment of a method of using the device of FIGS. 106A-B to fix a first material 10702 (e.g., ADM) to a second material 10704 (e.g., tissue). FIG. 107A shows the needle tip 10706 being used to target the fixation location on the first material 10702. As shown in FIG. 107B, the jaws 10604, 10606 are closed, causing the needle 10602 to puncture the first material by entering the hole in the second jaw (not shown). In FIG. 107C, the jaws 10604, 10606 are opened. As shown in FIG. 107D, the first material 10702 is positioned to the desired fixation location on the second material 10704 using the needle 10602, and the needle tip 10706 is used to target the fixation location on the second material 10704. In FIG. 107E, the jaws 10604, 10606 are closed, compressing the second material 10704 onto the needle tip 10706 by inserting the needle 10602 into the hole of the second jaw. The entire device 10600 may be maneuvered to retract the materials in order to avoid underlying structures during staple deployment. FIG. 107F shows the stapling mechanism 10708 telescoping to the fixation site and deploying the staple 10710 to fix the target materials to one another. As shown in FIG. 107G, the stapling mechanism 10708 is retracted. The jaws 10604, 10606 are opened, and the device 10600 is removed, as shown in FIG. 107H. In some embodiments, the device 10600 is modified so that the needle has a channel for the staple leg to travel and pass easily through the first material (e.g. tough ADM) and second material.

Figure 108A:
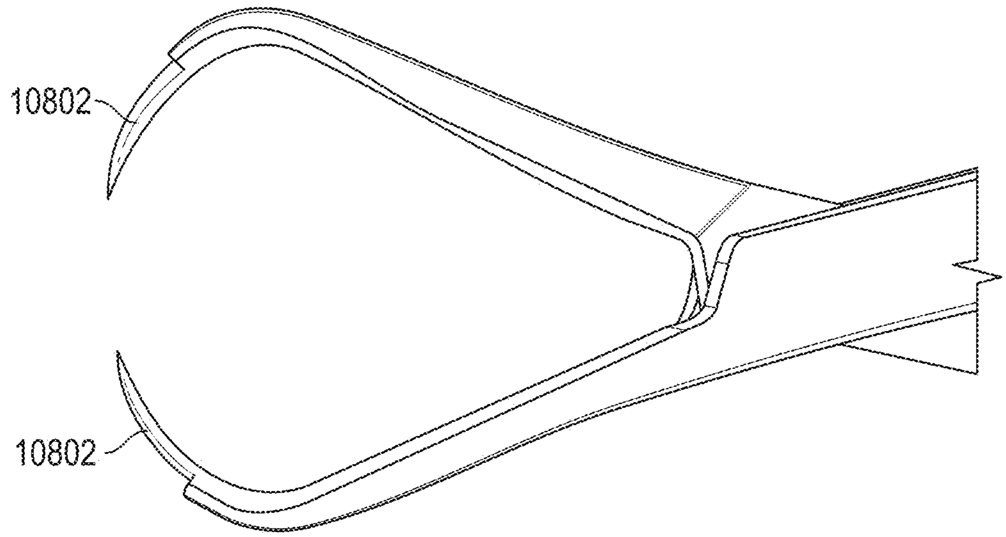
FIGS. 108A-108D show an embodiment of a device for grasping and positioning materials to be stapled.
Figure 108B:
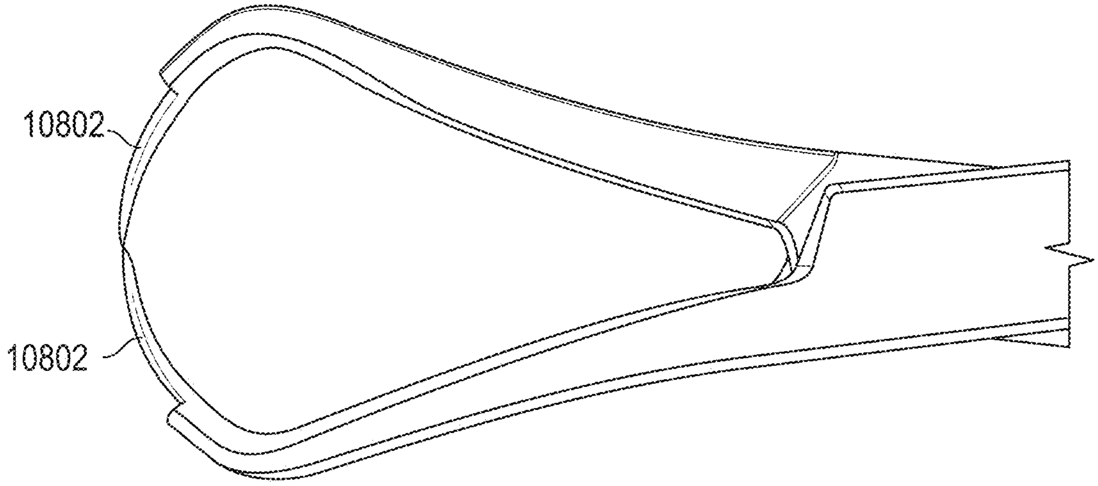
Figure 108C:
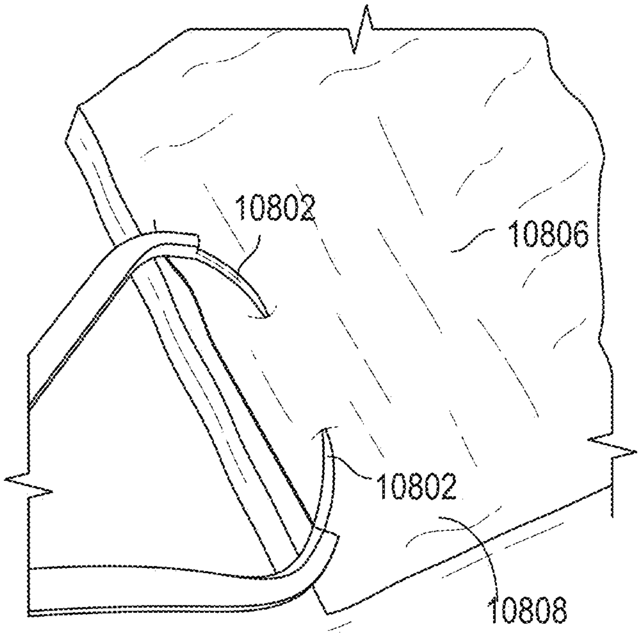
Figure 108D:
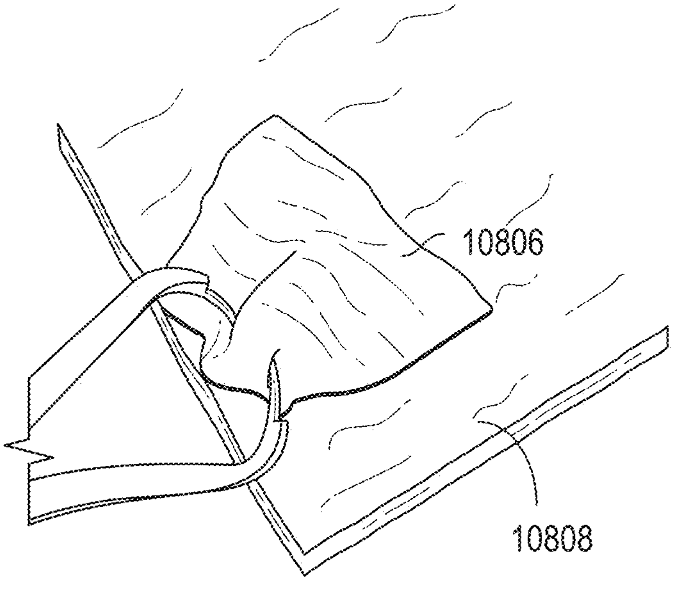

FIGS. 108A and 108B show an alternate jaw embodiment with two opposing sharp tips 10802. The tips 10802 can be used to position the first target material 10806 to the second target material 10808 and can then be used to puncture the first material and secure the second material, as shown in FIGS. 108C and 108D. The entire device 10800 may be maneuvered to retract the target materials (e.g., ADM and tissue) in order to avoid underlying structures during staple deployment. The stapling mechanism telescopes to the fixation site and deploys the staple to fix the materials. The device could be modified so the each sharp tip has a channel for the corresponding staple leg to travel and pass easily through the first material (e.g. tough ADM) and second material. The tips could also be modified to serve as a guard to prevent the staple legs from grabbing unintended material during staple formation.

Figure 109A:
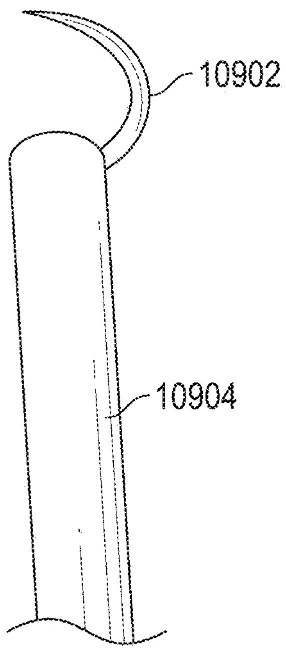
FIGS. 109A-109B show an embodiment of a stapling device.
Figure 109B:
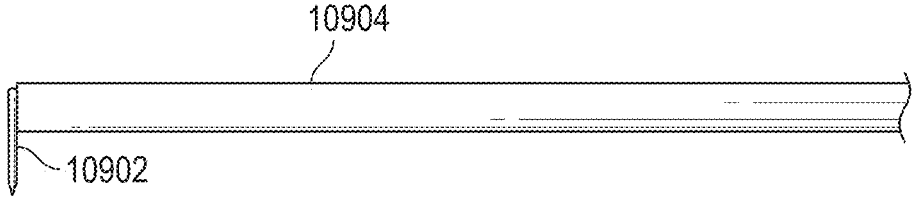

FIGS. 109A and 109B show an embodiment in which the staple 10902 is mounted on the end of a shaft 10904. The staple 10902 can be curved, with one end mounted to the end of the shaft 10904 and the sharp end free from the shaft. The staple can be curved within a plane that is perpendicular (or at some angle) to the shaft 10904. This positioning can allow rotation of the shaft to drive the staple through adjacent material(s).

Figure 110A:
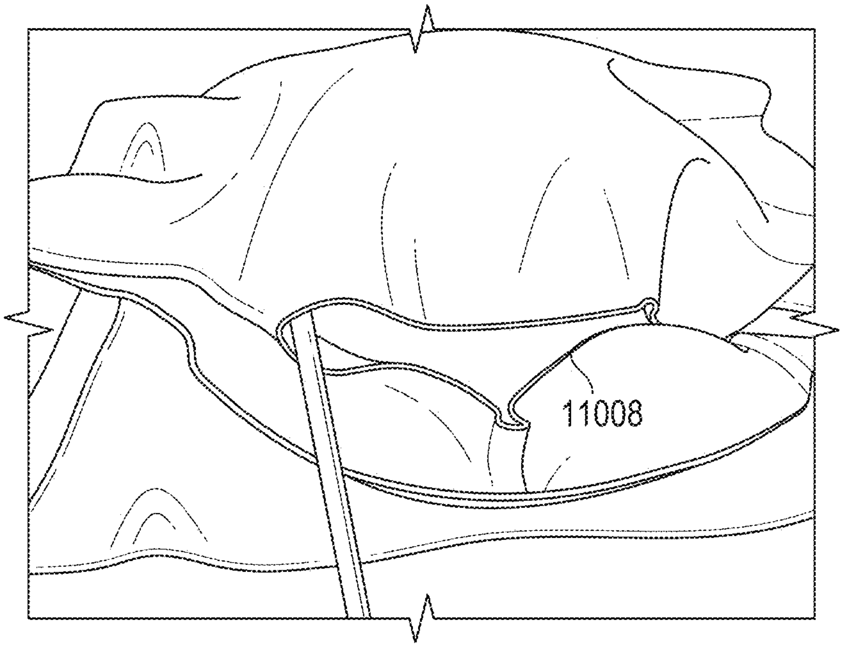
FIGS. 110A-110L show an embodiment of using the device of FIGS. 9A-9B.
Figure 110B:
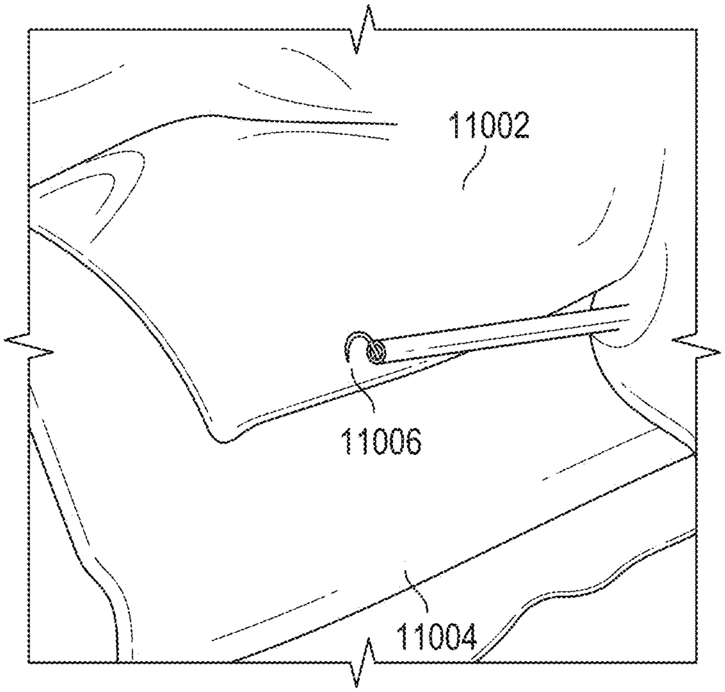
Figure 110C:
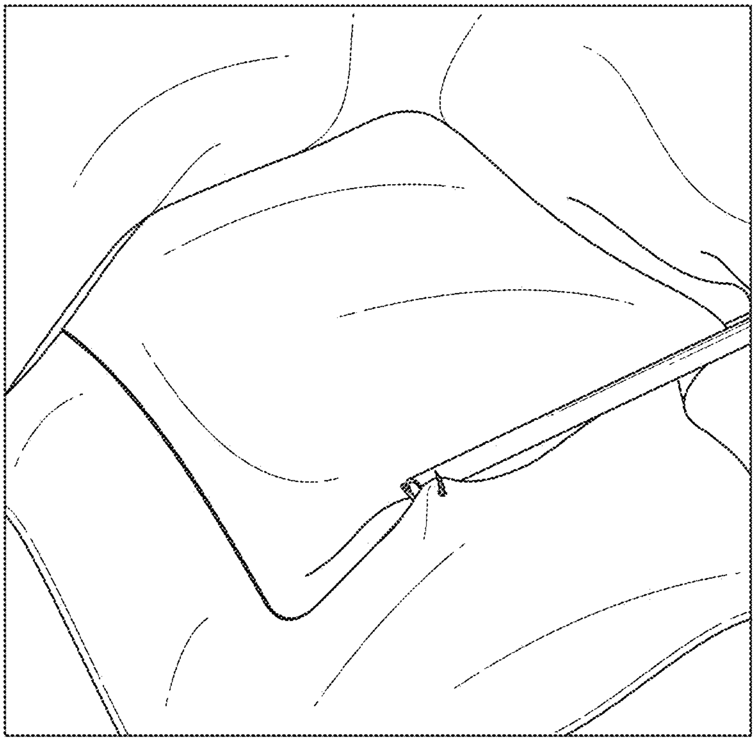
Figure 110D:
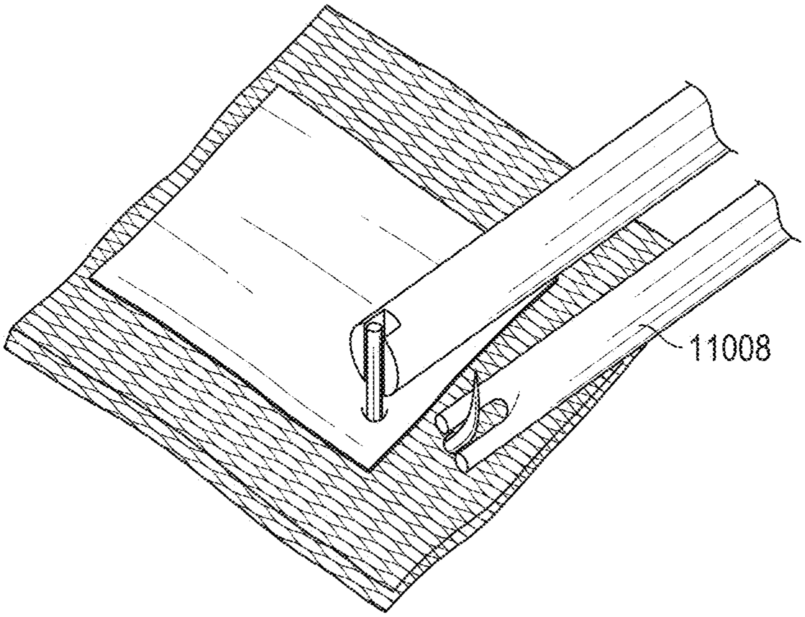
Figure 110E:
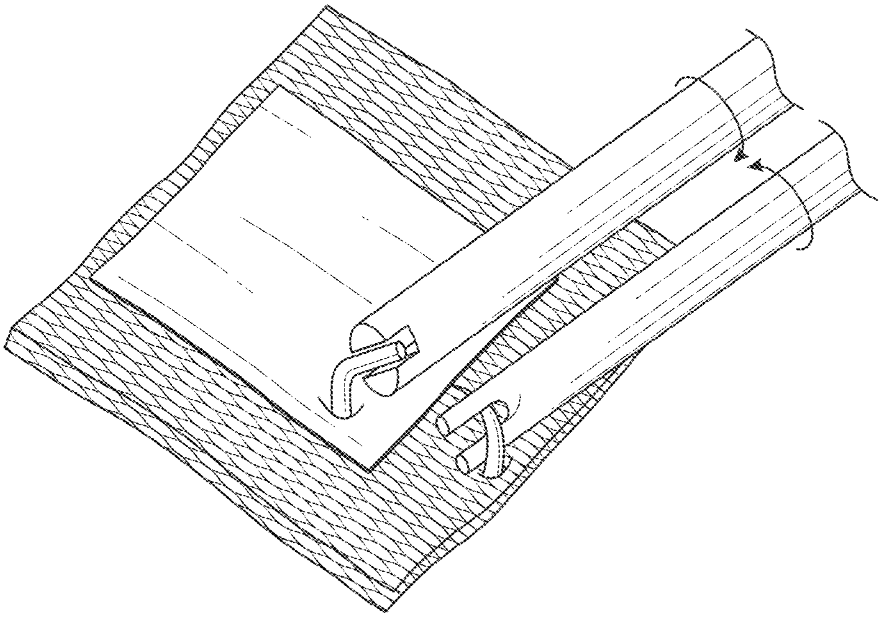
Figure 110F:
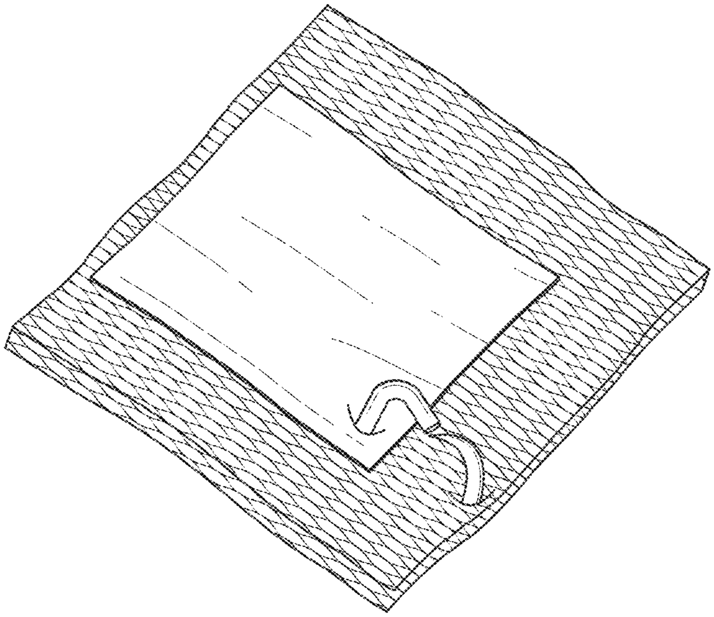

An example application for such a device is shown in FIG. 110A where the staple and shaft are inserted into an incision 11008. In FIG. 110B, the staple and shaft are inserted to the location where the ADM is to be attached to tissue. In FIG. 110C, the shaft drives the staple through the ADM and tissue. Prior to closing the staple, the entire device may be maneuvered to lift the tissue/ADM and check if underlying structures were grabbed unintentionally. In FIG. 110D, a fork 11008 advances around the staple tip. In FIG. 110E, the shaft and fork actuate to bend and close the staple. In FIG. 110F, the device is removed, and the closed staple secures ADM to tissue.

Figure 110G:
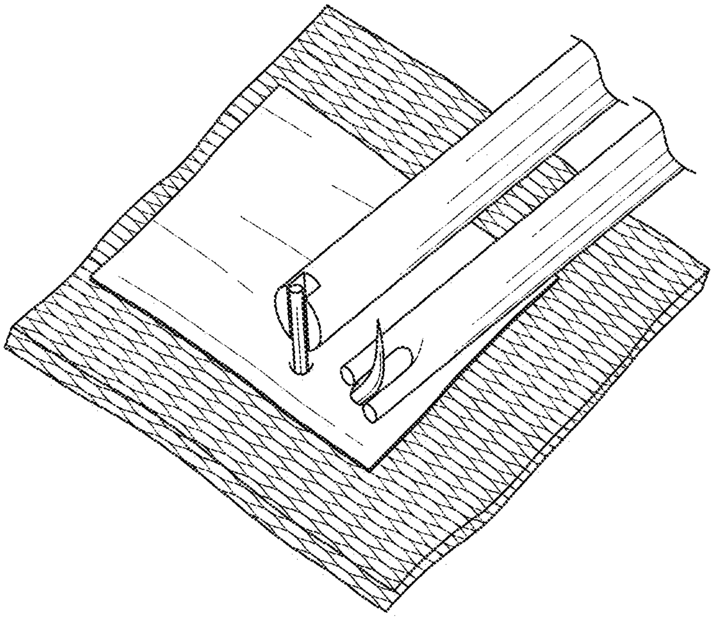
Figure 110H:
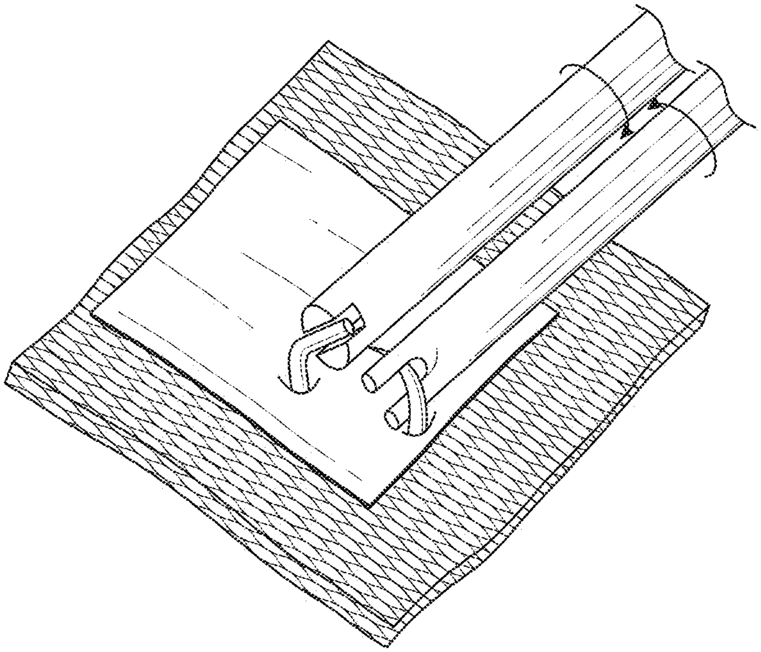
Figure 110I:
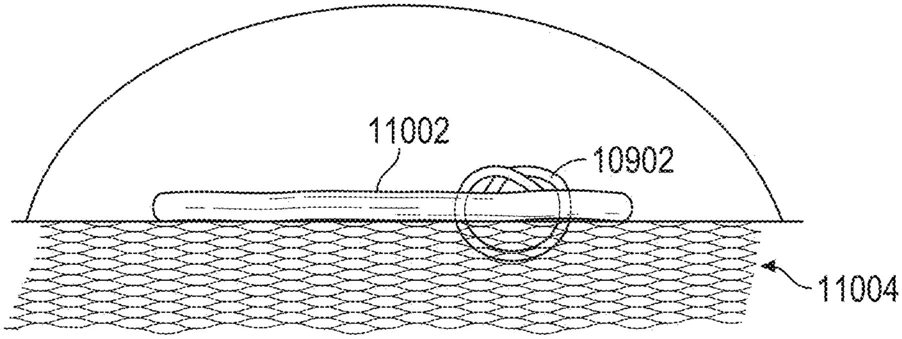

A device with this configuration could also be used to place a staple away from the edges of the target material (e.g., ADM). In FIG. 110G, the staple 10902 pierced through ADM 11002 and tissue 11004. The fork 11008 was used as a backstop on top of the ADM to apply countertraction so the staple tip can penetrate back up through the ADM 11002. Prior to closing the staple, the entire device may be maneuvered to lift the tissue/ADM and check if underlying structures were grabbed unintentionally. In FIG. 110H, the shaft and fork actuate to bend and close the staple 10902, securing the ADM 11002 to tissue 11004 as shown in FIG. 110I.

Figure 110J:
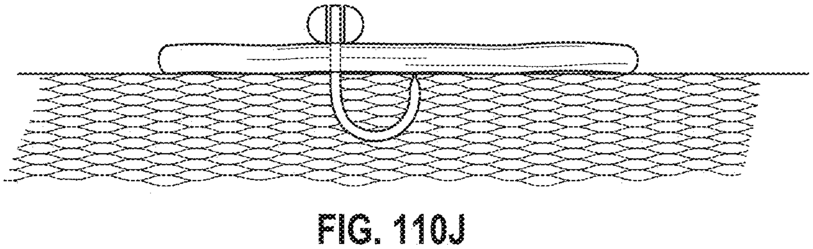
Figure 110K:
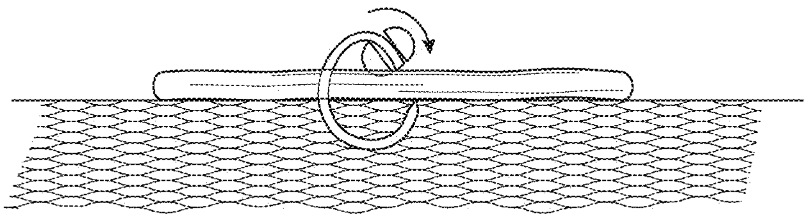
Figure 110L:
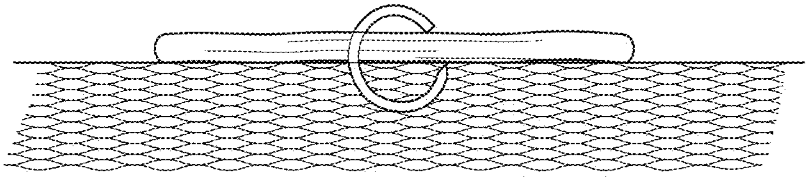

Alternatively, the staple 10902 could pierce through ADM 11002 and tissue 11004 without piercing back up through the ADM 11002, as shown in FIG. 110J. Prior to closing the staple, the entire device may be maneuvered to lift the tissue/ADM and check if underlying structures were grabbed unintentionally. The staple 10902 leg above the ADM 11002 could then be bent to fix the ADM 11002 to tissue 11004, as shown in FIGS. 110K and 110L.

Figure 111A:
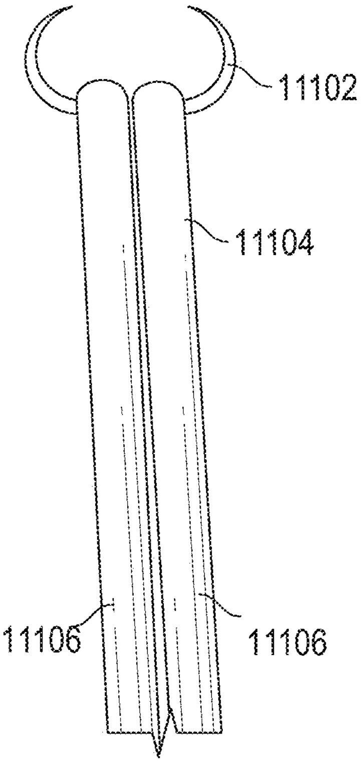
FIGS. 111A-111D show an embodiment of a stapling device.
Figure 111B:
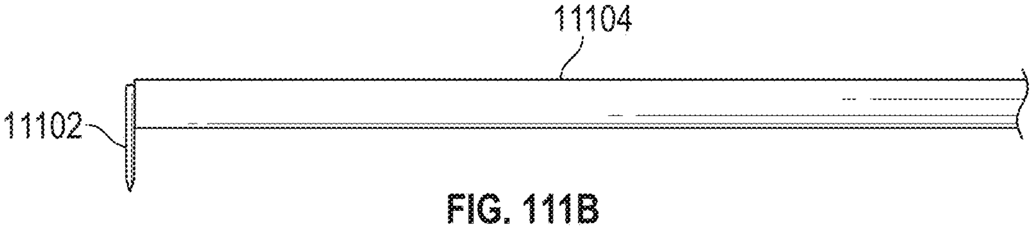

FIGS. 111A and 111B show another embodiment in which the staple 11102 is mounted on the end of a shaft 11104. The shaft 11104 can comprise 2 rods 11106, each rod connected to a side of the staple. This architecture could be used to place a staple on the edges of the target material (e.g., ADM) or away from the edges of the target material (e.g., ADM).

Figure 111C:
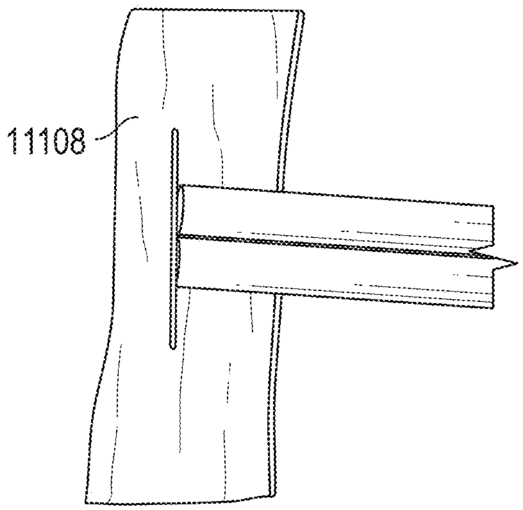
Figure 111D:
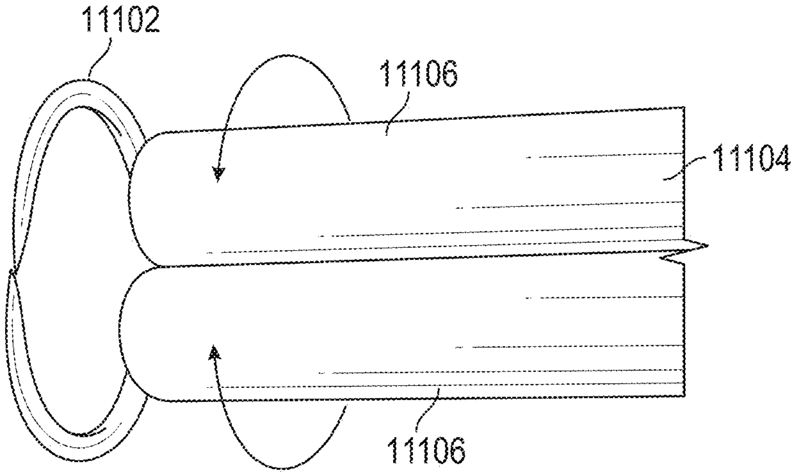

The staple tips are placed on the ADM/tissue 11108, as shown in FIG. 111C. The rods 11106 of the shaft 11104 are rotated to close the staple 11102, as shown in FIG. 111D. The staple can then be released from the rods. This can be performed using a variety of methods (e.g., a push rod pushing the staple off the shaft, a spring that pushes the staple off the shaft, etc.).

Figure 112A:
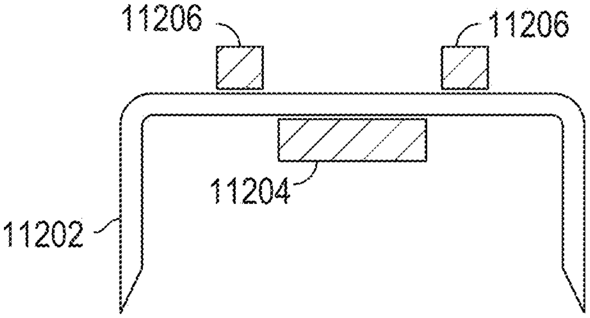
FIGS. 112A-112B shows an embodiment of a staple closing mechanism.
Figure 112B:
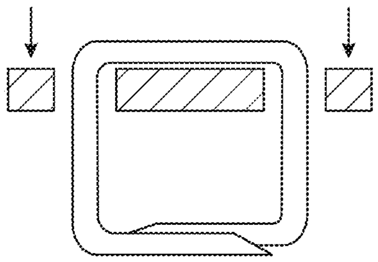

FIG. 112 illustrates an alternate mechanism that closes the staple 11202. The staple span rests on die 11204. Dies 11206 are actuated toward die 11204 causing the staple 11202 to close.

Figure 113A:
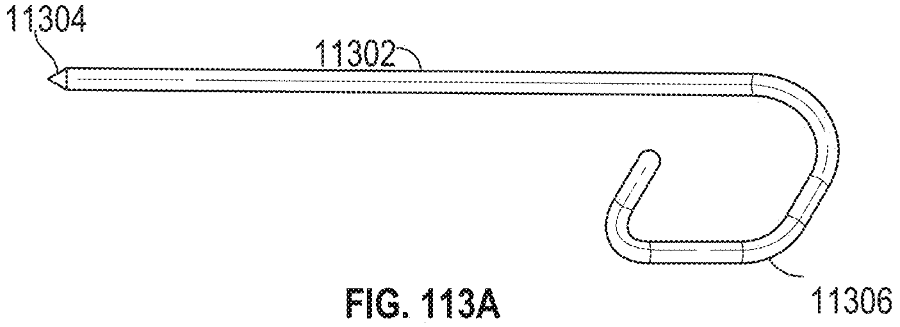
FIGS. 113A-113J show an embodiment of a stapling device using a staple with pre-formed features.
Figure 113B:
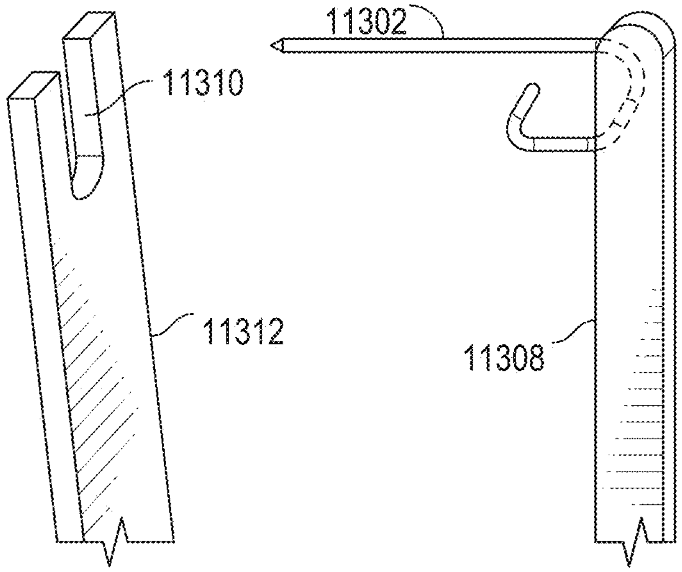

FIG. 113A shows an embodiment of a staple 11302 with tip 11304 and pre-formed features 11306. FIG. 113B shows the staple 11302 held by a first jaw 11308. FIG. 113B also shows slot 11310 in a second jaw 11312 such that the staple tip 11304 enters the slot 11310 when the jaws 11308, 11312 are closed.

Figure 113C:
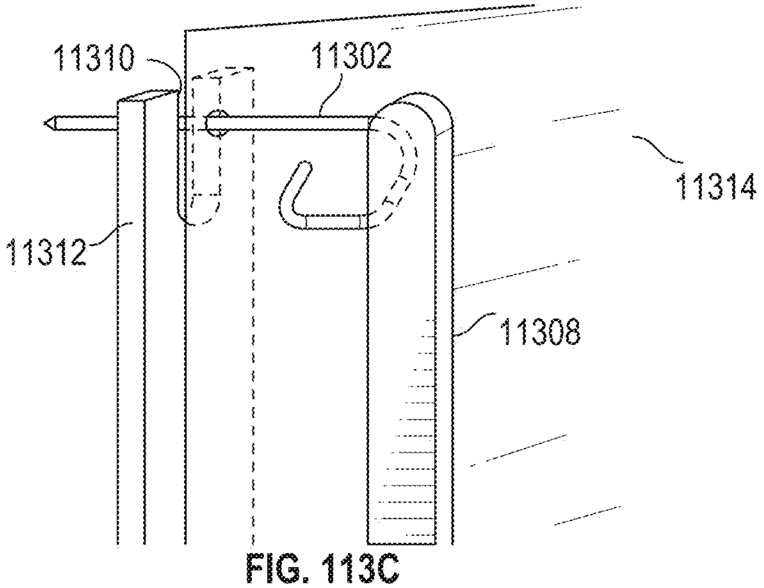
Figure 113D:
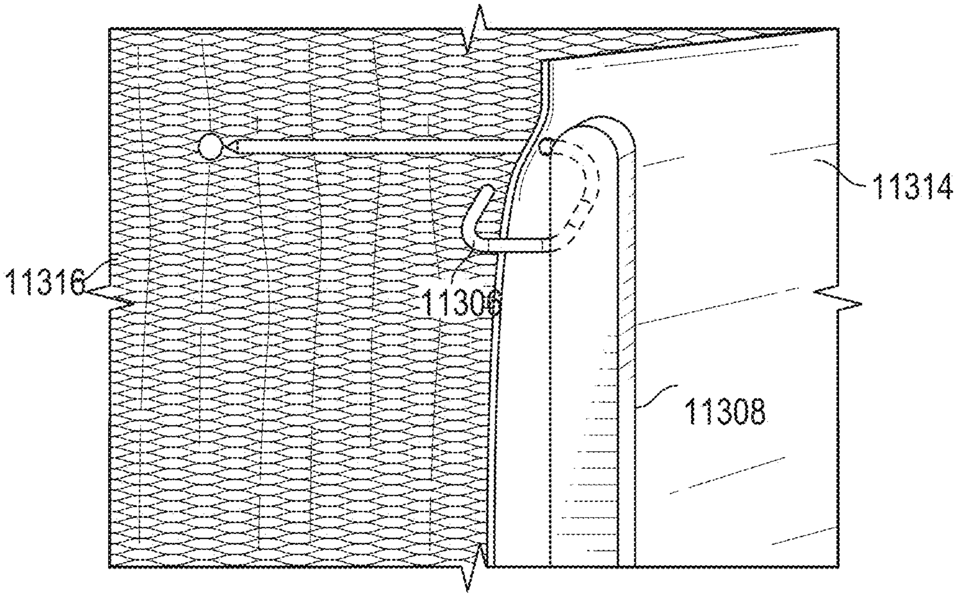
Figure 113E:
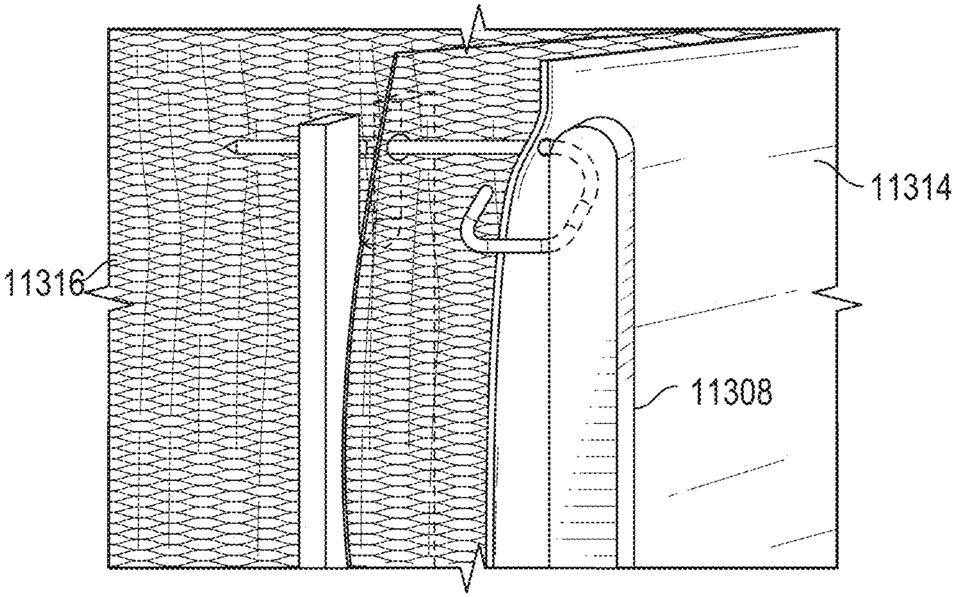

The staple tip 11304 is used to target the fixation location on the target material 11314 (e.g., ADM). The jaws 11308, 11312 are closed, causing the staple tip 11304 to puncture the ADM 11314 by entering the slot 11310 in the second jaw 11312, as shown in FIG. 113C. The ADM 11314 is moved inside the pre-formed staple features 11306 by sliding the staple through until the ADM is positioned within the pre-formed staple features, as shown in FIG. 113D. The jaws 11308, 11312 are opened, the ADM 11314 is moved into position, and the staple tip 11304 is used to target the fixation location on tissue as shown in FIG. 113D. In FIG. 113E, the jaws 11308, 11312 are closed, causing the staple tip 11304 to pierce tissue. The tissue 11316 is compressed onto the staple 11302 as the staple tip 11304 enters the slot 11310 of the second jaw 11312. The entire device may be maneuvered to lift the tissue/ADM and check if underlying structures were grabbed unintentionally.

Figure 113F:
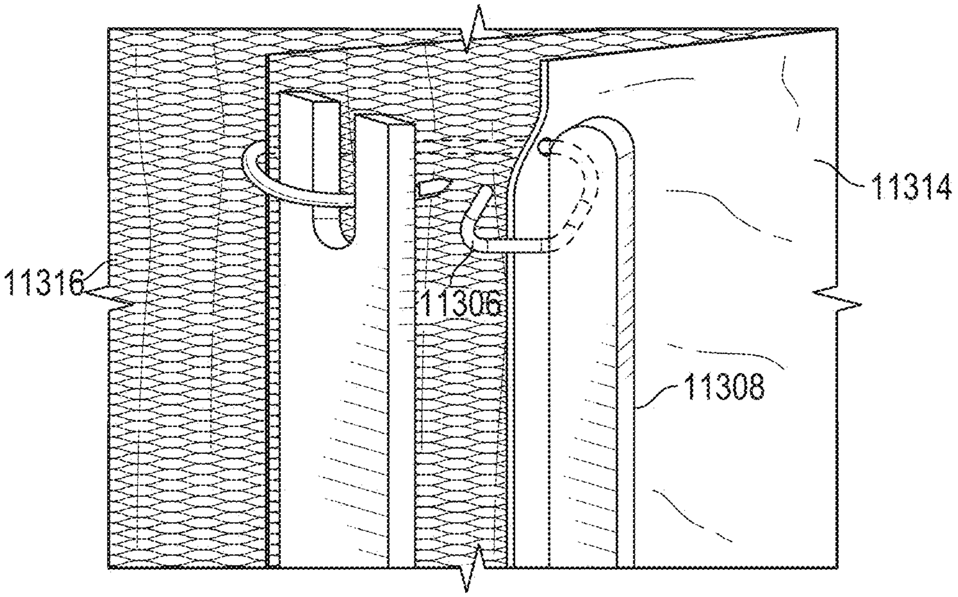
Figure 113G:
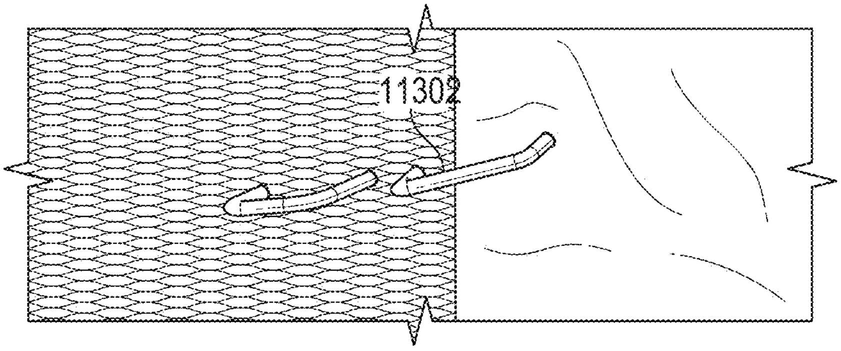
Figure 113H:
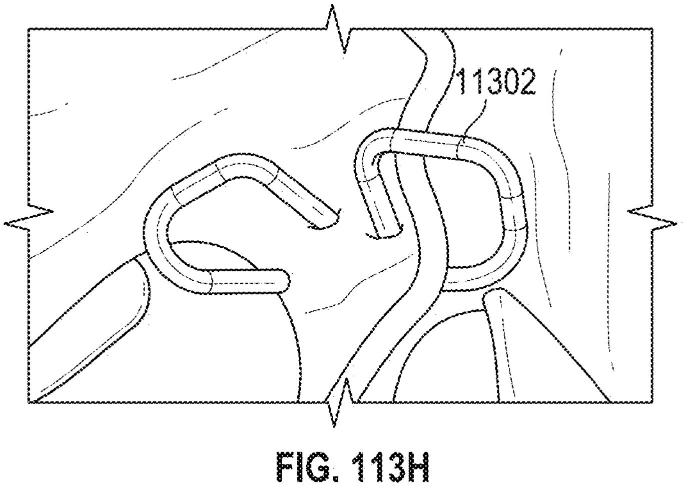
Figure 113I:
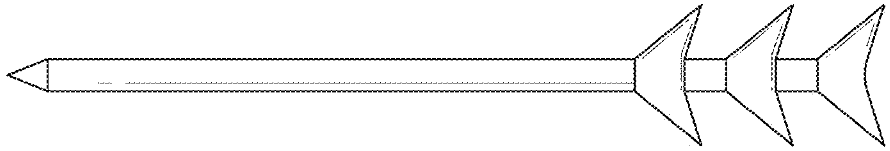
Figure 113J:
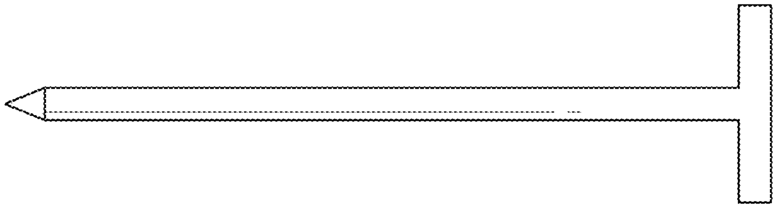

With the staple leg in the slot of the second jaw 11312, the second jaw 11312 is rotated to close the staple (FIG. 113F) and fix the ADM to tissue. The pre-formed staple features and the closed staple leg secure the ADM to tissue as shown in FIGS. 113G and 113H. In some embodiments, the pre-formed staple feature(s) may differ from that shown in FIGS. 113A-H, so long as the pre-formed feature serves to prevent the target material (e.g., ADM) from disconnecting from the staple. Examples could include a barb or barbs (FIG. 1131) or a stopper feature (FIG. 113J).

Figure 114A:
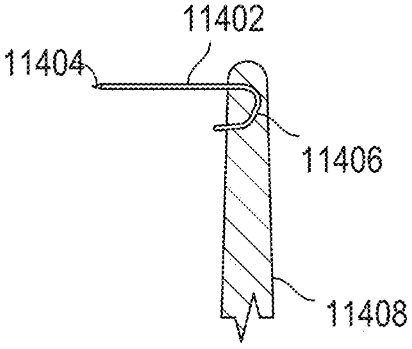
FIGS. 114A-114C show another embodiment of a stapling device using a staple with pre-formed features.
Figure 114B:
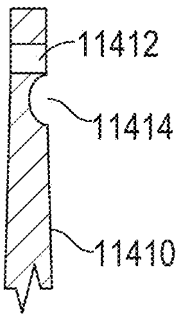
Figure 114C:
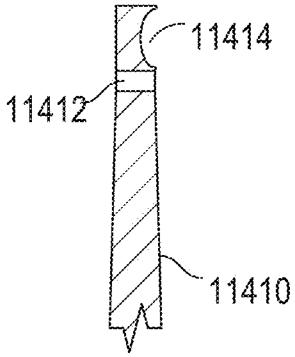

FIG. 114A shows another embodiment of a staple 11402 with a staple tip 11404 and pre-formed features 11406. The staple 11402 is held by a first jaw 11408, as shown in FIG. 114A. A second jaw 11410 comprises a hole 11412 and an anvil 11414, as shown in FIGS. 114B and 114C. As shown in FIG. 114B, the hole 11412 can be positioned distal to the anvil 11414, in some embodiments. Alternatively, the anvil 11414 can be positioned distal to the hole 11412, as shown in FIG. 114C.

Figure 115A:
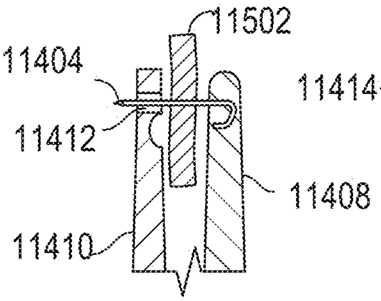
FIGS. 115A-F show an embodiment of using the device of FIGS. 114A-114C.
Figure 115B:
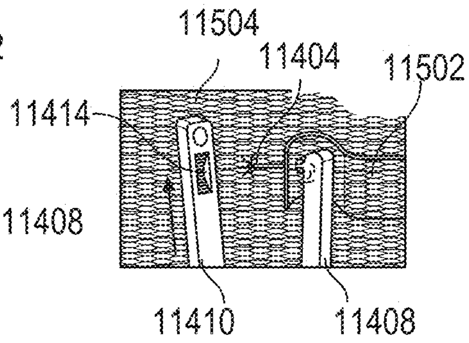

FIGS. 115A-G show an embodiment of a method of using the staple 11402 and jaws 11410, 11408, described with respect to FIGS. 114A-C. The staple tip 11404 is used to target the fixation location on the target material 11502 (e.g., ADM). As shown in FIG. 115A, the jaws 11408, 11410 are closed, causing the staple tip 11404 to puncture the ADM 11502 by entering the hole 11412 in the second jaw 11410. In FIG. 115B, the jaws 11408, 11410 are opened, and the second jaw 11410 is actuated to align the anvil 11414 with the staple tip 11404. The ADM 11502 is positioned, and the staple tip 11404 is used to target the fixation location on the second target material 11504 (e.g., tissue).

Figure 115C:
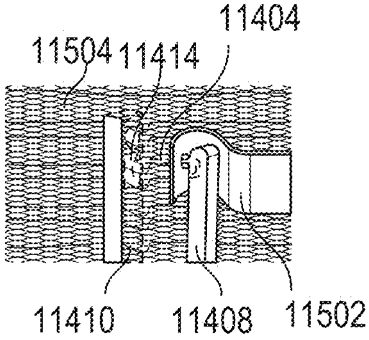
Figure 115D:
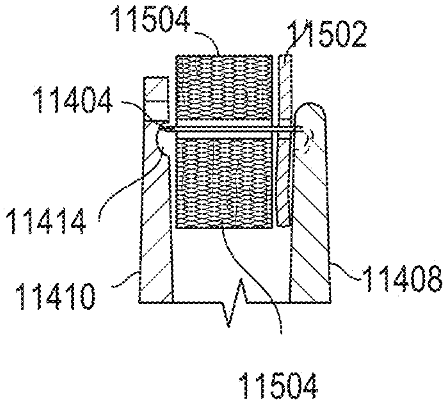
Figure 115E:
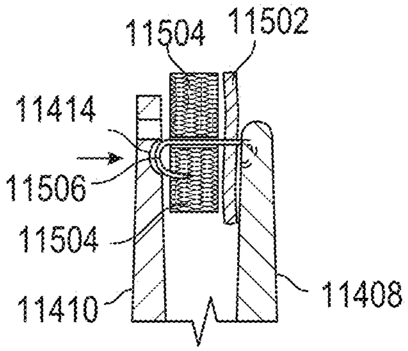
Figure 115F:
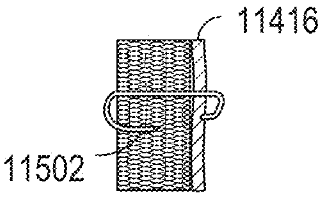

In FIG. 115C and FIG. 115D, the jaws 11408, 11410 are closed, compressing tissue 11504 onto the staple tip 11404 and sending the staple tip 11404 into the anvil 11414 on the second jaw 11410. The entire device may be maneuvered to lift the tissue/ADM and check if underlying structures were grabbed unintentionally. In FIG. 115E, the jaws 11408, 11410 continue to close, causing the anvil 11414 to curl/close the staple leg 11506 and fix the ADM 11502 to tissue 11504. The anvil 11414 also serves as a guard to prevent the staple leg from grabbing unintended material during staple formation. FIG. 115F shows the staple 11402 in place with the jaws withdrawn.

Figure 116A:
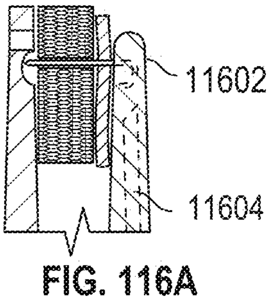
FIGS. 116A-116B shows an alternative embodiment for closing a staple.
Figure 116B:
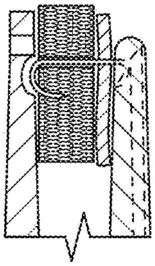

FIGS. 116A and 116B illustrate an alternative embodiment for closing the staple. In the first jaw 11602, an element 11604 (such as a wedge or other mechanism) is actuated. This advances the staple within the first jaw towards the anvil (where the anvil is in the second jaw), causing anvil to curl/close the staple leg and fix the ADM to tissue. This mechanism could be used solely on its own to close the staple, or it could be used in conjunction with closing the jaws as described in FIG. 115.

Figure 117:
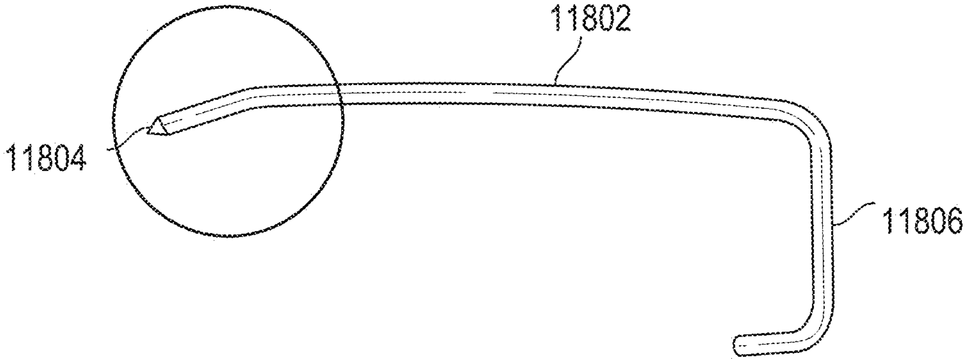
FIG. 117 shows an embodiment of a staple with pre-formed features and a pre-bent tip.

FIG. 117 shows an alternative embodiment of a staple 11802 with pre-formed features 11806 and a pre-bent tip 11804 that enables the staple leg to bend in the proper direction in the anvil (instead of jamming or buckling in the anvil).

Figure 118A:
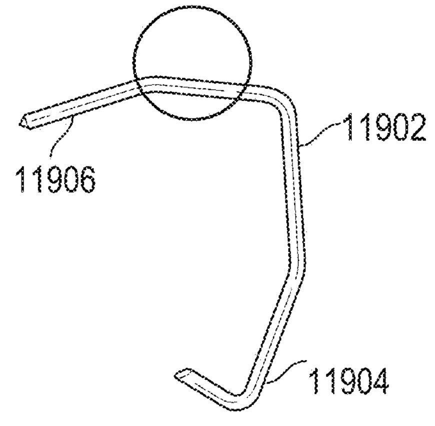
FIGS. 118A-118C show an embodiment of a staple with pre-formed features and a pre-bent tip.
Figure 118B:
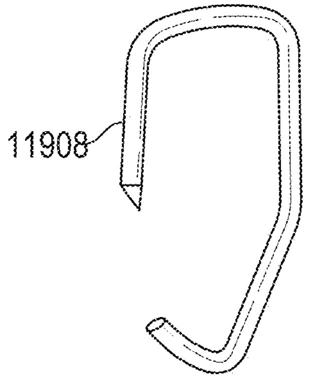
Figure 118C:
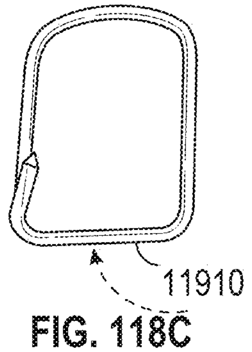

FIGS. 118A-C show an alternative embodiment of a staple 11902 with pre-formed features 11904 and a pre-bent tip 11906 that enables the staple leg 11908 to bend in the proper direction in the anvil (not shown). This pre-bent tip 11906 can help prevent jamming or buckling in the anvil. Staple closing is accomplished by bending the distal end or leg 11908 in the anvil, as shown in FIG. 118B, and bending the proximal end or leg 11910 with a plunger or other mechanism, as shown in FIG. 118C.

Figure 119A:
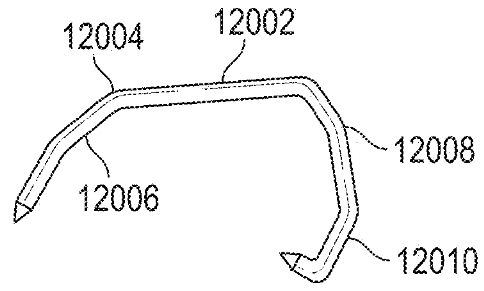
FIGS. 119A-119C show an embodiment of a staple comprising multiple pre-bends.
Figure 119B:
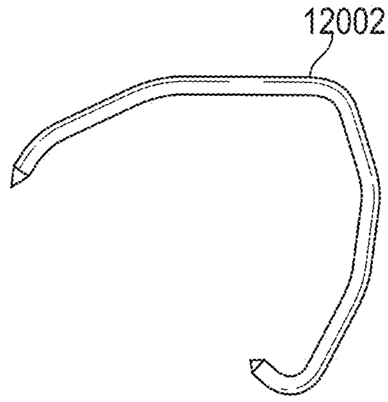
Figure 119C:
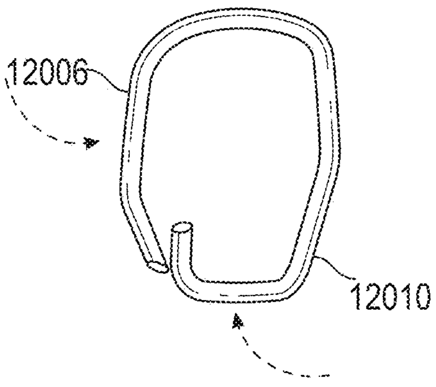

FIGS. 119A-C show an alternative embodiment of a staple 12002 containing multiple pre-bends 12004 on the distal leg 12006 and multiple pre-bends 12008 on the proximal leg 12010. Staple closing is accomplished by bending the distal end or leg in the anvil and bending the proximal end or leg with a plunger or other mechanism. The staple 12002 is shown in its closed configuration in FIG. 119C.

Figure 120:
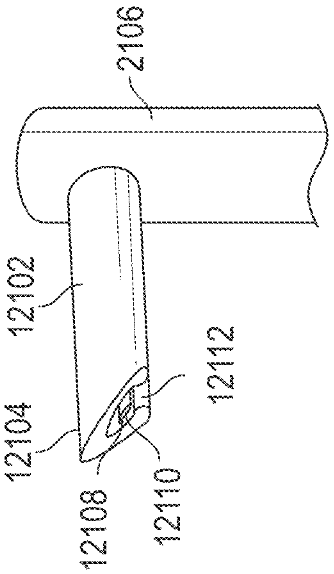
FIG. 120 shows an embodiment of a jaw comprising a shroud configured to cover a staple.

FIG. 120 illustrates a shroud 12102 with a sharpened tip 12104 attached to a jaw 12106. The staple 12108 resides in the lumen 12110 of the shroud. The sharpened shroud tip facilitates penetration through a target material (e.g., ADM). The shroud 12102 provides rigidity for the staple 12108. This design mitigates undesired staple leg bending or deforming from user applied forces (e.g. that may cause the staple leg to miss the staple forming features on the second jaw, or that may cause improper staple closing). The shroud slot 12112 allows the staple to close. The staple may or may not have a sharpened tip. The rigid shroud could also allow for smaller staples since the shroud takes the user applied forces instead of the staple.

Figure 121A:
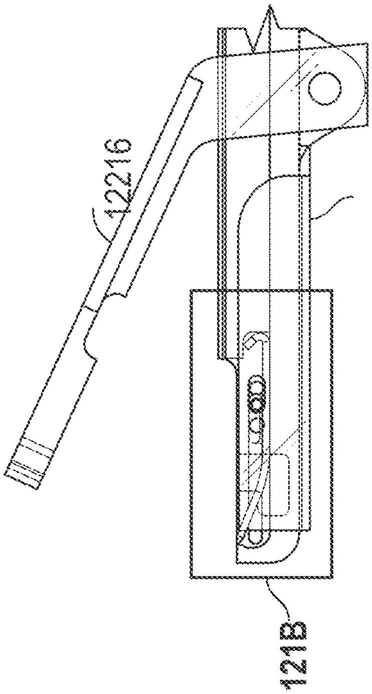
FIGS. 121A-121C show an embodiment of a stapling device.
Figure 121C:
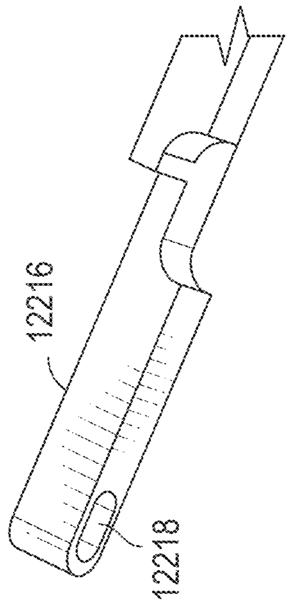
Figure 121B:
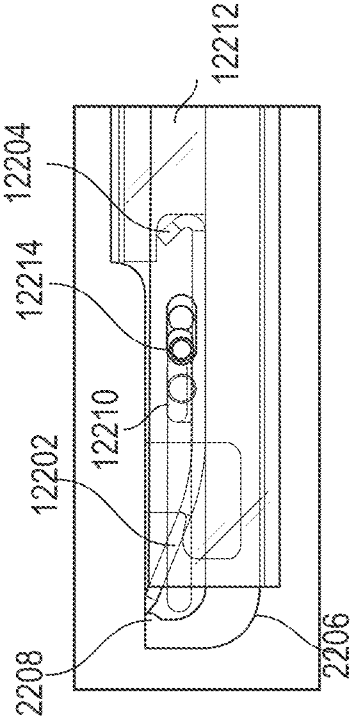

FIGS. 121A-C show various views of an embodiment of a device 12200 with staple 12202 with staple barb 12204 residing in a first jaw 12206. As shown in FIG. 121A, a first end of the staple is bent at an angle, causing it to extend towards the exit of the first jaw. The first jaw comprises a forming feature 12208. The device also comprises sliding forming member 12210, push rod 12212, stop 12214, cover (transparent to enable visibility of internal features), and second jaw 12216. FIG. 121C shows the hole 12218 in the second jaw 12216.

Figure 122A:
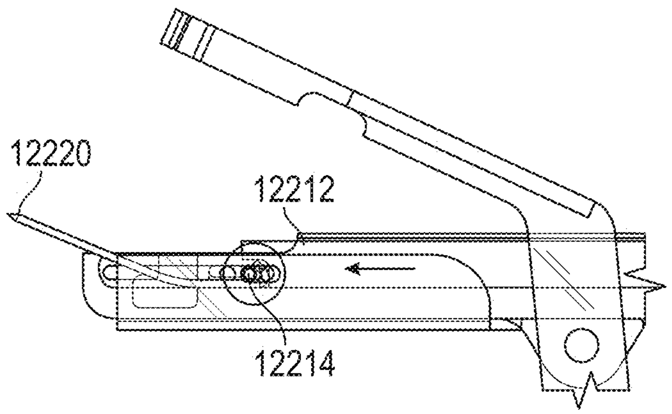
FIGS. 122A-122M show an embodiment of using the device of FIGS. 121A-121C.

FIGS. 122A-M show an embodiment of a method of using the device 12200 of FIGS. 121A-C. The device 12200 is inserted to the surgical site with the staple tip residing in the lower jaw 12206. As shown in FIG. 122A, the push rod 12212 is advanced until the staple barb 12204 contacts the stop 12214, causing the staple tip 12220 to extend out of the first jaw 12206.

Figure 122B:
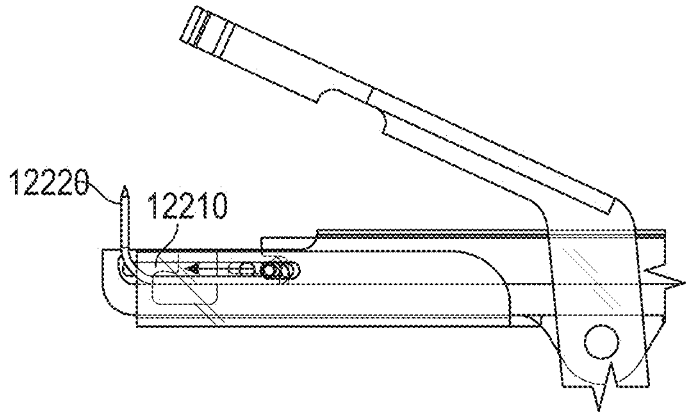
Figure 122C:
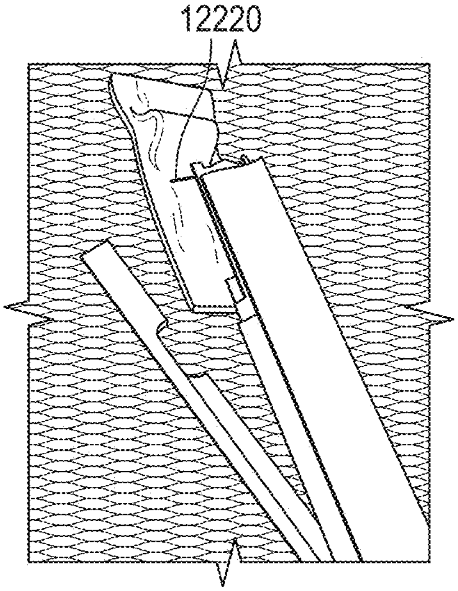

FIGS. 122B and 122C show the sliding forming member 12210 advanced, causing the staple tip to bend by pressing the staple 12202 against the forming feature 12208. FIG. 122B shows a schematic view of the device 12200, such that the internal components are visible, while FIG. 122C shows the device being used in a procedure, such that the internal components are not visible. Alternatively, the staple tip bending described above could be done prior to inserting to the surgical site, and the second jaw could be closed to conceal the staple tip while the device is inserted to the surgical site.

Figure 122D:
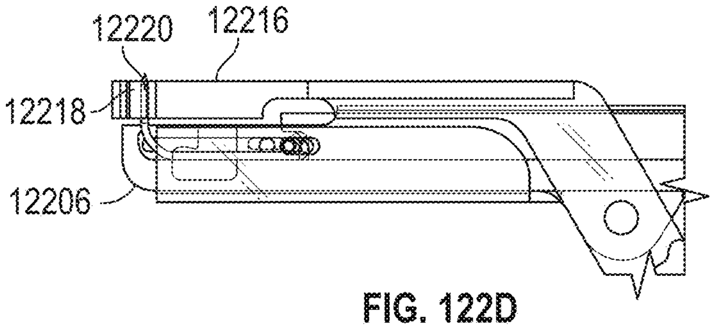
Figure 122E:
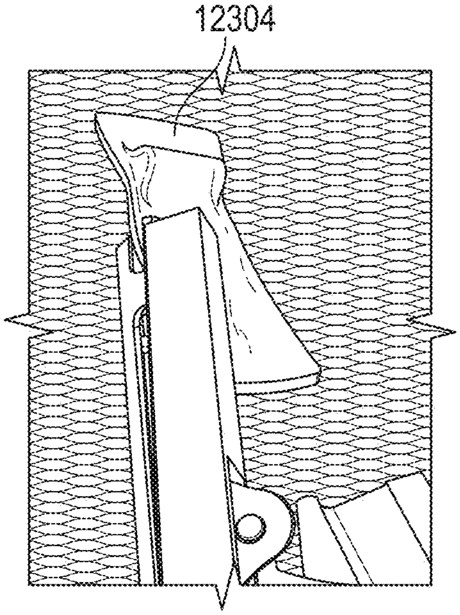

FIGS. 122D and E show the staple tip 12220 being used to target the fixation location on the target material 12304, in this case, ADM. Then the jaws 12206, 12216 are closed, causing the staple tip 12220 to puncture the ADM 12304 by entering the hole 12218 in the second jaw 12216.

Figure 122F:
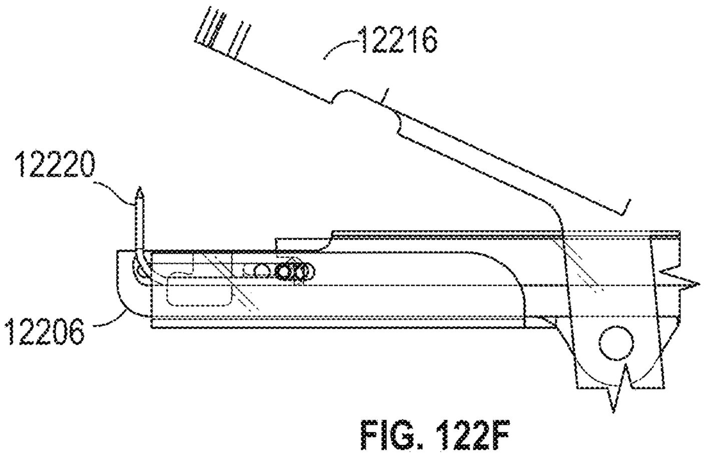
Figure 122G:
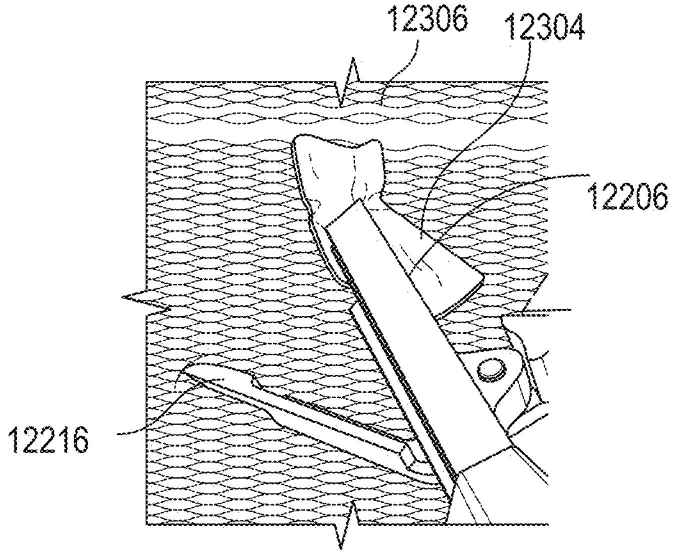

As shown in FIGS. 122F and G, the stop 12214 (contacting the staple barb) is disengaged. The jaws 12206, 12216 are then opened. The target material, in this case, ADM, is positioned to the second target material 12306 (e.g. tissue). The staple tip 12220 is used to target the fixation location on the second target material 12306. FIG. 122F shows a schematic view of the device 12200, while FIG. 122G shows the device 12200 while it is performing a stapling procedure.

Figure 122H:
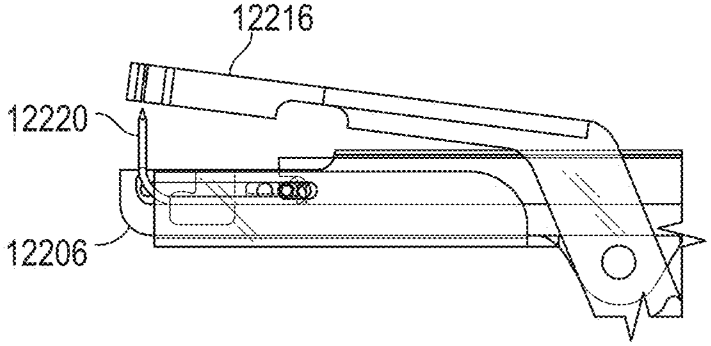
Figure 122I:
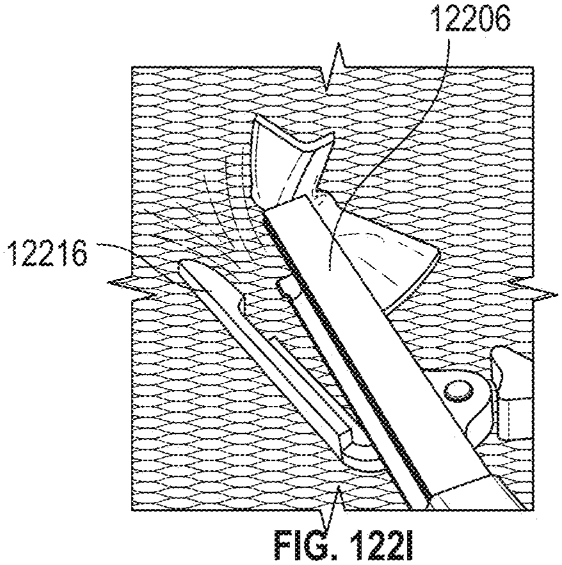

In FIGS. 122H and 122I, the jaws 12206, 12216 are closed, compressing tissue 12306 onto the staple tip 12220. The entire device may be maneuvered to retract the tissue/ADM in order to avoid underlying structures during staple deployment. FIG. 122H shows a schematic view of the device 12200, while FIG. 122I shows the device 12200 while it is performing a stapling procedure.

Figure 122J:
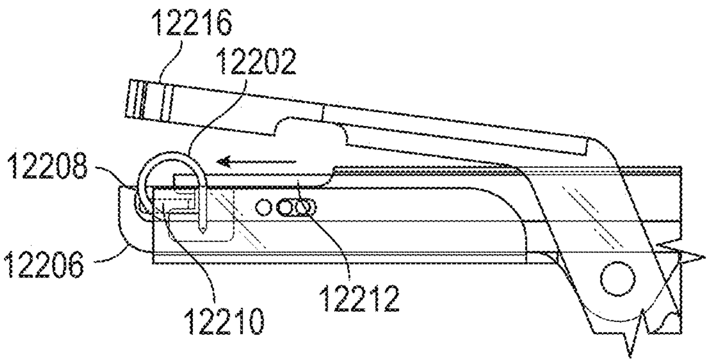
Figure 122K:
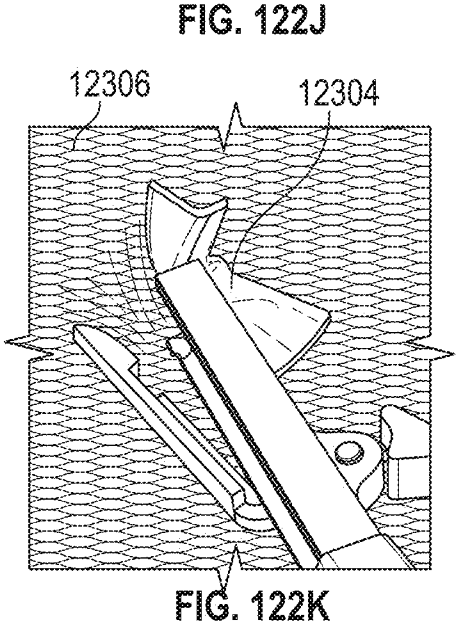

In FIGS. 122J and 122K, the push rod 12212 is advanced. When the sliding forming member 12210 is in its forward position, it bends the staple by compressing it against the forming feature 12208 in the first jaw 12206. As the push rod 12212 advances the staple, the compression zone (created by the forming feature 12208 and the sliding forming member 12210) continuously deforms the staple as the staple advances through the compression zone, causing the staple to curl. The curled staple fixes the ADM 12304 to tissue 12306. The second jaw 12216 also serves as a guard to prevent the staple leg from grabbing unintended material during staple formation. FIG. 122J shows a schematic view of the device 12200, while FIG. 122K shows the device 12200 while it is performing a stapling procedure.

Figure 122L:
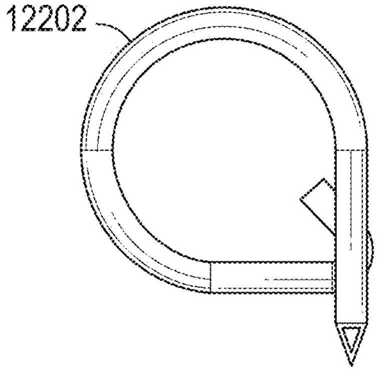
Figure 122M:
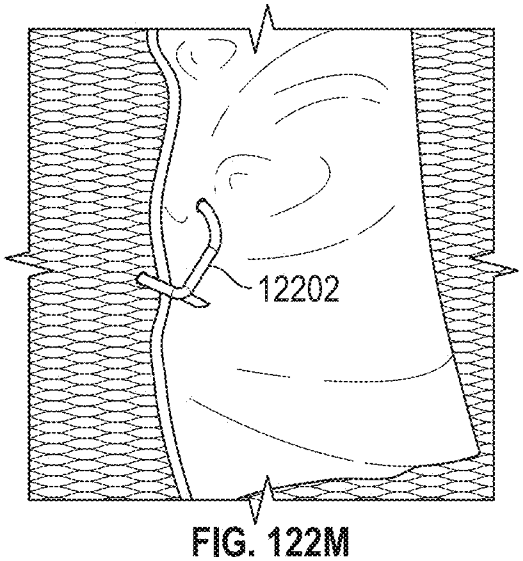

FIGS. 122L and 122M show the staple 12202 after release from the device 12200. FIG. 122L shows a schematic view of the closed staple 12202, while FIG. 122M shows the closed staple 12202 after performing the stapling procedure.

Figure 123A:
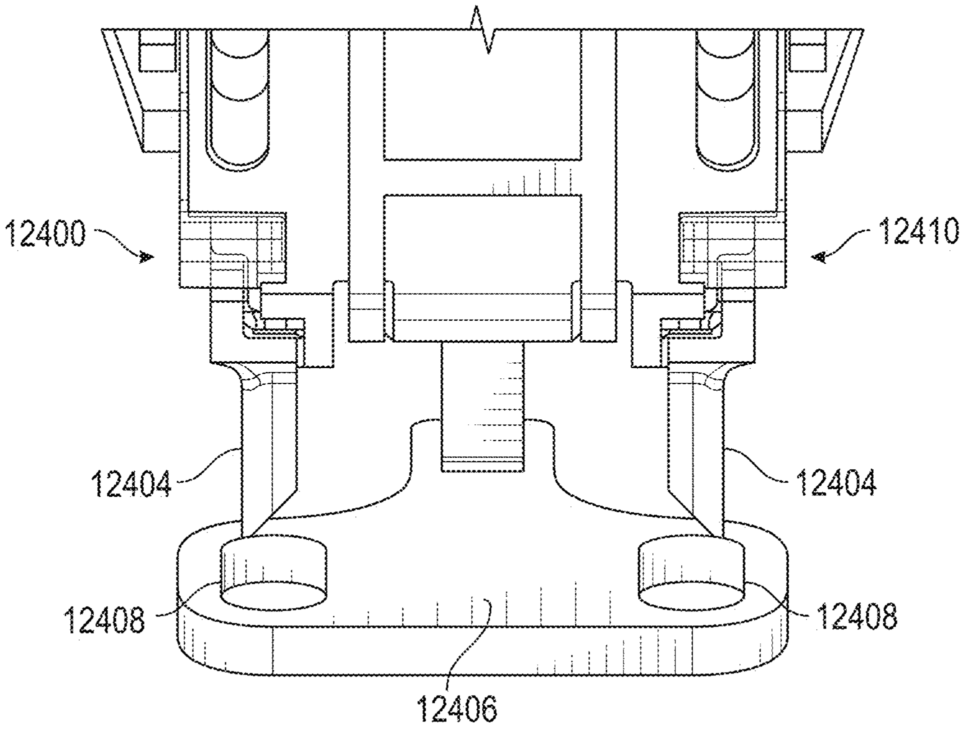
FIGS. 123A-123B show an embodiment of a stapling device.
Figure 123B:
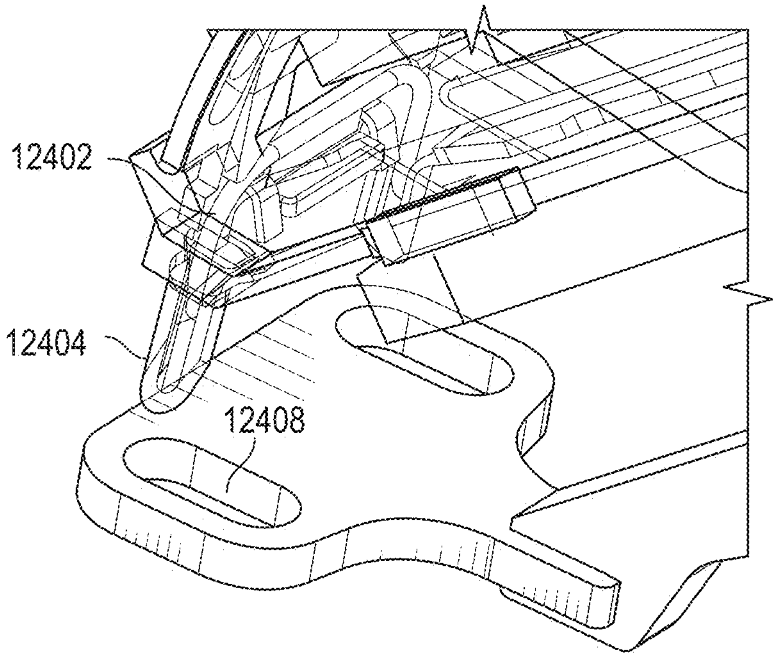

FIGS. 123A and 123B show a portion of a device 12400 with staple 12402 residing in fangs 12404. The fangs 12404 are part of a head 12410 portion of the device. The device 12400 also comprises a retractable backstop 12406. The backstop 12406 has holes 12408 that are shaped to accept the fangs 12404. The backstop 12406 retracts relative to the fangs 12404 of the device. When it is retracted, the backstop 12406 moves proximally relative to the fangs 12404 (shown best in FIG. 124E). Using the backstop with holes shaped to accept the piercing element (e.g., the fangs), allows the device to pierce a tough material, such as ADM, without having to apply high force or pressure to the tissue. In some embodiments, the staple itself can function as the piercing element.

Figure 124A:
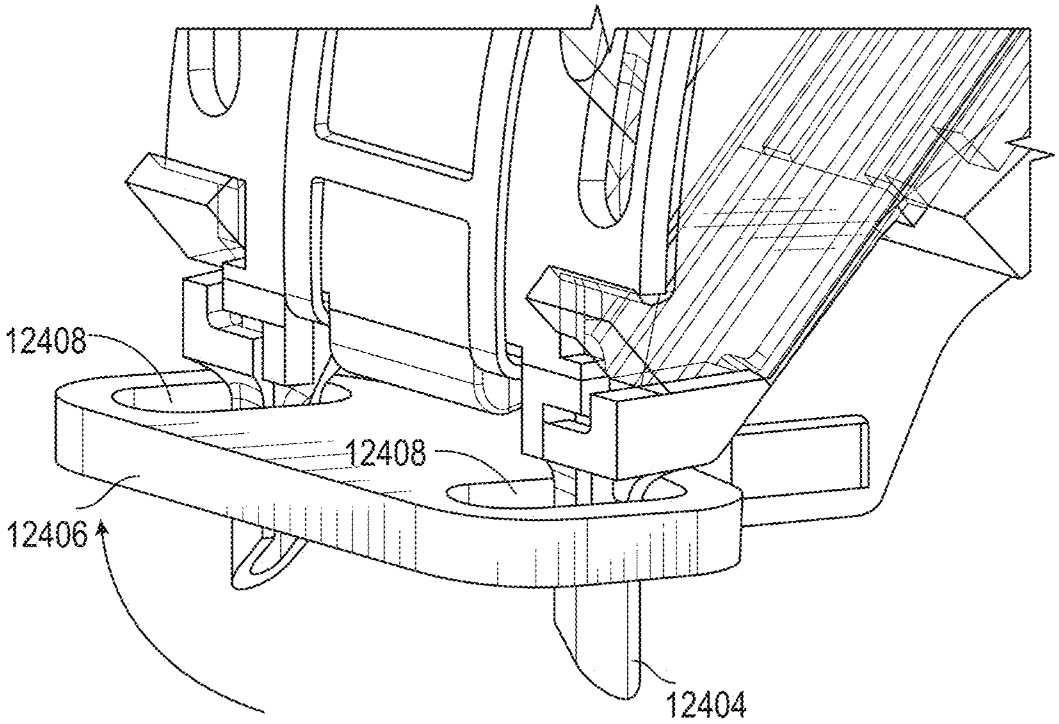
FIGS. 124A-124K show an embodiment of using the device of FIGS. 123A and 123B.
Figure 124B:
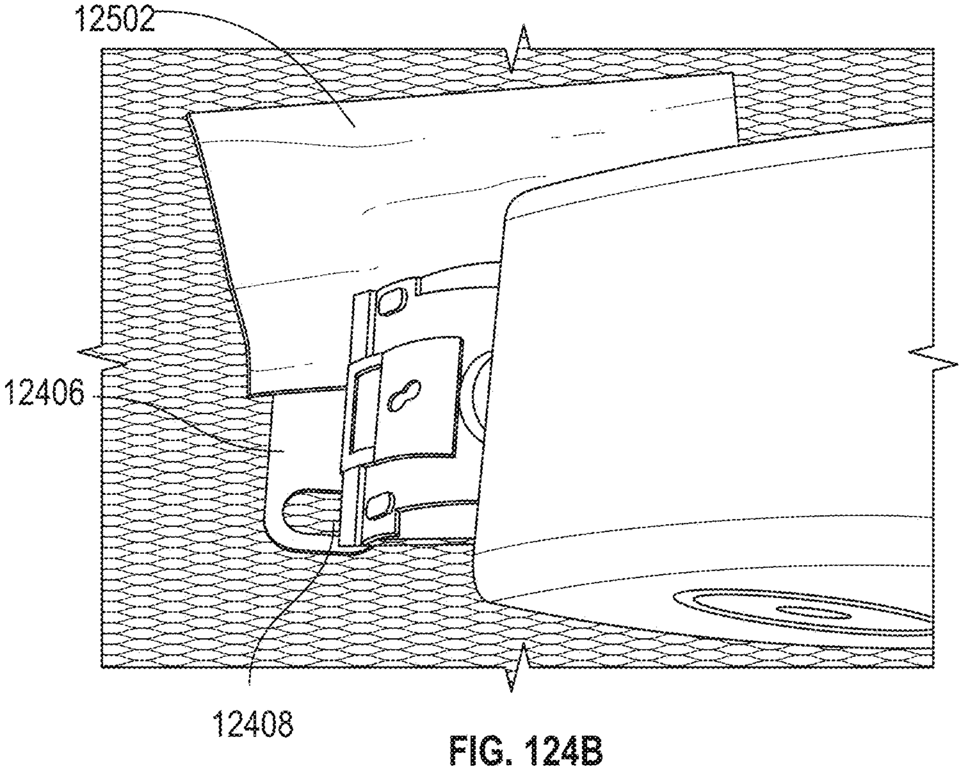

FIGS. 124A-L show an embodiment of a method of using device 12400 shown in FIGS. 123A and 123B. FIGS. 124A and B show the device 12400 maneuvered so that a target material to be joined 12502 (e.g., ADM) is positioned between the fang 12404 and its associated backstop hole 12408. The fang 12404 is used to target the fixation location on the ADM 12502. The backstop 12406 is then actuated to push the ADM 12502 onto the fang 12404. Similar to FIGS. 122A-L, FIG. 124A shows a schematic view of the device 12400, while FIG. 124B shows the device while it is performing a stapling procedure.

Figure 124C:
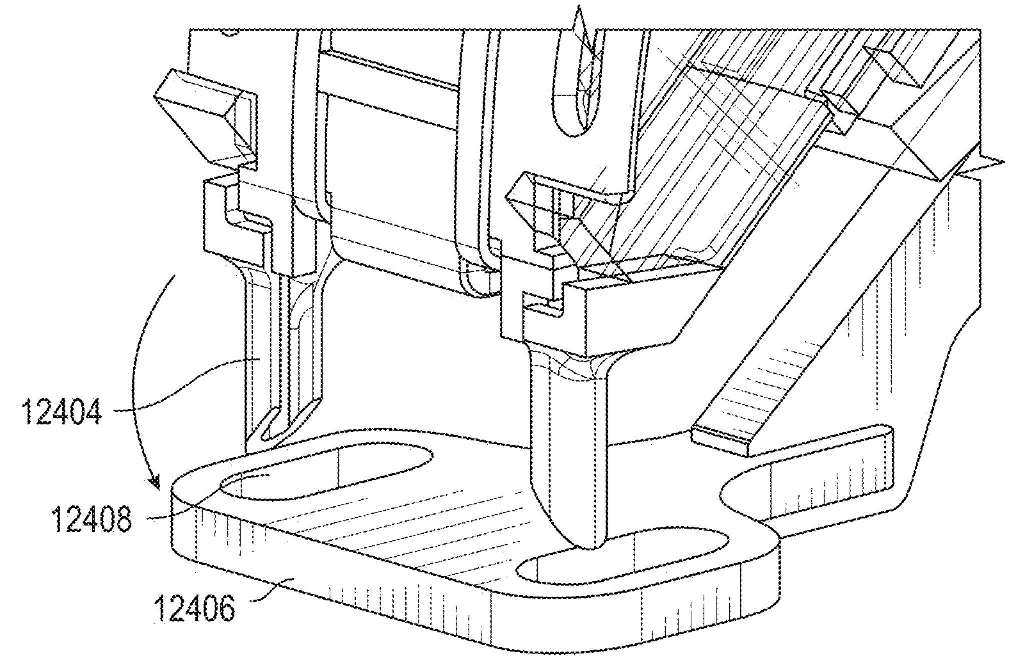
Figure 124D:
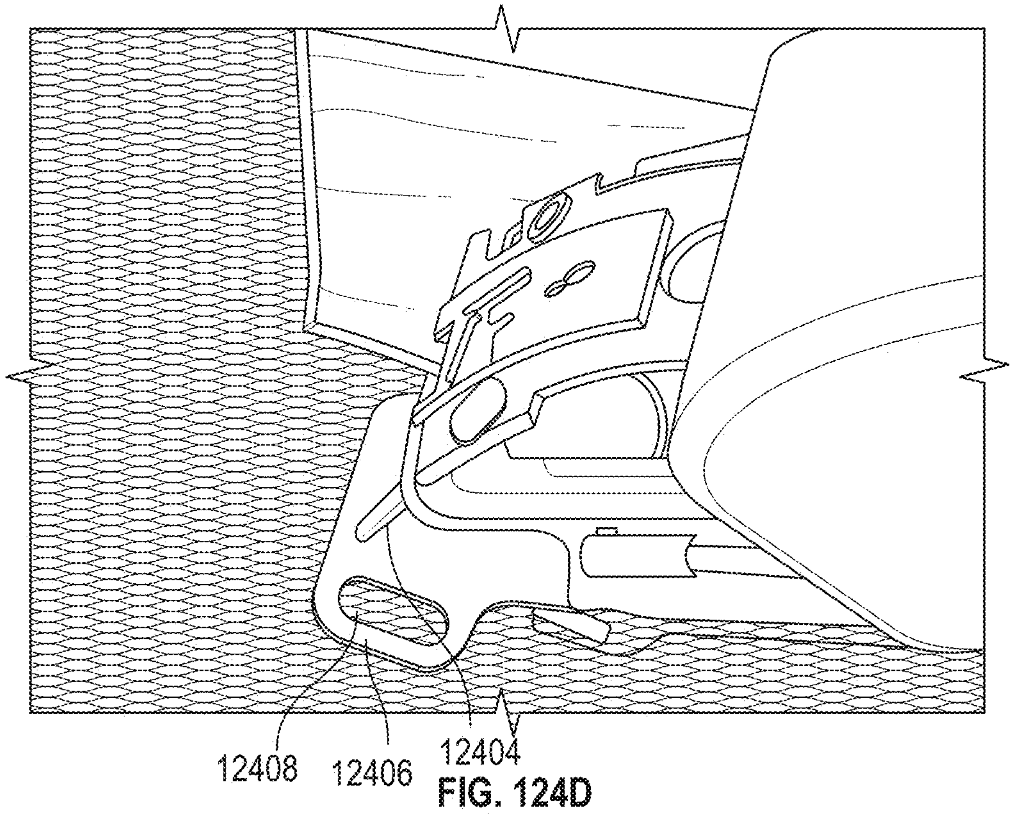

FIGS. 124C and 124D show the backstop 12406 opened to disengage from the fangs 12404, causing the holes 12408 to be withdrawn from the fangs 12404. FIG. 124C shows a schematic view of the device 12400, while FIG. 124D shows the device while it is performing a stapling procedure.

Figure 124E:
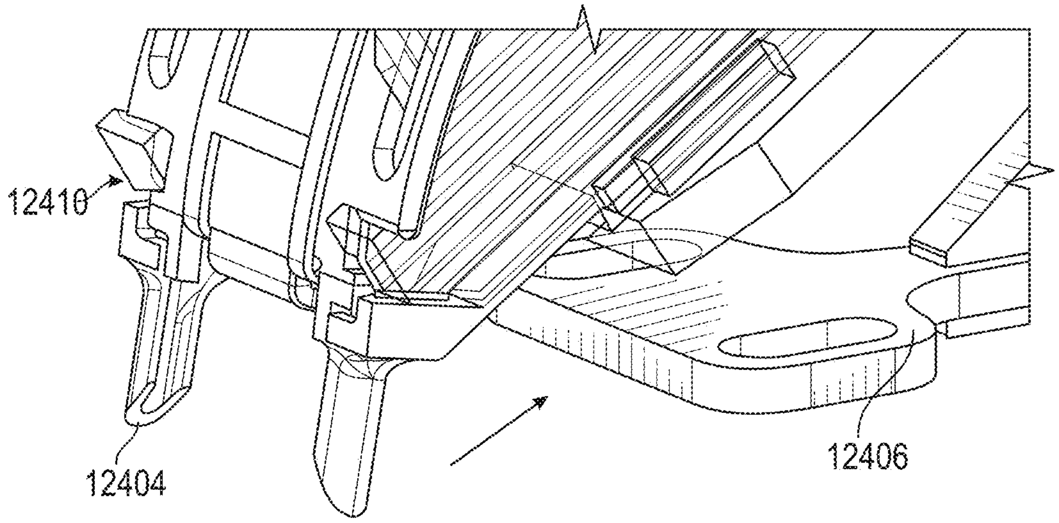
Figure 124F:
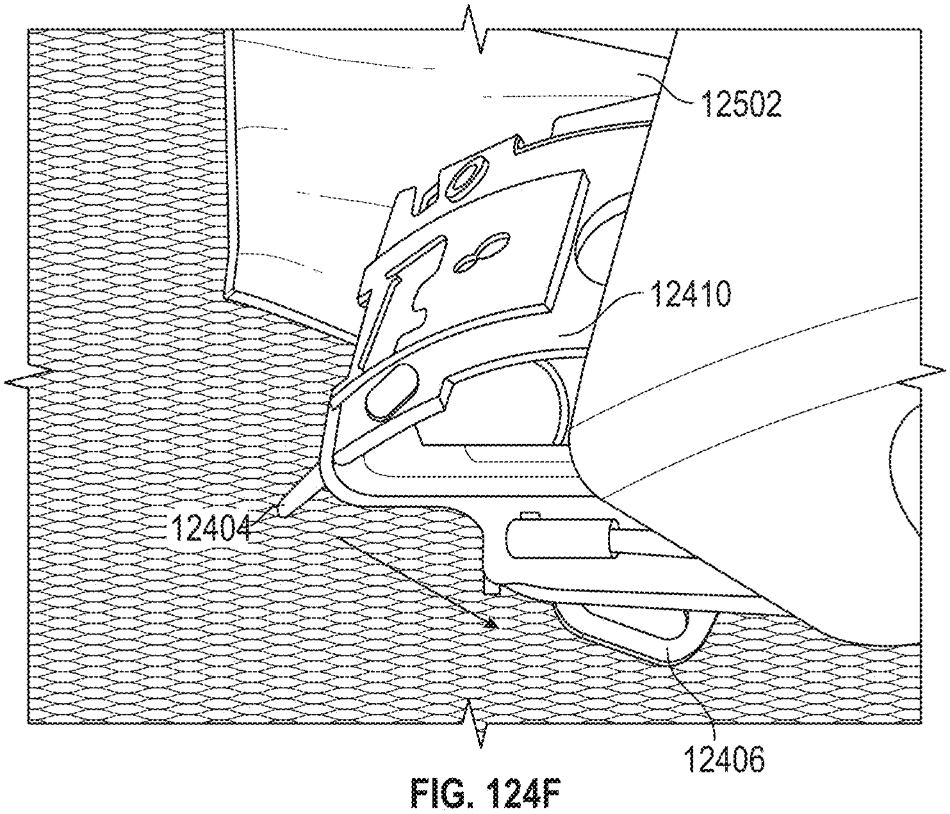

FIGS. 124E and 124F show the backstop 12406 being retracted, such that it is moved proximally relative to the fangs 12404, exposing fangs 12404. FIG. 124E shows a schematic view of the device 12400, while FIG. 124F shows the device while it is performing a stapling procedure.

Figure 124G:
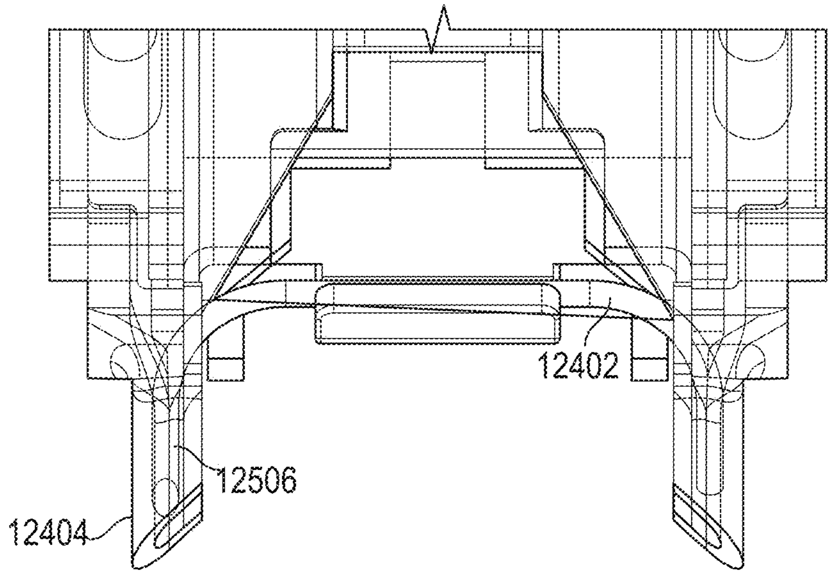
Figure 124H:
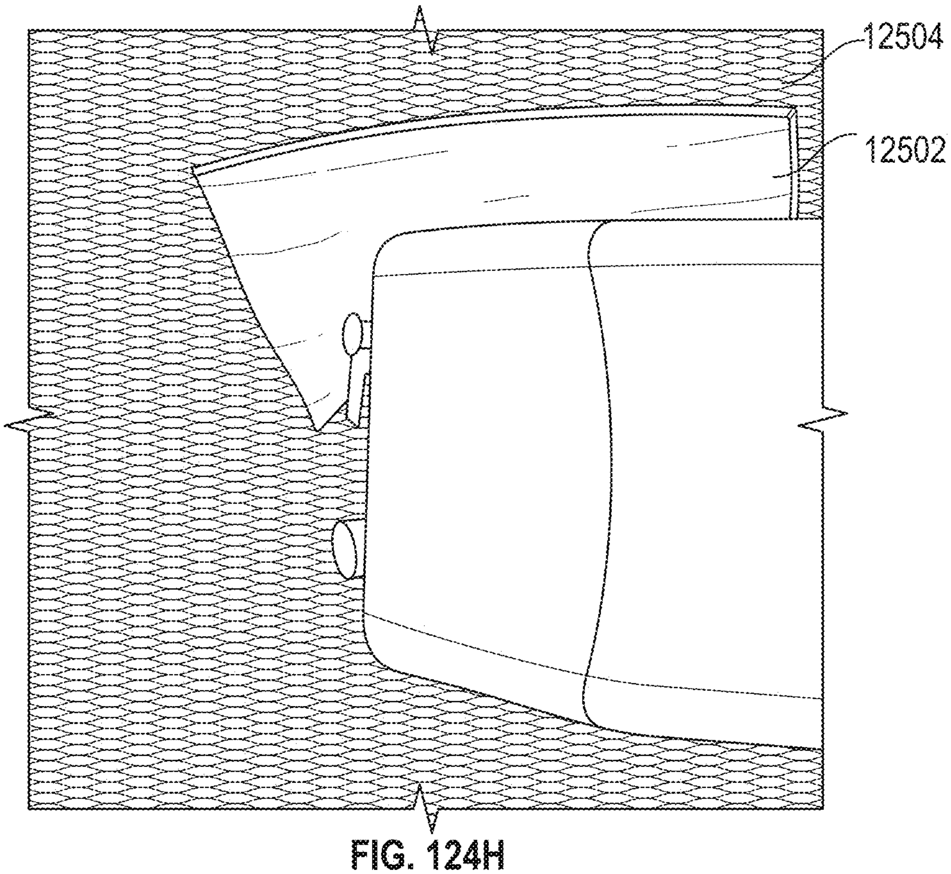

In FIGS. 124G and 124H, the fang 12404 was used to target the fixation location on the second target material, in this case, tissue 12504, and position the ADM 12502. The fangs 12404 are then inserted into tissue 12504. The length of the fangs 12404 is sized to penetrate tissue 12504 to a certain depth. The fangs 12404 prevent the staple 12402 from grabbing/damaging underlying structures.

Figure 124I:
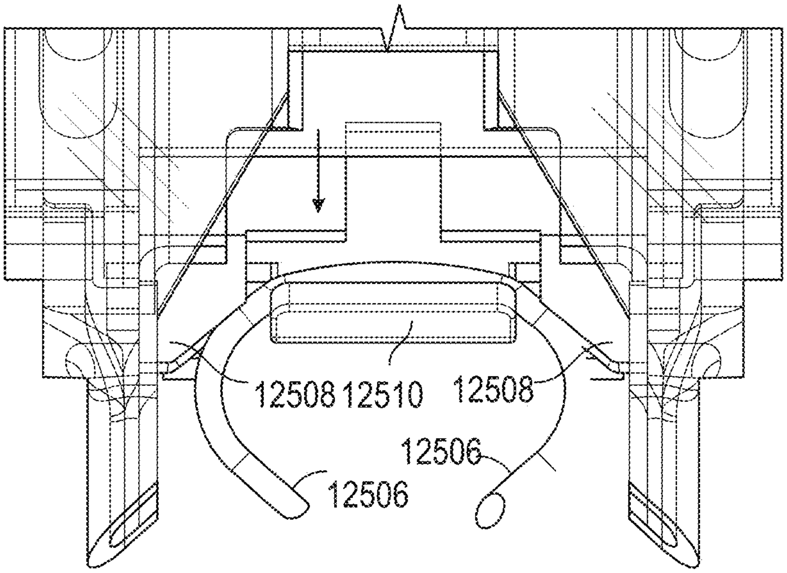
Figure 124J:
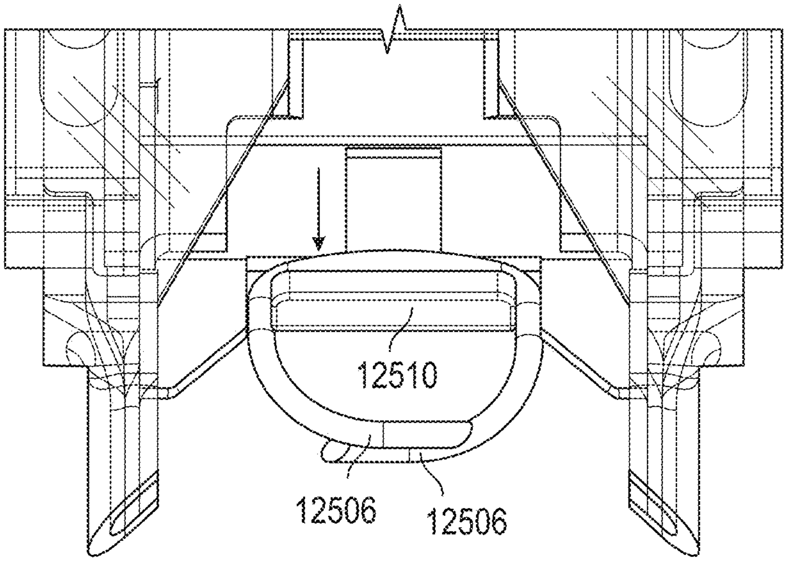

FIGS. 124I and 124J show the staple 12402 being formed. The span of the staple 12402 rests on a center die 12510. The outer dies 12508 are actuated to bend the staple on center die 12510. Actuating the outer dies 12508 comprises moving them in the direction indicated by the arrow in FIGS. 124I and 124J. The staple legs 12506 bend inward to gather, compress and fix the ADM to tissue.

The staple could also be deployed in stages. In the first stage, shown in FIG. 124I, the staple 12402 grasps ADM 12502 and tissue 12504. Prior to fully closing the staple, the device may be maneuvered to retract the tissue/ADM in order to avoid underlying structures prior to fully closing the staple. While holding the tissue/ADM away from underlying structures, the staple can be fully closed, as shown in FIG. 124J.

Figure 124K:
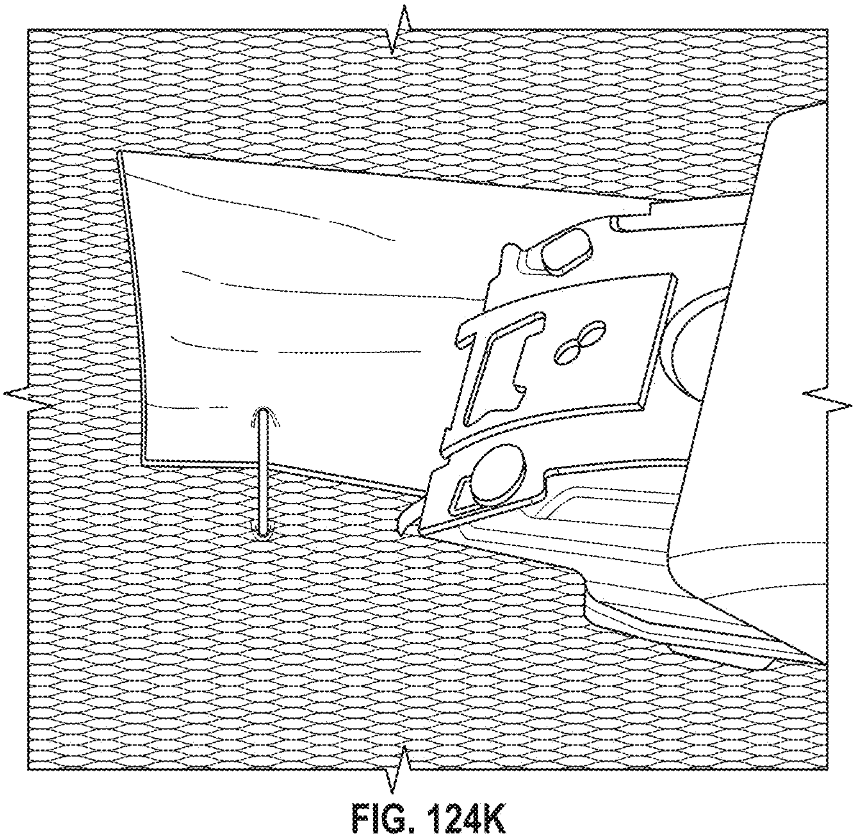

In FIG. 124K, the staple comes off of the center die and is detached from the stapler. Ejectors could assist with pushing the staple off the center die.

An alternative method for using the device described in FIGS. 123A-124K is excluding the use of the backstop by piercing the onlay material and underlying tissue directly with the fangs such that the fangs pierce through the onlay material and into the underlying tissue. The staple can then be fully deployed and closed as described in FIGS. 124I-124J. The staple could also be deployed in stages. In the first stage, shown in FIG. 124I, the staple 12402 grasps ADM 12502 and tissue 12504. Prior to fully closing the staple, the device may be maneuvered to retract the tissue/ADM in order to avoid underlying structures prior to fully closing the staple. While holding the tissue/ADM away from underlying structures, the staple can be fully closed, as shown in FIG. 124J.

Figure 125:
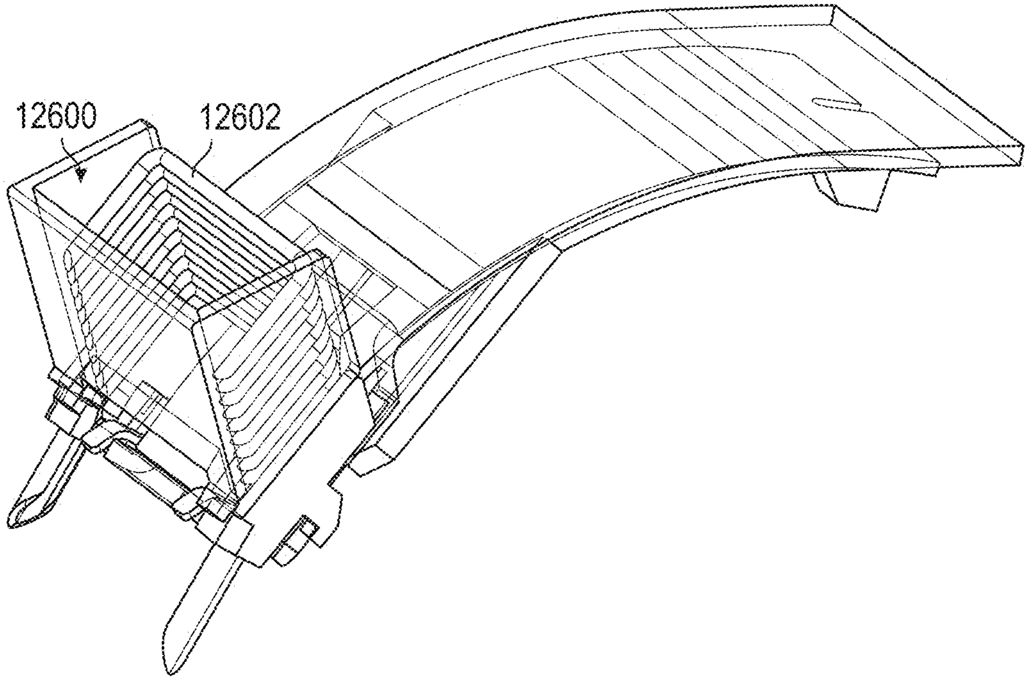
FIG. 125 shows an embodiment of a staple reservoir.

In some embodiments, the device 12400 comprises a staple reservoir 12600 shaped and configured to hold a plurality of staples, as shown in FIG. 125. The staple reservoir 12600 can be fixed to the stapler device 12400 or could be a replaceable cartridge.

Figure 126:
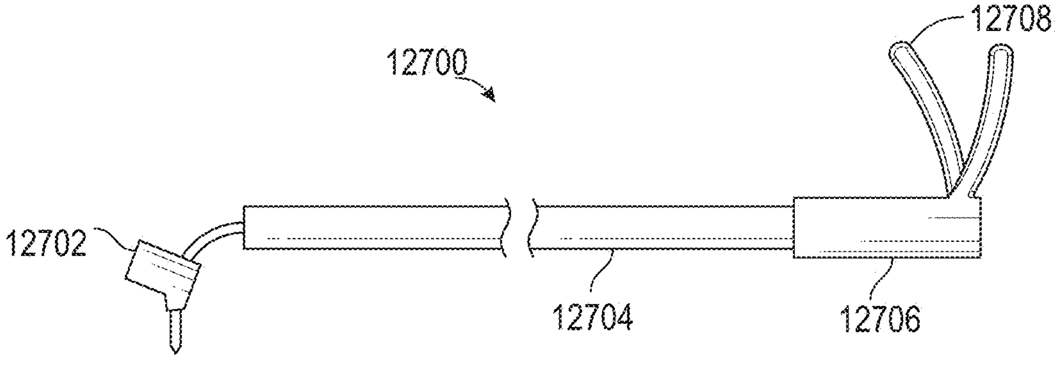
FIG. 126 shows an embodiment of a device 12700 comprising a stapler head 12702 similar to the structure shown in FIG. 125

FIG. 126 shows an embodiment of a device 12700 comprising a stapler head 12702 similar to the structure shown in FIG. 125. The stapler head 12702 is positioned at a distal end of a shaft 12704 which enables staple placement in confined locations. The device 12700 comprises a handle 12706 and actuator 12708, which can be used to control the function of the stapling mechanism.

Figure 127A:
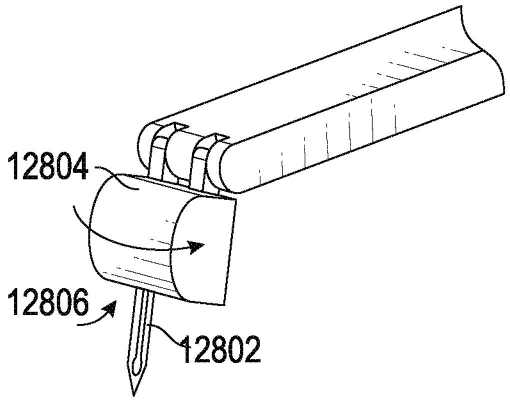
FIGS. 127A and 127B show an embodiment of a device comprising a stapler head similar to the structure shown in FIGS. 123A and 123B.
Figure 127B:
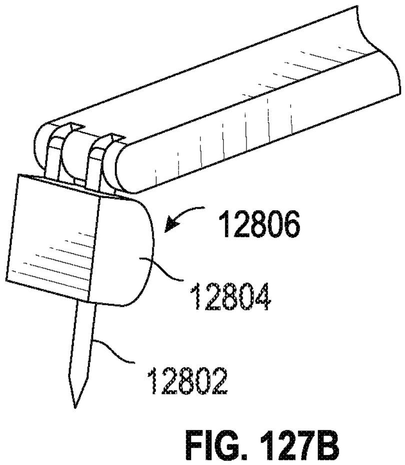

FIGS. 127A and 127B show an embodiment of a device 12800 with one fang 12802 on a rotating head 12804 to enable staple placement on, for example, both sides of a breast implant and/or in confined locations. FIG. 127A shows the device 12800 with the rotating head positioned so that the fang 12802 is on a first side of the device 12806. FIG. 127B shows the device 12800 with the rotating head rotated about 180°, such that the fang 12802 is on a second side of the device 12806. The head can also rotate through a range of angles.

Figure 128A:
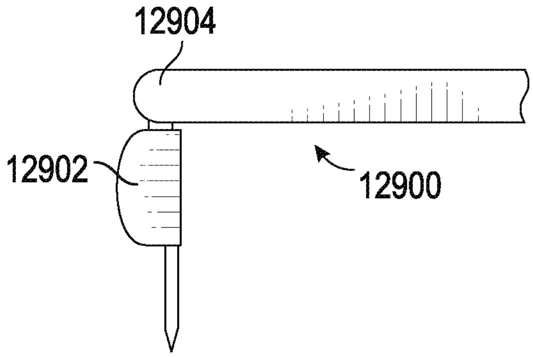
FIGS. 128A-128C show an embodiment of a stapling device with an articulating head.
Figure 128B:
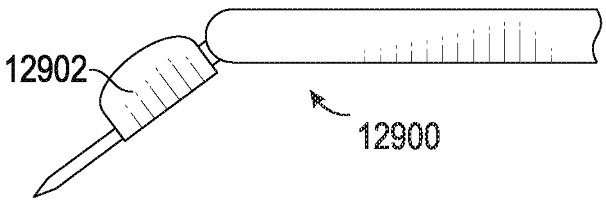
Figure 128C:
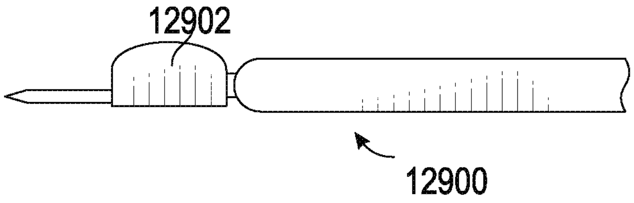

FIGS. 128A-C show an embodiment of a device 12900 with an articulating head 12902. The articulating head 12902 can enable staple placement in confined locations. The head 12902 can articulate, in some embodiments, by rotating around hinge point 12904. FIGS. 128A-C show the head 12902 articulated through a first, second, and third position, respectively.

Figure 129A:
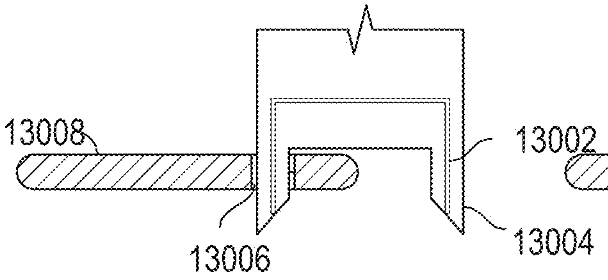
FIGS. 129A-129B show an embodiment of a fang and staple stretching a hole in a target material.
Figure 129B:
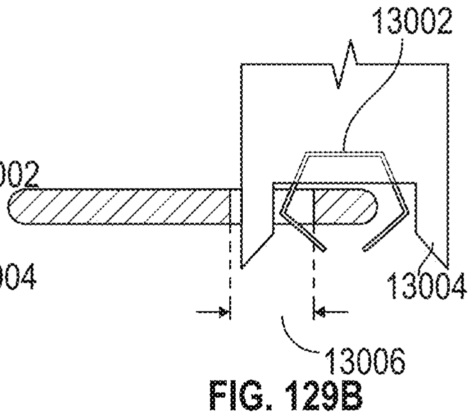

In the embodiments of staple formation described herein, as shown more clearly in FIGS. 129A and 129B, the fang 13004 and staple 13002 stretch the hole 13006 in the target material 13008 (e.g., ADM) as the staple 13002 forms. The stretching hole 13006 resists the closing staple. In some embodiments, the devices or mechanisms comprise further features to enhance or improve staple formation.

Figure 130A:
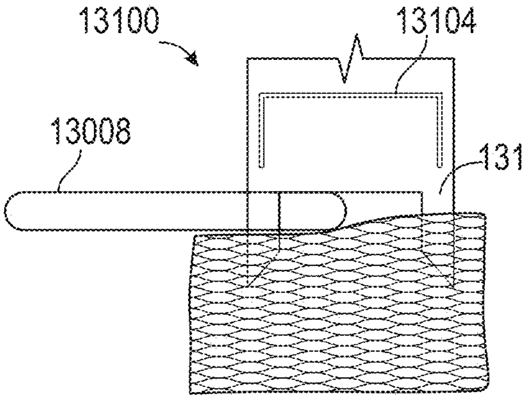
FIGS. 130A-130C show an embodiment of a device with retractable fangs.
Figure 130B:
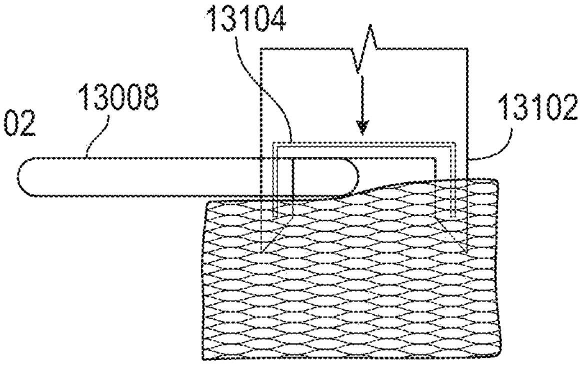
Figure 130C:
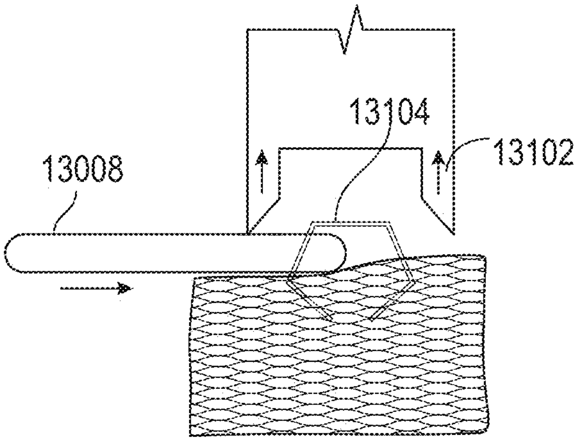

FIGS. 130A-C show a device 13100 with retractable fangs 13102. When the staple 13104 starts to clinch (the staple closing dies are not shown), the fangs 13102 retract, as shown in FIG. 130C. With the fangs retracted, the ADM can more easily comply with the forming staple leg.

Figure 131A:
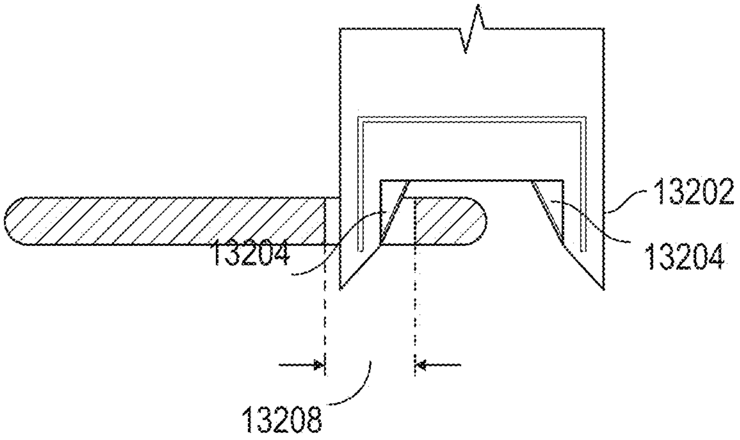
FIGS. 131A-131C show an embodiment of a fang comprising a blade.
Figure 131B:
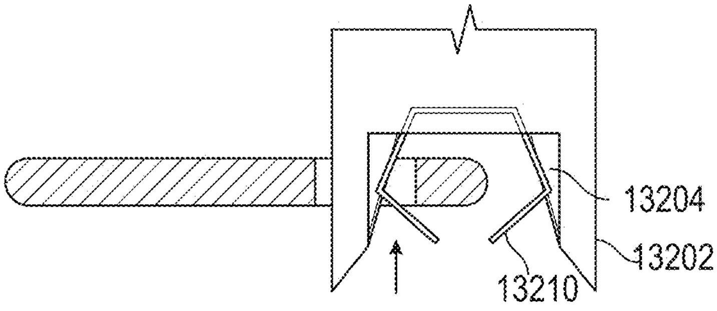
Figure 131C:
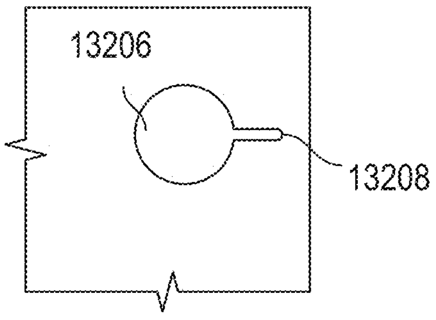

FIGS. 131A-B show an embodiment of an optional feature that could exist on a fang or device. In some embodiments, the fang 13202 comprises a blade 13204 that creates a slit 13208 in the fang hole 13206 (the hole created by the fang in the target material). As shown the blade can extend along the length of the fang (e.g., at its shorter side), and can comprise a tapered shape. When the staple forms, the staple leg 13210 can enter the slit so that the leg can fully close. FIG. 131C shows a top view of an exemplary fang hole 13206 and slit 13208 created by the fang 13202 and blade 13204 combination of FIGS. 131A and 131B.

Figure 132:
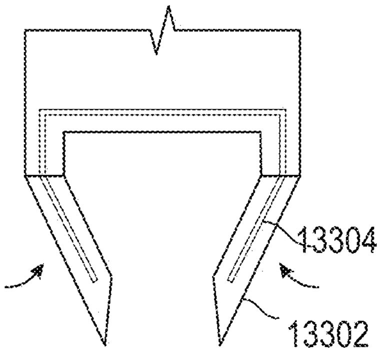
FIG. 132 shows an embodiment of an articulating fang.

FIG. 132 shows an embodiment of fangs 13302 that articulate. The fangs 13302 can serve to bend the staple tips 13304 inward and aide staple closing. The articulating fangs can also grasp two target materials to be joined. The entire device may be maneuvered to retract the materials in order to avoid underlying structures during staple deployment. The fangs 13302 can also serve as a guard to prevent the staple legs from grabbing unintended material during staple formation.

Figure 133A:
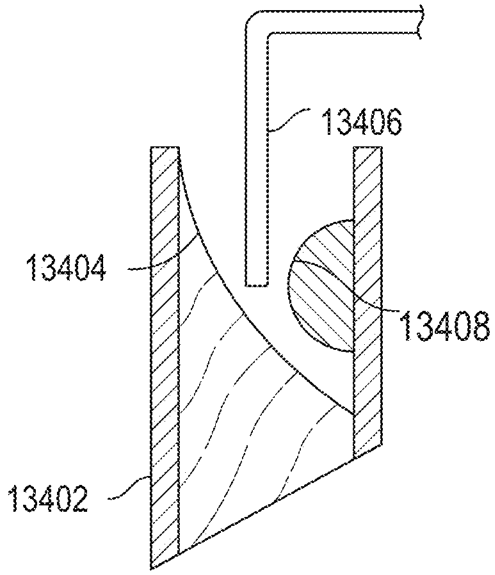
FIGS. 133A-133B show an embodiment of a fang comprising internal features configured to close a staple.
Figure 133B:
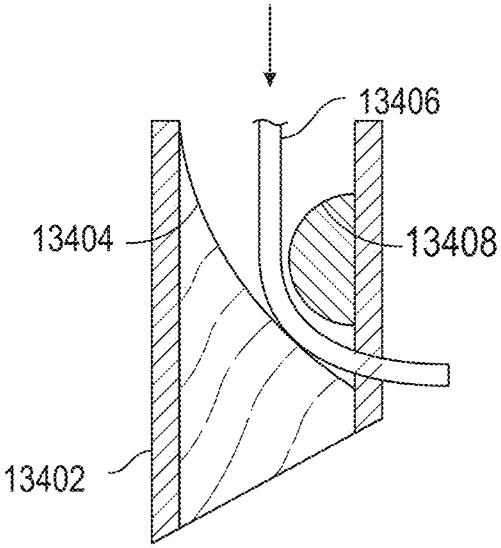

FIGS. 133A and 133B show an embodiment of fangs 13402 comprising internal features configured to close a staple. The features also serve as a guard to prevent the staple legs from grabbing unintended material during staple formation. As shown in FIGS. 133A and 133B, the features can comprise a slanted edge or surface 13404 configured to urge the staple leg 13406 inward upon moving the staple leg 13406 towards the edge or surface 13404. The features can further comprise another edge or surface 13408, around which the staple leg 13406 is configured to bend, when urged in that direction and vicinity by the slanted edge or surface 13404.

Figure 134A:
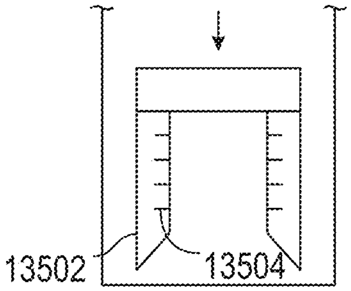
FIGS. 134A-134C show embodiments of fangs with adjustable positions.
Figure 134B:
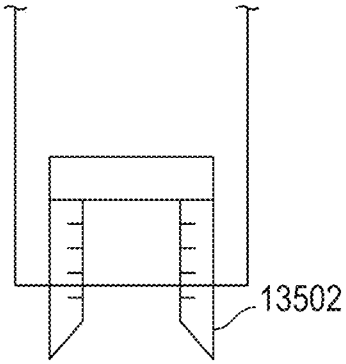
Figure 134C:
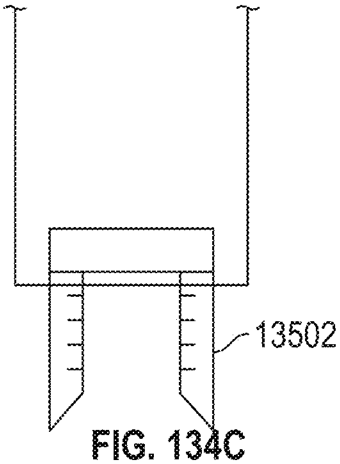

FIGS. 134A-C show fangs 13502 with adjustable positions. At a first position, shown in FIG. 134A, the fangs 13502 are concealed during device insertion and removal to prevent injury to surrounding structures. At a second position, shown in FIG. 134B, the fangs 13502 are slightly exposed, set to penetrate tissue at a shallow depth. At a third position, shown in FIG. 134C, the fangs 13502 are further exposed, set to penetrate tissue at a deeper depth. The staple can be configured to not extend past the tips of the fangs, thereby protecting underlying structures. Optional depth markers 13504 on the fangs can aid the user in setting the fangs at the proper length.

Figure 135:
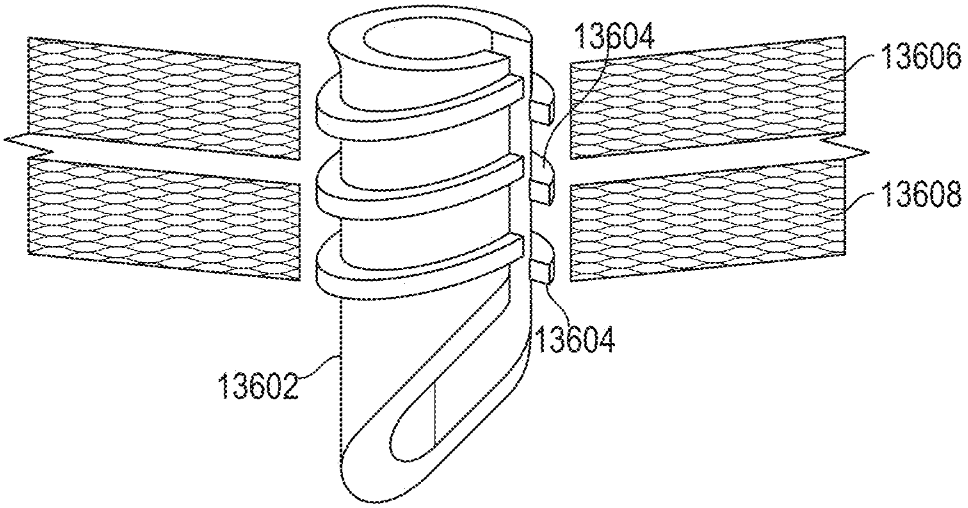
FIG. 135 shows an embodiment of a fang comprising external threads.

FIG. 135 shows an embodiment of a fang 13602 with external threads 13604. When the fang is placed on top of a first target material 13606, such as ADM, and second target material 13608, such as tissue, the fang 13602 is rotated to thread into the materials. The fang 13602 can be rotated until the desired depth into the materials is attained, avoiding underlying structures. With the threads engaged in ADM and tissue, the fang can be used to pull the ADM and tissue away to protect underlying structures during staple deployment.

Figures 136A, 136B, 136C:
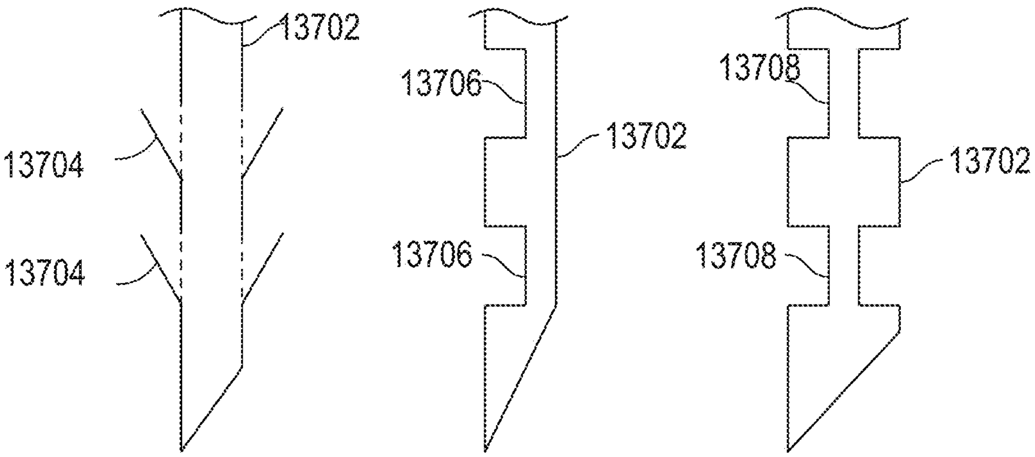
FIGS. 136A-136C show various embodiments of fangs.

FIGS. 136A-C show various embodiments of fangs 13702. FIG. 136A shows a fang 13702 with barbs 13704 positioned along a length of the fang 13702. FIG. 136B shows a fang 13702 with a plurality of notches 13706 positioned along a length of the fang 13702. FIG. 136C shows a fang 13702 with a plurality of necks 13708 positioned along a length of the fang 13702. When the fang(s) is inserted into a target material to the desired depth, the barbs, notches, and/or necks grip the target material. The fangs can be used to pull the material(s) away to protect underlying structures during staple deployment.

In some embodiments, the fang tips have various sharpened tip designs, such as lancet tip, vet (reverse grind) tip, trocar tip, etc. These various tip designs can aid in case of insertion through a tough material, such as ADM.

In some embodiments, the fangs can be replaceable. For example, the fangs can be part of a replaceable staple cartridge, as described herein. In other embodiments, the fangs are replaceable themselves, irrespective of the use of a cartridge.

Figure 137:
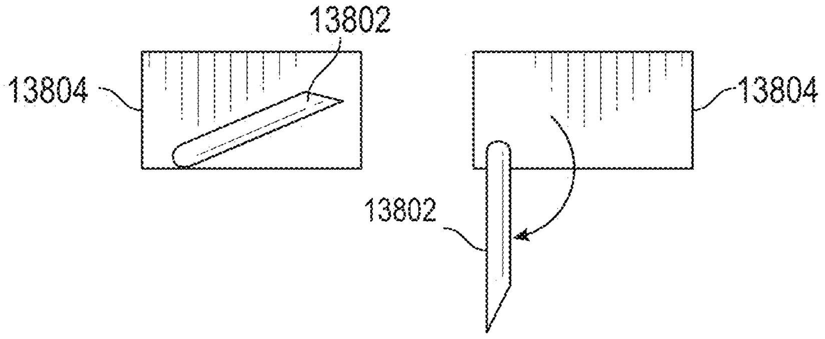
FIG. 137 shows an embodiment of a fang configured to flip down.

FIG. 137 shows an embodiment of a fang 13802 that is configured to flip (or rotate, or snap, or articulate, etc.) down. The fang can be configured to be concealed within a head 13804 of a device to protect surrounding structures. The fang 13802 can then be configured to flip down when needed, as shown in FIG. 137.

Figure 138:
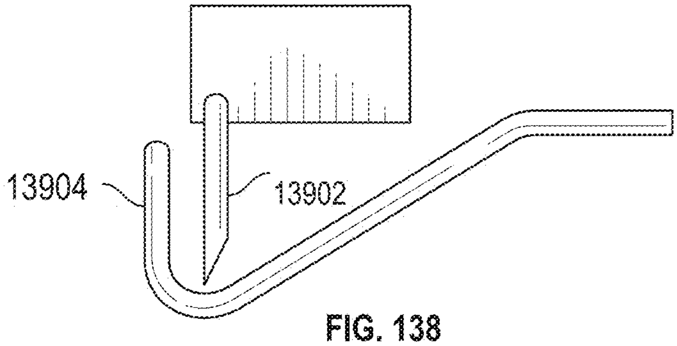
FIG. 138 shows an embodiment of a fang covered by a shroud.

In some embodiments, the fang 13902 is covered by a shroud 13904 to protect surrounding structures as shown in FIG. 138. The shroud 13904 is configured to retract when the fangs are needed.

Figure 139:
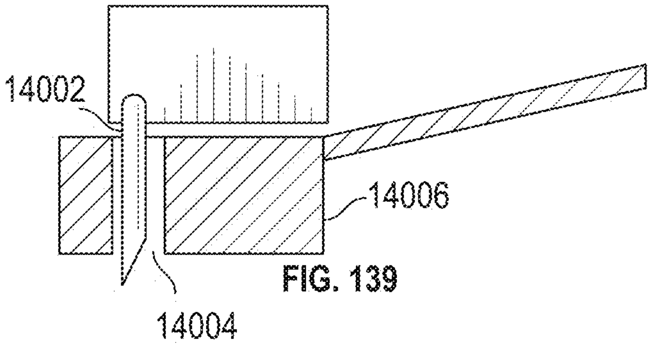
FIG. 139 shows an embodiment of a fang concealed in holes in a backstop.

In some embodiments, the fangs 14002 can be concealed in the backstop holes 14004, as shown in FIG. 139. The backstop 14006 can be configured to actuate and retract when the fangs 14002 are needed.

The embodiments described herein in which fangs are used to penetrate the target material can be adapted such that the staple legs perform the function of the fangs. In other words, the staple legs can be configured to penetrate the target materials instead of the fangs, thereby eliminating the fangs.

Figure 140A:
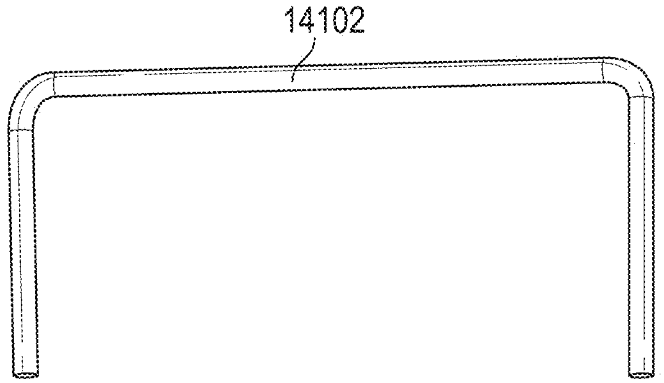
FIGS. 140A and 140B show embodiments of staple with varying shapes.
Figure 140B:
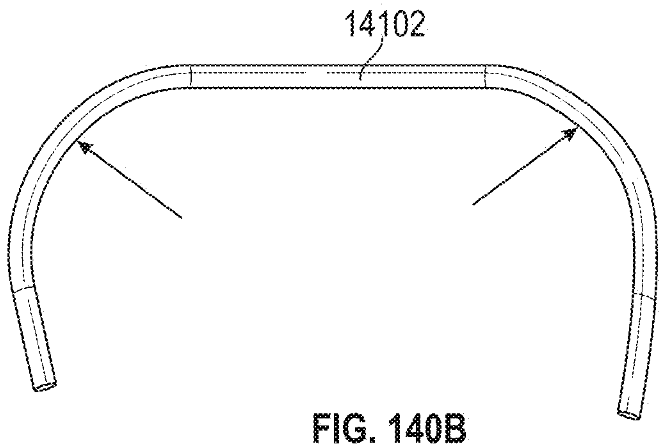

FIGS. 140A and 140B show embodiments of staples with varying shapes. The staple 14102 of FIG. 140A has a more square shape, while the staple 14102 of FIG. 140B has a more rounded shape. The radii on the staple 14102 of FIG. 140B can enable the target material to slide more easily along the staple leg (e.g., to prevent snagging) during staple formation.

Figure 141A:
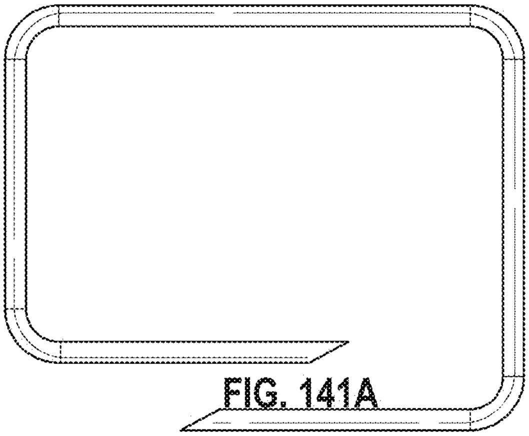
FIGS. 141A and 141B show an embodiment of a closed staple shape.
Figure 141B:
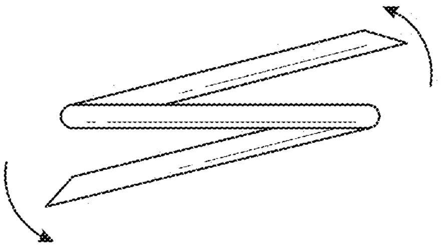

In some embodiments, the stapler or the staple is configured such that staple formation results in one staple leg residing above the other leg, as shown in the front view of FIG. 141A. This configuration can help prevent the staple legs from flaring out of plane, as shown in the top view of FIG. 141B.

Figure 142C:
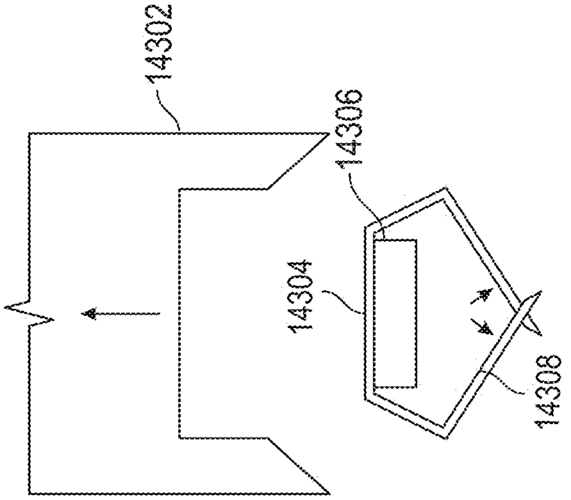
FIGS. 142A-142D show an embodiment of a staple springing open.
Figure 142B:
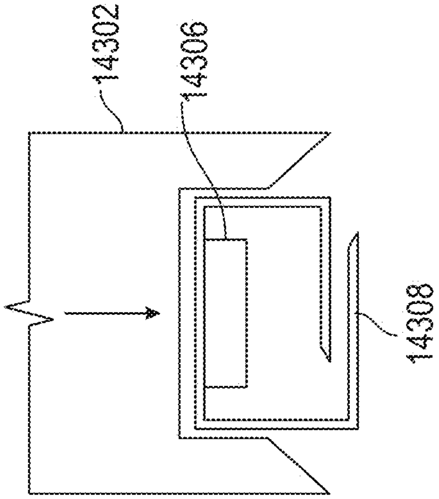
Figure 142D:
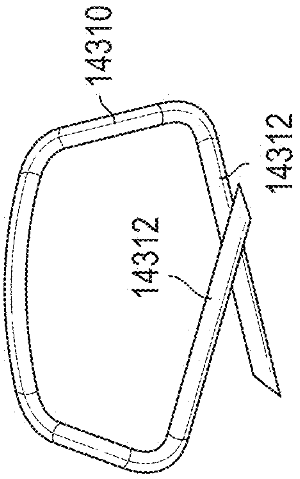
Figure 142A:
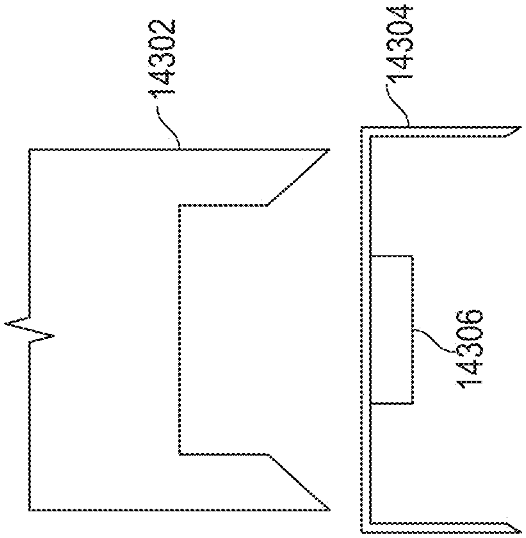
Figure 143A:
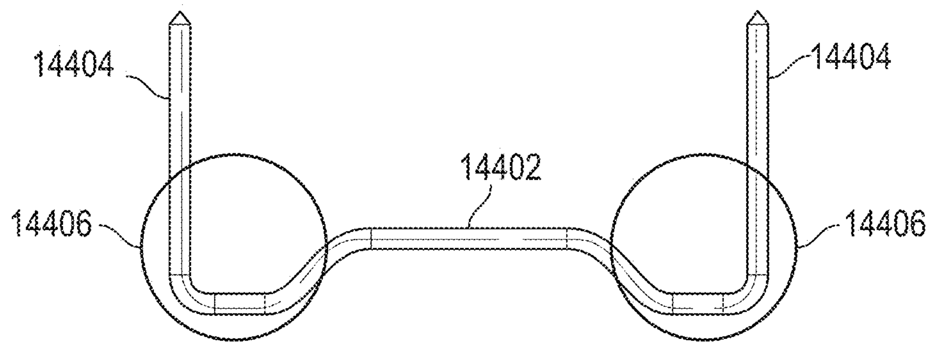
FIGS. 143A-143C shows an embodiment of a staple comprising legs configured to stay in the closed position.
Figure 143B:
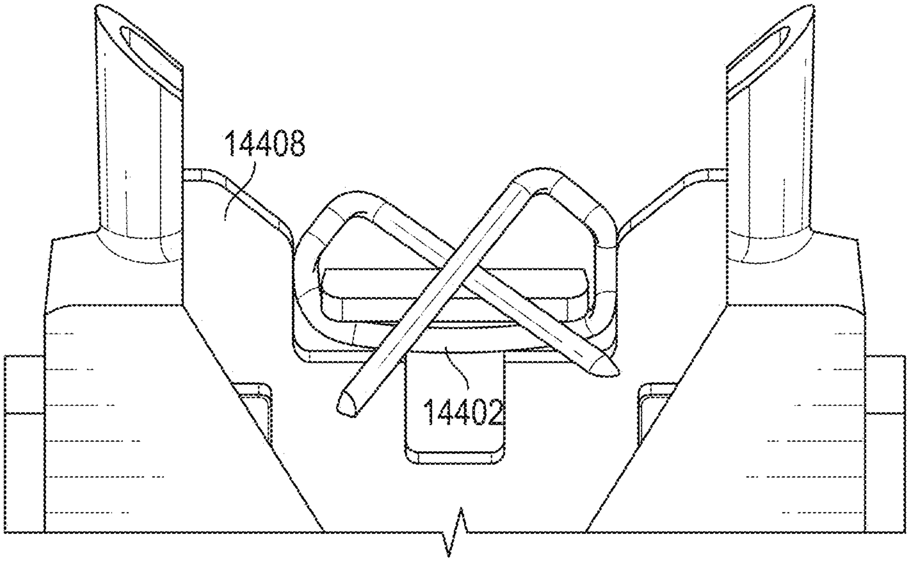
Figure 143C:
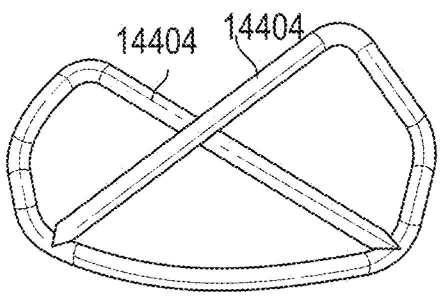

After forming a staple and the forming dies are retracted, the staple legs could spring open slightly, as shown in FIGS. 142A-D. FIGS. 143A-C show staple formation. In FIG. 142A, the forming mechanism 14302 is positioned above the staple 14304 and center die 14306. In FIG. 142B, the forming mechanism is lowered onto the staple, bending the staple legs 14308 around the center die 14306. In FIG. 142C, the forming mechanism 14302 is raised away from the staple 14304. Removing the compressing force of the forming mechanism 14302 causes the staple legs 14308 to spring open slightly. FIG. 142D shows another embodiment of a staple 14310 with the legs 14312 sprung open slightly.

FIG. 143A shows an embodiment of a staple 14402 with features to keep the staple legs 14404 closed after the forming dies are retracted. As shown in FIG. 143A, the staple 14402 comprises humps 14406, the geometry, dimensions, and locations of which can be changed to tune the positioned of the closed staple legs. FIG. 143B shows the staple 14402 being compressed into a closed position by the dies 14408. FIG. 143C shows the staple 14402 with the dies removed and the legs 14404 remaining closed.

Figure 144:
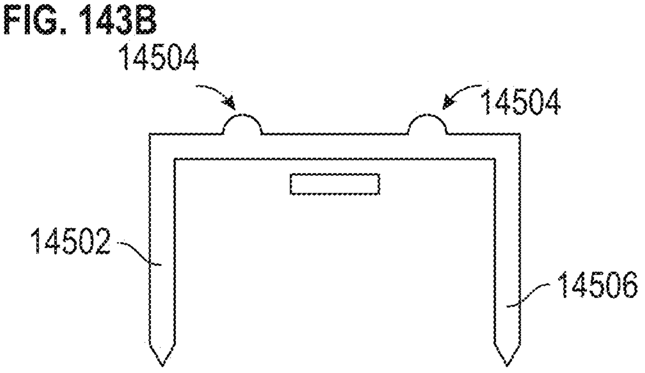
FIG. 144 shows an embodiment of a staple comprising legs configured to stay in the closed position.

FIG. 144 shows another embodiment of a staple 14502, in which the staple legs remain closed after the forming dies are retracted. The staple 14502 comprises bumps 14504. The geometry, dimensions, and locations of the bumps can be changed to tune the position of the closed legs 14506.

In some embodiments, staples are made from resorbable materials.

The embodiments shown in FIGS. 123A-144 can allow a single user to approximate an incision and place a staple. Currently, it could take up to two people to approximate and staple an incision: two hands to grasp and approximate the tissue on both sides of the incision, and another hand to deploy the staple (total of three hands). One user could operate the device described with respect to FIGS. 123A-124K to secure the tissue on side 1 of the incision in one fang, approximate it to the tissue on side 2 of the incision, secure the tissue on side 2 of the incision in the other fang, then deploy the staple.

Figure 145A:
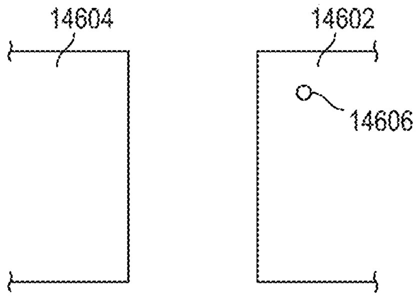
FIGS. 145A-145D show an embodiment of a single user using a stapling devices as disclosed herein.
Figure 145B:
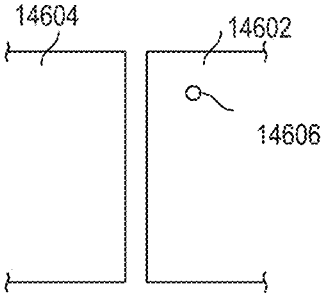
Figure 145C:
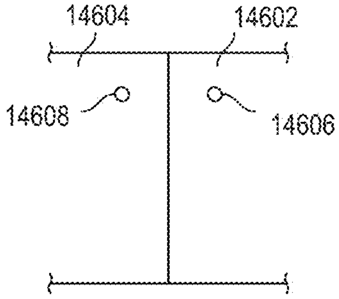
Figure 145D:
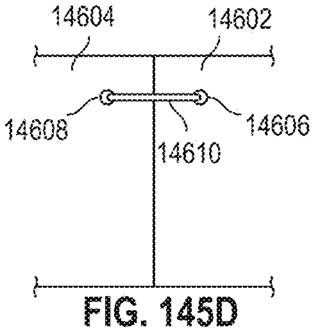

FIGS. 145A-D show an embodiment of a single user using such a device. In FIG. 145A, a first 14602 and second 14604 material to be joined are shown. A fang (not shown) holds the first material 14602 at point 14606. FIG. 145B shows the materials as the device is used to approximate the materials. The first and second materials 14602, 14604 are brought closer together. FIG. 145C shows the materials next to one another. A second fang (not shown) holds the second material 14604 at point 14608. FIG. 145D shows the materials 14602, 14604 after staple 14610 has been deployed to join the materials 14602, 14604.

Figure 146A:
FIGS. 146A-146D show an embodiment of a method of using a stapler to form staple legs at different times.
Figure 146B:
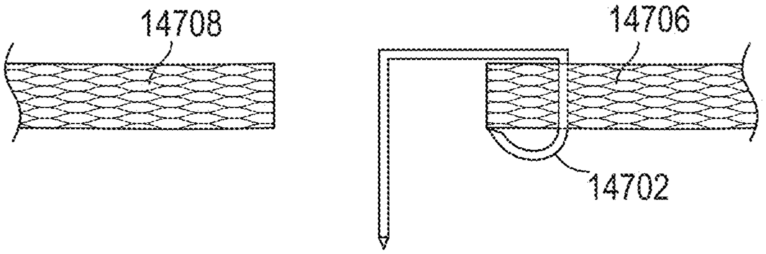
Figure 146C:
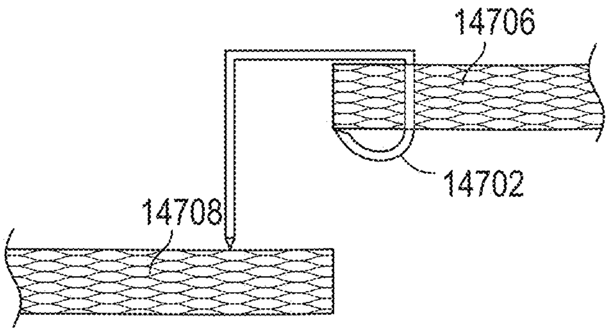
Figure 146D:
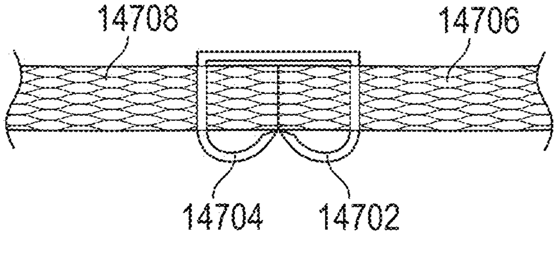

FIGS. 146A-D show a method of using a stapler (not shown) that forms the staple legs 14702, 14704 at different times. FIG. 146A shows two pieces of material 14706, 14708 to be joined. As shown in FIG. 146B, the surgeon could actuate the stapler to close one leg 14702 of the staple in one tissue 14706 (or material). As shown in FIG. 146C, the surgeon can then move the stapler to approximate the tissues (or materials). FIG. 146D shows the materials 14706, 14708 after a second actuation of the stapler to close the other leg 14704 of the staple in the second tissue 14708 (or material). This approach could be applied to a stapler with fangs, or to a stapler without fangs that uses the staple legs to perform the function of the fangs.

Figure 147A:
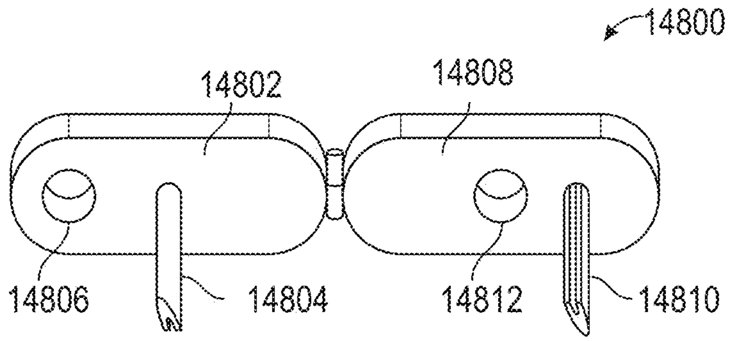
FIGS. 147A-147E show an embodiment of a stapling mechanism.

FIGS. 147A-D illustrate another embodiment of a stapling mechanism 14800 like that described with respect to FIGS. 101A-101G. FIG. 147A shows a first arm 14802 with a first fang or pincer 14804, and first backstop hole 14806. The stapling mechanism 14800 also comprises a second arm 14808 with second fang or pincer 14810 and second backstop hole 14812.

Figure 147B:
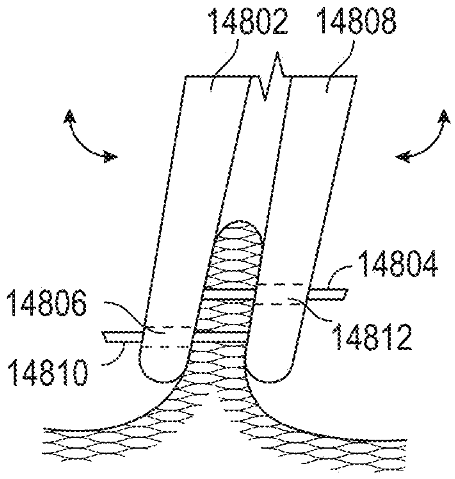

FIG. 147B shows, the fangs 14804, 14810 are placed on the first target material 14814 (e.g., ADM) and used to target the fixation locations on the ADM. The arms 14802, 14808 are actuated, folding the ADM. This causes fang 14804 to pierce the folded ADM 14814 and enter backstop hole 14812, and fang 14810 to pierce the folded ADM and enter backstop hole 14806.

Figure 147C:
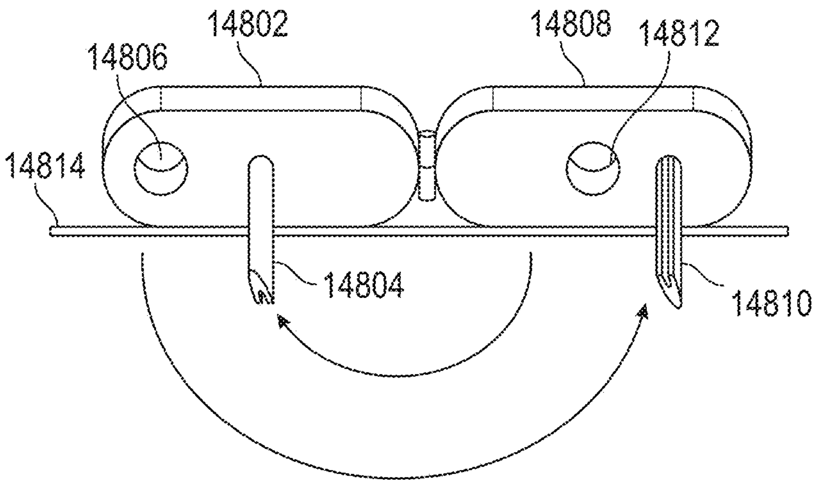
Figure 147D:
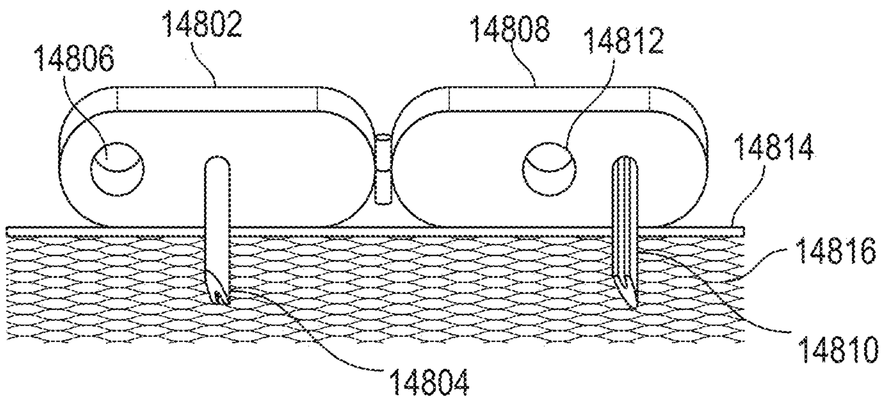

In FIG. 147C, the arms 14802, 14808 are opened, such that fang 14804 pulls out of backstop hole 14812 and the corresponding location of ADM, and fang 14810 pulls out of backstop hole 14806 and the corresponding location of ADM. The ADM adjacent to the base of the fangs are still attached to fang 14804 and fang 14810. In FIG. 147D, the ADM 14814 is positioned, the fangs 14804, 14810 are used to target the fixation location on a second target material 14816 (e.g., tissue), and the fangs 14804, 14810 are inserted into tissue. If the device has staple forming dies (e.g., as described with respect to FIGS. 112 and 124I-J), the staple can be deployed to gather, compress and fix the ADM to tissue. The staple could also be deployed in stages (as described in FIGS. 124I-J) to pull the tissue/ADM away and protect underlying structures prior to closing the staple.

Figure 147E:
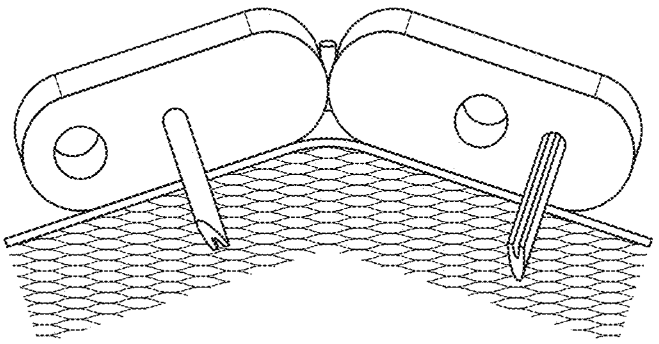

If the device uses the fangs to form the staple (e.g., as described with respect to FIGS. 101A-101G), the arms 14802, 14808 are partially actuated, as shown in FIG. 147E. The device may be maneuvered to retract the tissue 14816 and ADM 14814 to avoid underlying structures during staple deployment. In some embodiments, to cause staple closure, a push rod is advanced to deploy the staple; the staple legs advance and track along the fang grooves, and the staple closes to gather, compress and fix the ADM to tissue. The fangs also serve as a guard to prevent the staple legs from grabbing unintended material during staple formation.

Figure 148A:
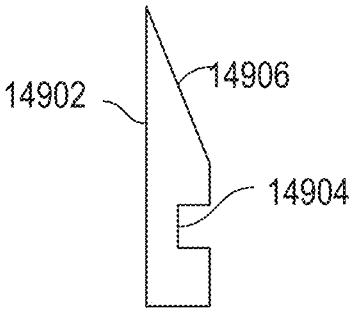
FIGS. 148A-148D show embodiment of fangs.
Figure 148B:
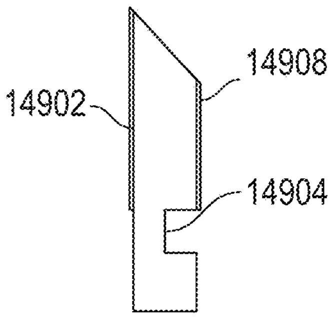
Figure 148C:
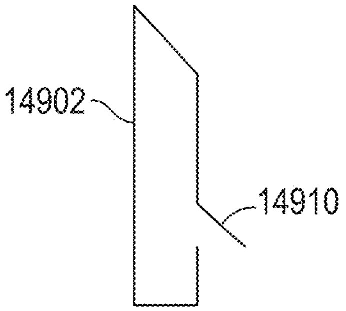
Figure 148D:
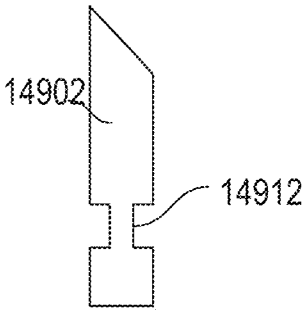

FIGS. 148A-D illustrate embodiments of fangs comprising features configured to enhance performance of the device in FIG. 147. For example, FIG. 148A shows an embodiment of a fang 14902 comprising a notch 14904 to better retain a material (e.g., ADM) at the fang's base. The fang 14902 also comprises a taper 14906 to enable the distal end of the fang 14902 to pull easily out of material, such as ADM. FIG. 148B shows an embodiment of a fang 14902 comprising a lubricious coating 14908, configured to allow the distal end of the fang 14902 to pull easily out of material, such as ADM. The fang 14902 of FIG. 148B also comprises a notch 14904. FIG. 148C illustrates an embodiment of a fang 14902 comprising a barb 14910 configured to better retain a material, such as ADM, at the fang's base. FIG. 148D shows an embodiment of a fang 14902 comprising a neck 14912 configured to better retain a material, such as ADM, at the fang's base.

In some embodiments, the stapling mechanism can use an energy source to aid in the fang or staple piercing material, such as ADM. In some embodiments, high-frequency (e.g. radio frequency) electrical current can be applied to the fang or staple. In some embodiments, a laser can be used to cut a hole in the material (e.g., ADM). In some embodiments, ultrasonic energy is applied to the fang or staple.

Figure 149:
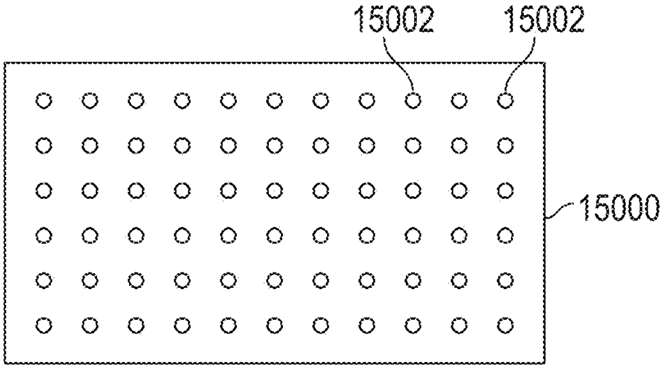
FIG. 149 shows an embodiment of a material comprising a plurality of prepared holes.

FIG. 149 shows a sheet 15000 of material (e.g., ADM) that has been prepared with multiple holes 15002. The prepared holes 15002 remove the burden on the fang or staple from having to puncture through the toughness of a material like ADM. With the prepared holes 15002, the staple leg can easily pass through a hole.

Figure 150A:
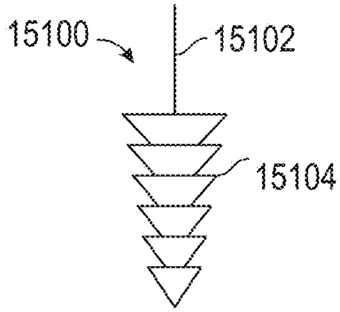
FIGS. 150A-150D show an embodiment of a bone anchor staple.

FIG. 150A shows a bone anchor staple 15100 intended to fix soft tissue (or ADM, mesh, membrane, etc.) to bone. The bone anchor staple has a staple wire feature 15102 that extends from a bone anchor feature 15104.

Figure 150B:
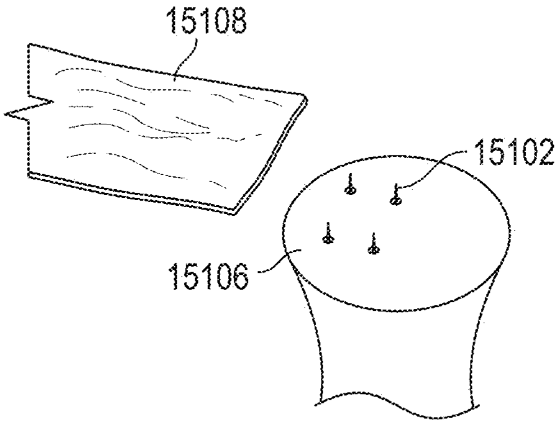
Figure 150C:
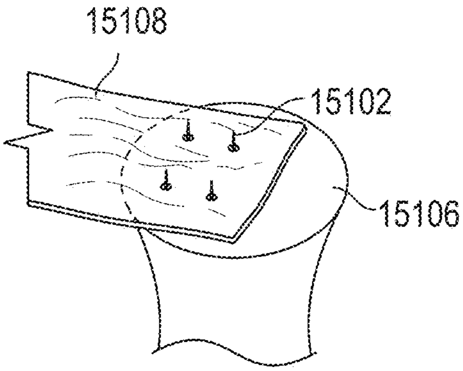
Figure 150D:
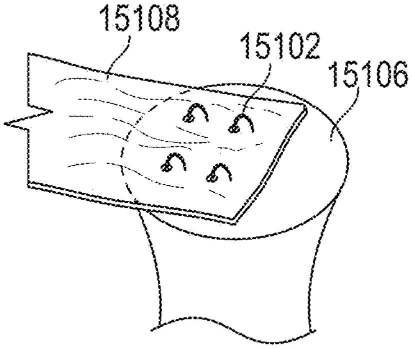

This device 15100 could be utilized in procedures to simplify/eliminate complex suture management (e.g. arthroscopic rotator cuff repair). FIG. 150B shows the bone anchor feature 15104 inserted into bone 15106 with the staple wire feature 15102 protruding from the bone 15106. FIG. 150C shows the material 15108 (e.g., tissue) pushed onto the staple wire features 15102. FIG. 150D shows the formed staple wire features 15102 securing the tissue 15108 to bone 15106.

Figure 151A:
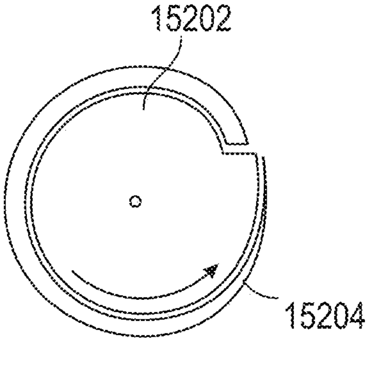
FIGS. 151A-151C show an embodiment of a stapling device.
Figure 151B:
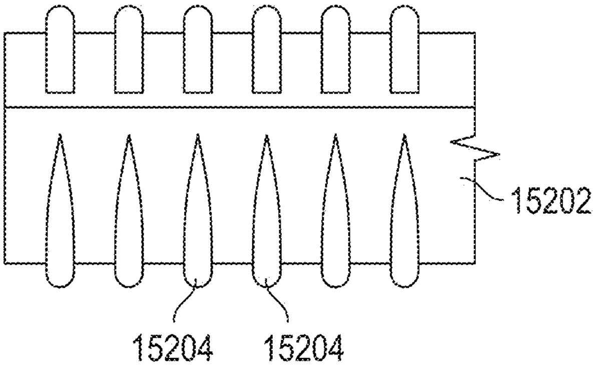

FIGS. 151A and 151B show views of a stapler concept that has a shaft 15202 keeping multiple spring staples 15204 open. The shaft 15202 rotates and drives the staple 15204 through a material such as tissues (or ADM, mesh, membrane, etc.) that are to be fixed together. When the staple comes off the end of the shaft, the staple 15204 contracts to a smaller size to gather, compress and fix the materials

Figure 151C:
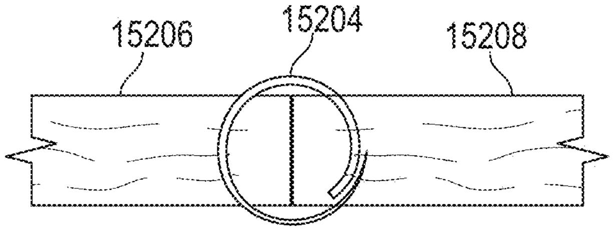

15206, 15208 together, as shown in FIG. 151C. The next staple is advanced to the end of the shaft and is ready to be deployed.

Figure 152A:
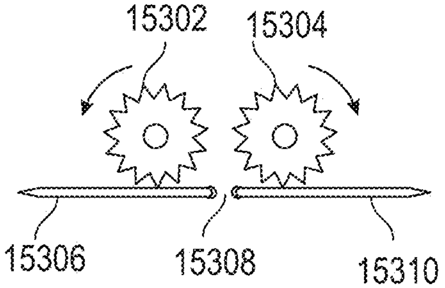
FIGS. 152A-152C shows an embodiment of a device configured to approximate materials.
Figure 152B:
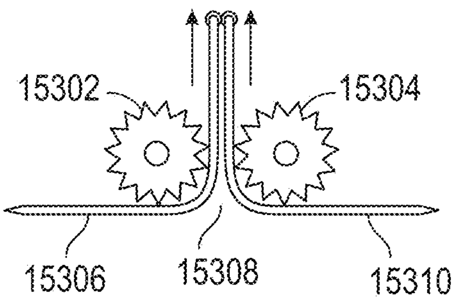
Figure 152C:
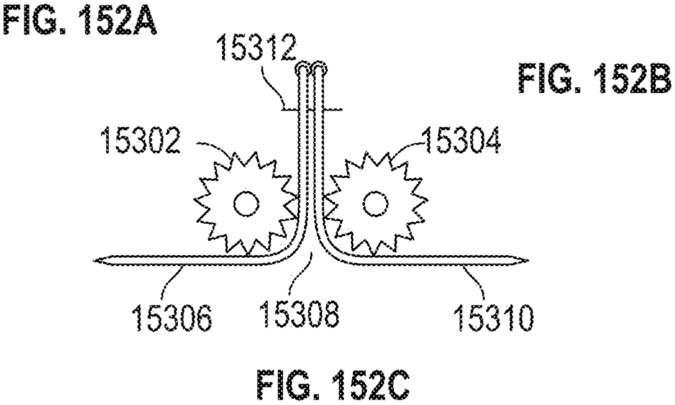

FIGS. 152A-C show an embodiment of a device 15300 that approximates materials, such as tissues (or ADM, mesh, membrane, etc.) so a staple can fix the tissues together. FIG. 152A shows textured wheels 15302, 15304 where one wheel is in contact with tissue 15306 on one side of the incision 15308 (or gap). The other wheel 15304 is in contact with tissue 15310 on the other side of the incision 15308 (or gap). The wheels 15302, 15304 are rotated (as shown by the arrows) to gather the tissue. FIG. 152B shows the textured wheels 15302, 15304 after they have been rotated, where the tissue 15306, 15310 from both sides of the incision 15308 have been approximated between the wheels. FIG. 152C shows the staple 15312 fixing the tissues 15306, 15310 together. The rotating wheels could be a separate device from the stapler or integrated into the stapler device.

Figure 153A:
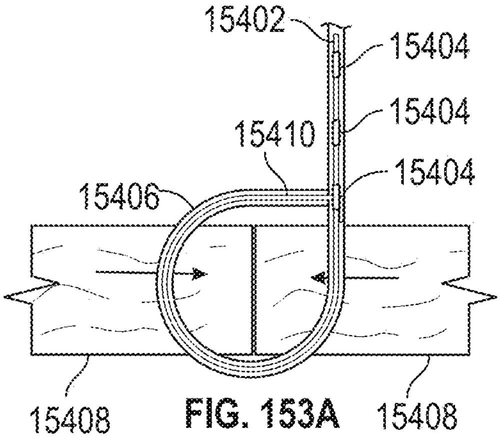
FIGS. 153A-153C shows an embodiment of using a polymer strand to join materials.

FIG. 153A shows a polymer strand 15402 with a series of openings 15404 at one end of the strand. A guide tube 15406 is used to puncture the materials 15408 (e.g., tissues) that are to be fixed together. The tissues could also be ADM, mesh, membrane, etc. The polymer strand 15402 is advanced in the guide tube 15406 until the distal end 15410 of the polymer strand 15402 goes through an opening 15404 in the strand.

Figure 153B:
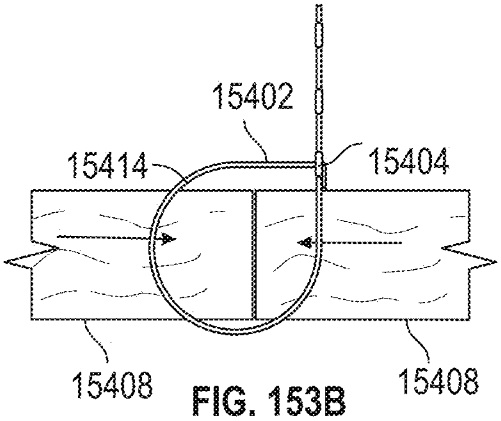
Figure 153C:
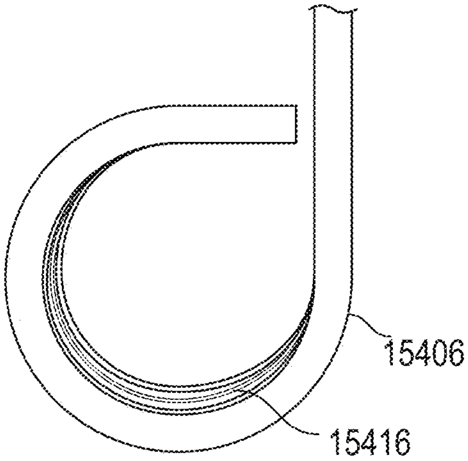

As shown in FIG. 153B, a heating element fused the strand 15402 at the opening 15404 to create a fixed loop 15414 that compresses and fixes the tissues together. A slot 15416, shown in FIG. 153C, along the length of the inner loop of the guide tube 15406 allows the guide tube to be removed, leaving the stitch. The excess length of polymer strand could be trimmed, leaving only the fixed loop/stitch.

Figure 154A:
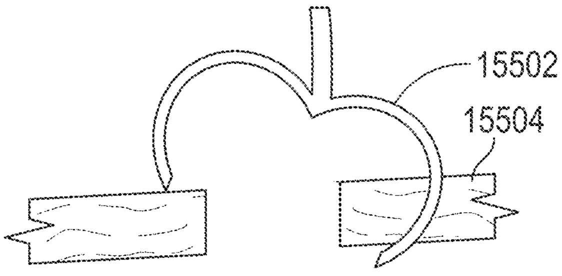
FIGS. 154A-154E show an embodiment of a device configured to join materials.
Figure 154B:
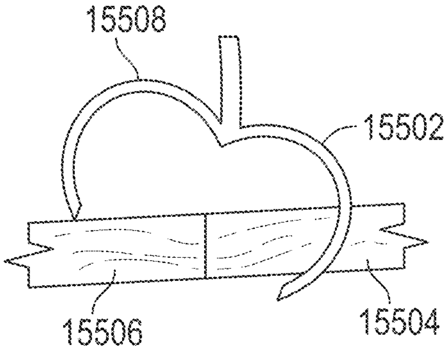
Figure 154C:
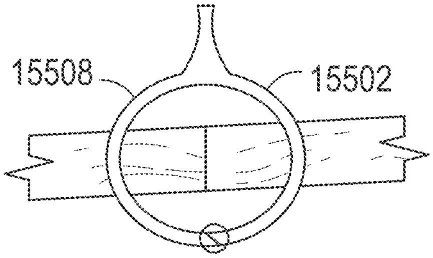
Figure 154D:
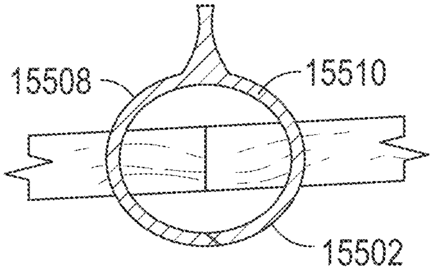
Figure 154E:
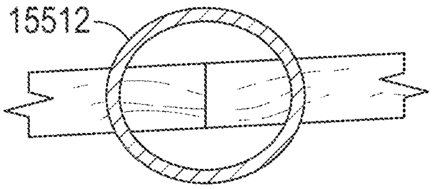

FIGS. 154A-E show an embodiment of a device 15500 configured to approximate and join tissue. As shown in FIG. 154A, the device 15500 comprises a sharpened hollow or tube arm 15502 that is shown penetrating material or tissue 15504. The material can be ADM, mesh, membrane, etc. FIG. 154B shows the arm 15502 being used to approximate the material 15504 to the material 15506 to be joined. In FIG. 154C, sharpened arm 15508 (tube arm, hollow arm) has penetrated material 15506 so that the tips of the arms 15502, 15508 mate. The tips can be shaped such that they are configured to mate with one another, forming the arms 15502, 15508 into a loop. As shown in FIG. 154D, a material such as a heated polymeric material is injected into the lumen 15510 of the arms 15502, 15508. As shown in FIG. 154E, the material cools and hardens to form a fastener 15512. The arms are removed leaving just the fastener in place.

Figure 155A:
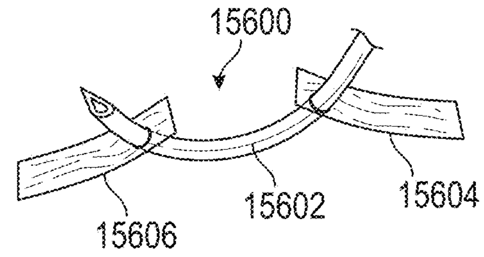
FIGS. 155A-155E show an embodiment of a device configured to join materials.
Figure 155B:
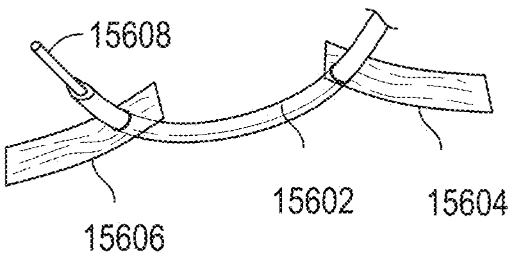
Figure 155C:
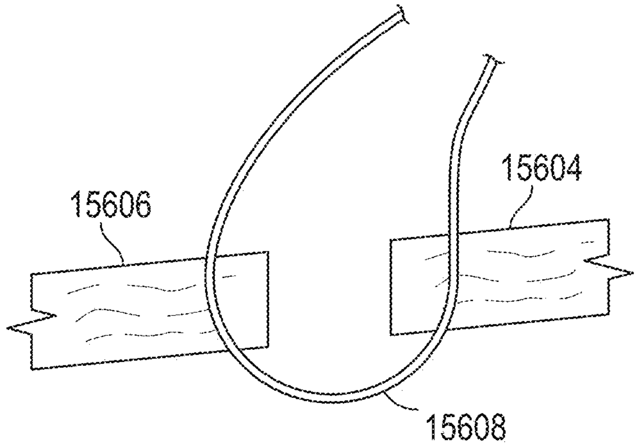
Figure 155D:
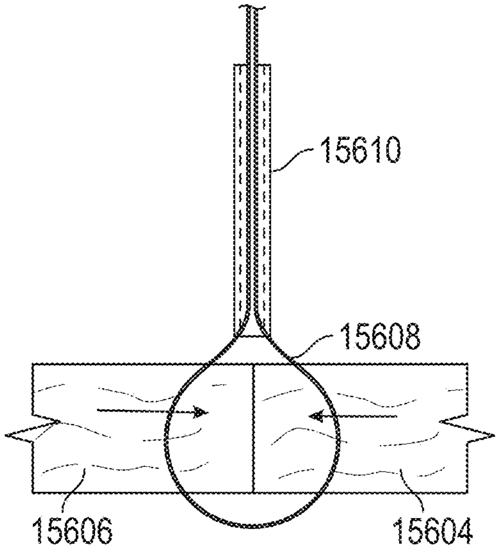
Figure 155E:
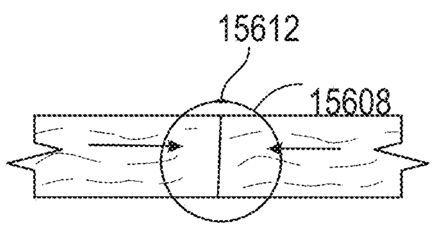

FIGS. 155A-E show another embodiment of a device 15600 configured to approximate and join materials. FIG. 155A shows a sharpened hollow fang 15602 penetrating a first material 15604 and a second material 15606. The materials can be tissue, ADM, mesh, membrane, etc. As shown in FIG. 155B, a strand 15608 (e.g., a polymer strand) is advanced out from the end of the fang 15602. FIG. 155C shows the fang 15602 removed, leaving just the strand 15608 in place penetrating both materials 15604, 15606. In FIG. 155D, a fusing tube or device 15610 is shown advanced over the ends or limbs of the strand 15608 and to the repair site. Advancing the device 15610 can result in approximating and compressing materials 15604, 15606. As shown in FIG. 155E, the strand 15608 is fused into a loop at union point 15612, and the device 15610 is removed.

Figure 156:
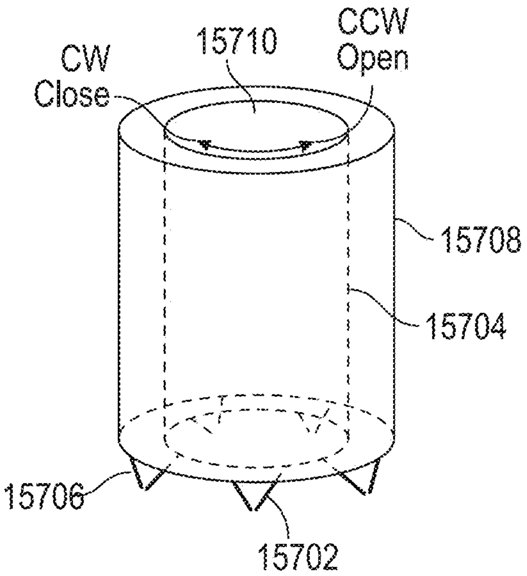
FIG. 156 shows an embodiment of a device configured to grip materials.

FIG. 156 shows an embodiment of a device 15700 configured to grip material such as tissue (or ADM, mesh, membrane, etc.) so that the user can pull the tissue for countertraction when performing various procedures (e.g. stapling). Pincers 15702 are located at the end of inner tube 15704. Pincers 15706 are located at the end of outer tube 15708. The tips of the pincers 15702 on the inner tube 15704 point towards the tips of the pincers 15706 on the outer tube 15708. The inner tube 15704 is rotated one direction (e.g. counterclockwise in FIG. 156) to open the gap between the outer tube pincers 15706 and inner tube pincers 15702. The pincers 15702, 15706 are placed on the material or tissue of interest, and the inner tube 15704 is rotated the opposite direction (e.g. clockwise in FIG. 156) to close the gap between the outer tube pincers 15706 and inner tube pincers 15702, causing the pincers 15702, 15706 to grip the material. The user can pull on the tubes 15704, 15708 to lift the material or tissue as needed. A surgical device (e.g. stapler or scope) can be inserted down the lumen 15710 of the inner tube 15704 to work on the material or tissue (e.g. place a staple). This tissue retraction device can be made with small (micro) pincers or larger pincers. Windows can also be cut in the sides of the tubes to provide visibility and access to the tissue and work site. This mechanism could be separate from a stapler (or other device) or integrated into a stapler (or other device).

Figure 157A:
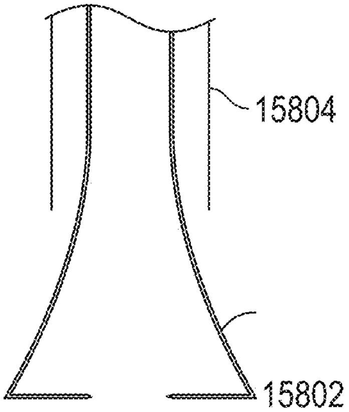
FIGS. 157A-157D show an embodiment of a device configured to grip material.
Figure 157B:
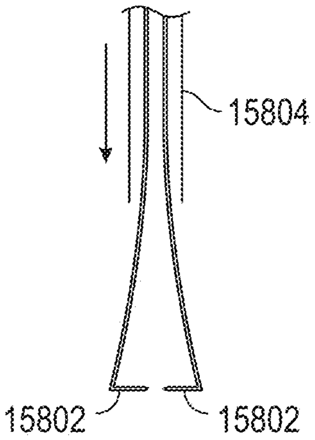
Figure 157C:
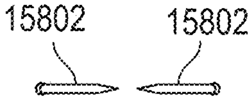
Figure 157D:
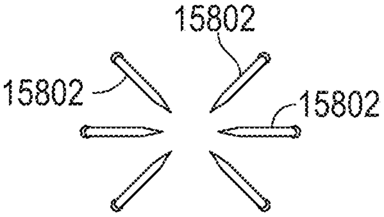

FIGS. 157A-D show a device 15800 configured to grip material (e.g., tissue, ADM, mesh, membrane, etc.) so that the user can pull the tissue for countertraction when performing various procedures (e.g., stapling). Pincers 15802 are positioned within sleeve 15804, as shown in FIG. 157A. The pincers are biased (e.g., spring loaded) outward. The pincers 15802 are placed on the tissue of interest. The sleeve 15804 is advanced, causing the pincers 15802 to move toward one another and grip the material, as shown in FIG. 157B. The number of pincers could vary, as shown in FIGS. 157C (2 pincers) and 157D (6 pincers). Other amounts of pincers are also possible (e.g., 3, 4, 5, 6, 7, 8, more, etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A fastening device comprising:

a shaft;

a needle extending from the shaft, the needle comprising a slot extending along at least a portion of the needle;

the device configured to receive at least one fastener comprising a first bar and a second bar connected by a bar connector, the first bar configured to be positioned within the needle and the second bar configured to be positioned outside the needle;

a push member configured to push the fastener out of the needle, wherein the fastener is manipulated to reorient the second bar relative to the first bar prior to exiting the needle;

one or more control rods comprising a connector, the connector configured for connection to a surgical robot; and a control system for actuating the push member, wherein the control system is configured to execute a deployment cycle in which the push member is advanced to a full extension to deploy the fastener and is prevented from retracting until said full extension is reached.

2. The fastening device of claim 1, wherein the shaft is configured to rotate and/or articulate.

3. The fastening device of claim 1, wherein at least one control rod provides motion for moving a fastener from a conveyance zone through a transition zone.

4. The fastening device of claim 1, wherein at least one control rod is configured to provide motion for moving a fastener from a transition zone through a manipulation zone and deploying the fastener.

5. The fastening device of claim 1, wherein the one or more control rod connectors are configured for connection to one or more control rods of the surgical robot.

6. The fastening device of claim 1, wherein the one or more control rod connectors comprise a connection clamp or union configured to interact with a ball or end feature on the surgical robot.

7. The fastening device of claim 6, wherein the connection clamp or union comprises a first position in the device to receive the ball or end feature on the surgical robot.

8. The fastening device of claim 6, wherein the connection clamp or union comprises a second position in the device to secure the control rod connection to the surgical robot.

9. The fastening device of claim 1, wherein the connector on the fastening device comprises a collar that attaches to the surgical robot.

10. The fastening device of claim 1, wherein the connector on the fastening device threads onto the surgical robot.

11. The fastening device of claim 1, configured to receive a fastener cartridge comprising one or more fasteners.

12. The fastening device of claim 11, wherein the fastener cartridge is replaceable.

13. The fastening device of claim 11, wherein the fastener cartridge is configured for replacement while the device remains connected to the surgical robot.

14. The fastening device of claim 11, wherein the fastener cartridge comprises features to secure the cartridge to the device.

15. The fastening device of claim 11, wherein the fastener cartridge comprises spring loading features to secure the cartridge to the device.

16. The fastening device of claim 11, wherein the fastener cartridge comprises features that align the cartridge to a transition zone of the device.

17. The fastening device of claim 11, wherein the fastener cartridge comprises features that align the cartridge to the control rods or push rods of the device.

18. The fastening device of claim 11, wherein the fastener cartridge is flexible.

19. The fastening device of claim 1, wherein the needle of the device is configured for replacement while the device remains connected to the surgical robot.

* * * * *